(12) United States Patent
Sturino et al.

(10) Patent No.: US 8,349,839 B2
(45) Date of Patent: Jan. 8, 2013

(54) INHIBITORS OF HIV REPLICATION

(75) Inventors: Claudio Sturino, Laval (CA); Patrick Deroy, Laval (CA); Martin Duplessis, Laval (CA); Paul J. Edwards, Laval (CA); Anne-Marie Faucher, Laval (CA); Teddy Halmos, Laval (CA); Clint James, Laval (CA); Jean-Eric Lacoste, Laval (CA); Eric Malenfant, Laval (CA); Joannie Minville, Laval (CA); Louis Morency, Laval (CA); Sebastien Morin, Laval (CA); Martin Tremblay, Laval (CA); Christiane Yoakim, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 291 days.

(21) Appl. No.: 12/756,276

(22) Filed: Apr. 8, 2010

(65) Prior Publication Data

US 2010/0261714 A1    Oct. 14, 2010

Related U.S. Application Data

(60) Provisional application No. 61/168,032, filed on Apr. 9, 2009, provisional application No. 61/263,689, filed on Nov. 23, 2009.

(51) Int. Cl.
*A61K 31/501* (2006.01)
*A61K 31/34* (2006.01)
*C07D 237/36* (2006.01)
*C07D 307/92* (2006.01)

(52) U.S. Cl. .................... 514/252.01; 514/468; 544/234; 549/458

(58) Field of Classification Search ............. 514/252.01, 514/468; 544/234; 549/458
See application file for complete search history.

(56) References Cited

U.S. PATENT DOCUMENTS

| | | |
|---|---|---|
| 2003/0139427 A1 | 7/2003 | Castelhano et al. |
| 2006/0074124 A1 | 4/2006 | Napper et al. |
| 2006/0167290 A1 | 7/2006 | Kawachi |
| 2008/0160028 A1 | 7/2008 | Reichelt et al. |

FOREIGN PATENT DOCUMENTS

| | | |
|---|---|---|
| EP | 1209158 A1 | 5/2002 |
| JP | 06220059 A | 8/1994 |
| WO | 03099206 A2 | 12/2003 |
| WO | 2004046143 A1 | 6/2004 |
| WO | 2004046163 A1 | 6/2004 |
| WO | 2005111034 A1 | 11/2005 |
| WO | 2005111035 A1 | 11/2005 |
| WO | 2005111044 A1 | 11/2005 |
| WO | 2005111047 A1 | 11/2005 |
| WO | 2006044425 A2 | 4/2006 |
| WO | 2006064355 A2 | 6/2006 |
| WO | 2006074192 A2 | 7/2006 |
| WO | 2007025090 A2 | 3/2007 |
| WO | 2007088214 A2 | 8/2007 |
| WO | 2008037783 A1 | 4/2008 |
| WO | 2008119070 A1 | 10/2008 |
| WO | 2009085185 A1 | 7/2009 |

OTHER PUBLICATIONS

Martinez A, Gil C, Castro A, Bruno AM, Pérez C, Prieto C, Otero J. Benzothiadiazine dioxide human cytomegalovirus inhibitors: synthesis and antiviral evaluation of main heterocycle modified derivatives. Antivir Chem Chemother. Mar. 2003;14(2):107-14.*
Seo YJ, Bhuniya S, Tapadar S, Yi JW, Kim BH. Expanded Fluorescent Nucleoside Analog as Hybridization Probe. Bull. Korean Chem. Soc. 2007; 28(11): 1923-1924.*
Rastorgueva, N.A. et al, Synthesis and Chemical Properties of 1-Aryl-substituted Pyrimido[5,4-b]indole, Pharmaceutical Chemistry Journal (translationof Khimiko-Farmatsevticheski Zhumal) (2004), 38(2), 109-112 CODEN: PCJOAU; ISSN: 00910150X.
Lantsetti, N.A. et al., Synthesis and properties of [1,4]diazepino[6,5-b]indoles, Russian Chemical Bulletin (Translation of Izvestiya Akademii Nauk, Seriya Khimicheskaya) (2002), 51(3), 506-512 CODEN: RCBUEY: ISSN 1066-5285.
Sangapure, S.S., Synthesis of some biologically active 4-amino-1,2-dihydro-2-oxo/mercaptobenzofuro[3,2-d]pyrimidine derivatives via Dimroth rearrangement, Indian Journal of Heterocyclic Chemistry (2000), 10(1), 27-30 CODEN: IJCHEI: ISSN 0971-1627.
Basavaraja, K.M. et al., Synthesis of some biologically active 2&2,2-disubstituted 1,2,3,4-tetrahydro-4-thiobenzofuro [3,2-d]pyrimidines and their reactions, Indian Journal of Heterocyclic Chemistry (2007), 17(1), 27-32 CODEN: IJCHI; ISSN:0971-1627.
Pyrimidines XXII interaction of benzalbisurea with ya-indanone and its O- and S- analogs, Mamaev, V.P. et al., Izvestiya Sibirskogo Otdeleniya Akademii Nauk SSSR, Seriya Khimicheskikh Nauk (1969), (2) 96-0 CODEN: IZSKAB; ISSN: 0002-3426.
Rateb, N.M. et al., Convenient synthesis and antimicrobial evaluation of multicyclic thienopyridines, Phosphorus, Sulfur and Silicon, 2007, 182, 10, pp. 2393-2407.
International Search Report, Form PCT/ISA/210, for application PCT/CA2010/000478, date of mailing Jul. 8, 2010.

* cited by examiner

*Primary Examiner* — Paul Zarek
(74) *Attorney, Agent, or Firm* — Michael P. Morris; Alan R. Stempel

(57) ABSTRACT

Compounds of formula (I):

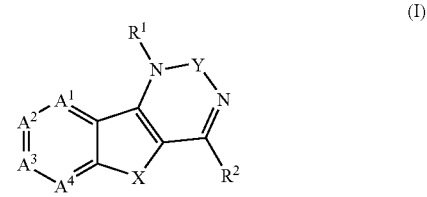

wherein $R^1$, $R^2$, $A^1$, $A^2$, $A^3$, $A^4$, X and Y are as defined herein, are useful as inhibitors of HIV replication.

14 Claims, No Drawings

INHIBITORS OF HIV REPLICATION

RELATED APPLICATIONS

This application claims benefit of U.S. Ser. No. 61/168,032, filed Apr. 9, 2009 and U.S. Ser. No. 61/263,689, filed Nov. 23, 2009, the contents of which are incorporated by reference herein.

FIELD OF THE INVENTION

The present invention relates to compounds, compositions and methods for the treatment of human immunodeficiency virus (HIV) infection. In particular, the present invention provides novel inhibitors of HIV replication, pharmaceutical compositions containing such compounds and methods for using these compounds in the treatment of HIV infection.

BACKGROUND OF THE INVENTION

Acquired immune deficiency syndrome (AIDS) is caused by the human immunodeficiency virus (HIV), particularly the HIV-1 strain. Most currently approved therapies for HIV infection target the viral reverse transcriptase and protease enzymes, with additional approved drugs targeting the viral integrase enzyme and the viral gp41 protein, to inhibit viral entry. Within the reverse transcriptase inhibitor and protease inhibitor classes, resistance of HIV to existing drugs is a problem. Therefore, it is important to discover and develop new antiretroviral compounds.

V. P. Mamaev and E. N. Lyubimova (*Siberian Chemistry Journal* (*translation of Izvestiya Sibirskogo Otdeleniya Akademii Nauk SSSR, Seriya Khimicheskikh Nauk*) (1969) (1): 77-9) describe a compound of the formula:

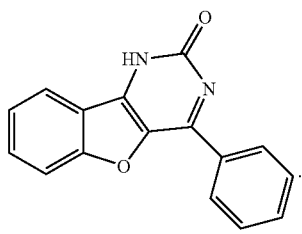 [SMILES: O=c1nc(-c2ccccc2)c2oc3ccccc3c2[nH]1]

K. M. Basavaraja et al (*Indian Journal of Heterocyclic Chemistry* (2007) 17(1): 27-32) describe compounds with antibacterial activity, including compounds of the formula:

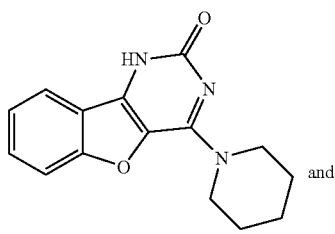
and

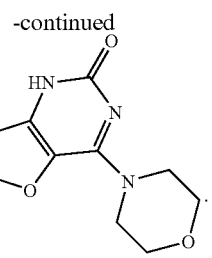

International Patent Application No. WO 2007/088214 describes compounds with anti-HIV activity, of the general formula:

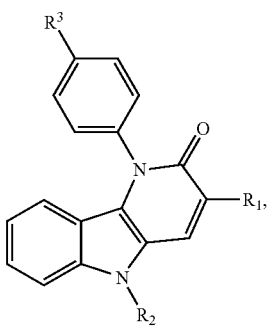

wherein $R_1$, $R_2$ and $R_3$ are as defined in WO 2007/088214.

SUMMARY OF THE INVENTION

The present invention provides a novel series of compounds having inhibitory activity against HIV replication. Further objects of this invention arise for the one skilled in the art from the following description and the examples.

One aspect of the invention provides compounds of formula (I):

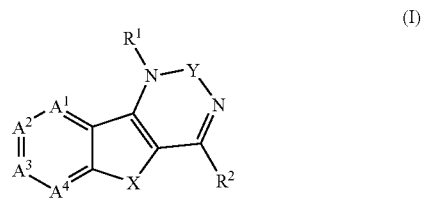

wherein $R^1$ is H, $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het or Het-$(C_{1-6})$alkyl-, wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is optionally substituted with 1 to 3 substituents each independently selected from $R^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

$R^2$ is $R^{21}$, —OR$^{21}$, —N(R$^{12}$)R$^{21}$, —C(=O)R$^{21}$, —C(=O)OR$^{21}$, —C(=O)N(R$^{12}$)R$^{21}$, —O(=O)N(R$^{12}$)—SO$_2$R$^{21}$,

—N(R$^{12}$)—C(=O)R$^{21}$, —N(R$^{12}$)—C(=O)OR$^{21}$, —N(R$^{12}$)—C(=O)N(R$^{12}$)R$^{21}$, —N(R$^{12}$)—SO$_2$R$^{21}$, —SR$^{21}$, —SOR$^{21}$, —SO$_2$R$^{21}$ or —SO$_2$N(R$^{12}$)R$^{21}$;

wherein R$^{21}$ is H, (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-;

wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from R$^{11}$, halo, oxo, —CN, —NO$_2$, —OR$^{11}$, —N(R$^{12}$)R$^{11}$, —C(O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR, —SOR$^{11}$, —SO$_2$R$^{11}$ and —SO$_2$N(R$^{12}$)R$^{11}$;

or wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is substituted with (C$_{1-6}$)alkyl or Het, wherein each of the (C$_{1-6}$)alkyl and Het is substituted with 1 to 3 substituents each independently selected from R$^{11}$, halo, oxo, —CN, —NO$_2$, —OR$^{11}$, —N(R$^{12}$)R$^{11}$, —(N((C$_{1-6}$)alkyl)$_2$R$^{11}$)$^+$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR, —SOR$^{11}$, —SO$_2$R$^{11}$ and —SO$_2$N(R$^{12}$)R$^{11}$;

A$^1$, A$^2$, A$^3$ and A$^4$ are each independently selected from N and CR$^3$, wherein R$^3$ is independently in each instance selected from H and R$^{33}$, wherein R$^{33}$ is independently in each instance selected from R$^{32}$, halo, —CN, —NO$_2$, —OR$^{31}$, —N(R$^{12}$)R$^{31}$, —C(=O)R$^{31}$, —C(=O)OR$^{31}$, —C(=O)N(R$^{12}$)R$^{31}$, —C(=O)N(R$^{12}$)—SO$_2$R$^{31}$, —N(R$^{12}$)—C(=O)R$^{31}$, —N(R$^{12}$)—C(=O)OR$^{31}$, —N(R$^{12}$)—C(=O)N(R$^{12}$)R$^{31}$, —N(R$^{12}$)—SO$_2$R$^{31}$, —SR$^{31}$, —SOR$^{31}$, —SO$_2$R$^{31}$ and —SO$_2$N(R$^{12}$)R$^{31}$;

wherein R$^{31}$ is independently in each instance selected from H and R$^{32}$, and R$^{32}$ is independently in each instance selected from (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from R$^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —C(=NH)N(R$^{12}$)R$^{11}$, —N(R$^{12}$)—C(=O)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is substituted with (C$_{1-6}$)alkyl or Het, wherein each of the (C$_{1-6}$)alkyl and Het is substituted with 1 to 3 substituents each independently selected from R$^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)OR$^{11}$, —N(R$^{12}$)—C(=O)N(R$^{12}$)R$^{11}$, —N(R$^{12}$)—C(=O)—(C$_{1-3}$)alkyl-N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

X is O, S or NR$^4$, wherein R$^4$ is R$^{41}$, —C(=O)R$^{41}$, or —SO$_2$R$^{41}$, wherein R$^{41}$ is H, (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from R$^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

Y is C=O or SO$_2$;

R$^{11}$ is independently in each instance selected from H, (C$_{1-6}$)alkyl, (C$_{1-6}$)haloalkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and R$^{12}$ is independently in each instance selected from R$^{11}$, —OH, —O(C$_{1-6}$)alkyl, —NH$_2$, —NH(C$_{1-6}$)alkyl and —N((C$_{1-6}$)alkyl)$_2$;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

or a salt thereof;

provided that when R$^1$ is H, A$^1$, A$^2$, A$^3$ and A$^4$ are each CR$^3$ wherein R$^3$ is H, X is O, and
Y is C=O, R$^2$ is not

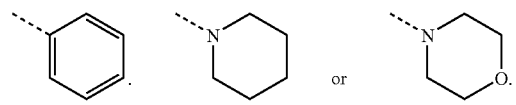

Another aspect of the invention provides compounds of formula (II):

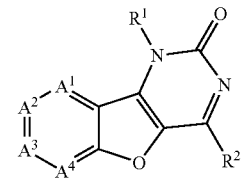

(II)

wherein
R$^1$ is H, (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)

alkyl-, Het or Het-($C_{1-6}$)alkyl-, wherein each of the ($C_{1-6}$) alkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl- is optionally substituted with 1 to 3 substituents each independently selected from $R^{11}$, halo, oxo, —CN, —$NO_2$, —$OR^{11}$, —$N(R^{12})R^{11}$, —C(=O)$R^{11}$, —C(=O)$OR^{11}$, —C(=O)N($R^{12}$)$R^{11}$, —C(=O)N($R^{12}$)—$SO_2R^{11}$, —N($R^{12}$)—C(=O)$R^{11}$, —N($R^{12}$)—C(=O)$OR^{11}$, —N($R^{12}$)—C(=O)N($R^{12}$)$R^{11}$, —N($R^{12}$)—$SO_2R^{11}$, —$SR^{11}$, —$SOR^{11}$, —$SO_2R^{11}$ and —$SO_2N(R^{12})R^{11}$;

$R^2$ is $R^{21}$, wherein $R^{21}$ is ($C_{3-7}$)cycloalkyl, ($C_{3-7}$)cycloalkyl-($C_{1-6}$)alkyl-, aryl, aryl-($C_{1-6}$)alkyl-, Het or Het-($C_{1-6}$)alkyl-;

wherein each of the ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl- is optionally substituted with 1 to 3 substituents each independently selected from $R^{11}$, halo, oxo, —CN, —$NO_2$, —$OR^{11}$, —$N(R^{12})R^{11}$, —C(=O)$R^{11}$, —C(=O)$OR^{11}$, —C(=O)N($R^{12}$)$R^{11}$, —C(=O)N($R^{12}$)—$SO_2R^{11}$, —N($R^{12}$)—C(=O)$R^{11}$, —N($R^{12}$)—C(=O)—($C_{1-3}$)alkyl-N($R^{12}$)$R^{11}$, —N($R^{12}$)—C(=O)$OR^{11}$, —N($R^{12}$)—C(=O)N($R^{12}$)$R^{11}$, —N($R^{12}$)—$SO_2R^{11}$, —$SR^{11}$, —$SOR^{11}$, —$SO_2R^{11}$ and —$SO_2N(R^{12})R^{11}$;

or wherein each of the ($C_{1-6}$)alkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl- is substituted with ($C_{1-6}$)alkyl or Het, wherein each of the ($C_{1-6}$)alkyl and Het is substituted with 1 to 3 substituents each independently selected from $R^{11}$, halo, oxo, —CN, —$NO_2$, —$OR^{11}$, —$N(R^{12})R^{11}$, —(N(($C_{1-6}$)alkyl)$_2R^{11}$)$^+$, —C(=O)$R^{11}$, —C(=O)$OR^{11}$, —C(=O)N(R C(=O)N($R^{12}$)—$SO_2R^{11}$, —N($R^{12}$)—C(=O)$R^{11}$, —N($R^{12}$)—C(=O)—($C_{1-3}$)alkyl-N($R^{12}$)$R^{11}$, —N($R^{12}$)—C(=O)$OR^{11}$, —N($R^{12}$)—C(=O)N($R^{12}$)$R^{11}$, —N($R^{12}$)—$SO_2R^{11}$, —$SR^{11}$, —$SOR^{11}$, —$SO_2R^{11}$ and —$SO_2N(R^{12})R^{11}$;

Provided that when $R^{21}$ is unsubstituted ($C_{3-7}$)cycloalkyl, ($C_{3-7}$)cycloalkyl-($C_{1-6}$)alkyl-, aryl, aryl-($C_{1-6}$)alkyl-, Het or Het-($C_{1-6}$)alkyl-; then $R^1$ is ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het or Het-($C_{1-6}$)alkyl-, all of which being mono-, di- or tri-substituted with at least one substituent selected from $R^{11}$, halo, —$OR^{11}$, oxo, —CN, —$NO_2$, —$N(R^{12})R^{11}$, —C(=O)$R^{11}$, —C(=O)$OR^{11}$, —C(=O)N($R^{12}$)$R^{11}$, —C(=O)N($R^{12}$)—$SO_2R^{11}$, —N($R^{12}$)—C(=O)$R^{11}$, —N($R^{12}$)—C(=O)$OR^{11}$, —N($R^{12}$)—C(=O)N($R^{12}$)$R^{11}$, —N($R^{12}$)—$SO_2R^{11}$, —$SR^{11}$, —$SOR^{11}$, —$SO_2R^{11}$ and —$SO_2N(R^{12})R^{11}$; or $R^1$ is $R^{1a}$, wherein $R^{1a}$ is ($C_{1-6}$)alkyl substituted with 1 to 3 substituents selected from $R^{11}$, halo, —$OR^{11}$, oxo, —CN, —$NO_2$, —$N(R^{12})R^{11}$, —C(=O)$R^{11}$, —C(=O)$OR^{11}$, $R^{12}$)$R^{11}$, —C(=O)N($R^{12}$)—$SO_2R^{11}$, —N($R^{12}$)—C(=O)$R^{11}$, —N($R^{12}$)—C(=O)$OR^{11}$, —N($R^{12}$)—C(=O)N($R^{12}$)$R^{11}$, —N($R^{12}$)—$SO_2R^{11}$, —$SR^{11}$, —$SOR^{11}$, —$SO_2R^{11}$ and —$SO_2N(R^{12})R^{11}$; and provided that $R^{1a}$ cannot be haloalkyl, haloalkoxy or alkoxy;

$A^1$, $A^2$, $A^3$ and $A^4$ are each independently selected from N and $CR^3$, wherein $R^3$ is independently in each instance selected from H and $R^{33}$, wherein $R^{33}$ is independently in each instance selected from $R^{32}$, halo, —CN, —$NO_2$, —$N(R^{12})R^{31}$, —C(=O)$R^{31}$, —C(=O)$OR^{31}$, —C(=O)N($R^{12}$)$R^{31}$, —C(=O)N($R^{12}$)—$SO_2R^{31}$, —N($R^{12}$)—C(=O)$R^{31}$, —N($R^{12}$)—C(=O)$OR^{31}$, —N($R^{12}$)—C(=O)N($R^{12}$)$R^{31}$, —N($R^{12}$)—$SO_2R^{31}$, —$SR^{31}$, —$SOR^{31}$, —$SO_2R^{31}$ and —$SO_2N(R^{12})R^{31}$;

wherein $R^{31}$ is independently in each instance selected from H and $R^{32}$, and $R^{32}$ is independently in each instance selected from ($C_{1-6}$)alkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl-, wherein each of the ($C_{1-6}$)alkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl- is optionally substituted with 1 to 3 substituents each independently selected from $R^{11}$, halo, oxo, —CN, —$NO_2$, —$OR^{11}$, —$N(R^{12})R^{11}$, —C(=O)$R^{11}$, —C(=O)$OR^{11}$, —C(=O)N($R^{12}$)$R^{11}$, —C(=O)N($R^{12}$)—$SO_2R^{11}$, —C(=NH)N($R^{12}$)$R^{11}$, —N($R^{12}$)—C(=O)$R^{11}$, —N($R^{12}$)—C(=O)$OR^{11}$, —N($R^{12}$)—C(=O)N($R^{12}$)$R^{11}$, —N($R^{12}$)—$SO_2R^{11}$, $SR^{11}$, —$SOR^{11}$, —$SO_2R^{11}$ and —$SO_2N(R^{12})R^{11}$;

or wherein each of the ($C_{1-6}$)alkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl- is substituted with ($C_{1-6}$)alkyl or Het, wherein each of the ($C_{1-6}$)alkyl and Het is substituted with 1 to 3 substituents each independently selected from $R^{11}$, halo, oxo, —CN, —$NO_2$, —$OR^{11}$, —$N(R^{12})R^{11}$, —C(=O)$R^{11}$, —C(=O)$OR^{11}$, —C(=O)N($R^{12}$)$R^{11}$, —C(=O)N($R^{12}$)—$SO_2R^{11}$, —N($R^{12}$)—C(=O)$R^{11}$, —N($R^{12}$)—C(=O)$OR^{11}$, —N($R^{12}$)—C(=O)N($R^{12}$)$R^{11}$, —N($R^{12}$)—C(=O)—($C_{1-3}$)alkyl-N($R^{12}$)$R^{11}$, —N($R^{12}$)—$SO_2R^{11}$, —$SR^{11}$, —$SOR^{11}$, —$SO_2R^{11}$ and —$SO_2N(R^{12})R^{11}$;

$R^{11}$ is independently in each instance selected from H, ($C_{1-6}$)alkyl, ($C_{1-6}$)haloalkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl-, wherein each of the ($C_{1-6}$)alkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl- are optionally substituted with 1 to 3 substituents each independently selected from ($C_{1-6}$)alkyl, halo, oxo, —CN, —$NO_2$, —OH, —O($C_{1-6}$)alkyl, —$NH_2$, —NH($C_{1-6}$)alkyl, —N(($C_{1-6}$)alkyl)$_2$, —C(=O)—($C_{1-6}$)alkyl, —COOH, —COO($C_{1-6}$)alkyl, —C(=O)$NH_2$, —C(=O)NH($C_{1-6}$)alkyl, —C(=O)N(($C_{1-6}$)alkyl)$_2$, —SH, —S($C_{1-6}$)alkyl, —SO($C_{1-6}$)alkyl, —$SO_2$($C_{1-6}$)alkyl, —$SO_2NH_2$, —$SO_2$NH($C_{1-6}$)alkyl, —$SO_2$N(($C_{1-6}$)alkyl)$_2$, —NHC(=O)—($C_{1-6}$)alkyl, —N(($C_{1-6}$)alkyl)C(=O)—($C_{1-6}$)alkyl, —NH$SO_2$—($C_{1-6}$)alkyl and —N(($C_{1-6}$)alkyl)$SO_2$—($C_{1-6}$)alkyl; and $R^{12}$ is independently in each instance selected from $R^{11}$, —OH, —O($C_{1-6}$)alkyl, —$NH_2$, —NH($C_{1-6}$)alkyl and —N(($C_{1-6}$)alkyl)$_2$;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$;

or a salt thereof.

A further aspect of the invention provides compounds of formula (I) wherein $R^1$ is ($C_{1-6}$)alkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het or Het-($C_{1-6}$)alkyl-, wherein each of the ($C_{1-6}$)alkyl, ($C_{2-6}$)alkenyl, ($C_{2-6}$)alkynyl, ($C_{3-7}$)cycloalkyl, ($C_{3-7}$)cycloalkyl-($C_{1-6}$)alkyl-, aryl, aryl-($C_{1-6}$)alkyl-, Het and Het-($C_{1-6}$)alkyl- is optionally substituted with 1 to 3 substituents each independently selected from $R^{11}$, halo, oxo, —CN, —$NO_2$, —$OR^{11}$, —$N(R^{12})R^{11}$, —C(=O)

$R^{11}$, —C(=O)O$R^{11}$, —C(=O)N($R^{12}$)$R^{11}$, —C(=O)N($R^{12}$)—SO$_2$$R^{11}$, —N($R^{12}$)—C(=O)$R^{11}$, —N($R^{12}$)—C(=O)O$R^{11}$, —N($R^{12}$)—C(=O)N($R^{12}$)$R^{11}$, —N($R^{12}$)—SO$_2$$R^{11}$, —S$R^{11}$, —SO$R^{11}$, —SO$_2$$R^{11}$ and —SO$_2$N($R^{12}$)$R^{11}$; wherein $R^{11}$, $R^{12}$, and Het are as defined herein.

A further aspect of the invention provides compounds of formula (I) wherein $R^2$ is $R^{21}$, —O$R^{21}$, —N($R^{12}$)$R^{21}$, —C(=O)$R^{21}$, —C(=O)O$R^{21}$, —C(=O)N($R^{12}$)$R^{21}$, —C(=O)N($R^{12}$)—SO$_2$$R^{21}$, —N($R^{12}$)—C(=O)$R^{21}$, —N($R^{12}$)—C(=O)O$R^{21}$, N($R^{12}$)—C(=O)N($R^{12}$)$R^{21}$, —N($R^{12}$)—SO$_2$$R^{21}$, —S$R^{21}$, —SO$R^{21}$, —SO$_2$$R^{21}$ or —SO$_2$N($R^{12}$)$R^{21}$; wherein $R^{21}$ is (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-; wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from $R^{11}$, halo, oxo, —CN, —NO$_2$, —O$R^{11}$, —N($R^{12}$)$R^{11}$, —C(=O)$R^{11}$, —C(=O)O$R^{11}$, —C(=O)N($R^{12}$)$R^{11}$, —C(=O)N($R^{12}$)—SO$_2$$R^{11}$, —N($R^{12}$)—C(=O)$R^{11}$, —N($R^{12}$)—C(=O)—(C$_{1-3}$)alkyl-N($R^{12}$)$R^{11}$, —N($R^{12}$)—C(=O)O$R^{11}$, —N($R^{12}$)—C(=O)N($R^{12}$)$R^{11}$, —N($R^{12}$)—SO$_2$$R^{11}$, —S$R^{11}$, —SO$R^{11}$, —SO$_2$$R^{11}$ and —SO$_2$N($R^{12}$)$R^{11}$;

or wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is substituted with (C$_{1-6}$)alkyl or Het, wherein each of the (C$_{1-6}$)alkyl and Het is substituted with 1 to 3 substituents each independently selected from $R^{11}$, halo, oxo, —CN, —NO$_2$, —O$R^{11}$, —N($R^{12}$)$R^{11}$, —(N((C$_{1-6}$)alkyl)$_2$$R^{11}$)$^+$, —C(=O)O$R^{11}$, —C(=O)N($R^{12}$)$R^{11}$, —C(=O)N($R^{12}$)—SO$_2$$R^{11}$, —N($R^{12}$)—C(=O)$R^{11}$, —N($R^{12}$)—C(=O)—(C$_{1-3}$)alkyl-N($R^{12}$)$R^{11}$, —N($R^{12}$)—C(=O)O$R^{11}$, —N($R^{12}$)—C(=O)N($R^{12}$)$R^{11}$, —N($R^{12}$)—SO$_2$$R^{11}$, —S$R^{11}$, —SO$R^{11}$, —SO$_2$$R^{11}$ and —SO$_2$N($R^{12}$)$R^{11}$;

wherein $R^{11}$, $R^{12}$, and Het are as defined herein.

A further aspect of the invention provides compounds of formula (I) wherein $A^1$, $A^2$, $A^3$ and $A^4$ are each C$R^3$ wherein $R^3$ is as defined above.

A further aspect of the invention provides compounds of formula (I) wherein at least one of $A^1$, $A^2$, $A^3$ and $A^4$ is N.

A further aspect of the invention provides compounds of formula (I) wherein at least one of $A^1$, $A^2$, $A^3$ and $A^4$ is C$R^3$ wherein $R^3$ is $R^{33}$, wherein $R^{33}$ is as defined above.

Another aspect of this invention provides a compound of formula (I) or a pharmaceutically acceptable salt thereof, as a medicament.

Still another aspect of this invention provides a pharmaceutical composition comprising a therapeutically effective amount of a compound of formula (I) or a pharmaceutically acceptable salt thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of an HIV infection in a human being having or at risk of having the infection.

A further aspect of the invention involves a method of treating an HIV infection in a human being having or at risk of having the infection, the method comprising administering to the human being a therapeutically effective amount of a compound of formula (I), a pharmaceutically acceptable salt thereof, or a composition thereof as described hereinabove.

Another aspect of the invention involves a method of treating an HIV infection in a human being having or at risk of having the infection, the method comprising administering to the human being a therapeutically effective amount of a combination of a compound of formula (I) or a pharmaceutically acceptable salt thereof, and at least one other antiviral agent; or a composition thereof.

Also within the scope of this invention is the use of a compound of formula (I) as described herein, or a pharmaceutically acceptable salt thereof, for the treatment of an HIV infection in a human being having or at risk of having the infection.

Another aspect of this invention provides the use of a compound of formula (I) as described herein, or a pharmaceutically acceptable salt thereof, for the manufacture of a medicament for the treatment of an HIV infection in a human being having or at risk of having the infection.

An additional aspect of this invention refers to an article of manufacture comprising a composition effective to treat an HIV infection; and packaging material comprising a label which indicates that the composition can be used to treat infection by HIV; wherein the composition comprises a compound of formula (I) according to this invention or a pharmaceutically acceptable salt thereof.

Still another aspect of this invention relates to a method of inhibiting the replication of HIV comprising exposing the virus to an effective amount of the compound of formula (I), or a salt thereof, under conditions where replication of HIV is inhibited.

Further included in the scope of the invention is the use of a compound of formula (I), or a salt thereof, to inhibit the replication of HIV.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "(C$_{1-n}$)alkyl" as used herein, wherein n is an integer, either alone or in combination with another radical, is intended to mean acyclic, straight or branched chain alkyl radicals containing from 1 to n carbon atoms. "(C$_{1-6}$)alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "(C$_{2-n}$)alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of (C$_{2-6}$)alkenyl radicals include, but are not limited to, ethenyl (vinyl), 1-propenyl, 2-propenyl, and 1-butenyl. Unless specified otherwise, the term "(C$_{2-n}$)alkenyl" is understood to encompass individual stereoisomers where possible, including but not limited to (E) and (Z) isomers, and mixtures thereof. When a $(C_{2-n})$ alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of $(C_{2-6})$alkynyl radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "$(C_{3-m})$cycloalkyl" as used herein, wherein m is an integer, either alone or in combination with another radical, is intended to mean a cycloalkyl substituent containing from 3 to m carbon atoms. Examples of $(C_{3-7})$cycloalkyl radicals include, but are not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise, such that the substitution would give rise to a chemically stable compound, such as are recognized by those skilled in the art.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-6})$alkyl- include, but are not limited to, phenylmethyl (benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise, such that the substitution would give rise to a chemically stable compound, such as are recognized by those skilled in the art.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$, unless specified otherwise. When a Het group is substituted, it is understood that substituents may be attached to any carbon atom or heteroatom thereof which would otherwise bear a hydrogen atom, unless specified otherwise, such that the substitution would give rise to a chemically stable compound, such as are recognized by those skilled in the art.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-6})$alkyl- include, but are not limited to, thienylmethyl, furylmethyl, piperidinylethyl, 2-pyridinylmethyl, 3-pyridinylmethyl, 4-pyridinylmethyl, quinolinylpropyl, and the like. When an Het-$(C_{1-n})$alkyl- group is substituted, it is understood that substituents may be attached to either the Het or the alkyl portion thereof or both, unless specified otherwise, such that the substitution would give rise to a chemically stable compound, such as are recognized by those skilled in the art.

The term "heteroatom" as used herein is intended to mean O, S or N.

The term "heterocycle" as used herein and unless specified otherwise, either alone or in combination with another radical, is intended to mean a 3- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine and pyrimidine, and saturated, unsaturated and aromatic derivatives thereof, and the following heterocycle:

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzodioxole, benzothiazole, quinoline, isoquinoline, and naphthyridine and saturated, unsaturated and aromatic derivatives thereof, and the following heterocycles:

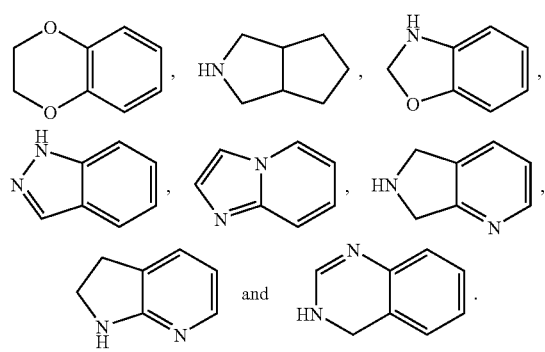

The term "halo" as used herein is intended to mean a halogen substituent selected from fluoro, chloro, bromo and iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. When two or more hydrogen atoms are replaced by halo substituents, the halo substituents may be the same or different. Examples of $(C_{1-6})$haloalkyl include but are not limited to chloromethyl, chloroethyl, dichloroethyl, bromomethyl, bromoethyl, dibromoethyl, chlorobromoethyl, fluoromethyl, difluoromethyl, trifluoromethyl, fluoroethyl and difluoroethyl.

The terms "—O—$(C_{1-n})$alkyl" or "$(C_{1-n})$alkoxy" as used herein interchangeably, wherein n is an integer, either alone or in combination with another radical, are intended to mean an oxygen atom further bonded to an alkyl radical having 1 to n carbon atoms as defined above. Examples of —O—$(C_{1-6})$ alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—$(C_{1-n})$alkyl radical is substituted, it is understood to be substituted on the $(C_{1-n})$alkyl portion thereof, such that the substitution would give rise to a chemically stable compound, such as are recognized by those skilled in the art.

The terms "—S—$(C_{1-n})$alkyl" or "$(C_{1-n})$alkylthio" as used herein interchangeably, wherein n is an integer, either alone or in combination with another radical, are intended to mean an sulfur atom further bonded to an alkyl radical having 1 to n carbon atoms as defined above. Examples of —S—$(C_{1-6})$ alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—$(C_{1-n})$alkyl radical, or an oxidized derivative thereof, such as an —SO—$(C_{1-n})$alkyl radical or an —$SO_2$—$(C_{1-n})$ alkyl radical, is substituted, each is understood to be substituted on the $(C_{1-n})$alkyl portion thereof, such that the substitution would give rise to a chemically stable compound, such as are recognized by those skilled in the art.

The term "oxo" as used herein is intended to mean an oxygen atom attached to a carbon atom as a substituent by a double bond (=O).

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides ($RCONHSO_2NR_2$), and N-acylsulfonamides ($RCONHSO_2R$).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof.

As used herein, the designation whereby a bond to a substituent R is drawn as emanating from the center of a ring, such as, for example,

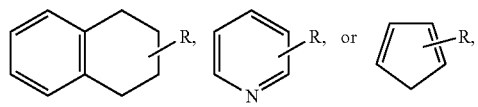

is intended to mean that the substituent R may be attached to any free position on the ring that would otherwise be substituted with a hydrogen atom, unless specified otherwise.

The following designation - - - is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Berge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids or organic acids. Suitable inorganic acids include but are not limited to hydrochloric acid, hydrobromic acid, sulfuric acid, sulfamic acid, nitric acid, phosphoric acid and the like. Suitable organic acids include but are not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases or organic bases. Suitable inorganic bases include but are not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV-1 from mother to baby, by administration to the mother before giving birth and to the child within the first days of life.

The term "antiviral agent" as used herein is intended to mean an agent that is effective to inhibit the formation and/or replication of a virus in a human being, including but not limited to agents that interfere with either host or viral mechanisms necessary for the formation and/or replication of a virus in a human being.

Preferred Embodiments

In the following preferred embodiments, groups and substituents of the compounds according to this invention are described in detail.

Any and each individual definition as set out herein may be combined with any and each individual definition as set out herein.

$R^1$:

$R^1$-A: In at least one embodiment, $R^1$ is $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het or Het-$(C_{1-6})$alkyl-, wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is optionally substituted with 1 to 3 substituents each independently selected from $R^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

wherein $R^{11}$ is independently in each instance selected from H, $(C_{1-6})$alkyl, $(C_{1-6})$haloalkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl-, wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- are optionally substituted with 1 to 3 substituents each independently selected from $(C_{1-6})$alkyl, halo, oxo, —CN, —NO$_2$, —OH, —O$(C_{1-6})$alkyl, —NH$_2$, —NH$(C_{1-6})$alkyl, —N$((C_{1-6})$alkyl$)_2$, —C(=O)—$(C_{1-6})$alkyl, —COOH, —COO$(C_{1-6})$alkyl, —C(=O)NH$_2$, —C(=O)NH$(C_{1-6})$alkyl, —C(=O)N$((C_{1-6})$alkyl$)_2$, —SH, —S$(C_{1-6})$alkyl, —SO$(C_{1-6})$alkyl, —SO$_2(C_{1-6})$alkyl, —SO$_2$NH$_2$, —SO$_2$NH$(C_{1-6})$alkyl, —SO$_2$N$((C_{1-6})$alkyl$)_2$, —NHC(=O)—$(C_{1-6})$alkyl, —N$((C_{1-6})$alkyl$)$C(=O)—$(C_{1-6})$alkyl, —NHSO$_2$—$(C_{1-6})$alkyl and —N$((C_{1-6})$alkyl$)$SO$_2$—$(C_{1-6})$alkyl; and $R^{12}$ is independently in each instance selected from $R^{11}$, —OH, —O$(C_{1-6})$alkyl, —NH$_2$, —NH$(C_{1-6})$alkyl and —N$((C_{1-6})$alkyl$)_2$; and Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$.

$R^1$-B: In at least one embodiment, $R^1$ is $(C_{1-6})$alkyl, $(C_{2-6})$alkenyl, aryl, Het or Het-$(C_{1-6})$alkyl-, wherein Het and the Het portion of Het-$(C_{1-6})$alkyl- are each independently selected from a 5- or 6-membered saturated, unsaturated or aromatic heterocycle having 1 to 3 heteroatoms each independently selected from O, N and S, or an 8- or 9-membered saturated, unsaturated or aromatic heteropolycycle having 1 or 2 N heteroatoms and wherein each of the $(C_{1-6})$alkyl, $(C_{2-6})$alkenyl, aryl, Het and Het-$(C_{1-6})$alkyl- is optionally substituted with 1 to 3 substituents each independently selected from $R^{11}$, halo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —N(R$^{12}$)—C(=O)R$^{11}$ and —N(R$^{12}$)—C(=O)OR$^{11}$;

wherein $R^{11}$ and $R^{12}$ are each independently in each instance selected from H, $(C_{1-6})$alkyl, $(C_{1-6})$haloalkyl, $(C_{2-6})$alkynyl, $(C_{3-7})$cycloalkyl-$(C_{1-6})$alkyl-, aryl-$(C_{1-6})$alkyl-, Het and Het-$(C_{1-6})$alkyl-, wherein Het and the Het portion of Het-$(C_{1-6})$alkyl- are each independently selected from a 5- or 6-membered saturated, unsaturated or aromatic heterocycle having 1 or 2 heteroatoms each independently selected from O and N, and wherein each of the $(C_{1-6})$alkyl, $(C_{2-6})$alkynyl, $(C_{3-7})$cycloalkyl-$(C_{1-6})$alkyl-, aryl-$(C_{1-6})$alkyl-, Het and Het-$(C_{1-6})$alkyl- are optionally substituted with 1 to 3 substituents each independently selected from $(C_{1-6})$alkyl, halo, —CN, —OH, —O$(C_{1-6})$alkyl and —N$((C_{1-6})$alkyl$)_2$.

$R^1$—C: In at least one embodiment, $R^1$ is $(C_{1-6})$alkyl, $(C_{2-6})$alkenyl, aryl, Het or Het-$(C_{1-6})$alkyl-, wherein Het and the Het portion of Het-$(C_{1-6})$alkyl- are each independently selected from

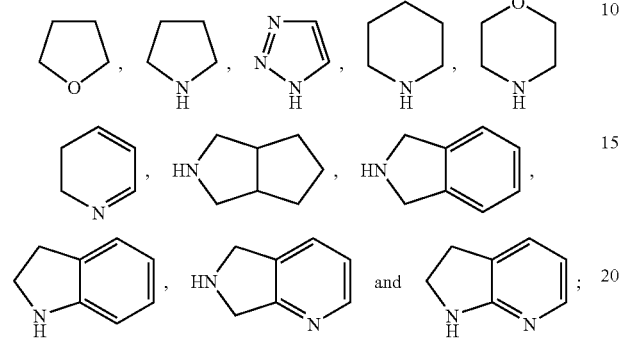

and wherein each of the $(C_{1-6})$alkyl, $(C_{2-6})$alkenyl, aryl, Het and Het-$(C_{1-6})$alkyl- is optionally substituted with 1 to 3 substituents each independently selected from $R^{11}$, halo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —N(R$^{12}$)—C(=O) R$^{11}$ and —N(R$^{12}$)—C(=O)OR$^{11}$;

wherein $R^{11}$ is independently in each instance selected from H, $(C_{1-6})$alkyl, $(C_{1-6})$haloalkyl, $(C_{2-6})$alkynyl, $(C_{3-7})$ cycloalkyl-$(C_{1-6})$alkyl-, aryl-$(C_{1-6})$alkyl-, Het and Het-$(C_{1-6})$ alkyl-, wherein Het and the Het portion of Het-$(C_{1-6})$alkyl- are each independently selected from and wherein each of the $(C_{1-6})$alkyl, $(C_{2-6})$alkynyl, $(C_{3-7})$ cycloalkyl-$(C_{1-6})$alkyl-, aryl-$(C_{1-6})$alkyl-, Het and Het-$(C_{1-6})$ alkyl- are optionally substituted with 1 to 3 substituents each independently selected from $(C_{1-6})$alkyl, halo, —CN, —OH, —O$(C_{1-6})$alkyl and —N$((C_{1-6})$alkyl$)_2$; and $R^{12}$ is independently in each instance selected from H and $(C_{1-6})$alkyl.

$R^1$-D: In at least one embodiment, $R^1$ is selected from:

H, CH$_3$—, CH$_3$CH$_2$—, CH$_3$CH$_2$CH$_2$—, (CH$_3$)$_2$CH—, H$_2$C=CH—CH$_2$—, ClCH$_2$CH$_2$—, HOCH$_2$CH$_2$—, CH$_3$OCH$_2$CH$_2$—, CH$_3$OCH$_2$CH$_2$CH$_2$—,

-continued
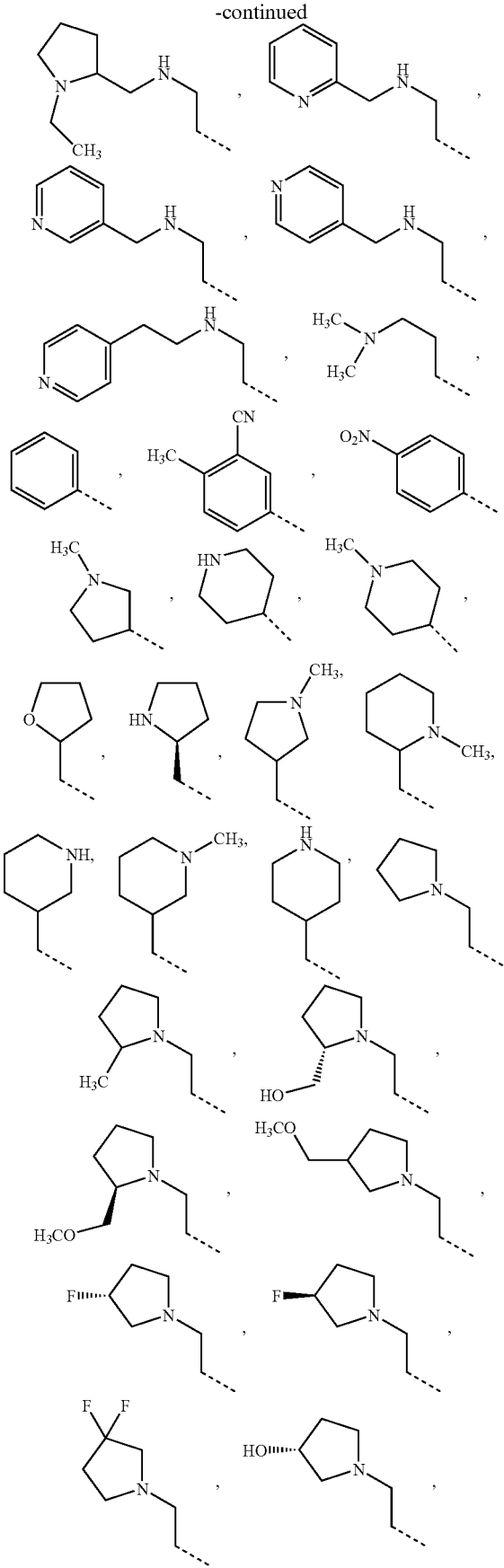
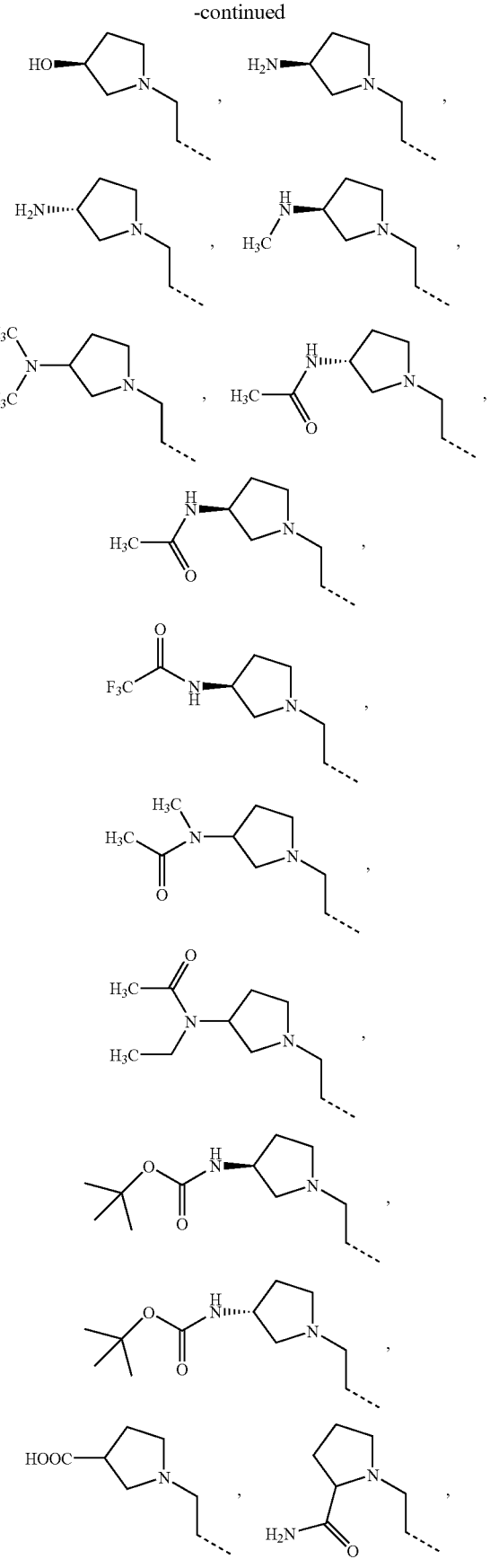

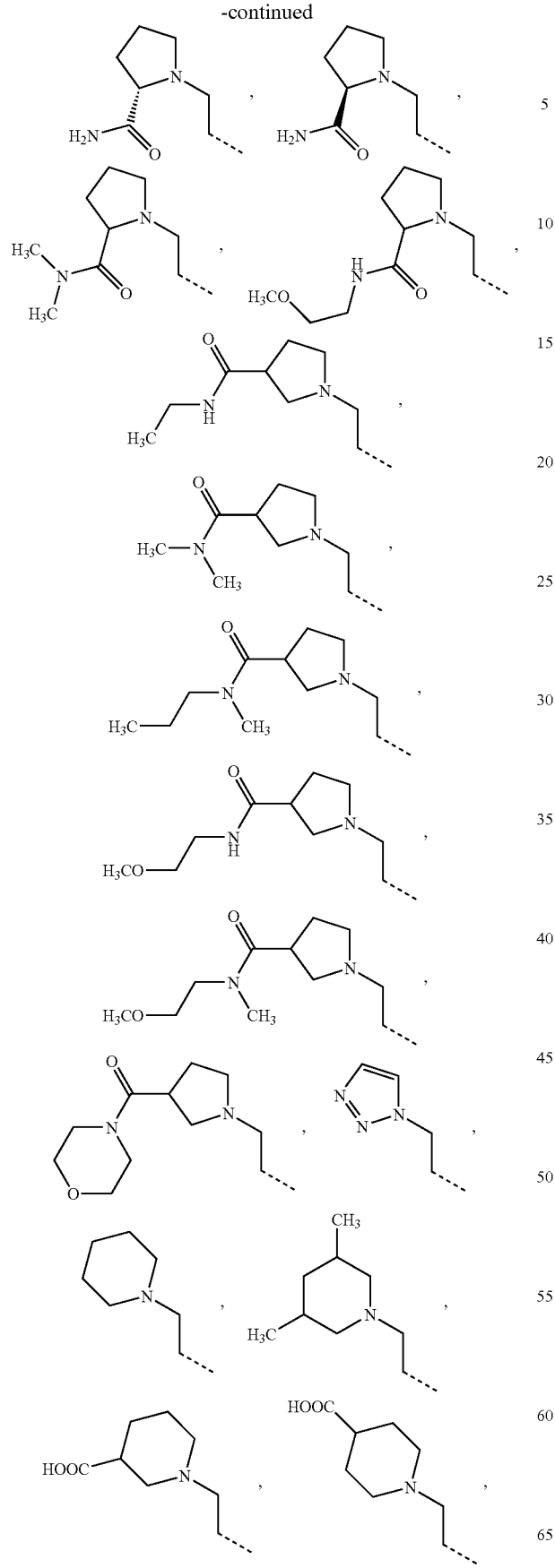
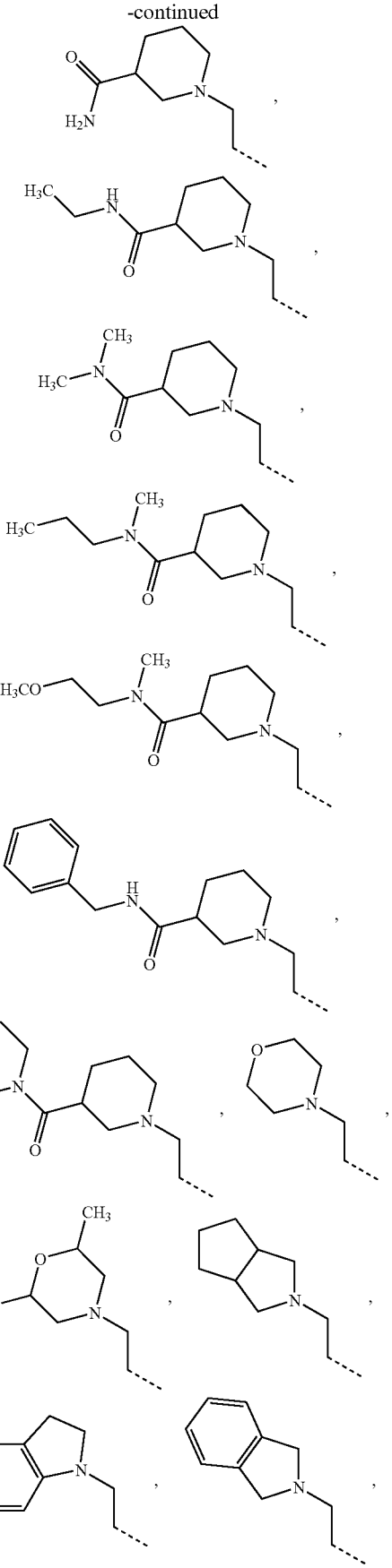

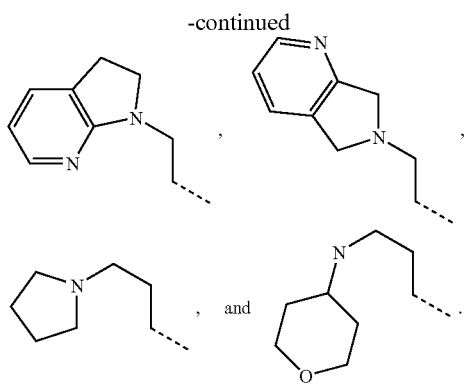

R¹-E: In at least one embodiment, R¹ is $(C_{1-6})$alkyl, $(C_{2-6})$ alkenyl, aryl, Het or Het-$(C_{1-6})$alkyl-, wherein Het and the Het portion of Het-$(C_{1-6})$alkyl- are each independently selected from a 5- or 6-membered saturated, unsaturated or aromatic heterocycle having 1 to 3 heteroatoms each independently selected from O, N and S, or an 8- or 9-membered saturated, unsaturated or aromatic heteropolycycle having 1 or 2 N heteroatoms and wherein each of the $(C_{1-6})$alkyl, $(C_{2-6})$alkenyl, aryl, Het and Het-$(C_{1-6})$alkyl- is optionally substituted with 1 to 3 substituents each independently selected from $R^{11}$, halo, —CN, —NO₂, —OR¹¹, —N(R¹²)R¹¹, —C(=O)R¹¹, —C(=O)OR¹¹, —C(=O)N(R¹²)R¹¹, —N(R¹²)—C(=O)R¹¹ and —N(R¹²)—C(=O)OR¹¹;

wherein $R^{11}$ and $R^{12}$ are each independently in each instance selected from H, $(C_{1-6})$alkyl, $(C_{1-6})$haloalkyl, $(C_{2-6})$alkynyl, $(C_{3-7})$cycloalkyl-$(C_{1-6})$alkyl-, aryl-$(C_{1-6})$alkyl-, Het and Het-$(C_{1-6})$alkyl-, wherein Het and the Het portion of Het-$(C_{1-6})$alkyl- are each independently selected from a 5- or 6-membered saturated, unsaturated or aromatic heterocycle having 1 or 2 heteroatoms each independently selected from O and N, and wherein each of the $(C_{1-6})$alkyl, $(C_{2-6})$alkynyl, $(C_{3-7})$cycloalkyl-$(C_{1-6})$alkyl-, aryl-$(C_{1-6})$alkyl-, Het and Het-$(C_{1-6})$alkyl- are optionally substituted with 1 to 3 substituents each independently selected from $(C_{1-6})$alkyl, halo, —CN, —OH, —O$(C_{1-6})$alkyl and —N(($C_{1-6}$)alkyl)₂;

Provided that when R² is R²¹ and R²¹ is unsubstituted $(C_{3-7})$ cycloalkyl, $(C_{3-7})$cycloalkyl-$(C_{1-6})$alkyl-, aryl, aryl-$(C_{1-6})$ alkyl-, Het or Het-$(C_{1-6})$alkyl-; then R¹ is $(C_{2-6})$alkenyl, $(C_{2-6})$alkynyl, $(C_{3-7})$cycloalkyl, $(C_{3-7})$cycloalkyl-$(C_{1-6})$ alkyl-, aryl, aryl-$(C_{1-6})$alkyl-, Het or Het-$(C_{1-6})$alkyl-, all of which being mono-, di- or tri-substituted with at least one substituent selected from $R^{11}$, halo, —OR¹¹, oxo, —CN, —NO₂, —N(R¹²)R¹¹, —C(=O)R¹¹, C(=O) OR¹¹, —C(=O)N(R¹²)R¹¹, —C(=O)N(R¹²)—SO₂R¹¹, —N(R¹²)—C(=O)R¹¹, —N(R¹²)—C(=O)OR¹¹, —N(R¹²)—C(=O)N(R¹²)R¹¹, —N(R¹²)—SO₂R¹¹, —SR¹¹, SOR¹¹, —SO₂R¹¹ and —SO₂N(R¹²)R¹¹; or R¹ is $R^{1a}$, wherein $R^{1a}$ is $(C_{1-6})$alkyl substituted with 1 to 3 substituents selected from $R^{11}$, halo, —OR¹¹, oxo, —CN, —NO₂, —N(R¹²)R¹¹, —C(=O)OR¹¹, —C(=O)N(R¹²) R¹¹, —C(=O)N(R¹²)—SO₂R¹¹, —N(R¹²)—C(=O)R¹¹, —N(R¹²)—C(=O)OR¹¹, —N(R¹²)—C(=O)N(R¹²)R¹¹, —N(R¹²)—SO₂R¹¹, —SR¹¹, —SOR¹¹, —SO₂R¹¹ and —SO₂N(R¹²)R¹¹; and provided that $R^{1a}$ cannot be haloalkyl, haloalkoxy or alkoxy.

R²:

R²-A: In at least one embodiment, R² is R²¹, —OR²¹, —N(R¹²)R²¹, —C(=O)R²¹, —C(=O)OR²¹, —C(=O)N (R¹²)R²¹, —C(=O)N(R¹²)—SO₂R²¹, —N(R¹²)—C (=O)R²¹, —N(R¹²)—C(=O)OR²¹, —N(R¹²)—C(=O) N(R¹²)R²¹, —N(R¹²)—SO₂R²¹, —SR²¹, —SOR²¹, —SO₂R²¹ or —SO₂N(R¹²)R²¹;

wherein R²¹ is $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het or Het-$(C_{1-6})$alkyl-; wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is optionally substituted with 1 to 3 substituents each independently selected from $R^{11}$, halo, oxo, —CN, —NO₂, —OR¹¹, —N(R¹²)R¹¹, —C(=O)R¹¹, —C(=O) OR¹¹, —C(=O)N(R¹²)R¹¹, —C(=O)N(R¹²)—SO₂R¹¹, —N(R¹²)—C(=O)R¹¹, —N(R¹²)—C(=O)—$(C_{1-3})$alkyl-N(R¹²)R¹¹, —N(R¹²)—C(=O)OR¹¹, —N(R¹²)—C(=O)N (R¹²)R¹¹, —N(R¹²)—SO₂R¹¹, —SR¹¹, —SOR¹¹, —SO₂R¹¹ and —SO₂N(R¹²)R¹¹;

or wherein each of the $(C_{1-6})$alkyl, $(C_{2-6})$alkenyl, $(C_{2-6})$ alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is substituted with $(C_{1-6})$alkyl or Het, wherein each of the $(C_{1-6})$alkyl and Het is substituted with 1 to 3 substituents each independently selected from $R^{11}$, halo, oxo, —CN, —NO₂, —OR¹¹, —N(R¹²)R¹¹, —(N(($C_{1-6})$alkyl)₂R¹¹)⁺, —C(=O)R¹¹, —C(=O)OR¹¹, —C(=O)N(R¹²)R¹¹, —C(=O)N(R¹²)— SO₂R¹¹, —N(R¹²)—C(=O)R¹¹, —N(R¹²)—C(=O)— $(C_{1-3})$alkyl-N(R¹²)R¹¹, —N(R¹²)—C(=O)OR¹¹, —N(R¹²)—C(=O)N(R¹²)R¹¹, —N(R¹²)—SO₂R¹¹, —SR¹¹, —SOR¹¹, —SO₂R¹¹ and —SO₂N(R¹²)R¹¹;

$R^{11}$ is independently in each instance selected from H, $(C_{1-6})$alkyl, $(C_{1-6})$haloalkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl-, wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- are optionally substituted with 1 to 3 substituents each independently selected from $(C_{1-6})$alkyl, halo, oxo, —CN, —NO₂, —OH, —O$(C_{1-6})$alkyl, —NH₂, —NH $(C_{1-6})$alkyl, —N(($C_{1-6})$alkyl)₂, —C(=O)—$(C_{1-6})$alkyl, —COOH, —COO$(C_{1-6})$alkyl, —C(=O)NH₂, —C(=O)NH $(C_{1-6})$alkyl, —C(=O)N(($C_{1-6})$alkyl)₂, —SH, —S$(C_{1-6})$ alkyl, —SO$(C_{1-6})$alkyl, —SO₂$(C_{1-6})$alkyl, —SO₂NH₂, —SO₂NH$(C_{1-6})$alkyl, —SO₂N(($C_{1-6})$alkyl)₂, —NHC (=O)—$(C_{1-6})$alkyl, —N(($C_{1-6})$alkyl)C(=O)—$(C_{1-6})$alkyl, —NHSO₂—$(C_{1-6})$alkyl and —N(($C_{1-6})$alkyl)SO₂—$(C_{1-6})$ alkyl; and $R^{12}$ is independently in each instance selected from $R^{11}$, —OH, —O$(C_{1-6})$alkyl, —NH₂, —NH$(C_{1-6})$alkyl and —N(($C_{1-6})$alkyl)₂;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO₂;

provided that when R¹ is H, A¹, A², A³ and A⁴ are each CR³ wherein R³ is H, X is O, and Y is C=O, R² is not

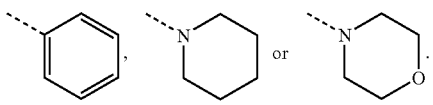 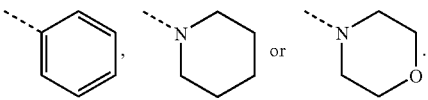

$R^2$-B: In at least one embodiment, $R^2$ is $R^{21}$;

wherein $R^{21}$ is $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het or Het-$(C_{1-6})$alkyl-; wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is optionally substituted with 1 to 3 substituents each independently selected from $R^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is substituted with $(C_{1-6})$alkyl or Het, wherein each of the $(C_{1-6})$alkyl and Het is substituted with 1 to 3 substituents each independently selected from $R^{11}$, halo, oxo, —CN, —NO$_2$, —OR$^{11}$, —N(R$^{12}$)R$^{11}$, —(N((C$_{1-6}$)alkyl)$_2$R$^{11}$)$^+$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

$R^{11}$ is independently in each instance selected from H, $(C_{1-6})$alkyl, $(C_{1-6})$haloalkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl-, wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- are optionally substituted with 1 to 3 substituents each independently selected from $(C_{1-6})$alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and $R^{12}$ is independently in each instance selected from $R^{11}$, —OH, —O(C$_{1-6}$)alkyl, —NH$_2$, —NH(C$_{1-6}$)alkyl and —N((C$_{1-6}$)alkyl)$_2$;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

provided that when $R^1$ is H, $A^1$, $A^2$, $A^3$ and $A^4$ are each CR$^3$ wherein $R^3$ is H, X is O, and Y is C=O, $R^2$ is not $R^2$-C: In at least one embodiment, $R^2$ is $R^{21}$, —OR$^{21}$, —N(R$^{12}$)R$^{21}$, —C(=O)R$^{21}$, —C(=O)OR$^{21}$, —C(=O)N(R$^{12}$)R$^{21}$, —C(=O)N(R$^{12}$)—SO$_2$R$^{21}$, —N(R$^{12}$)—C(=O)R$^{21}$, —N(R$^{12}$)—C(=O)OR$^{21}$, —N(R$^{12}$)—C(=O)N(R$^{12}$)R$^{21}$, —N(R$^{12}$)—SO$_2$R$^{21}$, —SR$^{21}$, —SOR$^{21}$, —SO$_2$R$^{21}$ or —SO$_2$N(R$^{12}$)R$^{21}$;

wherein $R^{21}$ is aryl or Het;

wherein each of the aryl and Het is optionally substituted with 1 to 3 substituents each independently selected from $R^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, SR$^{11}$, —SOR$^{11}$, —SO$_2$R$^{11}$ and —SO$_2$N(R$^{12}$)R$^{11}$;

or wherein each of the aryl and Het is substituted with $(C_{1-6})$alkyl or Het, wherein each of the $(C_{1-6})$alkyl and Het is substituted with 1 to 3 substituents each independently selected from $R^{11}$, halo, oxo, —CN, —NO$_2$, —OR$^{11}$, —N(R$^{12}$)R$^{11}$, —(N((C$_{1-6}$)alkyl)$_2$R$^{11}$)$^+$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

$R^{11}$ is independently in each instance selected from H, $(C_{1-6})$alkyl, $(C_{1-6})$haloalkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl-, wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- are optionally substituted with 1 to 3 substituents each independently selected from $(C_{1-6})$alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and $R^{12}$ is independently in each instance selected from $R^{11}$, —OH, —O(C$_{1-6}$)alkyl, —NH$_2$, —NH(C$_{1-6}$)alkyl and —N((C$_{1-6}$)alkyl)$_2$;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

provided that when $R^1$ is H, $A^1$, $A^2$, $A^3$ and $A^4$ are each CR$^3$ wherein $R^3$ is H, X is O, and Y is C=O, $R^2$ is not

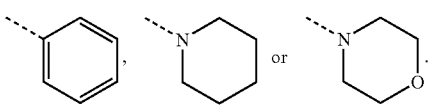

R²-D: In at least one embodiment, R² is aryl or Het;
wherein each of the aryl and Het is optionally substituted with 1 to 3 substituents each independently selected from $R^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or wherein each of the aryl and Het is substituted with (C$_{1-6}$)alkyl or Het, wherein each of the (C$_{1-6}$)alkyl and Het is substituted with 1 to 3 substituents each independently selected from $R^{11}$, halo, oxo, —CN, —NO$_2$, —OR$^{11}$, —N(R$^{12}$)R$^{11}$, —(N((C$_{1-6}$)alkyl)$_2$R$^{11}$)$^+$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

$R^{11}$ is independently in each instance selected from H, (C$_{1-6}$)alkyl, (C$_{1-6}$)haloalkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and $R^{12}$ is independently in each instance selected from $R^{11}$, —OH, —O(C$_{1-6}$)alkyl, —NH$_2$, —NH(C$_{1-6}$)alkyl and —N((C$_{1-6}$)alkyl)$_2$;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

provided that when $R^1$ is H, $A^1$, $A^2$, $A^3$ and $A^4$ are each CR$^3$ wherein $R^3$ is H, X is O, and Y is C=O, $R^2$ is not

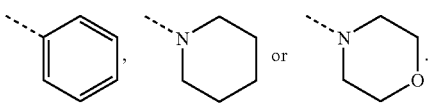

R²-E: In at least one embodiment, R² is aryl optionally substituted with 1 to 3 substituents each independently selected from $R^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or R² is aryl substituted with (C$_{1-6}$)alkyl or Het, wherein each of the (C$_{1-6}$)alkyl and Het is substituted with 1 to 3 substituents each independently selected from $R^{11}$, halo, oxo, —CN, —NO$_2$, —OR$^{11}$, —N(R$^{12}$)R$^{11}$, —(N((C$_{1-6}$)alkyl)$_2$R$^{11}$)$^+$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

wherein $R^{11}$ is independently in each instance selected from H, (C$_{1-6}$)alkyl, (C$_{1-6}$)haloalkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and $R^{12}$ is independently in each instance selected from $R^{11}$, —OH, —O(C$_{1-6}$)alkyl, —NH$_2$, —NH(C$_{1-6}$)alkyl and —N((C$_{1-6}$)alkyl)$_2$; and Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

provided that when $R^1$ is H, $A^1$, $A^2$, $A^3$ and $A^4$ are each CR$^3$ wherein $R^3$ is H, X is O, and Y is C=O, $R^2$ is not

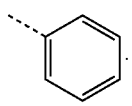

R²-F: In at least one embodiment, R² is aryl optionally substituted with 1 or 2 substituents each independently selected from $R^{11}$, halo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)N(R$^{12}$)R$^{11}$ and —N(R$^{12}$)—SO$_2$R$^{11}$; or R² is aryl substituted with (C$_{1-6}$)

alkyl wherein the (C$_{1-6}$)alkyl is substituted with 1 to 3 substituents each independently selected from R$^{11}$, —OR$^{11}$, —N(R$^{12}$)R$^{11}$, —(N((C$_{1-6}$)alkyl)$_2$R$^{11}$)$^+$ and —N(R$^{12}$)—C(=O)R$^{11}$;

wherein R$^{11}$ is independently in each instance selected from H, (C$_{1-6}$)alkyl, (C$_{1-6}$)haloalkyl, (C$_{3-7}$)cycloalkyl, aryl, aryl-(C$_{1-6}$)alkyl-, Het and Het-(C$_{1-6}$)alkyl-;

wherein Het and the Het portion of Het-(C$_{1-6}$)alkyl- are each independently selected from a 5- or 6-membered saturated, unsaturated or aromatic heterocycle having 1 to 4 heteroatoms each independently selected from O, N and S, or a 9-membered saturated, unsaturated or aromatic heteropolycycle having 1 O heteroatom;

and wherein each of the (C$_{1-6}$)alkyl, (C$_{3-7}$)cycloalkyl, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —OH, —O(C$_{1-6}$)alkyl, —NH$_2$, —NH(C$_{1-6}$)alkyl, —N((C$_{1-6}$)alkyl)$_2$, —COO(C$_{1-6}$)alkyl, —C(=O)NH(C$_{1-6}$)alkyl and —C(=O)N((C$_{1-6}$)alkyl)$_2$; and R$^{12}$ is independently in each instance selected from H, (C$_{1-6}$)alkyl, —NH$_2$, —NH(C$_{1-6}$)alkyl and —N((C$_{1-6}$)alkyl)$_2$;

provided that when R$^1$ is H, A$^1$, A$^2$, A$^3$ and A$^4$ are each CR$^3$ wherein R$^3$ is H, X is O, and Y is C=O, R$^2$ is not

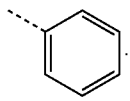

R$^2$-G: In at least one embodiment, R$^2$ is aryl optionally substituted with 1 or 2 substituents each independently selected from R$^{11}$, halo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)N(R$^{12}$)R$^{11}$ and —N(R$^{12}$)—SO$_2$R$^{11}$;

or R$^2$ is aryl substituted with (C$_{1-6}$)alkyl wherein the (C$_{1-6}$)alkyl is substituted with 1 to 3 substituents each independently selected from R$^{11}$, —OR$^{11}$, —N(R$^{12}$)R$^{11}$, —(N((C$_{1-6}$)alkyl)$_2$R$^{11}$)$^+$ and —N(R$^{12}$)—C(=O)R$^{11}$;

wherein R$^{11}$ is independently in each instance selected from H, (C$_{1-6}$)alkyl, (C$_{1-6}$)haloalkyl, (C$_{3-7}$)cycloalkyl, aryl, aryl-(C$_{1-6}$)alkyl-, Het and Het-(C$_{1-6}$)alkyl-;

wherein Het and the Het portion of Het-(C$_{1-6}$)alkyl- are each independently selected from

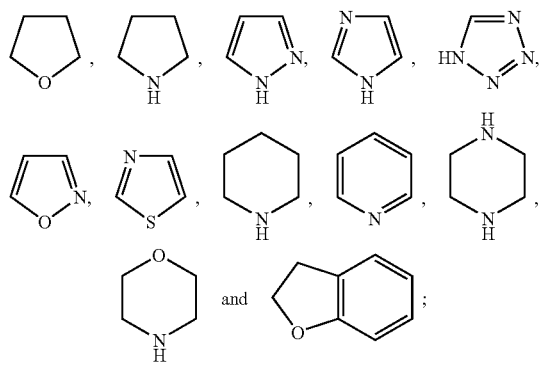

and wherein each of the (C$_{1-6}$)alkyl, (C$_{3-7}$)cycloalkyl, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —OH, —O(C$_{1-6}$)alkyl, —NH$_2$, —NH(C$_{1-6}$)alkyl, —N((C$_{1-6}$)alkyl)$_2$, —COO(C$_{1-6}$)alkyl, —C(=O)NH(C$_{1-6}$)alkyl and —C(=O)N((C$_{1-6}$)alkyl)$_2$; and R$^{12}$ is independently in each instance selected from H, (C$_{1-6}$)alkyl, —NH$_2$, —NH(C$_{1-6}$)alkyl and —N((C$_{1-6}$)alkyl)$_2$;

provided that when R$^1$ is H, A$^1$, A$^2$, A$^3$ and A$^4$ are each CR$^3$ wherein R$^3$ is H, X is O, and Y is C=O, R$^2$ is not

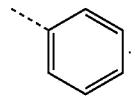

R$^2$-H: In at least one embodiment, R$^2$ is Het, wherein Het is a 5- or 6-membered aromatic heterocycle having 1 to 4 heteroatoms each independently selected from O, N and S, or a 9- or 10-membered aromatic heteropolycycle having wherever possible 1 to 5 heteroatoms, each independently selected from O, N and S; and wherein the Het is optionally substituted with 1 to 3 substituents each independently selected from R$^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—O(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or R$^2$ is Het, wherein Het is a 5- or 6-membered aromatic heterocycle having 1 to 4 heteroatoms each independently selected from O, N and S, or a 9- or 10-membered aromatic heteropolycycle having wherever possible 1 to 5 heteroatoms, each independently selected from O, N and S; and wherein the Het is substituted with (C$_{1-6}$)alkyl or Het, wherein each of the (C$_{1-6}$)alkyl and Het is substituted with 1 to 3 substituents each independently selected from R$^{11}$, halo, oxo, —CN, —NO$_2$, —OR$^{11}$, —N(R$^{12}$)R$^{11}$, —(N((C$_{1-6}$)alkyl)$_2$R$^{11}$)$^+$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR, —SOR$^{11}$, —SO$_2$R$^{11}$ and —SO$_2$N(R$^{12}$)R$^{11}$;

wherein R$^{11}$ is independently in each instance selected from H, (C$_{1-6}$)alkyl, (C$_{1-6}$)haloalkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and R$^{12}$ is independently in each instance selected from R$^{11}$, —OH, —O(C$_{1-6}$)alkyl, —NH$_2$, —NH(C$_{1-6}$)alkyl and —N((C$_{1-6}$)alkyl)$_2$; and Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or $SO_2$.

$R^2$-I: In at least one embodiment, $R^2$ is Het, wherein Het is a 6-membered aromatic heterocycle having 1 N heteroatom, or a 9- or 10-membered aromatic heteropolycycle having 1 or 2 heteroatoms, each independently selected from N and S; and wherein the Het is optionally substituted with 1 to 3 substituents each independently selected from $R^{11}$, —$OR^{11}$, —$N(R^{12})R^{11}$ and Het, wherein Het is selected from a 5- or 6-membered saturated, unsaturated or aromatic heterocycle having 1 or 2 heteroatoms each independently selected from O and N; and wherein the Het is substituted with 1 to 3 substituents each independently selected from $R^{11}$, —CN, —$OR^{11}$, —$N(R^{12})R^{11}$, —$N(R^{12})$—C(=O)$R^{11}$ and —$SO_2N(R^{12})R^{11}$;

wherein $R^{11}$ and $R^{12}$ are each independently in each instance selected from H, $(C_{1-6})$alkyl, aryl, Het and Het-$(C_{1-6})$alkyl-, wherein Het and the Het portion of Het-$(C_{1-6})$alkyl- are each independently selected from a 5- or 6-membered saturated, unsaturated or aromatic heterocycle having 1 or 2 heteroatoms each independently selected from O and N and wherein each of the $(C_{1-6})$alkyl, aryl, Het and Het-$(C_{1-6})$alkyl- are optionally substituted with 1 to 3 substituents each independently selected from $(C_{1-6})$alkyl, —CN, —OH, —O$(C_{1-6})$alkyl, —NH$(C_{1-6})$alkyl, —N$((C_{1-6})$alkyl$)_2$, —C(=O)NH$_2$ and —NHC(=O)—$(C_{1-6})$alkyl.

$R^2$-J: In at least one embodiment, $R^2$ is Het, wherein Het is selected from

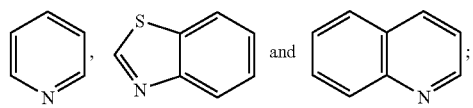

and wherein the Het is optionally substituted with 1 to 3 substituents each independently selected from $R^{11}$, —$OR^{11}$, —$N(R^{12})R^{11}$ and Het, wherein Het is selected from

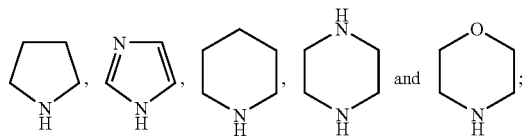

and wherein the Het is substituted with 1 to 3 substituents each independently selected from $R^{11}$, —CN, —$OR^{11}$, —$N(R^{12})R^{11}$, —$N(R^{12})$—C(=O)$R^{11}$ and —$SO_2N(R^{12})R^{11}$;

wherein $R^{11}$ is independently in each instance selected from H, $(C_{1-6})$alkyl, aryl, Het and Het-$(C_{1-6})$alkyl-, wherein Het and the Het portion of Het-$(C_{1-6})$alkyl- are each independently selected from

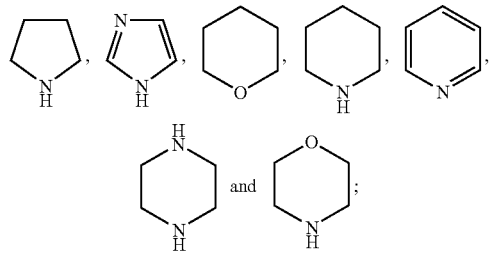

and wherein each of the $(C_{1-6})$alkyl, aryl, Het and Het-$(C_{1-6})$alkyl- are optionally substituted with 1 to 3 substituents each independently selected from $(C_{1-6})$alkyl, —CN, —OH, —O$(C_{1-6})$alkyl, —NH$(C_{1-6})$alkyl, —N$((C_{1-6})$alkyl$)_2$, —C(=O)NH$_2$ and —NHC(=O)—$(C_{1-6})$alkyl; and $R^{12}$ is independently in each instance selected from H and $(C_{1-6})$alkyl.

$R^2$-K: In at least one embodiment, $R^2$ is selected from:

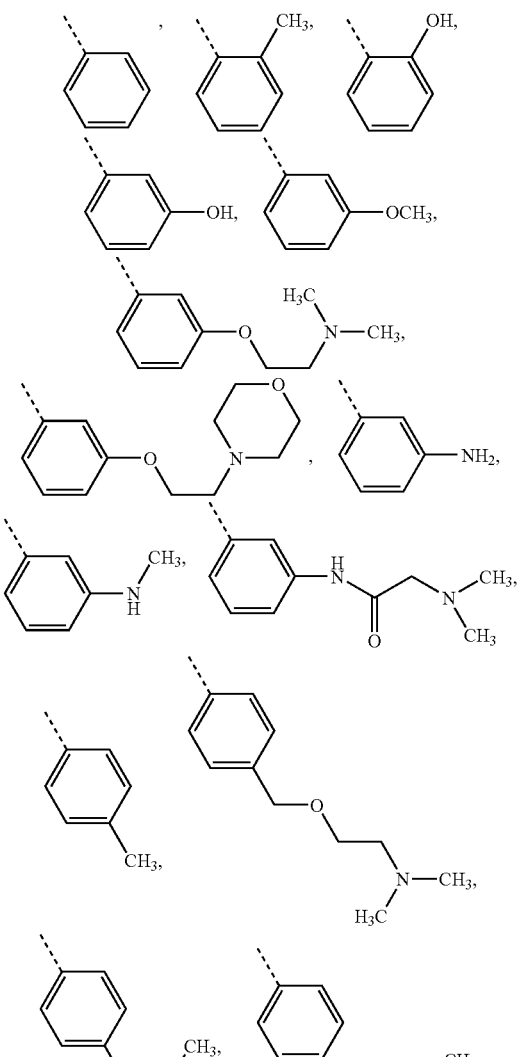

-continued
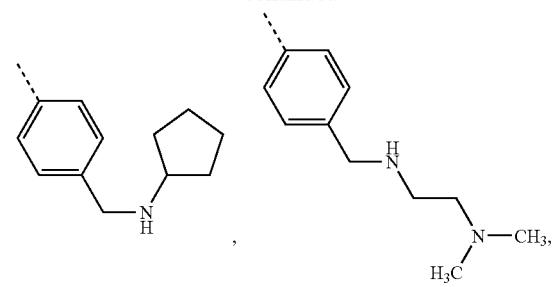
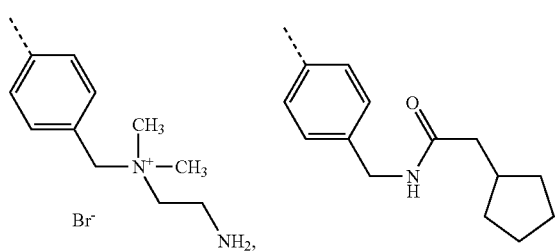
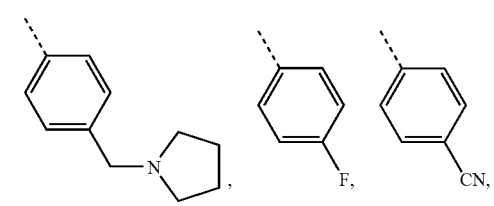
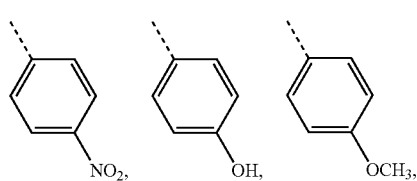
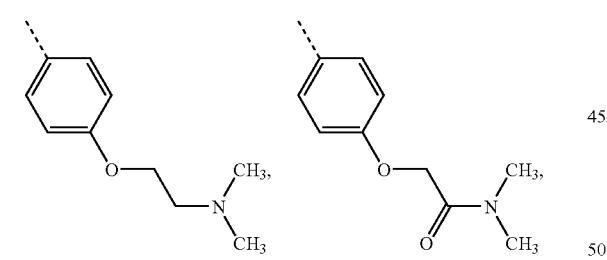
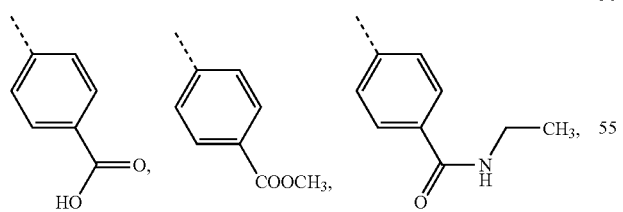
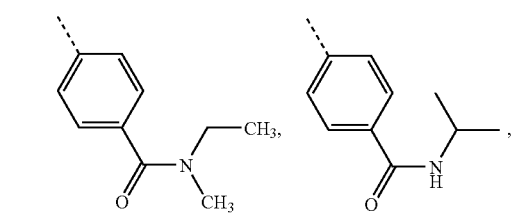
-continued
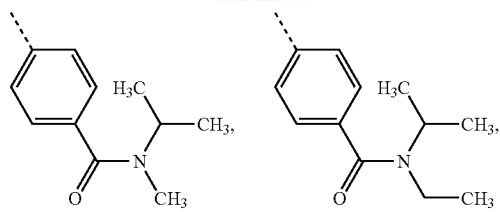
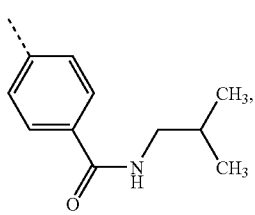
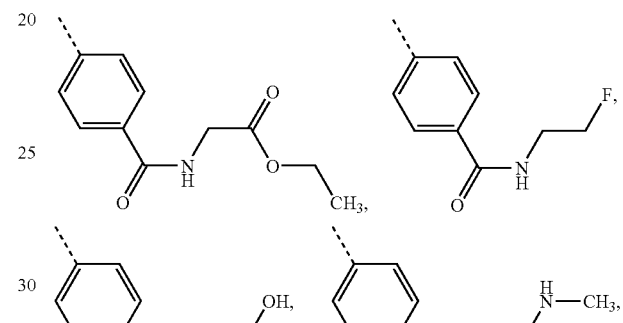

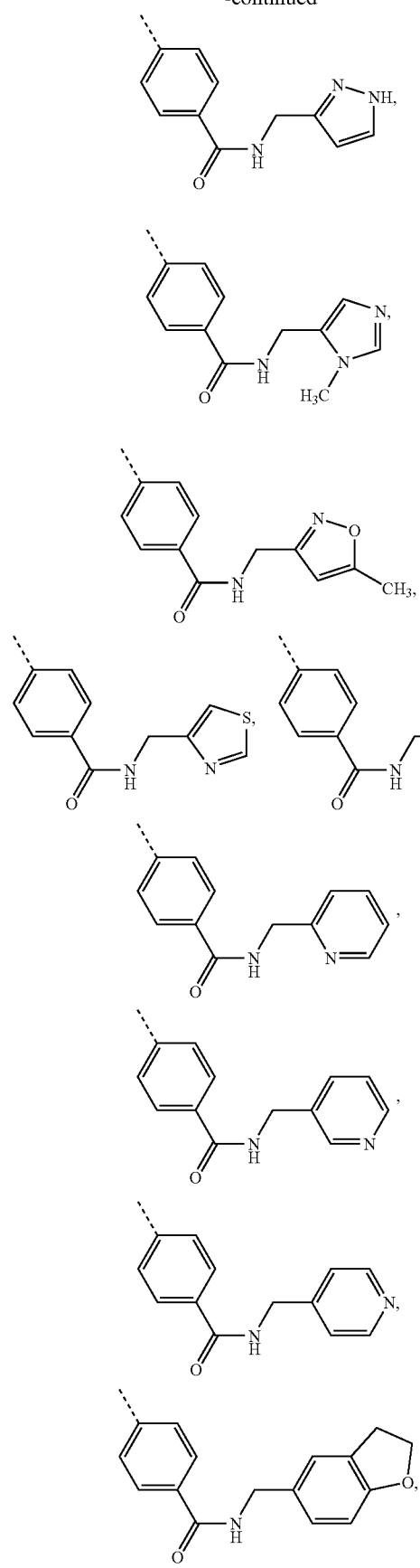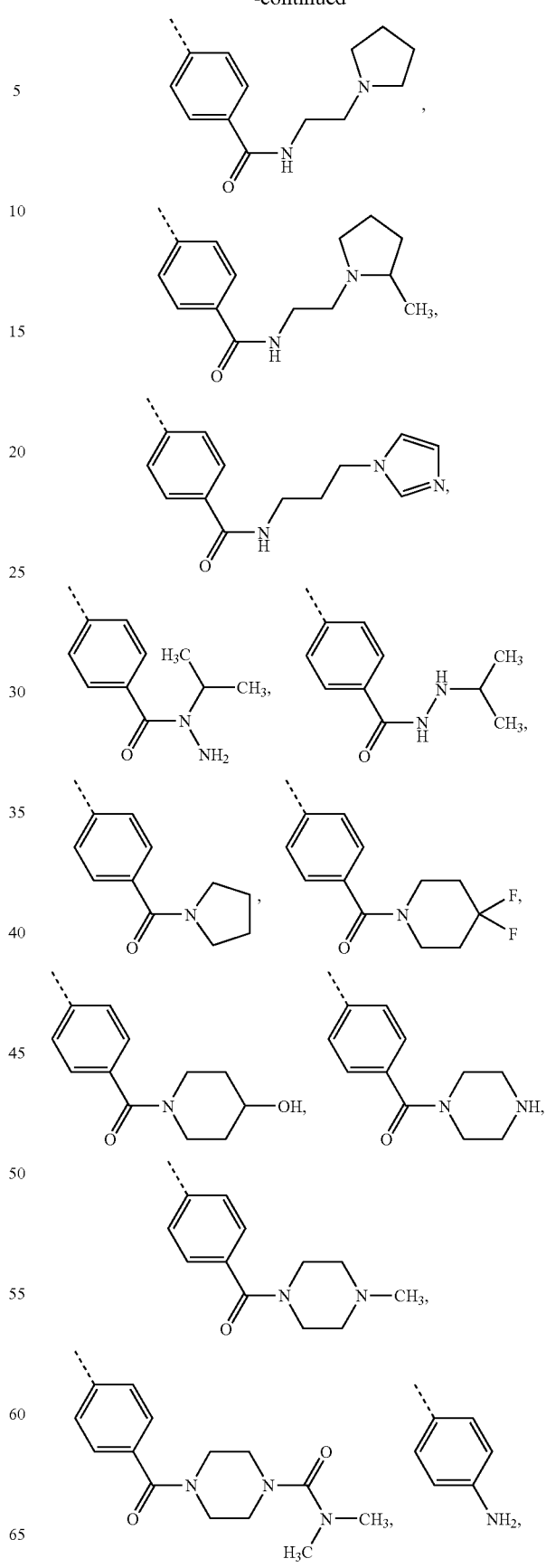

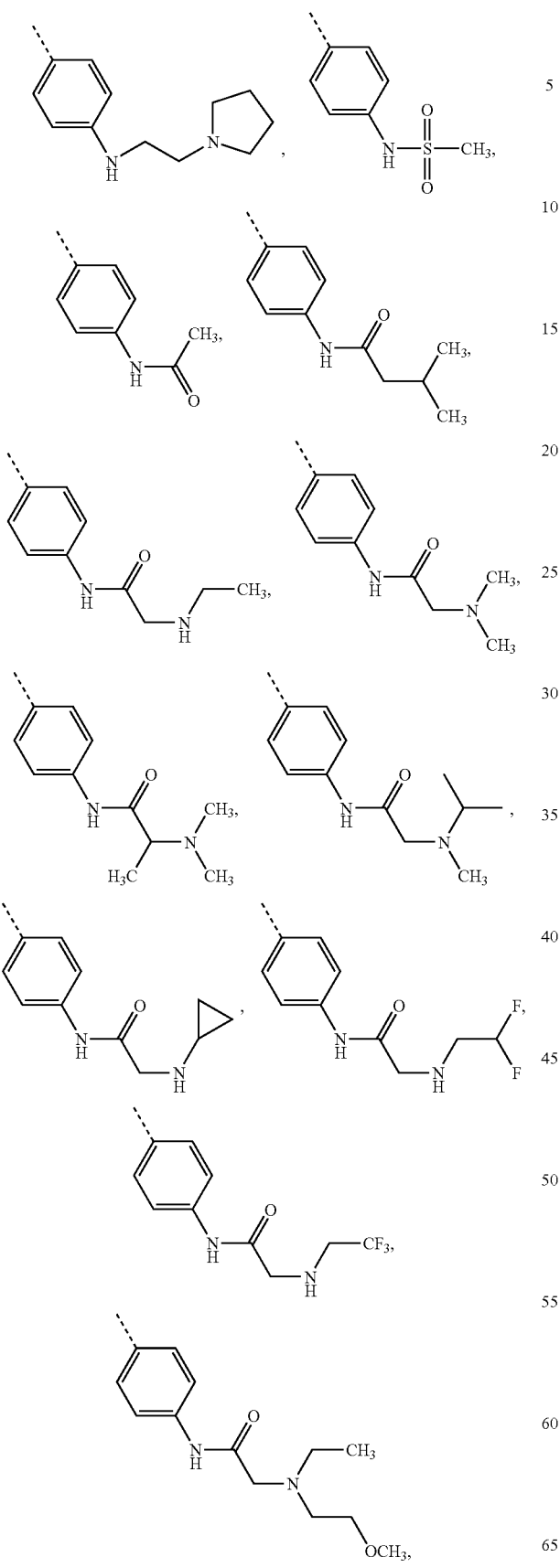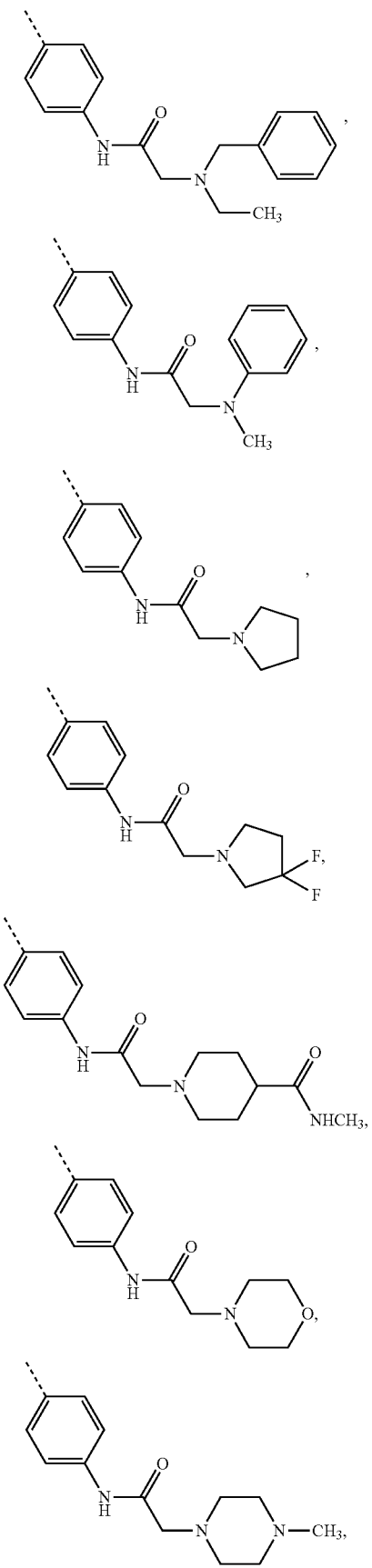

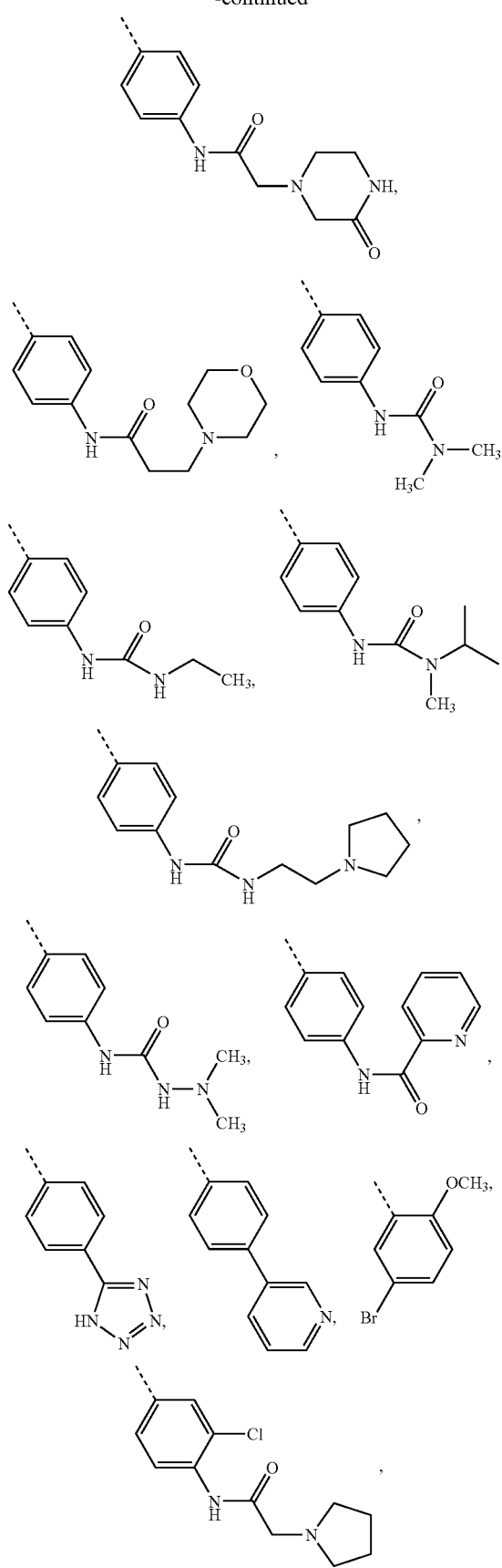
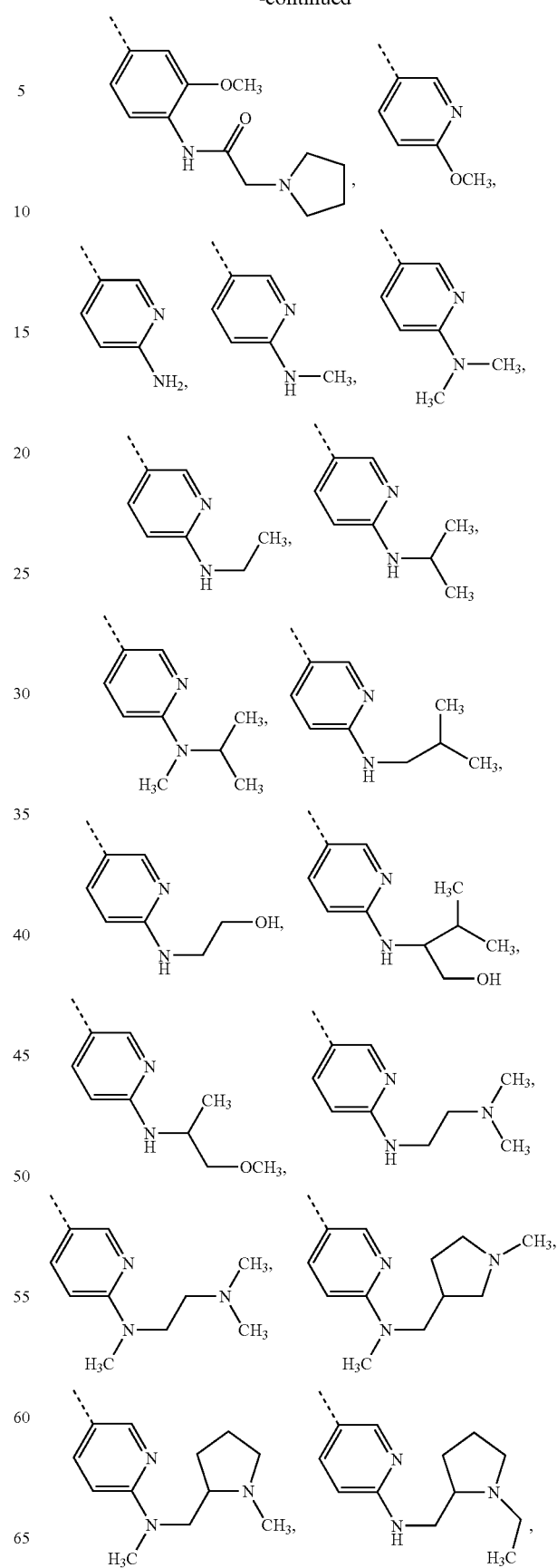

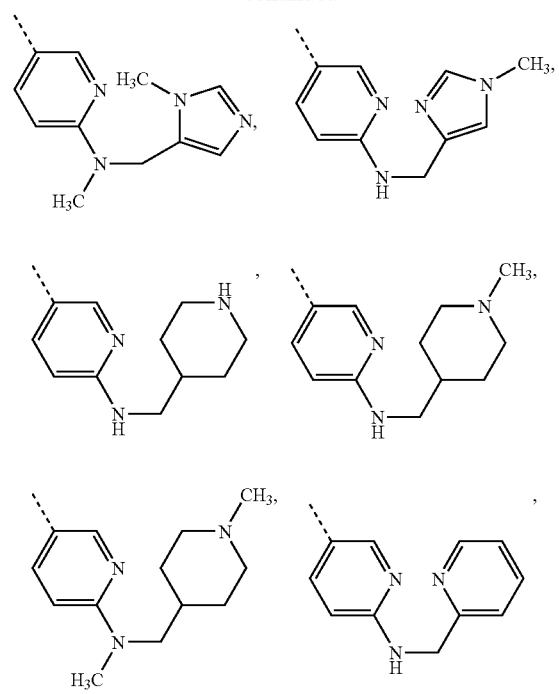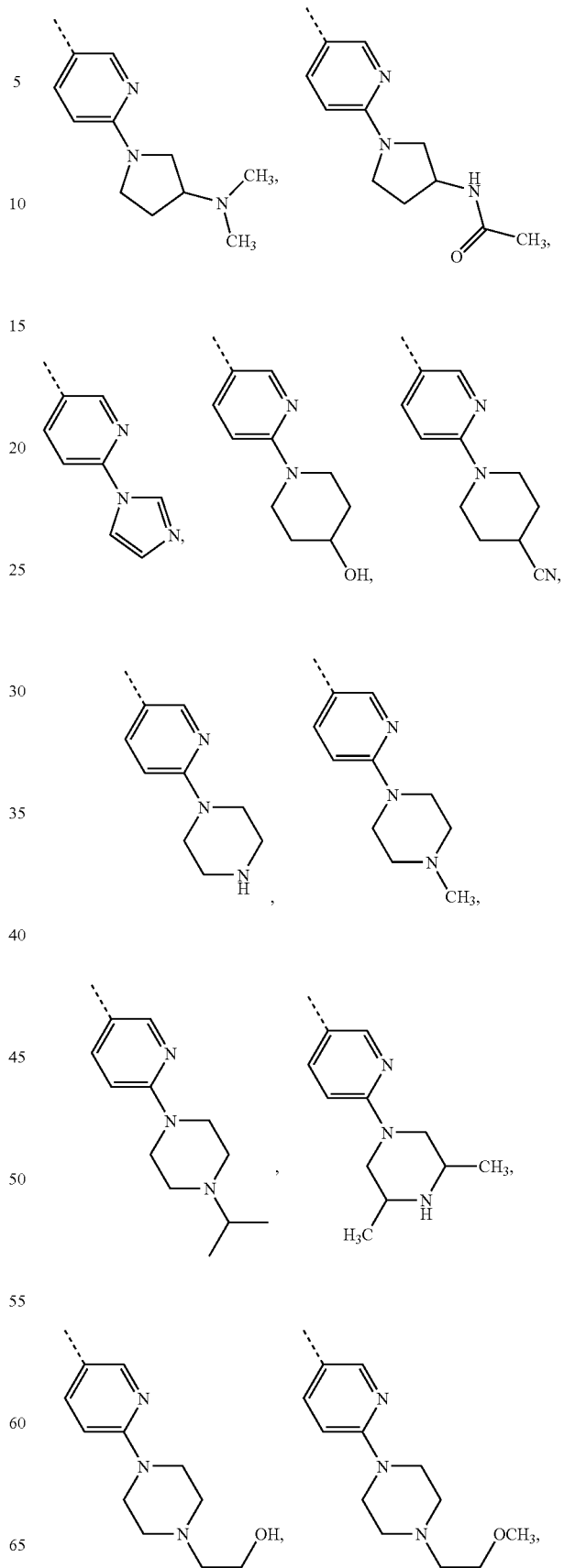

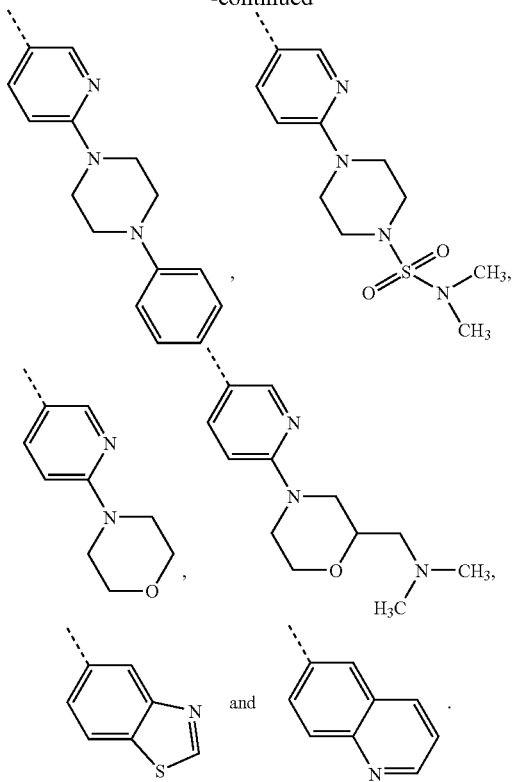

R²-L: In at least one embodiment, R² is phenyl or Het, wherein Het is a 5- or 6-membered aromatic heterocycle or a 9- or 10-membered aromatic heteropolycycle having 1 or 2 N heteroatom; and wherein the phenyl and Het are optionally substituted with 1 to 3 substituents each independently selected from $R^{11}$, $-OR^{11}$, $-N(R^{12})R^{11}$ and Het, wherein Het is selected from a 5- or 6-membered saturated, unsaturated or aromatic heterocycle having 1 or 2 heteroatoms each independently selected from O and N; and wherein the Het is substituted with 1 to 3 substituents each independently selected from $R^{11}$, $-CN$, $-OR^{11}$, $-N(R^{12})R^{11}$, $-N(R^{12})-C(=O)R^{11}$ and $-SO_2N(R^{12})R^{11}$;

wherein $R^{11}$ and $R^{12}$ are each independently in each instance selected from H, $(C_{1-6})$alkyl, aryl, Het and Het-$(C_{1-6})$alkyl-, wherein Het and the Het portion of Het-$(C_{1-6})$alkyl- are each independently selected from a 5- or 6-membered saturated, unsaturated or aromatic heterocycle having 1 or 2 heteroatoms each independently selected from O and N and wherein each of the $(C_{1-6})$alkyl, aryl, Het and Het-$(C_{1-6})$alkyl- are optionally substituted with 1 to 3 substituents each independently selected from $(C_{1-6})$alkyl, $-CN$, $-OH$, $-O(C_{1-6})$alkyl, $-NH(C_{1-6})$alkyl, $-N((C_{1-6})$alkyl$)_2$, $-C(=O)NH_2$ and $-NHC(=O)-(C_{1-6})$alkyl.

R²-M: In at least one embodiment, R² is phenyl or Het, wherein Het is a 5- or 6-membered aromatic heterocycle or a 9- or 10-membered aromatic heteropolycycle having 1 or 2 N heteroatom; and wherein the phenyl and Het are substituted with 1 to 3 substituents each independently selected from $R^{11}$, $-OR^{11}$, and Het, wherein Het is selected from a 5- or 6-membered saturated, unsaturated or aromatic heterocycle having 1 or 2 heteroatoms each independently selected from O and N; and wherein the Het is substituted with 1 to 3 substituents each independently selected from $R^{11}$, $-CN$, $-OR^{11}$, $-N(R^{12})R^{11}$, $-N(R^{12})-C(=O)R^{11}$ and $-SO_2N(R^{12})R^{11}$;

wherein $R^{11}$ and $R^{12}$ are each independently in each instance selected from H, $(C_{1-6})$alkyl, aryl, Het and Het-$(C_{1-6})$alkyl-, wherein Het and the Het portion of Het-$(C_{1-6})$alkyl- are each independently selected from a 5- or 6-membered saturated, unsaturated or aromatic heterocycle having 1 or 2 heteroatoms each independently selected from O and N and wherein each of the $(C_{1-6})$alkyl, aryl, Het and Het-$(C_{1-6})$alkyl- are optionally substituted with 1 to 3 substituents each independently selected from $(C_{1-6})$alkyl, $-CN$, $-OH$, $-O(C_{1-6})$alkyl, $-NH(C_{1-6})$alkyl, $-N((C_{1-6})$alkyl$)_2$, $-C(=O)NH_2$ and $-NHC(=O)-(C_{1-6})$alkyl.

Core:

Core-A: In at least one embodiment, at least one of $A^1$, $A^2$, $A^3$ and $A^4$ is $CR^3$ wherein $R^3$ is as defined herein.

Core-B: In at least one embodiment, $A^1$, $A^2$, $A^3$ and $A^4$ are each $CR^3$ wherein $R^3$ is as defined herein.

Core-C: In at least one embodiment, at least one of $A^1$, $A^2$, $A^3$ and $A^4$ is N.

Core-D: In at least one embodiment, one of $A^1$, $A^2$, $A^3$ and $A^4$ is N and the remaining three of $A^1$, $A^2$, $A^3$ and $A^4$ are $CR^3$ wherein $R^3$ is as defined herein.

It will be apparent to the skilled person that, when $A^1$, $A^2$, $A^3$ and $A^4$ are each independently selected from N and $CR^3$, compounds of the following formulas Ia to Ir are contemplated, wherein $R^3$ is as defined herein. Where more than one instance of $R^3$ occurs in a formula, $R^3$ at one instance can be the same as or different than $R^3$ at any other instance.

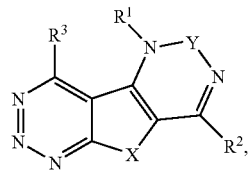

Ia

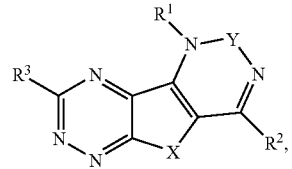

Ib

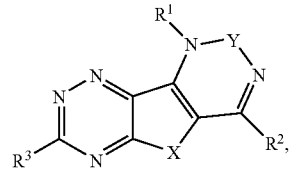

Ic

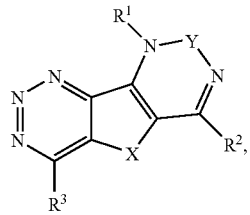

Id

Ie
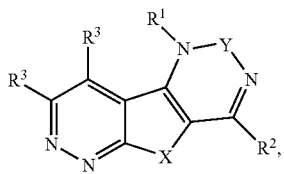

If
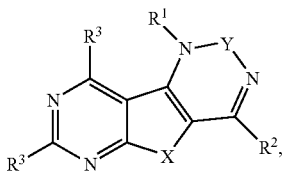

Ig
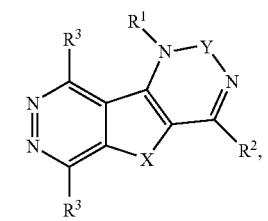

Ih
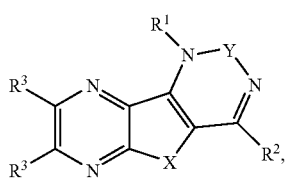

Ij
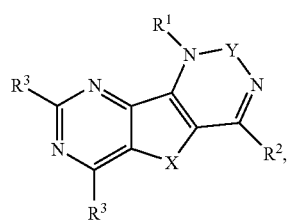

Ik
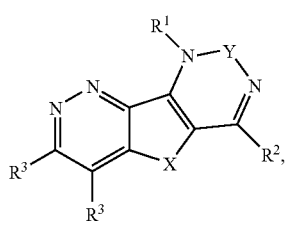

Im
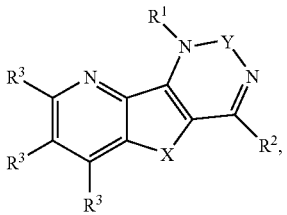

In
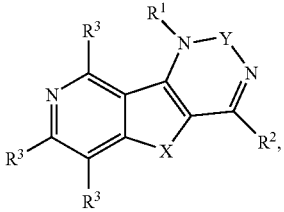

Io
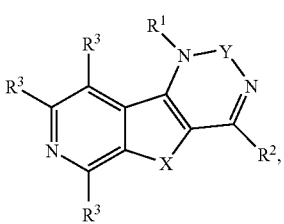

Ip
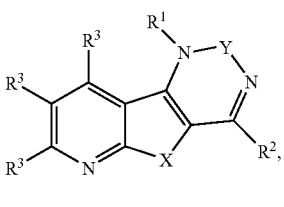

Iq
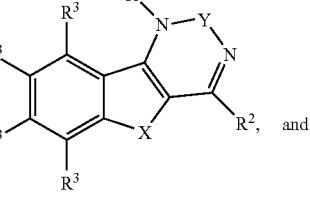

Ir
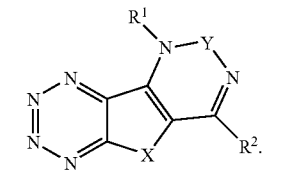

It will also be apparent to the skilled person that where one or more of $A^1$, $A^2$, $A^3$ and $A^4$ is $CR^3$, such as in formulas Ia to Iq above, $R^3$ is independently at each instance selected from H and $R^{33}$ wherein $R^{33}$ is as defined herein. Therefore, for example, when the compound of the invention has the formula Iq, compounds of the following formulas Iq1 to Iq16 are contemplated. Where more than one instance of $R^{33}$ occurs in a formula, $R^{33}$ at one instance can be the same as or different than $R^{33}$ at any other instance.

Iq1
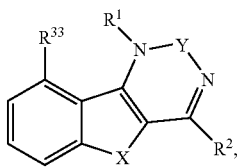

Iq2 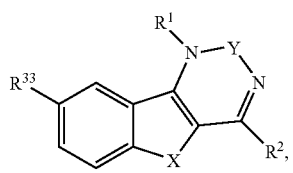
Iq3 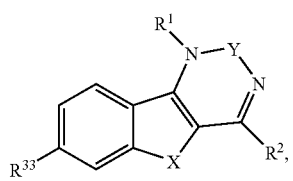
Iq4 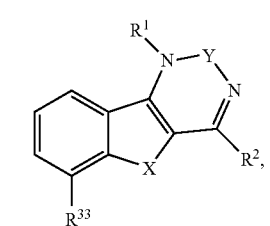
Iq5 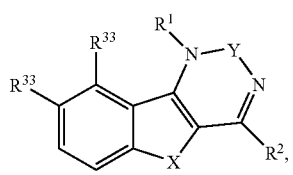
Iq6 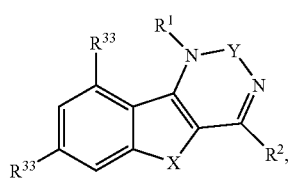
Iq7 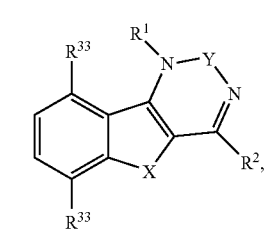
Iq8 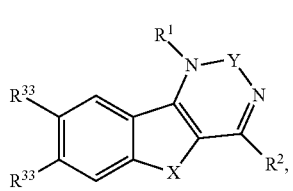
Iq9 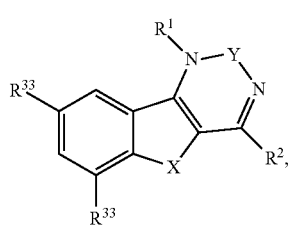
Iq10 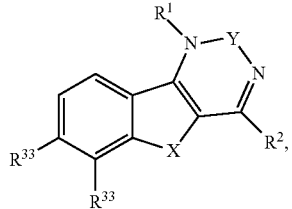
Iq11 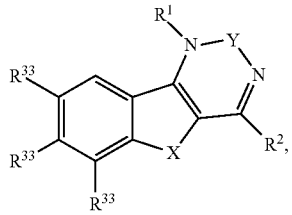
Iq12 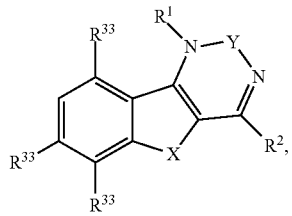
Iq13 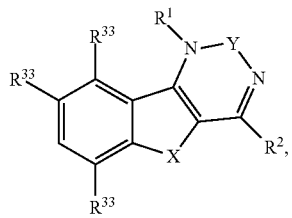
Iq14 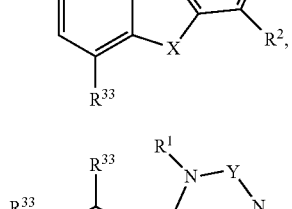
Iq15 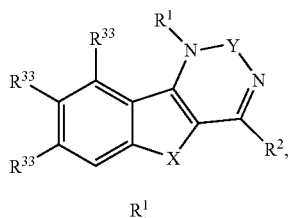
and
Iq16 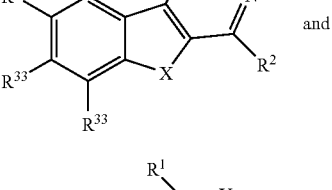
$R^3$:
$R^3$-A: In at least one embodiment, $R^3$ is H.
$R^3$-B: In at least one embodiment, $R^3$ is $R^{33}$ in at least one instance, wherein $R^{33}$ is as defined herein.
$R^3$-C: In at least one embodiment, $R^3$ is independently in each instance selected from H and $R^{33}$, wherein R³³ is independently in each instance selected from R³², halo, —CN, —NO₂, —OR³¹, —N(R¹²)R³¹, —C(=O)R³¹, —C(=O)OR³¹, —C(=O)N(R¹²)R³¹ and —N(R¹²)—C(=O)R³¹; wherein R³¹ is independently in each instance selected from H and R³² and R³² is independently in each instance selected from (C₁₋₆)alkyl, (C₂₋₆)alkenyl, (C₂₋₆)alkynyl, aryl, aryl-(C₁₋₆)alkyl-, Het and Het-(C₁₋₆)alkyl-, wherein Het and the Het portion of Het-(C₁₋₆)alkyl- are each independently selected from a 5- or 6-membered saturated, unsaturated or aromatic heterocycle having 1 to 4 heteroatoms each independently selected from O, N and S, or a 9- or 10-membered saturated, unsaturated or aromatic heteropolycycle having wherever possible 1 or 2 heteroatoms, each independently selected from O and N; wherein each N heteroatom may, independently and where possible, exist in an oxidized state such that it is further bonded to an oxygen atom to form an N-oxide group;

and wherein each of the (C₁₋₆)alkyl, (C₂₋₆)alkenyl, (C₂₋₆)alkynyl, aryl, aryl-(C₁₋₆)alkyl-, Het and Het-(C₁₋₆)alkyl- is optionally substituted with 1 to 3 substituents each independently selected from R¹¹, halo, oxo, —CN, —OR¹¹, —N(R¹²)R¹¹, —C(=O)R¹¹, —C(=O)OR¹¹, —C(=O)N(R¹²)R¹¹, —C(=NH)N(R¹²)R¹¹, —N(R¹²)—C(=O)R¹¹, —N(R¹²)—SO₂R¹¹, —SO₂R¹¹ and —SO₂N(R¹²)R¹¹; or wherein each of the (C₁₋₆)alkyl, (C₂₋₆)alkenyl, (C₂₋₆)alkynyl, aryl, aryl-(C₁₋₆)alkyl-, Het and Het-(C₁₋₆)alkyl- is substituted with (C₁₋₆)alkyl wherein the (C₁₋₆)alkyl is substituted with 1 to 3 substituents each independently selected from R¹¹, —OR¹¹, —N(R¹²)R¹¹, —C(=O)R¹¹, —C(=O)OR¹¹ and —C(=O)N(R¹²)R¹¹;

wherein R¹¹ is independently in each instance selected from H, (C₁₋₆)alkyl, (C₁₋₆)haloalkyl, (C₃₋₇)cycloalkyl, aryl, aryl-(C₁₋₆)alkyl-, Het and Het-(C₁₋₆)alkyl-;

wherein Het and the Het portion of Het-(C₁₋₆)alkyl- are each independently selected from a 5- or 6-membered saturated, unsaturated or aromatic heterocycle having 1 or 2 heteroatoms each independently selected from O and N; and wherein each of the (C₁₋₆)alkyl, (C₃₋₇)cycloalkyl, aryl, aryl-(C₁₋₆)alkyl-, Het and Het-(C₁₋₆)alkyl- are optionally substituted with 1 to 3 substituents each independently selected from —OH, —O(C₁₋₆)alkyl, —NH₂, —N((C₁₋₆)alkyl)₂, —COOH and —C(=O)NH₂; and R¹² is independently in each instance selected from H and (C₁₋₆)alkyl.

R³-D: In at least one embodiment, R³ is independently in each instance selected from H and R³³, wherein R³³ is independently in each instance selected from R³², halo, —CN, —NO₂, —OR³¹, —N(R¹²)R³¹, —C(=O)R³¹, —C(=O)OR³¹, —C(=O)N(R¹²)R³¹ and —N(R¹²)—C(=O)R³¹; wherein R³¹ is independently in each instance selected from H and R³², and R³² is independently in each instance selected from (C₁₋₆)alkyl, (C₂₋₆)alkenyl, (C₂₋₆)alkynyl, aryl, aryl-(C₁₋₆)alkyl-, Het and Het-(C₁₋₆)alkyl-, wherein Het and the Het portion of Het-(C₁₋₆)alkyl- are each independently selected from

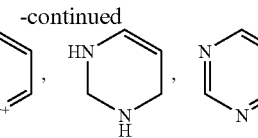

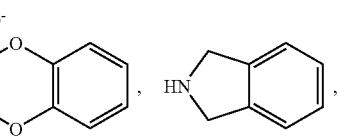

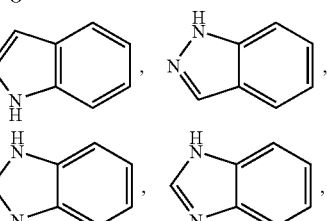

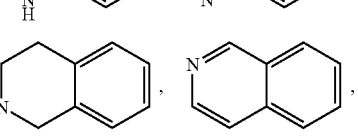

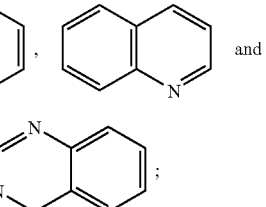

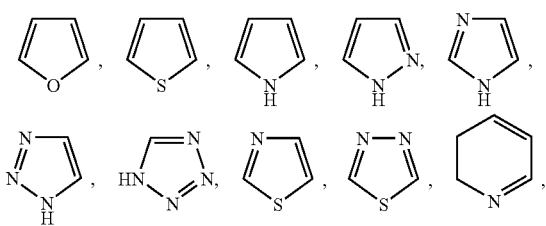

and wherein each of the (C₁₋₆)alkyl, (C₂₋₆)alkenyl, (C₂₋₆)alkynyl, aryl, aryl-(C₁₋₆)alkyl-, Het and Het-(C₁₋₆)alkyl- is optionally substituted with 1 to 3 substituents each independently selected from R¹¹, halo, oxo, —CN, —OR¹¹, —N(R¹²)R¹¹, —C(=O)R¹¹, —C(=O)OR¹¹, —C(=O)N(R¹²)R¹¹, —C(=NH)N(R¹²)R¹¹, —N(R¹²)—C(=O)R¹¹, —N(R¹²)—SO₂R¹¹, —SO₂R¹¹ and —SO₂N(R¹²)R¹¹;

or wherein each of the (C₁₋₆)alkyl, (C₂₋₆)alkenyl, (C₂₋₆)alkynyl, aryl, aryl-(C₁₋₆)alkyl-, Het and Het-(C₁₋₆)alkyl- is substituted with (C₁₋₆)alkyl wherein the (C₁₋₆)alkyl is substituted with 1 to 3 substituents each independently selected from R¹¹, —OR¹¹, —N(R¹²)R¹¹, —C(O)R¹¹, —C(=O)OR¹¹ and —C(=O)N(R¹²)R¹¹;

wherein R¹¹ is independently in each instance selected from H, (C₁₋₆)alkyl, (C₁₋₆)haloalkyl, (C₃₋₇)cycloalkyl, aryl, aryl-(C₁₋₆)alkyl-, Het and Het-(C₁₋₆)alkyl-;

wherein Het and the Het portion of Het-(C₁₋₆)alkyl- are each independently selected from

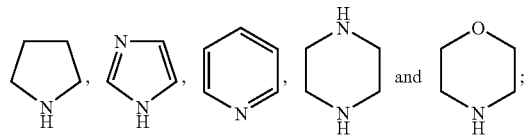

and wherein each of the (C₁₋₆)alkyl, (C₃₋₇)cycloalkyl, aryl, aryl-(C₁₋₆)alkyl-, Het and Het-(C₁₋₆)alkyl- are optionally substituted with 1 to 3 substituents each independently selected from —OH, —O(C₁₋₆)alkyl, —NH₂, —N((C₁₋₆)alkyl)₂, —COOH and —C(=O)NH₂; and R¹² is independently in each instance selected from H and (C₁₋₆)alkyl.

$R^3$-E: In at least one embodiment, $R^3$ is independently in each instance selected from:
—H, —Cl, —Br, —OH, —OCH₃, —NO₂, —NH₂, —NHC(=O)—CH₃,
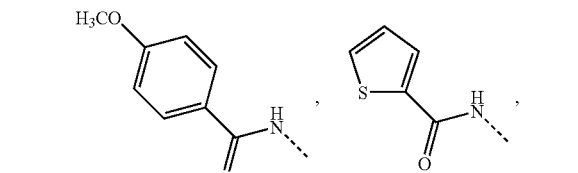
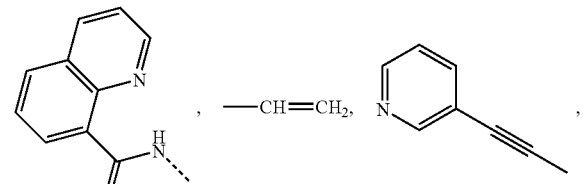
—C(=O)—CH₃, —COOH, —COOCH₃, —CONH₂, —CONHCH₂CH₃,
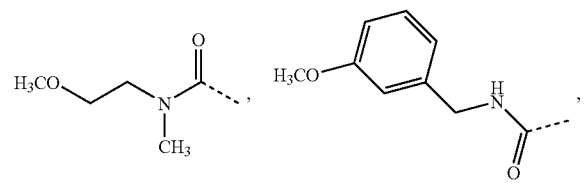
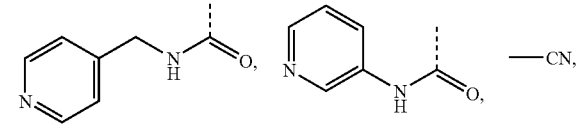
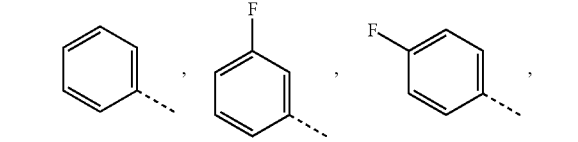, —CN,
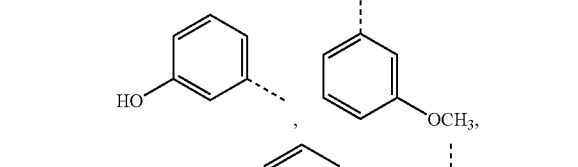
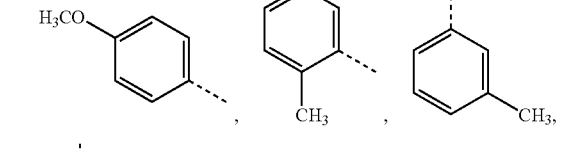
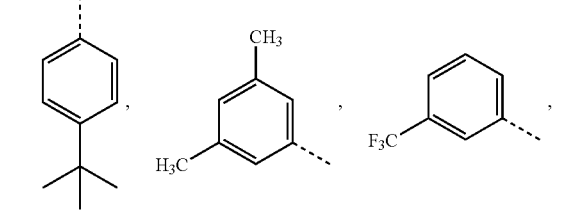
-continued
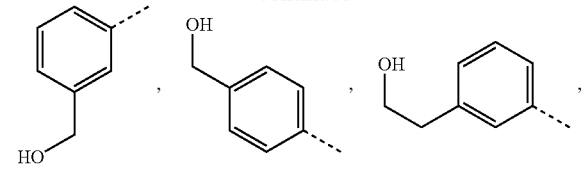
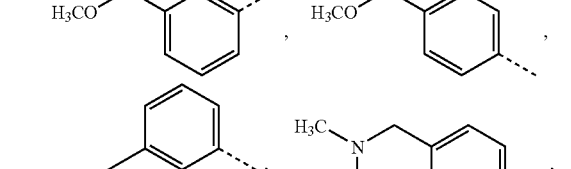
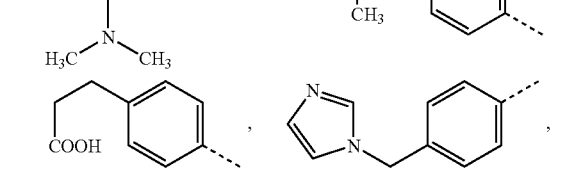
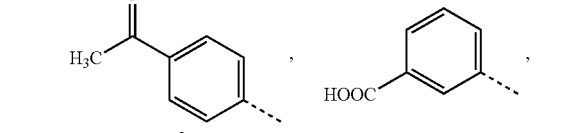
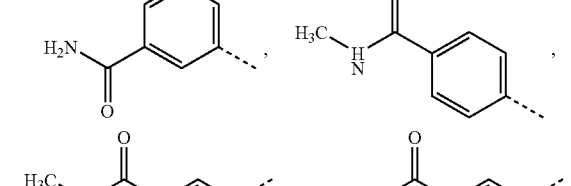
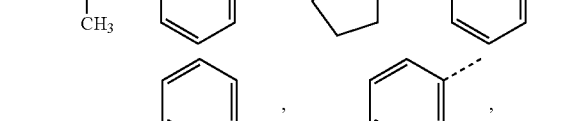
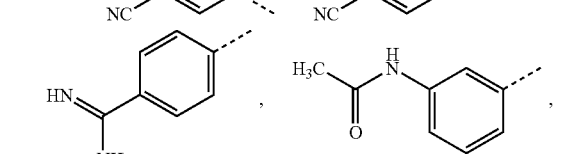
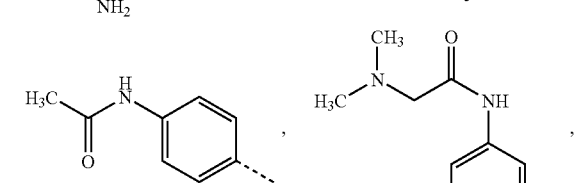
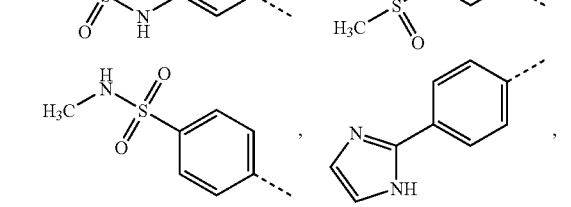

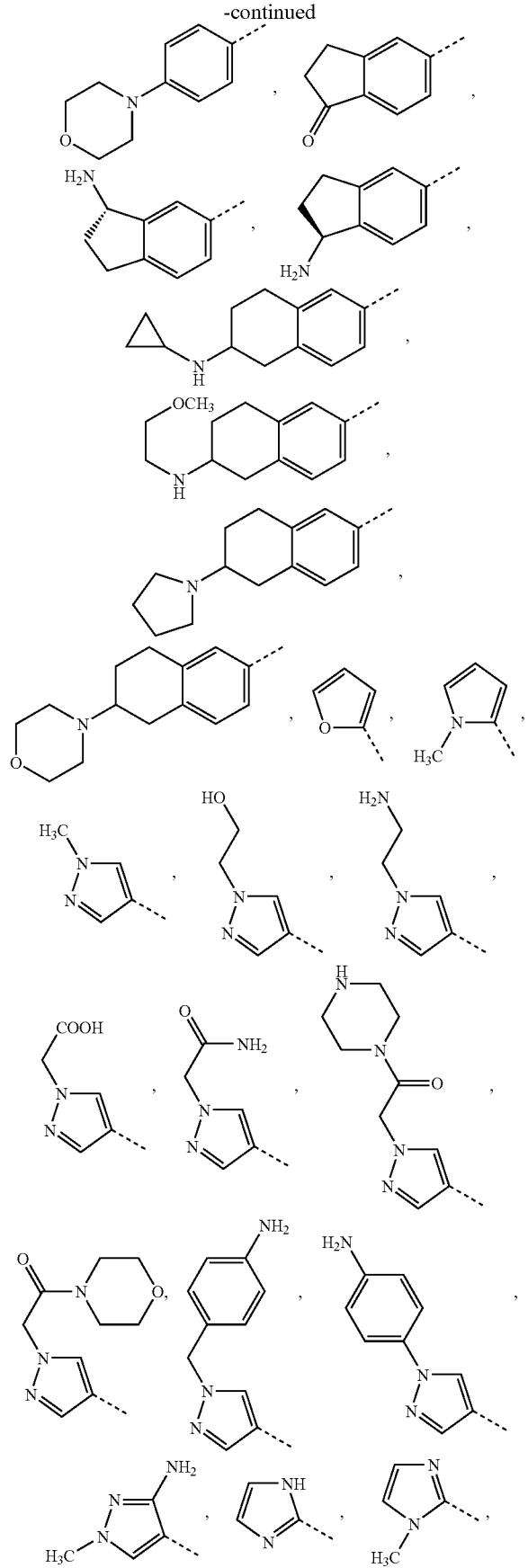
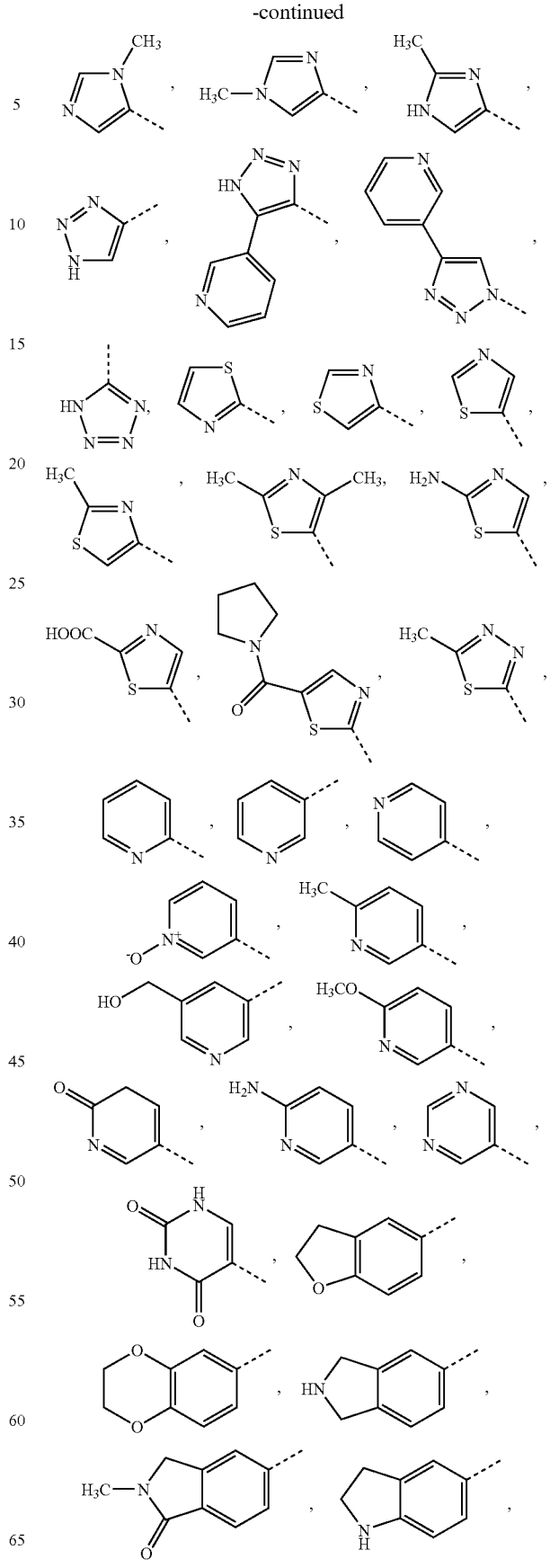

-continued

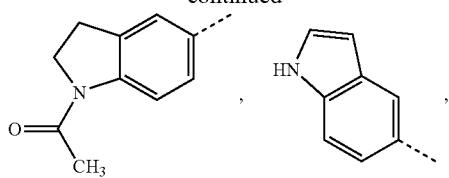
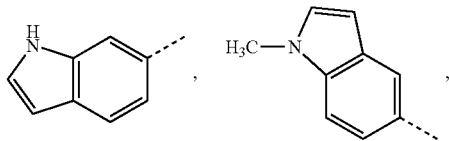
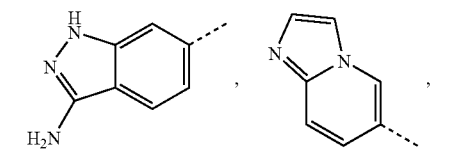
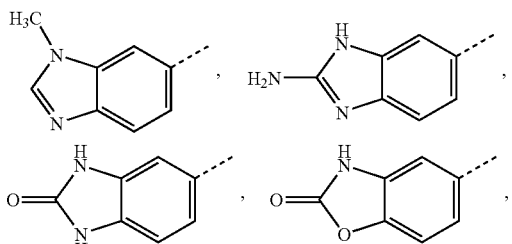
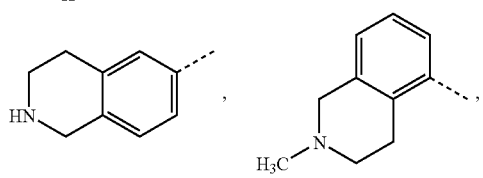
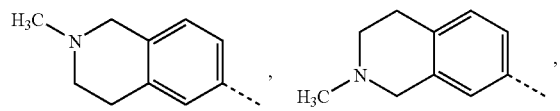
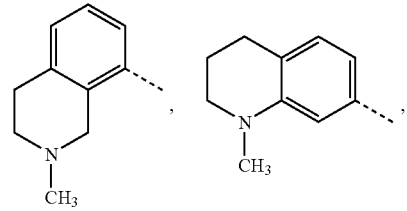
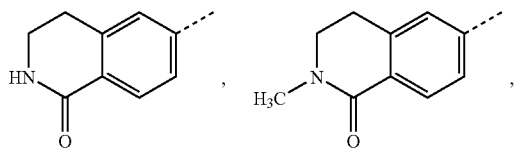
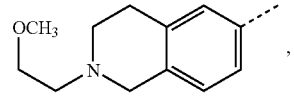
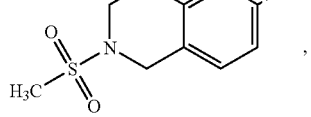

-continued

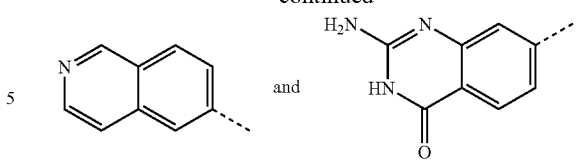

$R^3$-F: In at least one embodiment, $R^3$ is independently in each instance selected from H, halo, —CN, —NO$_2$, —CH=CH$_2$, —CF, —N(R$^{12}$)R$^{31}$, —C(=O)R$^{31}$, —C(=O)OR$^{31}$, —C(=O)N(R$^{12}$)R$^{31}$ and —N(R$^{12}$)—C(=O)R$^{31}$, phenyl and Het; wherein the phenyl and Het are optionally substituted with 1 to 3 substituents each independently selected from R$^{11}$, halo, oxo, —CN, —OR$^{11}$, —N(R$^{12}$)R$^{11}$, —C(=O)R$^{11}$, —C(=O)OR$^{11}$, —C(=O)N(R$^{12}$)R$^{11}$, —C(=NH)N(R$^{12}$)R$^{11}$, —N(R$^{12}$)—C(=O)R$^{11}$, —N(R$^{12}$)—SO$_2$R$^{11}$, —SO$_2$R$^{11}$ and —SO$_2$N(R$^{12}$)R$^{11}$;

or wherein each of the phenyl and Het is substituted with (C$_{1-6}$)alkyl wherein the (C$_{1-6}$)alkyl is substituted with 1 to 3 substituents each independently selected from R$^{11}$, —OR, —N(R$^{12}$)R$^{11}$, —C(=O)R$^{11}$, —C(=O)OR$^{11}$ and —C(=O)N(R$^{12}$)R$^{11}$; wherein $R^{31}$ is independently in each instance selected from H, (C$_{1-6}$)alkyl, aryl and Het; wherein $R^{11}$ is independently in each instance selected from H, (C$_{1-6}$)alkyl, optionally substituted with 1 to 3 substituents each independently selected from —OH, —O(C$_{1-6}$)alkyl, —NH$_2$, —N((C$_{1-6}$)alkyl)$_2$, —COOH and —C(=O)NH$_2$; and $R^{12}$ is independently in each instance selected from H and (C$_{1-6}$)alkyl.

wherein Het is selected from

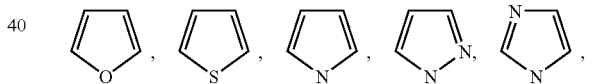
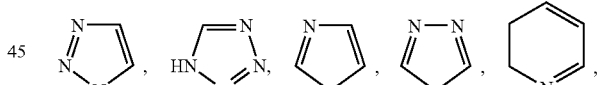
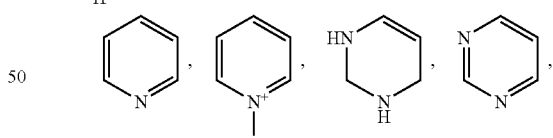
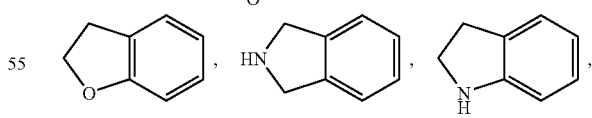
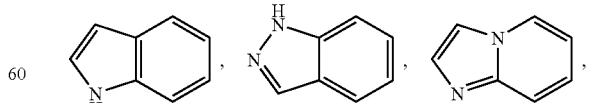
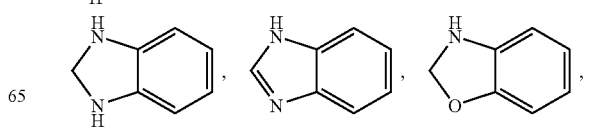

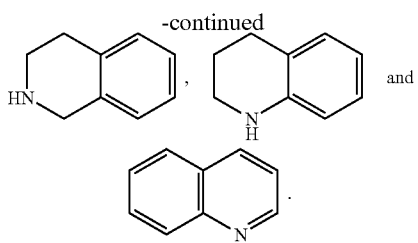

X:
X-A: In at least one embodiment, X is O.
X-B: In at least one embodiment, X is S.
X-C: In at least one embodiment, X is $NR^4$;
  wherein $R^4$ or is $R^{41}$, —C(=O)$R^{41}$, or —SO$_2R^{41}$,
  wherein $R^{41}$ is H, (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from $R^{11}$, halo, oxo, —CN, —NO$_2$, —O$R^{11}$, —N($R^{12}$)$R^{11}$, —C(=O)$R^{11}$, —C(=O)O$R^{11}$, —C(=O)N($R^{12}$)$R^{11}$, —C(=O)N($R^{12}$)—SO$_2R^{11}$, —N($R^{12}$)—C(=O)$R^{11}$, —N($R^{12}$)—C(=O)O$R^{11}$, —N($R^{12}$)—C(=O)N($R^{12}$)$R^{11}$, —N($R^{12}$)—SO$_2R^{11}$, —S$R^{11}$, —SO$R^{11}$, —SO$_2R^{11}$ and —SO$_2$N($R^{12}$)$R^{11}$;
  $R^{11}$ is independently in each instance selected from H, (C$_{1-6}$)alkyl, (C$_{1-6}$)haloalkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and
  $R^{12}$ is independently in each instance selected from $R^{11}$, —OH, —O(C$_{1-6}$)alkyl, —NH$_2$, —NH(C$_{1-6}$)alkyl and —N((C$_{1-6}$)alkyl)$_2$;
  wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$.

X-D: In at least one embodiment, X is $NR^4$;
  wherein $R^4$ is $R^{41}$, wherein $R^{41}$ is H, (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from $R^{11}$, halo, oxo, —CN, —NO$_2$, —O$R^{11}$, —N($R^{12}$)$R^{11}$, —C(=O)$R^{11}$, —C(=O)O$R^{11}$, —C(=O)N($R^{12}$)$R^{11}$, —C(=O)N($R^{12}$)—SO$_2R^{11}$, —N($R^{12}$)—C(=O)$R^{11}$, —N($R^{12}$)—C(=O)O$R^{11}$, —N($R^{12}$)—C(=O)N($R^{12}$)$R^{11}$, —N($R^{12}$)—SO$_2R^{11}$, —S$R^{11}$, —SO$R^{11}$, —SO$_2R^{11}$ and —SO$_2$N($R^{12}$)$R^{11}$;
  $R^{11}$ is independently in each instance selected from H, (C$_{1-6}$)alkyl, (C$_{1-6}$)haloalkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and
  $R^{12}$ is independently in each instance selected from $R^{11}$, —OH, —O(C$_{1-6}$)alkyl, —NH$_2$, —NH(C$_{1-6}$)alkyl and —N((C$_{1-6}$)alkyl)$_2$;
  wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$.

X-E: In at least one embodiment, X is $NR^4$;
  wherein $R^4$ is H, (C$_{1-6}$)alkyl, aryl-(C$_{1-6}$)alkyl- or Het-(C$_{1-6}$)alkyl-, wherein the Het portion of Het-(C$_{1-6}$)alkyl- is a 5- or 6-membered saturated, unsaturated or aromatic heterocycle having 1 or 2 heteroatoms each independently selected from N, O and S; and wherein each of the (C$_{1-6}$)alkyl, aryl-(C$_{1-6}$)alkyl- and Het-(C$_{1-6}$)alkyl- is optionally substituted with —COOH.

X-F: In at least one embodiment, X is $NR^4$;
  wherein $R^4$ is selected from:

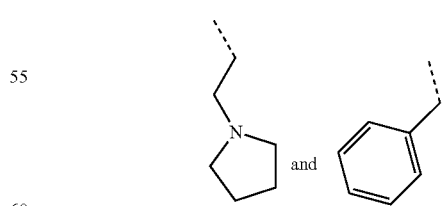

H, CH$_3$, —CH$_2$COOH,

X-G: In at least one embodiment, X is $NR^4$;
  wherein $R^4$ is selected from: H, CH$_3$ and —CH$_2$COOH.

Y:
Y-A: In at least one embodiment, Y is C=O.
Y-B: In at least one embodiment, Y is SO$_2$.

Examples of preferred subgeneric embodiments of the present invention are set forth in the following table, wherein each substituent group of each embodiment is defined according to the definitions set forth above:

| Embodiment | R¹ | R² | Core | R³ | X | Y |
|---|---|---|---|---|---|---|
| E1 | R¹-A | R²-A | Core-A | R³-A | X-A | Y-A |
| E2 | R¹-A | R²-A | Core-A | R³-A | X-A | Y-B |
| E3 | R¹-A | R²-A | Core-A | R³-A | X-B | Y-A |
| E4 | R¹-A | R²-A | Core-A | R³-A | X-B | Y-B |
| E5 | R¹-A | R²-A | Core-A | R³-A | X-C | Y-A |
| E6 | R¹-A | R²-A | Core-A | R³-A | X-C | Y-B |
| E7 | R¹-A | R²-A | Core-A | R³-B | X-A | Y-A |
| E8 | R¹-A | R²-A | Core-A | R³-B | X-A | Y-B |
| E9 | R¹-A | R²-A | Core-A | R³-B | X-B | Y-A |
| E10 | R¹-A | R²-A | Core-A | R³-B | X-B | Y-B |
| E11 | R¹-A | R²-A | Core-A | R³-B | X-C | Y-A |
| E12 | R¹-A | R²-A | Core-A | R³-B | X-C | Y-B |
| E13 | R¹-A | R²-D | Core-B | R³-A | X-A | Y-A |
| E14 | R¹-A | R²-D | Core-B | R³-A | X-A | Y-B |
| E15 | R¹-A | R²-D | Core-B | R³-A | X-B | Y-A |
| E16 | R¹-A | R²-D | Core-B | R³-A | X-B | Y-B |
| E17 | R¹-A | R²-D | Core-B | R³-A | X-D | Y-A |
| E18 | R¹-A | R²-D | Core-B | R³-A | X-D | Y-B |
| E19 | R¹-A | R²-D | Core-B | R³-B | X-A | Y-A |
| E20 | R¹-A | R²-D | Core-B | R³-B | X-A | Y-B |
| E21 | R¹-A | R²-D | Core-B | R³-B | X-B | Y-A |
| E22 | R¹-A | R²-D | Core-B | R³-B | X-B | Y-B |
| E23 | R¹-A | R²-D | Core-B | R³-B | X-D | Y-A |
| E24 | R¹-A | R²-D | Core-B | R³-B | X-D | Y-B |
| E25 | R¹-A | R²-D | Core-C | R³-A | X-A | Y-A |
| E26 | R¹-A | R²-D | Core-C | R³-A | X-A | Y-B |
| E27 | R¹-A | R²-D | Core-C | R³-A | X-B | Y-A |
| E28 | R¹-A | R²-D | Core-C | R³-A | X-B | Y-B |
| E29 | R¹-A | R²-D | Core-C | R³-A | X-D | Y-A |
| E30 | R¹-A | R²-D | Core-C | R³-A | X-D | Y-B |
| E31 | R¹-A | R²-D | Core-C | R³-B | X-A | Y-A |
| E32 | R¹-A | R²-D | Core-C | R³-B | X-A | Y-B |
| E33 | R¹-A | R²-D | Core-C | R³-B | X-B | Y-A |
| E34 | R¹-A | R²-D | Core-C | R³-B | X-B | Y-B |
| E35 | R¹-A | R²-D | Core-C | R³-B | X-D | Y-A |
| E36 | R¹-A | R²-D | Core-C | R³-B | X-D | Y-B |
| E37 | R¹-B | R²-F | Core-B | R³-C | X-A | Y-A |
| E38 | R¹-B | R²-F | Core-B | R³-C | X-A | Y-B |
| E39 | R¹-B | R²-F | Core-B | R³-C | X-B | Y-A |
| E40 | R¹-B | R²-F | Core-B | R³-C | X-B | Y-B |
| E41 | R¹-B | R²-F | Core-B | R³-C | X-E | Y-A |
| E42 | R¹-B | R²-F | Core-B | R³-C | X-E | Y-B |
| E43 | R¹-B | R²-I | Core-B | R³-C | X-A | Y-A |
| E44 | R¹-B | R²-I | Core-B | R³-C | X-A | Y-B |
| E45 | R¹-B | R²-I | Core-B | R³-C | X-B | Y-A |
| E46 | R¹-B | R²-I | Core-B | R³-C | X-B | Y-B |
| E47 | R¹-B | R²-I | Core-B | R³-C | X-E | Y-A |
| E48 | R¹-B | R²-I | Core-B | R³-C | X-E | Y-B |
| E49 | R¹-E | R²-L | Core-B | R³-F | X-A | Y-A |
| E50 | R¹-E | R²-L | Core-D | R³-F | X-A | Y-A |
| E51 | R¹-E | R²-M | Core-B | R³-F | X-A | Y-A |
| E52 | R¹-E | R²-M | Core-D | R³-F | X-A | Y-A |
| E53 | R¹-E | R²-D | Core-B | R³-F | X-A | Y-A |
| E54 | R¹-E | R²-G | Core-D | R³-F | X-A | Y-A |
| E55 | R¹-E | R²-J | Core-B | R³-F | X-A | Y-A |

Examples of most preferred compounds according to this invention are each single compound listed in the following Tables 1 to 5.

In general, all tautomeric and isomeric forms and mixtures thereof, including but not limited to individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

For example, it is well known in the art that pyridones of formula P1 and hydroxypyridines of formula P2 are different tautomeric forms of the same species and interconvertible by proton transfer. Therefore, when a molecule or a substituent thereof is represented by either formula P1 or P2, either and both forms are intended.

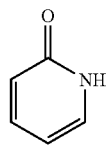

P1

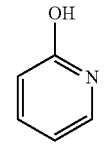

P2

It is well-known in the art that the biological and pharmacological activity of a compound is sensitive to the stereochemistry of the compound. Thus, for example, enantiomers often exhibit strikingly different biological activity including but not limited to differences in pharmacokinetic properties, including but not limited to metabolism, protein binding, and the like, and pharmacological properties, including but not limited to the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Furthermore, a compound according to the present invention may be used to treat or prevent viral contamination of materials and therefore reduce the risk of viral infection of laboratory or medical personnel or patients who come in contact with such materials (including but not limited to blood, tissue, surgical instruments and garments, laboratory instruments and garments, and blood collection apparatuses and materials).

Pharmaceutical Composition

Compounds of the present invention may be administered to a human being in need of treatment for HIV infection as a pharmaceutical composition comprising a therapeutically effective amount of a compound according to the invention or a pharmaceutically acceptable salt thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally, topically or systemically.

When one enantiomer of a chiral active ingredient has a different biological activity than the other, it is contemplated that the pharmaceutical composition according to the invention may comprise a racemic mixture of the active ingredient, a mixture enriched in one enantiomer of the active ingredient or a pure enantiomer of the active ingredient. The mixture enriched in one enantiomer of the active ingredient is contemplated to contain from about 50% to about 100% of one enantiomer of the active ingredient and from about 0% to about 50% of the other enantiomer of the active ingredient. Preferably, when the composition comprises a mixture enriched in one enantiomer of the active ingredient or a pure enantiomer of the active ingredient, the composition comprises from about 50% to about 100% of, or only, the more physiologically active enantiomer and/or the less toxic enantiomer. It is well known that one enantiomer of an active ingredient may be the more physiologically active for one therapeutic indication while the other enantiomer of the active ingredient may be the more physiologically active for a different therapeutic indication; therefore the preferred enantiomeric makeup of the pharmaceutical composition may differ for use of the composition in treating different therapeutic indications.

For oral administration, the compound, or a pharmaceutically acceptable salt thereof, can be formulated in any orally acceptable dosage form including but not limited to aqueous suspensions and solutions, capsules or tablets. For topical administration, the compound, or a pharmaceutically acceptable salt may be formulated in a pharmaceutically acceptable vehicle as a solution, cream or lotion. For systemic administration, including but not limited to administration by subcutaneous, intracutaneous, intravenous, intramuscular, intraperitoneal, intra-articular, intrasynovial, intrasternal, intrathecal, and intralesional injection or infusion techniques, it is preferred to use a solution of the compound, or a pharmaceutically acceptable salt thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004, herein incorporated by reference.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.001 to about 1000 milligrams per kilogram of body weight, with the preferred dose being about 0.01 to about 100 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Combination Therapy

Combination therapy is contemplated wherein a compound according to the invention, or a pharmaceutically acceptable salt thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being. Such agents can be selected from:

NRTIs (nucleoside or nucleotide reverse transcriptase inhibitors) including but not limited to zidovudine/RETROVIR® (GSK), didanosine/VIDEX® (BMS), stavudine/ZERIT® (BMS), lamivudine/EPIVIR® (GSK/Shire), emtricitabine/EMTRIVA® (Gilead Sciences), abacavir/ZIAGEN® (GSK), and tenofovir/VIREAD® (Gilead Sciences), apricitabine (Avexa), elvucitabine (Achillion) and OBP-601 (Oncolys), amdoxovir (RFS Pharma);

NNRTIs (non-nucleoside reverse transcriptase inhibitors) including but not limited to nevirapine/VIRAMUNE® (Boehringer Ingelheim), delavirdine/Rescriptor® (Pfizer), efavirenz/SUSTIVA® (BMS), etravirine/INTELENCE® (Johnson & Johnson), rilpivirine (Johnson & Johnson), UK-453,061 (Pfizer) and RDEA806 (Ardea Biosciences), IDX-899 (GSK);

protease inhibitors including but not limited to ritonavir/NORVIR® (Abbott), tipranavir/APTIVUS® (Boehringer Ingelheim), saquinavir/INVIRASE® (Hoffmann LaRoche), nelfinavir/VIRACEPT® (Pfizer), indinavir/CRIXIVAN® (Merck), fosamprenavir/

LEXIVA® (GSK/Vertex), atazanavir/REYATAZ® (BMS), lopinavir/KALETRA® (Abbott), and darunavir/PREZISTA® (Johnson & Johnson);

entry inhibitors including but not limited to
  CCR5 antagonists including but not limited to maraviroc/SELZENTRY® (Pfizer), vicriviroc (Schering-Plough), INCB9471 (Incyte), PF-232798 (Pfizer), PRO-140 (Progenics Pharm), GSK706769 (GSK), PF-232798 (Pfizer), TBR-220 and TBR-652 (Tovira Therapeutics);
CXCR4 antagonists including but not limited to AMD-11070 (Genzyme),
  fusion inhibitors including but not limited to enfuvirtide/FUZEON® (Trimeris), sifuvirtide (Fasogen), albuvirtide (Frontier Bio), FRI-1144 (Trimeris); and
  others including but not limited to BMS-488043 (BMS);
integrase inhibitors including but not limited to raltegravir SENTRESS® (Merck), elvitegravir (Gilead Sciences), GSK1349572 and GSK1265744 (GSK), JTK-656 (Japan Tobacco);
TAT inhibitors;
maturation inhibitors including but not limited to bevirimat (Myriad Genetics), vivecon (Myriad Genetics); and
immunomodulating agents including but not limited to levamisole/ERGAMISOL® (Janssen-Ortho).

Furthermore, a compound according to the invention can be used with at least one other compound according to the invention or with one or more antifungal or antibacterial agents (including but not limited to fluconazole).

Therefore, according to one embodiment, the pharmaceutical composition of this invention additionally comprises one or more antiviral agents.

A further embodiment provides the pharmaceutical composition of this invention wherein the one or more antiviral agent comprises at least one NNRTI.

According to another embodiment of the pharmaceutical composition of this invention, the one or more antiviral agent comprises at least one NRTI.

According to yet another embodiment of the pharmaceutical composition of this invention, the one or more antiviral agent comprises at least one protease inhibitor.

According to still another embodiment of the pharmaceutical composition of this invention, the one or more antiviral agent comprises at least one entry inhibitor.

According to a further embodiment of the pharmaceutical composition of this invention, the one or more antiviral agent comprises at least one integrase inhibitor.

Methodology and Synthesis

The synthesis of compounds of formula (I) according to this invention is conveniently accomplished following the general procedures outlined in Schemes 1 to 5 below wherein $R^1$, $R^2$, $A^1$, $A^2$, $A^3$, $A^4$, $R^3$, $R^4$, X, and Y are as defined herein. Other procedures by which compounds of the invention may be prepared are well known in the art or are set forth in the examples below.

Compounds of formula (I) wherein $A^1$, $A^2$, $A^3$ and $A^4$ are each $CR^3$, X is O and Y is C=O are conveniently prepared using the general procedure illustrated in Scheme 1 below.

Scheme 1:

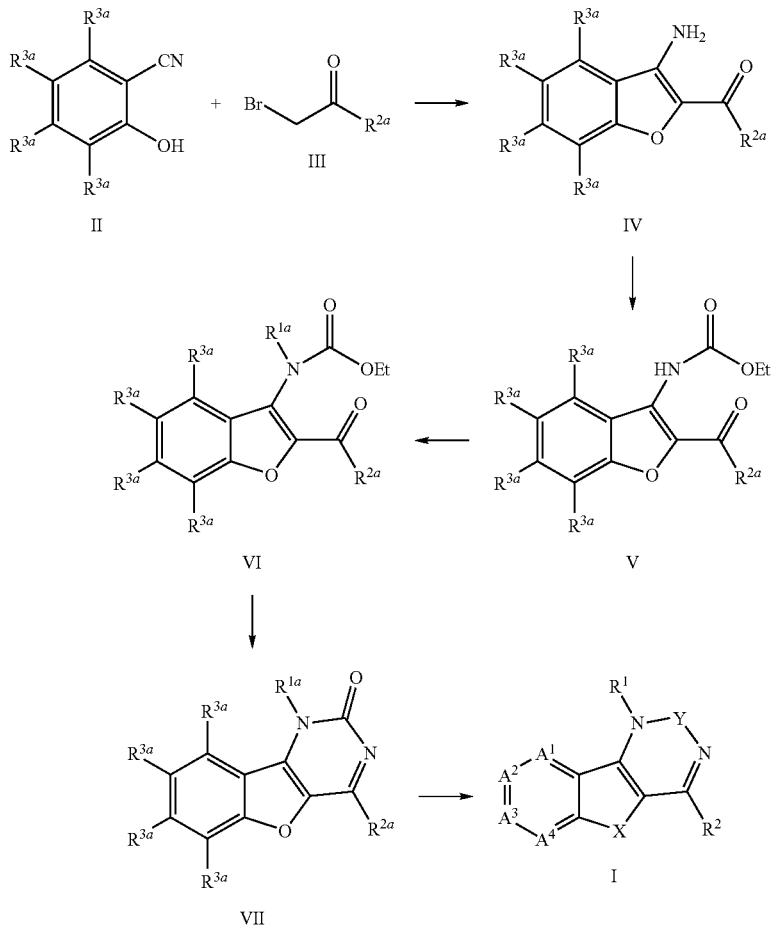

Intermediates II, wherein $R^{3a}$ is $R^3$ as defined herein or is a group transformable to $R^3$ as defined herein, and intermediates III, wherein $R^{2a}$ is $R^2$ as defined herein or is a group transformable to $R^2$ as defined herein, are commercially available or are prepared by reactions well known in the art or as set forth in the examples below. Intermediates II and III are allowed to react under basic conditions, including but not limited to treatment with $Na_2CO_3$ in acetone under reflux, followed by treatment with NaOH and MeOH, to give intermediates IV. Reaction of intermediates IV with a reagent such as ethyl chloroformate under basic conditions, including but not limited to treatment with $K_2CO_3$ or $Na_2CO_3$, provides intermediates V. Reaction of intermediates V with NaH, followed by alkylation with a reagent of formula $R^{1a}$-LG, wherein $R^{1a}$ is $R^1$ as defined herein or is a group transformable to $R^1$ as defined herein and wherein LG is a leaving group including but not limited to a halogen, mesylate or tosylate group, gives intermediates of formula VI; or intermediate IV can also be prepared via Mitsonobu reaction of intermediate V with a reagent of formula $R^{1a}$—OH. Heating of intermediates VI with ammonium acetate provides intermediates VII. Intermediates VII can be transformed to compounds of formula (I) wherein $A^1$, $A^2$, $A^3$ and $A^4$ are each $CR^3$, X is O and Y is C=O, using any reactions necessary to transform $R^{1a}$ to $R^1$, $R^{2a}$ to $R^2$ and $R^{3a}$ to $R^3$. Such reactions are well known in the art or are set forth in the examples below. For example, intermediates VII wherein $R^{3a}$ is a halogen atom, including but not limited to Br or Cl, can undergo a well known Stille or Suzuki coupling reaction to provide compounds of formula (I) wherein $R^3$ is an aryl or aromatic Het group. It will be clear to the skilled person that if $R^{1a}$ is $R^1$, $R^{2a}$ is $R^2$ and $R^{3a}$ is $R^3$ in intermediates VI, reaction of intermediates VI with ammonium acetate as described above will directly provide compounds of formula (I) wherein $A^1$, $A^2$, $A^3$ and $A^4$ are each $CR^3$, X is O and Y is C=O.

Alternatively, compounds of formula (I) wherein $A^1$, $A^2$, $A^3$ and $A^4$ are each $CR^3$, X is O and Y is C=O may be prepared by the general procedure outlined in Scheme 2 below.

Intermediates VIII, wherein $R^{2a}$ is $R^2$ as defined herein or is a group transformable to $R^2$ as defined herein, and intermediates X, wherein $R^{3a}$ is $R^3$ as defined herein or is a group transformable to $R^3$ as defined herein, are commercially available or are prepared by reactions well known in the art or as set forth in the examples below. Reaction of intermediates VIII with dimethylamine provides intermediates IX. Reaction of intermediates IX and intermediates X in the presence of $POCl_3$ gives intermediates XI. Intermediates XI react with intermediates of formula $R^{1a}$—$NH_2$, wherein $R^{1a}$ is $R^1$ as defined herein or is a group transformable to $R^1$ as defined herein, to provide intermediates XII. Intermediates XII are conveniently transformed to intermediates VII (Scheme 1) by reaction with oxalyl chloride followed by treatment with aqueous sodium azide. Intermediates VII are transformed to compounds of formula (I) wherein $A^1$, $A^2$, $A^3$ and $A^4$ are each $CR^3$, X is O and Y is C=O as described in Scheme 1 above and in the examples set forth below. It will be clear to the skilled person that if $R^{1a}$ is $R^1$, $R^{2a}$ is $R^2$ and $R^{3a}$ is $R^3$ in intermediates XII, reaction of intermediates XII with oxalyl chloride followed by treatment with aqueous sodium azide as described above will directly provide compounds of formula (I) wherein $A^1$, $A^2$, $A^3$ and $A^4$ are each $CR^3$, X is O and Y is C=O.

Compounds of formula (I) wherein $A^1$, $A^2$, $A^3$ and $A^4$ are each $CR^3$, X is O and Y is $SO_2$ are conveniently prepared using the general procedure illustrated in Scheme 3 below.

Scheme 3:

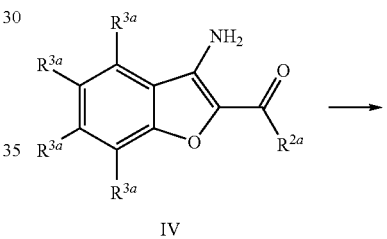

IV

Scheme 2:

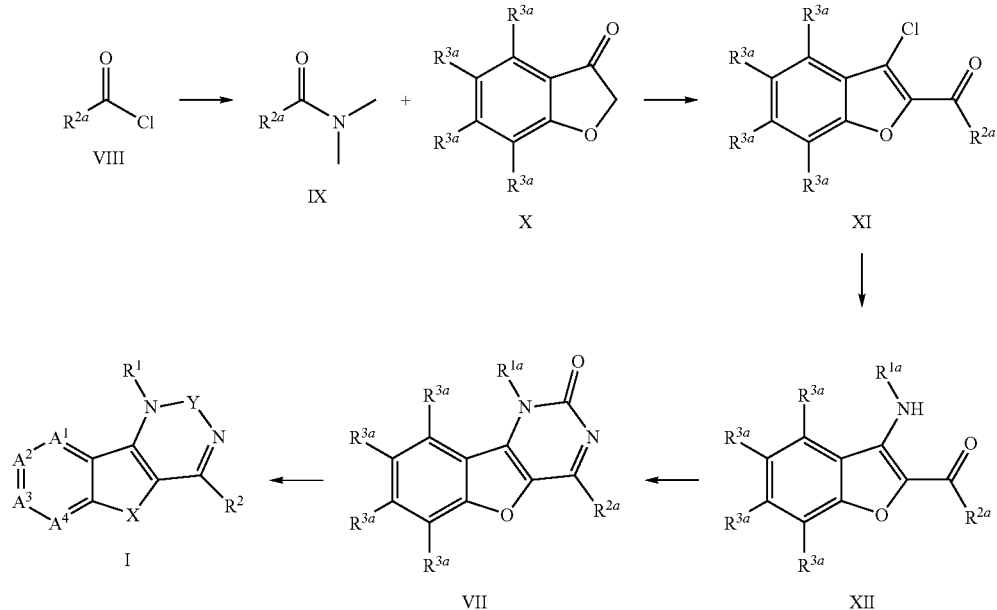

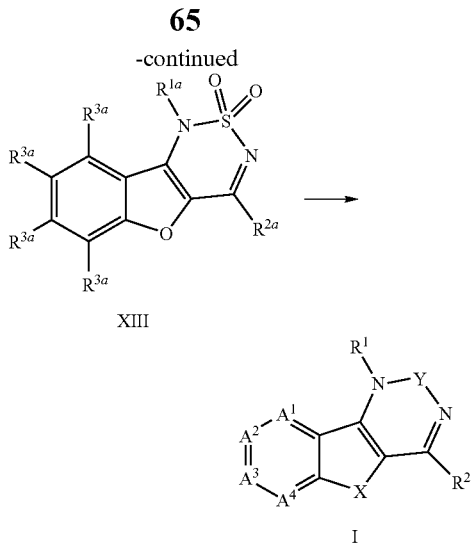

Intermediates IV (Scheme 1) are treated with ClSO$_2$NH$_2$ to provide intermediates XIII, wherein R$^{1a}$ is H. Reaction of intermediates XIII, wherein R$^{1a}$ is H, with reagents of formula R$^{1a}$-LG, wherein R$^{1a}$ is not H and wherein LG is a leaving group including but not limited to a halogen, mesylate or tosylate group, in the presence of basic reagents, including but not limited to pyridine, and/or sodium ethoxide in ethanol, provides intermediates XIII wherein R$^{1a}$ is not H. Furthermore, intermediates XIII can be transformed to compounds of formula (I) wherein A$^1$, A$^2$, A$^3$ and A$^4$ are each CR$^3$, X is O and Y is SO$_2$, using any reactions necessary to transform R$^{1a}$ to R$^1$, R$^{2a}$ to R$^2$ and/or R$^{1a}$ to R$^3$. It will be clear to the skilled person that if R$^{2a}$ is R$^2$ and R$^{3a}$ is R$^3$ in intermediates IV and/or XIII, reaction of intermediates IV with ClSO$_2$NH$_2$ and/or reaction of intermediates XIII, wherein R$^{1a}$ is H, with reagents of formula R$^{1a}$-LG, wherein R$^{1a}$ is R$^1$, as described above, will directly provide compounds of formula (I) wherein A$^1$, A$^2$, A$^3$ and A$^4$ are each CR$^3$, X is O and Y is SO$_2$.

Compounds of formula (I) wherein A$^1$, A$^2$, A$^3$ and A$^4$ are each CR$^3$, X is NR$^4$ and Y is C=O are conveniently prepared using the general procedure illustrated in Scheme 4 below.

Scheme 4:

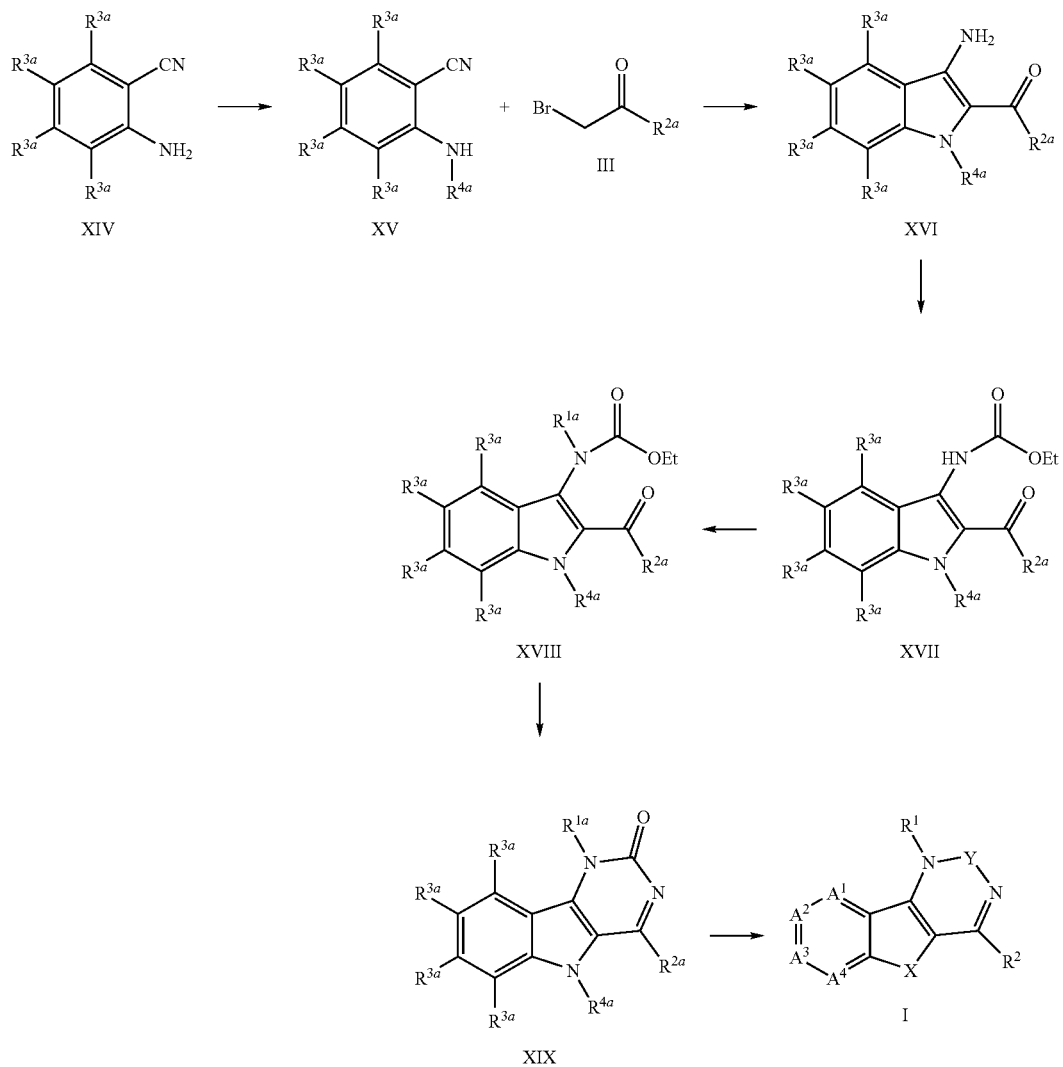

Intermediates XIV, wherein $R^{3a}$ is $R^3$ as defined herein or is a group transformable to $R^3$ as defined herein, are commercially available or are prepared by reactions well known in the art or as set forth in the examples below. Intermediates XIV can be transformed, by well known reactions, to intermediates XV wherein $R^{4a}$ is $R^4$ as defined herein or is a group transformable to $R^4$ as defined herein or wherein $R^{4a}$ is a protecting group well known in the art. For example, intermediates XIV may be treated with benzoyl chloride in the presence of pyridine, to provide intermediates XV wherein $R^{4a}$ is a benzoyl group. Reaction of intermediates XV with intermediates III (Scheme 1) in the presence of $Cs_2CO_3$ provides intermediates XVI, which can be transformed to intermediates XVII by reaction with a reagent such as ethyl chloroformate under basic conditions, including but not limited to treatment with $K_2CO_3$ or $Na_2CO_3$. Intermediates XVII, upon reaction with a reagent of formula $R^{1a}$-LG, wherein $R^{1a}$ is $R^1$ as defined herein or is a group transformable to $R^1$ as defined herein and wherein LG is a leaving group including but not limited to a halogen, mesylate or tosylate group, in the presence of a basic reagent such as $Cs_2CO_3$, provide intermediates of formula XVIII. Heating of intermediates XVIII with ammonium acetate provides intermediates XIX. Intermediates XIX can be transformed to compounds of formula (I) wherein $A^1$, $A^2$, $A^3$ and $A^4$ are each $CR^3$, X is $NR^4$ and Y is C=O, using any reactions necessary to transform $R^{1a}$ to $R^1$, $R^{2a}$ to $R^2$, $R^{3a}$ to $R^3$ and/or $R^{4a}$ to $R^4$. It will be clear to the skilled person that if $R^{1a}$ is $R^1$, $R^{2a}$ is $R^2$, $R^{3a}$ is $R^3$ and $R^{4a}$ is $R^4$ in intermediates XVIII, reaction of intermediates XVIII with ammonium acetate as described above will directly provide compounds of formula (I) wherein $A^1$, $A^2$, $A^3$ and $A^4$ are each $CR^3$, X is $NR^4$ and Y is C=O.

Compounds of formula (I) wherein $A^1$, $A^2$, $A^3$ and $A^4$ are each $CR^3$, X is S and Y is C=O are conveniently prepared using the general procedure illustrated in Scheme 5 below.

Scheme 5:

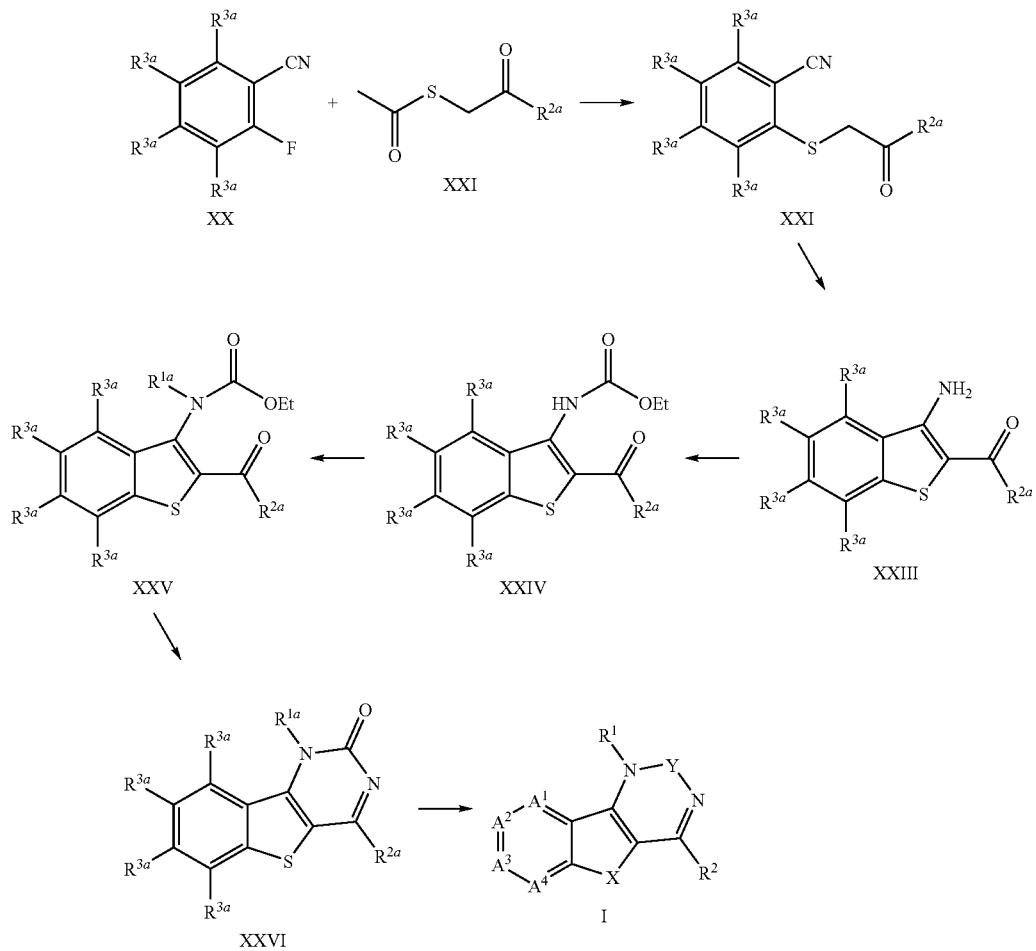

Intermediates XX, wherein $R^{3a}$ is $R^3$ as defined herein or is a group transformable to $R^3$ as defined herein, and intermediates XXI, wherein $R^{2a}$ is $R^2$ as defined herein or is a group transformable to $R^2$ as defined herein, are commercially available or are prepared by reactions well known in the art or as set forth in the examples below. Intermediates XX and XXI are heated under basic conditions, including but not limited to NaOMe in DMSO at, for example, 120° C. to give intermediates XXII. Reaction of intermediates XXII under basic conditions including but not limited to NaOMe in MeOH at reflux provides intermediates XXIII. Reaction of intermediates of formula XXIII with a reagent such as ethyl chloroformate under basic conditions, including but not limited to treatment with $K_2CO_3$ or $Na_2CO_3$, provides intermediates of formula XXIV. Reaction of intermediates XXIV with NaH, followed by alkylation with a reagent of formula $R^{1a}$-LG, wherein $R^{1a}$ is $R^1$ as defined herein or is a group transformable to $R^1$ as defined herein and wherein LG is a leaving group including but not limited to a halogen, mesylate or tosylate group, gives intermediates XXV. Heating of intermediates XXV with ammonium acetate provides intermediates XXVI. Intermediates XXVI can be transformed to compounds of formula (I) wherein $A^1$, $A^2$, $A^3$ and $A^4$ are each $CR^3$, X is S and Y is C=O, using any reactions necessary to transform $R^{1a}$ to $R^1$, $R^{ea}$ to $R^2$ and/or $R^{3a}$ to $R^3$. It will be clear to the skilled person that if $R^{1a}$ is $R^1$, $R^{2a}$ is $R^2$ and $R^{3a}$ is $R^3$ in intermediates XXV, reaction of intermediates XXV with ammonium acetate as described above will directly provide compounds of formula (I) wherein $A^1$, $A^2$, $A^3$ and $A^4$ are each $CR^3$, X is S and Y is C=O.

It will be apparent to one skilled in the art that a compound of formula (I), or any of the intermediates II to XXVI involved in its preparation, wherein any of the substituents $R^{1a}$, $R^1$, $R^{2a}$, $R^2$, $R^{3a}$, $R^3$, $R^{4a}$, $R^4$, X, and Y has one meaning as defined herein, may be transformed to another compound of formula (I), or to any of the intermediates II to XXVI involved in its preparation as appropriate, wherein any of the substituents $R^{1a}$, $R^1$, $R^{2a}$, $R^2$, $R^{3a}$, $R^3$, $R^{4a}$, $R^4$, X, and Y has a different meaning as defined herein, at any chemically convenient step in the preparation. In addition, the substituents $R^{1a}$, $R^{2a}$, $R^{3a}$, $R^{4a}$, X, and Y may be protected and/or deprotected at intermediate steps in the preparation of a compound of formula (I), as will be recognized by the skilled person.

EXAMPLES

Other features of the present invention will become apparent from the following non-limiting examples which illustrate, by way of example, the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923; or using Teledeyne Isco Flash Combiflash Companion or Rf instrument. Mass spectral analyses are recorded using electrospray mass spectrometry. Preparative HPLC is performed using a Waters instrument, Sunfire C18 column, OBD, 5 um, 30×75 mm, 5 μm, 120 Å, elution with a gradient of $CH_3CN/H_2O$ containing 0.06% TFA. Analytical HPLC and HPLC-MS are carried out under standard conditions using one of four instruments (Atlantis T3 column, Altantis T3C18 column, CombiScreen ODS-AQ column and Symmetry C18 column) with the specific measuring conditions shown below:
Column: Atlantis T3, 5 um, 4.6×30 mm
Eluent A: MeCN+0.1% TFA
Eluent B: $H_2O$+0.1% TFA
Gradient: Linear 2% A for 0.3 min, 2% to 50% A in 3.5 min, 50% to 100% A in 2 min, isocratic at 100% A for 0.2 min
Column: Atlantis T3C18, 3 um, 4.6×30 mm
Eluent A: MeCN+0.1% TFA
Eluent B: $H_2O$+0.1% TFA
Gradient: Linear 2% A for 0.8 min, 2% to 20% A in 0.7 min, 20% to 50% A in 1.4 min, 50 to 100% A in 1.5 min, isocratic at 100% A for 0.4 min.
Column: CombiScreen ODS-AQ, 5 um, 50×4.6 mm.
Eluent A: MeCN+0.06% TFA
Eluent B: $H_2O$+0.06% TFA
Gradient: 5-100% A in 12.5 min.
Column: Symmetry C18, 3.5 um, 30×4.6 mm
Eluent A: MeCN+0.06% TFA
Eluent B: $H_2O$+0.06% TFA
Gradient: Linear 5% A for 0.3 min, 5% to 50% A in 5.7 min, 50% to 100% A in 3 min.
Column: HSS T3, 1.8 um, 2.1×50 mm
Eluent A: MeCN+0.06% TFA
Eluent B: $H_2O$+0.06% TFA
Gradient: 2% to 50% A in 1.5 min, 50% to 100% A in 2.28 min.
Column: Sunfire, 3.5 um, 4.6×30 mm
Eluent A: MeCN+0.06% TFA
Eluent B: $H_2O$+0.06% TFA
Gradient: 5% to 30% A in 0.7 min, 30% to 50% A in 1.3 min, 50% to 100% A in 1.7 min.

Abbreviations or symbols used herein include:
Ac: acetyl; AcOH: acetic acid; $Ac_2O$: acetic anhydride; BOC or Boc: tert-butyloxycarbonyl; Bn: benzyl; Bu: butyl; CAN: ceric ammonium nitrate; DBU: diazabicyclo[5.4.0]undec-7-ene; DCM: dichloromethane; DIAD: diisopropyl azodicarboxylate; DIEA: n,n,diisopropylethylamine; DMA: dimethylacetamide; DMAP: 4-(N,N-dimethylamino)pyridine; DME: dimethoxyethane; DMF: N,N-dimethylformamide; DMSO: dimethylsulfoxide; DPPA: diphenylphosphoryl azide; dppf: 1,1'-bis(diphenylphosphino)ferrocene; $EC_{50}$: 50% effective concentration; Et: ethyl; $Et_3N$: triethylamine; $Et_2O$: diethyl ether; EtOAc: ethyl acetate; EtOH: ethanol; HATU: 2-(1H-7-Azabenzotriazol-1-yl)-1,1,3,3-tetramethyl uronium hexafluorophosphate methanaminium; Hex:hexanes; HPLC: high performance liquid chromatography; $IC_{50}$: 50% inhibitory concentration; $^i$Pr or i-Pr: 1-methylethyl (isopropyl); LDA: lithium diisopropylamide; Me: methyl; MeCN: acetonitrile; MeOH: methanol; MS: mass spectrometry (MALDI-TOF: Matrix Assisted Laser Desorption Ionization-Time of Flight, FAB: Fast Atom Bombardment, ES: electrospray); NaHMDS: sodium hexamethyldisilazide; NMP: N-methylpyrrolidone; NMR: nuclear magnetic resonance spectroscopy; Ph: phenyl; PG: protecting group; Prep: preparative; Pr: propyl; Pro: proline; RT: room temperature (approximately 18° C. to 25° C.); TBTU: O-benzotriazol-1-yl-N,N,N',N'-tetramethyluronium tetrafluoroborate; tert-Bu or t-Bu: 1,1-dimethylethyl (tert-butyl or t-butyl); TFA: trifluoroacetic acid; THF: tetrahydrofuran; TLC: thin layer chromatography; HPLC-MS: ultra performance liquid chromatography mass spectrometry.

Example 1

Preparation of Compound 1022 (Table 1)

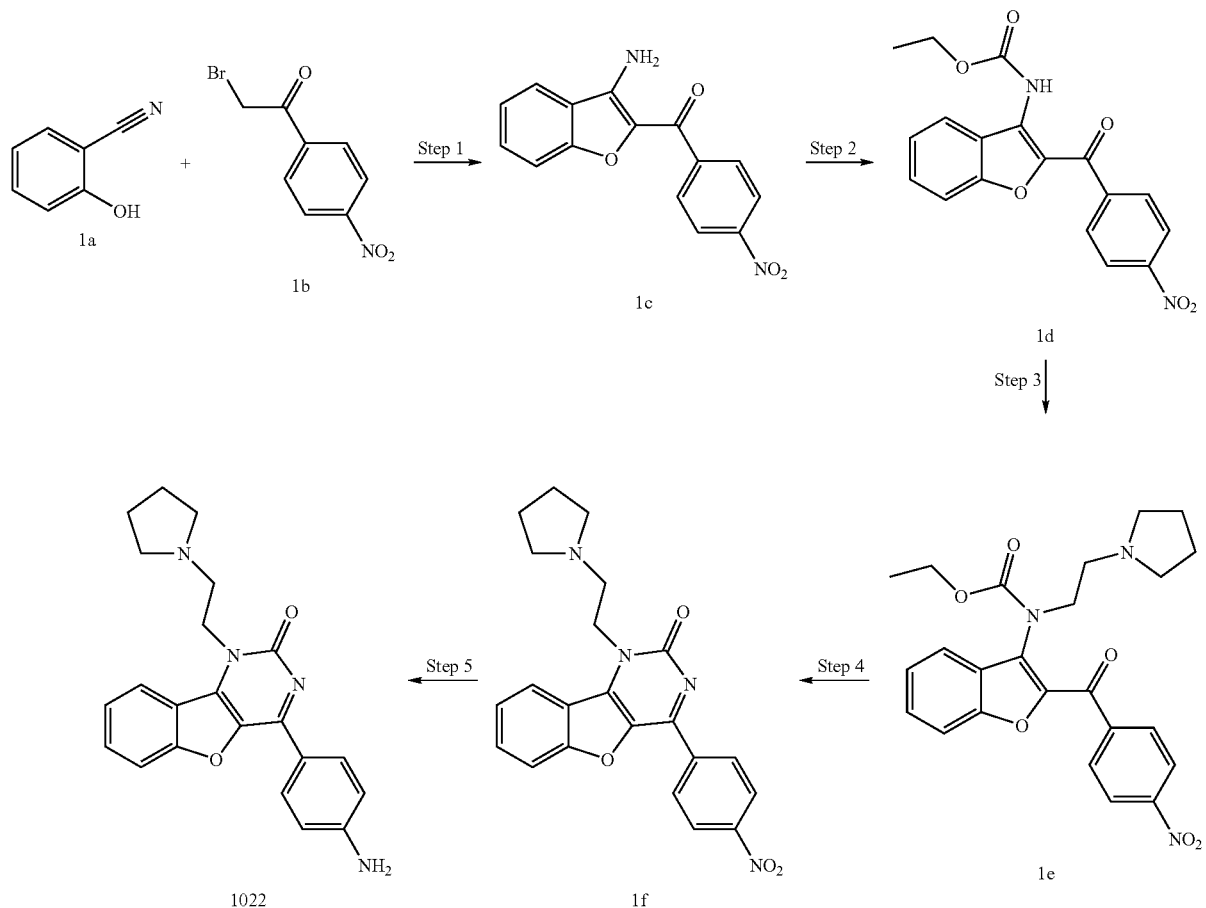

Step 1:

To a stirred mixture of compound 1a (1 g, 1.0 eq), compound 1b (2.07 g, 1.0 eq) and acetone (40 mL) at RT is added $Na_2CO_3$ (0.9 g, 1.0 eq). The mixture is stirred at reflux for 18 h and filtered, and the filtrate is concentrated. The residue is suspended in MeOH, then NaOH (1 N, 0.1 mL, 0.01 eq) is added. The mixture is stirred at reflux for 2 h and concentrated to give compound 1c.

Step 2:

To a stirred mixture of compound 1c (2.1 g, 1.0 eq), $K_2CO_3$ (7.5 g, 7.3 eq) and toluene (35 mL) at RT under $N_2$(g) is added ethyl chloroformate (5 mL, 7.0 eq), and the mixture is stirred at reflux for 18 h, then filtered. The filtrate is concentrated and the residue is triturated with hexanes to give compound 1d.

Step 3:

To a stirred suspension of NaH (60% dispersion, 27 mg, 1.2 eq) in DMF (2 mL) at RT under $N_2$(g) is added a solution of compound 1d (200 mg, 1.0 eq) in DMF (2 mL). The resulting mixture is stirred at RT for 1 h. To this solution is added a solution of 1-(2-chloroethyl)pyrrolidine hydrochloride salt (96.0 mg, 1.2 eq) in DMF (2 mL), which is previously neutralized with NaH. The mixture is stirred at RT for 30 min then heated at 90° C. for 1.5 h. The mixture is poured into water then extracted with EtOAc (2×50 mL). The combined organic layers are washed with brine, dried over $MgSO_4$, filtered and concentrated to give compound 1e.

Step 4:

A mixture of compound 1e (269 mg, 1.0 eq) and ammonium acetate (5 g, 100 eq) is heated at 130° C. (open to the air) with stirring for 1 h. The mixture is cooled to RT and adjusted to basic pH by addition of NaOH (1 N). The mixture is extracted with DCM, and the extract is dried ($MgSO_4$), filtered and concentrated. The residue is purified by silica gel chromatography (0-5% MeOH/DCM) to give compound 1f.

Step 5:

A mixture of compound 1f (175 mg, 1.0 eq), $Pd(OH)_2$/C, EtOH (50 mL) and TFA (few drops) is stirred under 1 atm of hydrogen for 45 min. The mixture is filtered through a Millex cartridge and the filtrate is concentrated in vacuo. The residue is purified by prep HPLC to give compound 1022 (Table 1).

Example 2

Preparation of Compound 1001 (Table 1)

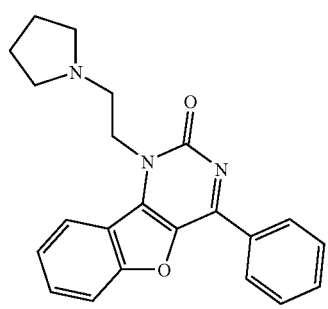

1001

Compound 1001 is prepared according to the method of Example 1 but replacing compound 1b in step 1 with 2-bromoacetophenone.

Example 3

Preparation of Compound 2001 (Table 2)

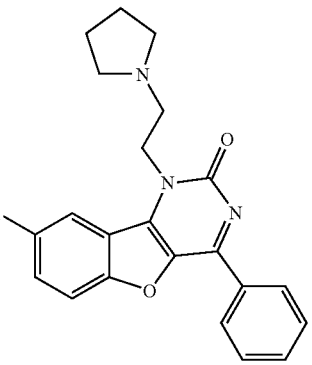

2001

Compound 2001 is prepared according to the method of Example 1 but replacing compound 1a in step 1 with 4-chloro-2-cyanophenol and replacing compound 1b in step 1 with 2-bromoacetophenone.

Example 4

Preparation of Compound 1005 (Table 1)

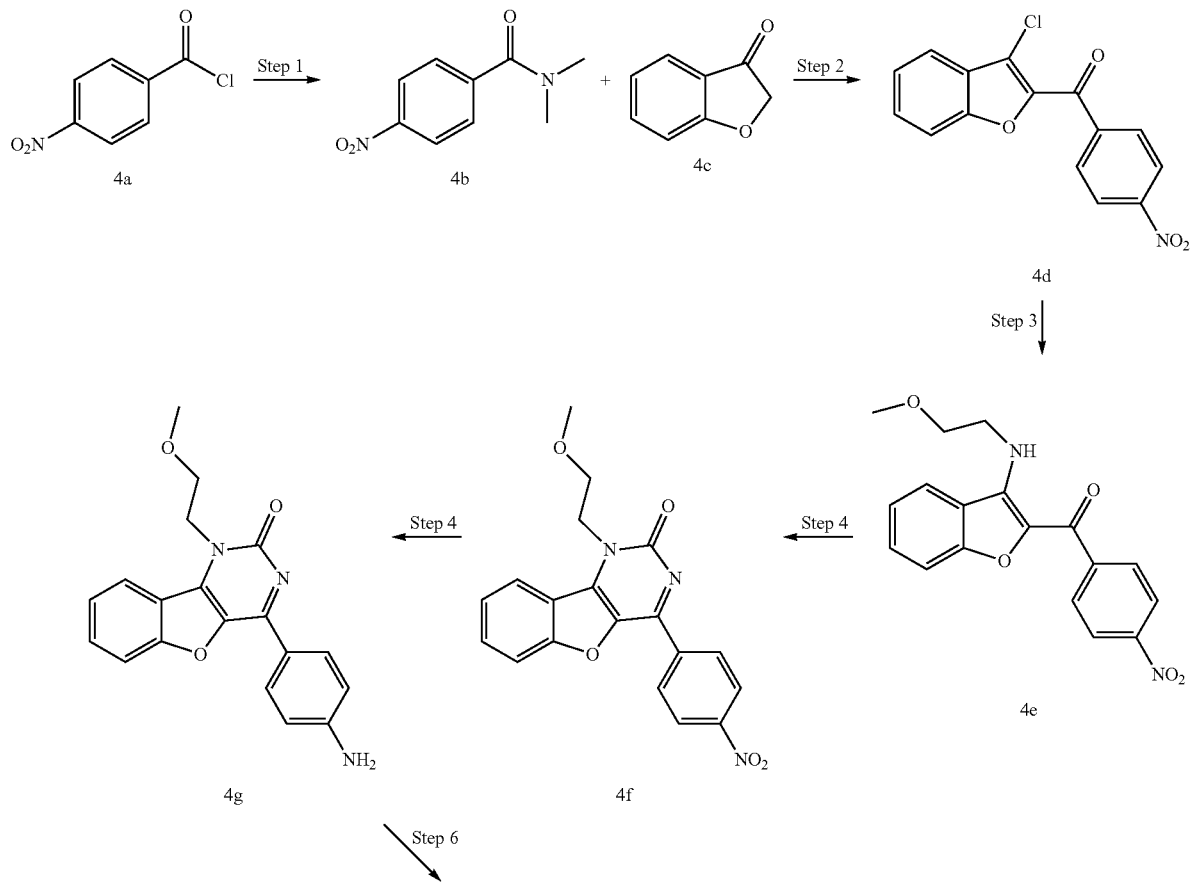

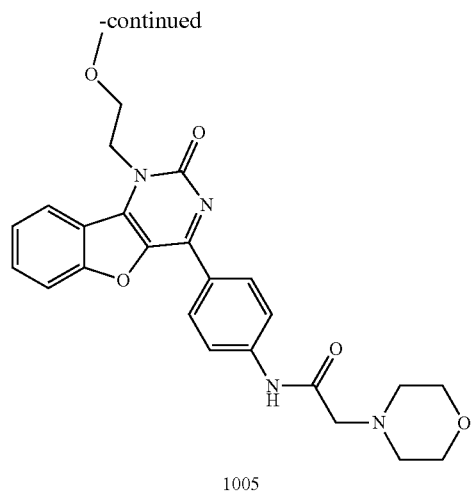

1005

Step 1:

To a solution of the acid chloride 4a (10.2 g, 1.0 eq) in THF (60 mL) is added 40% Me₂NH/water (15 mL, 2.2 eq). The mixture is stirred at RT for 1 h, then poured into saturated NaHCO₃/water (1:1) and extracted with EtOAc. The organic extract is washed with brine, dried with MgSO₄, filtered and concentrated under vacuum to give compound 4b (5.7 g, 53%).

Step 2:

A mixture of p-nitro-dimethylbenzamide 4b (1.91 g, 1.0 eq) and POCl₃ (10 mL) is stirred for 30 min at RT. Benzofuranone 4c (1.3 g, 1.0 eq) is added and the mixture is stirred for 30 min at RT. The mixture is heated at 90° C. for 2 h, then is poured into ice-water and extracted with EtOAc. The organic phase is washed with water and brine, dried and concentrated. The residue is triturated with ether, filtered and dried to afford compound 4d (1.8 g, 59%) that is used without further purification.

Step 3:

A mixture of the chlorobenzofuran 4d (1.3 g, 1.0 eq) and 2-methoxyethylamine (7 mL, 20 eq) in DMSO (20 mL) is heated at 100° C. for 2 h. The mixture is poured into water and extracted with EtOAc (2×). The organic layer is washed with water and brine, then dried with MgSO₄, filtered and concentrated under vacuum. The crude product is purified by flash chromatography on silica gel (30% EtOAc/Hex) to give compound 4e (748 mg, 52%).

Step 4:

A mixture of ketone 4e (1.4 g, 1.0 eq) and oxalyl chloride (18 mL) is stirred at RT for 1 h, then concentrated in vacuo. The residue is dissolved in acetone (30 mL) and NaN₃/water (655 mg, 2.4 eq, in 5 mL) is added. The mixture is stirred at RT for 24 h, then filtered, and the solid is washed with water and acetone to give compound 4f (1.1 g, 72%).

Step 5:

Compound 4f is transformed to compound 4g following the procedure of Example 1, step 5.

Step 6:

To a mixture of compound 4g (21 mg, 1 eq) in DCM (1 mL) at RT is added bromoacetyl bromide (20 μL, 3.6 eq), and the mixture is stirred for 30 min. The mixture is concentrated under reduced pressure, the residue is dissolved in DMF (1 mL) and morpholine (100 μL, 1.4 eq) is added at RT. After stirring for 3 h, the mixture is filtered through a 0.22 μm Millex™ filter, and purified by prep HPLC to give compound 1005 (29 mg, 83%).

Example 5

Preparation of Compound 1016 (Table 1)

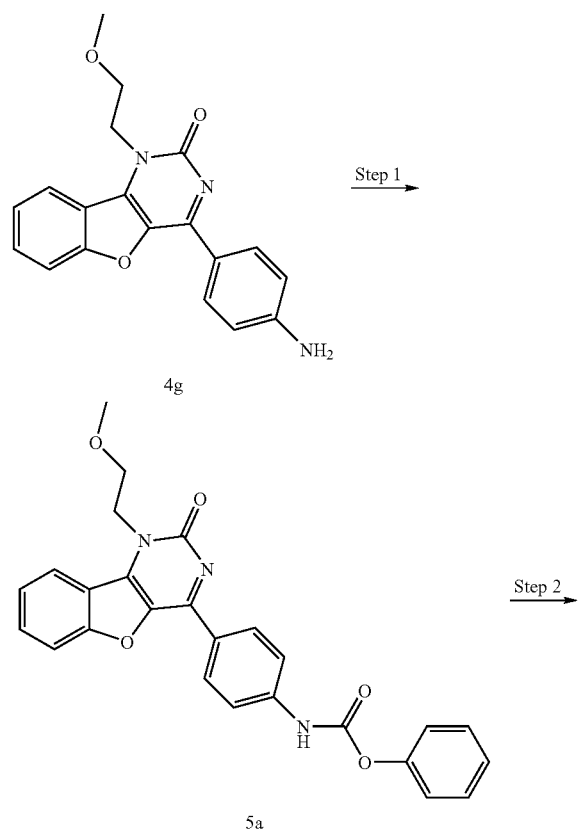

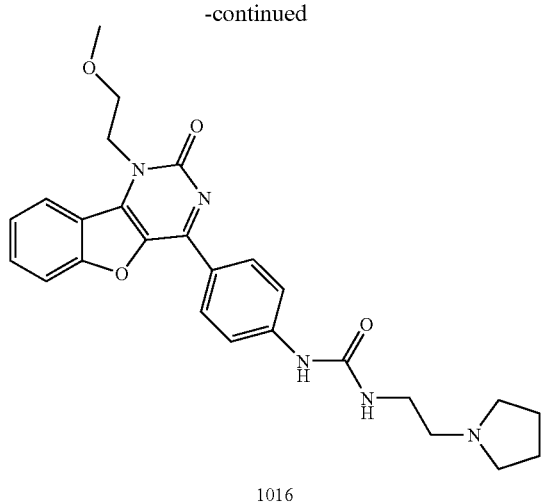

Step 1:

To a mixture of compound 4g (Example 4, step 5) (73 mg, 1 eq) in CH₃CN (1 mL) at RT is added phenyl chloroformate (60 μL, 2.1 eq), and the mixture is heated at 60° C. for 45 min. Concentration under reduced pressure affords intermediate 5a (115 mg, quant.).

Step 2:

To a mixture of intermediate 5a (34 mg, 1 eq) in DMSO is added 1-aminoethyl-N-pyrrolidine (60 μL, 6.7 eq) and the mixture is stirred for 1 h. The mixture is filtered through a 0.22 μm Millex filter, and purified by prep HPLC to give compound 1016 (Table 1) (12 mg, 34%).

Example 6

Preparation of Compound 1036 (Table 1)

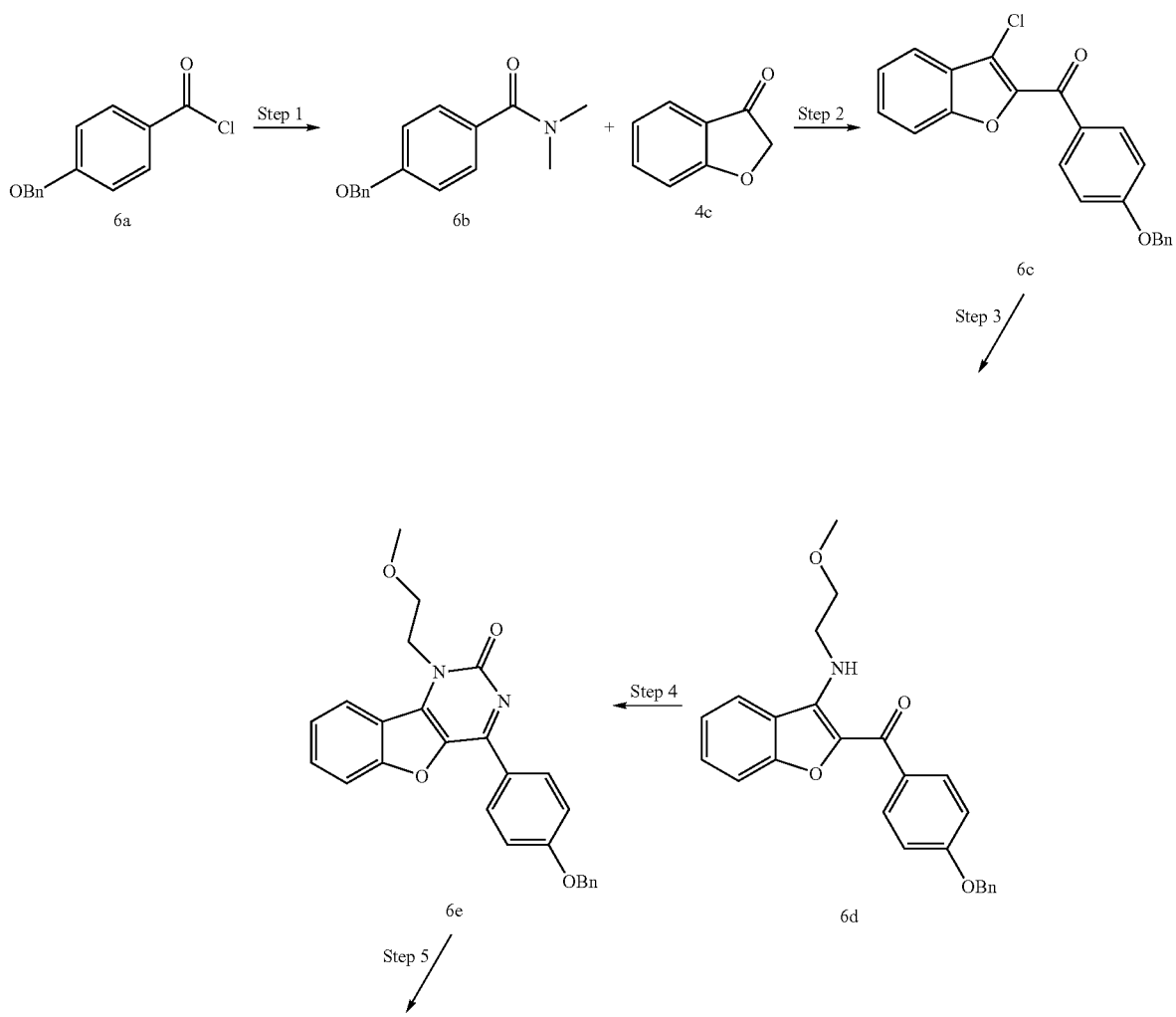

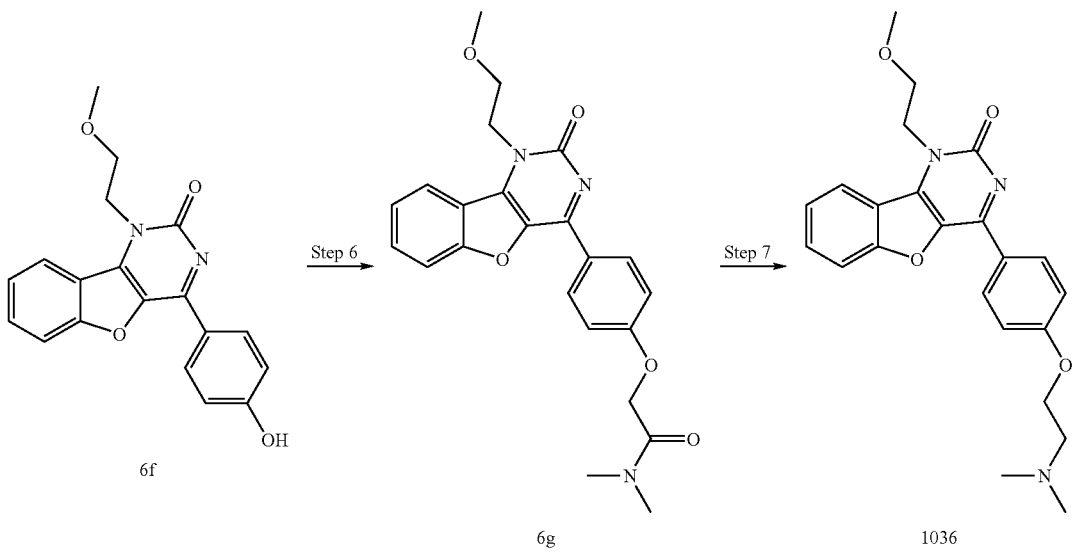

Step 1:

To a solution of the acid chloride 6a (9 g, 1.0 eq) in THF (75 mL) is added 40% Me$_2$NH/water (20 mL, 4.4 eq). The mixture is stirred at RT for 1 h, then poured into sat NaHCO$_3$/water (1:1) and extracted with EtOAc. The organic layer is washed with brine, dried with MgSO$_4$, filtered and concentrated under vacuum to give compound 6b (8.7 g, 93%).

Step 2:

A mixture of compound 6b (1.1 g, 0.4 eq) and POCl$_3$ (15 mL) is stirred for 30 min at RT. Benzofuranone 4c (Example 4) (1.5 g, 1.0 eq) is added and the mixture is stirred for 30 min at RT, then heated at 90° C. for 2 h, poured into ice-water and extracted with EtOAc. The organic phase is washed with water and brine, dried and concentrated and the residue is triturated with ether, filtered and dried to afford compound 6c (680 mg, 43%).

Step 3:

A mixture of chlorobenzofuran 6c (1.1 g, 1.0 eq) and 2-methoxyethylamine (3 mL, excess) in DMSO (17 mL) is heated at 135° C. for 5 h. The mixture is poured into water and extracted with EtOAc (2×). The organic layer is washed with water and brine, then dried with MgSO$_4$, filtered and concentrated under vacuum. The crude product is purified by flash chromatography (25 to 40% EtOAc in Hex) to give compound 6d (748 mg, 66%).

Step 4:

A mixture of the ketone 6d (805 mg, 1.0 eq) and oxalyl chloride (8 mL) is stirred at RT for 1 h, then concentrated in vacuo. The residue is dissolved in acetone (20 mL) and NaN$_3$/water (350 mg, 2.7 eq, in 3 mL) is added. The mixture is stirred at RT for 24 h, then filtered and the solid is washed with water and acetone to give compound 6e (361 mg, 42%).

Step 5:

A solution of the benzyl ether 6e (360 mg, 1.0 eq) and Pd(OH)$_2$/C (30 mg) in EtOH/THF (2:1, 30 mL) is stirred under an atmosphere of H$_2$ (balloon) for 2 h. The mixture is filtered through fiberglass and the filtrate is concentrated in vacuo to give compound 6f (336 mg, 93%).

Step 6:

A mixture of the phenol 6f (107 mg, 1 eq), N,N-dimethyl-2-chloroacetamide (80 µL, 2.5 eq) and Cs$_2$CO$_3$ (120 mg, 1.2 eq) in DMF (3 mL) is stirred at RT for 5 h. The mixture is poured into 1M HCl and extracted with EtOAc (2×). The organic extract is dried with MgSO$_4$, filtered and concentrated under vacuum. The aqueous phase is concentrated and purified by prep HPLC (20-35% CH$_3$CN/water) to give compound 6g (Table 1) (62 mg, 46%).

Step 7:

A mixture of the compound 6g (26 mg, 1 eq) and LiAlH$_4$ (10 mg, 4.4 eq) in THF (2.5 mL) is heated at 60° C. for 2.5 days. The mixture is poured into 1M HCl and concentrated in vacuo. DMF is added, then the mixture is shaken, filtered through Millex and is directly purified by prep HPLC (20-35% CH$_3$CN/water) to give compound 1036 (2 mg, 8%).

Example 7

Preparation of Compound 1046 (Table 1)

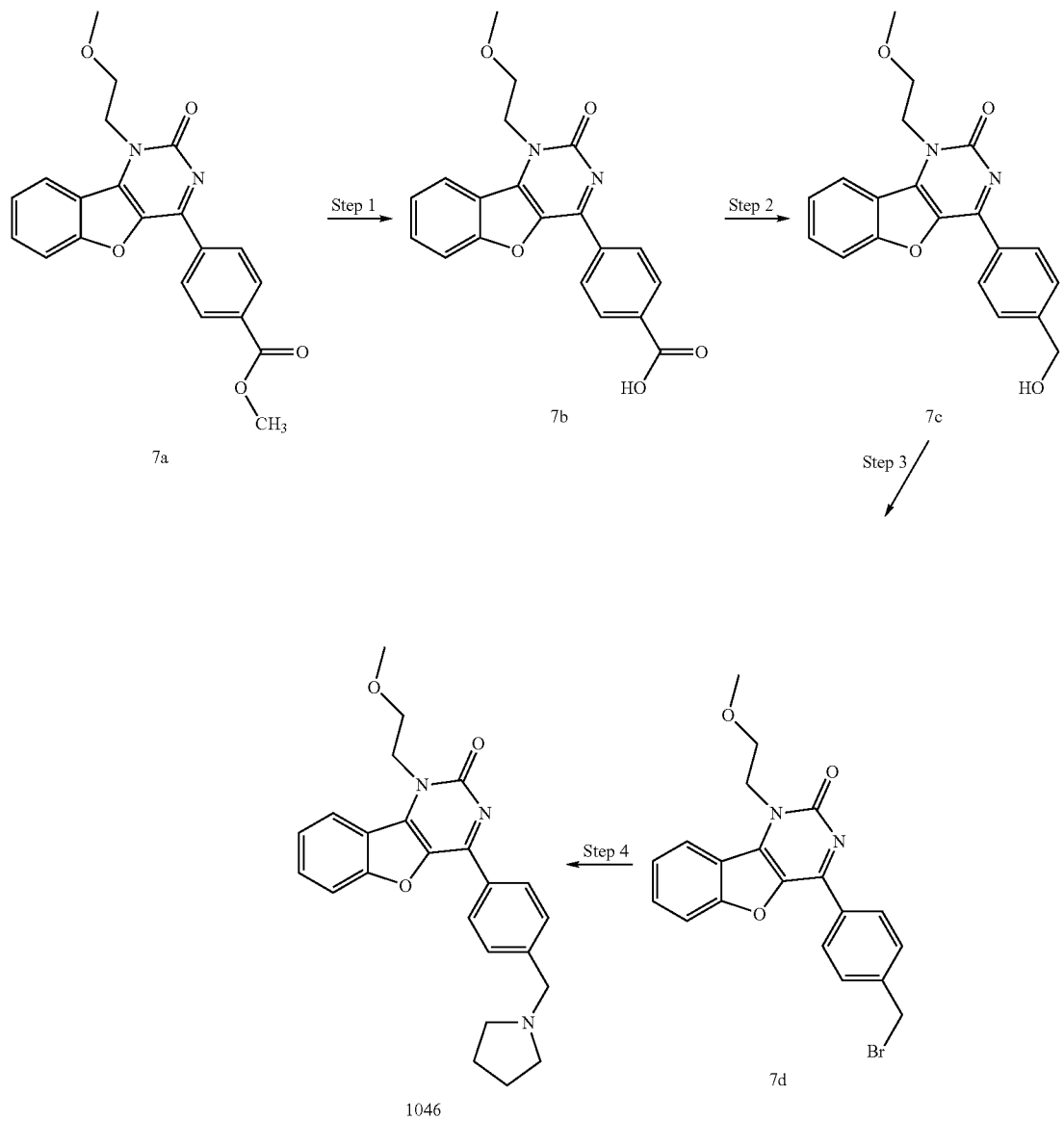

Step 1:

A mixture of compound 7a (prepared by the method of steps 1-4 of Example 4, but replacing compound 4a with 4-(methoxycarbonyl)benzoyl chloride in step 1) (1.7 g, 1 eq) and 1M NaOH (14 mL, 3 eq) in THF/MeOH (1:1, 30 mL) is stirred at RT for 20 h. The mixture is acidified with 1M HCl, filtered and the solid is washed with water to give compound 7b (1.6 g, 100%).

Step 2:

A mixture of compound 7b (400 mg, 1 eq) and 1M BH$_3$.THF (3 mL, 2.7 eq) in THF (10 mL) is heated at reflux for 1 h. The mixture is acidified with 1M HCl and extracted with EtOAc. The organic layer is washed with brine, then dried with MgSO$_4$, filtered and concentrated under vacuum. To a solution of the residue (375 mg, 1 eq) in CH$_3$CN/DMF (2:1, 6 mL) is added CAN/water (590 mg, 1 eq, in 1.5 mL). The mixture is stirred at RT for 1 h, then poured into 0.5M HCl and extracted with EtOAc (2×). The organic extract is washed with brine, then dried with MgSO$_4$, filtered and concentrated under vacuum to give compound 7c (297 mg, 80%).

83

Step 3:

To a mixture of the alcohol 7c (295 mg, 1 eq) and DCM (20 mL) is added PBr₃ (100 µL, 1.3 eq). The mixture is stirred at RT for 18 h, then is poured into water and extracted with EtOAc. The organic extract is washed with brine, then dried over MgSO₄, filtered and concentrated under vacuum to give compound 7d (287 mg, 83%).

Step 4:

A mixture of the benzylbromide 7d (35 mg, 1 eq) and pyrrolidine (40 µL, excess) in DMF (2 mL) is stirred at RT for 1 h, then directly purified by prep HPLC (20-35% acetonitrile/water) to give compound 1046 (Table 1) (20 mg, 59%) as a trifluoroacetic acid salt.

Example 8

Preparation of Compound 1056 (Table 1)

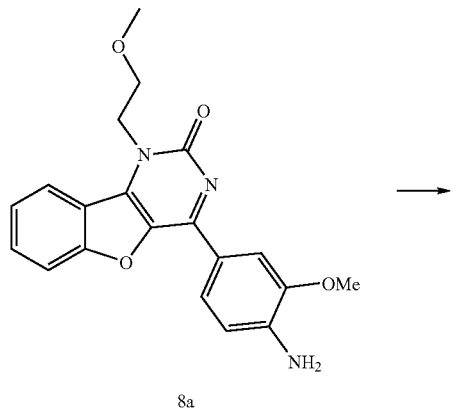

8a

→

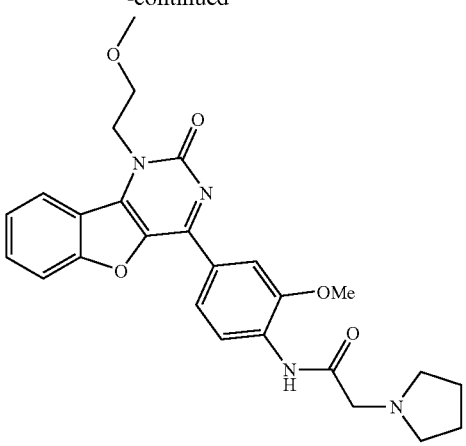

1056

To a mixture of compound 8a (prepared using the method of steps 1 to 5 of Example 4 but replacing compound 4a with 3-methoxy-4-nitrobenzoyl chloride in step 1) (15 mg, 1 eq) in DCM (1 mL) at RT is added bromoacetyl bromide (50 µL, 14 eq), and the mixture is stirred for 30 min, and then concentrated under reduced pressure. The residue is dissolved in DMF (1 mL) and pyrrolidine (200 µL, 1.4 eq) is added with stirring at RT. The mixture is stirred for 3 h, then filtered through a 0.22 µm Millex™ filter, and purified by prep HPLC to give compound 1056 (12 mg, 60%).

Example 9

Preparation of Compound 2029 (Table 2)

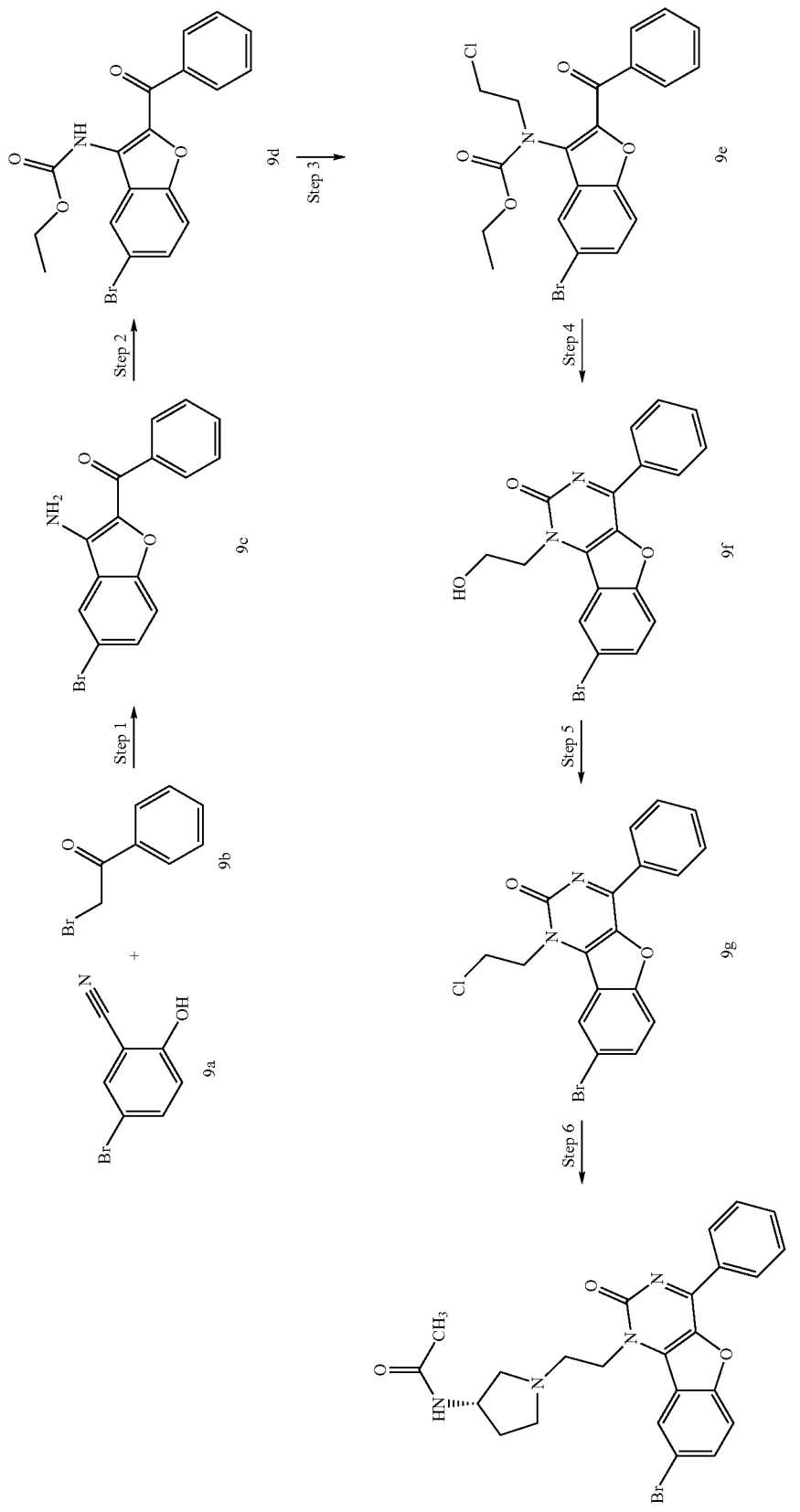

Step 1:

To a stirred mixture of compound 9a (5 g, 1.0 eq), compound 9b (5.05 g, 1.0 eq) and acetone (60 mL) at RT is added sodium carbonate (2.87 g, 1.1 eq), and the mixture is stirred at reflux for 18 h. The mixture is filtered and the filtrate is concentrated. The residue is suspended in MeOH and NaOH (1 N, 0.2 mL, 0.01 eq) is added. The mixture is stirred at reflux for 2 h and concentrated to give compound 9c.

Step 2:

To a stirred mixture of compound 9c (8.4 g, 1.0 eq), $K_2CO_3$ (34 g, 9.1 eq) and toluene (150 mL) at RT under $N_2(g)$ is added ethyl chloroformate (20 mL, 8.0 eq) and the mixture is stirred at reflux for 18 h. The mixture is filtered and the filtrate is concentrated. The residue is triturated with hexanes to give compound 9d.

Step 3:

To a stirred mixture of NaH (60% dispersion, 250 mg, 1.1 eq) in NMP (15 mL) at RT under $N_2$ (g) is added compound 9d (2.0 g, 1.0 eq). The mixture is stirred at RT for 1 h and 2-chloroethyl p-toluenesulfonate (1.3 mL, 1.4 eq) is added. The mixture is stirred at RT for 30 min then heated at 90° C. for 1.5 h. The mixture is poured into water then extracted with EtOAc (2×250 mL). The combined organic extracts are washed with brine, dried over $MgSO_4$, filtered, and concentrated. The residue is purified by chromatography (0-30% EtOAc/Hex) to give compound 9e.

Step 4:

A mixture of compound 9e (1.72 g, 1.0 eq) and ammonium acetate (20 g, 65 eq) is heated at 130° C. (open to the air) with stirring for 1 h. The mixture is cooled to RT then adjusted to basic pH with NaOH (1 N). The resulting mixture is extracted with DCM and the organic extract is concentrated. The residue is suspended in MeOH (50 mL), NaOH (1 N, 0.5 mL, 0.1 eq) is added and the mixture is allowed to stir at reflux for 30 min. The mixture is concentrated and the residue is purified by silica gel chromatography (0-10% MeOH/DCM) to give compound 9f.

Step 5:

To a cold stirred solution of compound 9f (1.38 g, 1.0 eq), $Et_3N$ (1.3 mL, 2.6 eq) and DCM (35 mL) is added slowly methanesulfonyl chloride (0.4 mL, 1.4 eq). The mixture is stirred at RT for 18 h, then poured into water (100 mL) and DCM (150 mL) is added. The aqueous layer is extracted with DCM (100 mL) and the combined organic layers are dried over $MgSO_4$ and concentrated. The residue is purified by silica gel chromatography (0.5% MeOH/DCM) to give compound 9g (Table 2).

Step 6:

A mixture of compound 9g (50 mg, 1.0 eq), $Et_3N$ (0.1 mL, 5.8 eq), NaI (5 mg, 0.2 eq), (3S)-(+)-3-acetamidopyrrolidine (60 mg, 3.8 eq) and NMP (2 mL) is stirred at 70° C. for 18 h. The mixture is neutralized with TFA and purified by prep HPLC to give compound 2029.

Example 10

Preparation of Compound 2009 (Table 2)

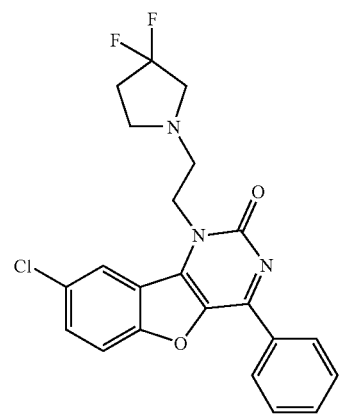

Compound 2009 is prepared according to the method of Example 9 but replacing compound 9a in step 1 with 4-chloro-2-cyanophenol and replacing (3S)-(+)-3-acetamidopyrrolidine in step 6 with 3,3-difluoropyrrolidine hydrochloride salt.

Example 11

Preparation of Compound 2038 (Table 2)

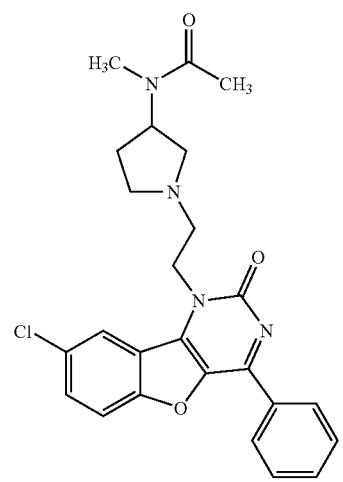

Compound 2038 is prepared according to the method of Example 9 but replacing (3S)-(+)-3-acetamidopyrrolidine in step 6 with 3-(N-acetyl-N-methylamino)pyrrolidine.

Example 12

Preparation of Compound 2214 (Table 2)

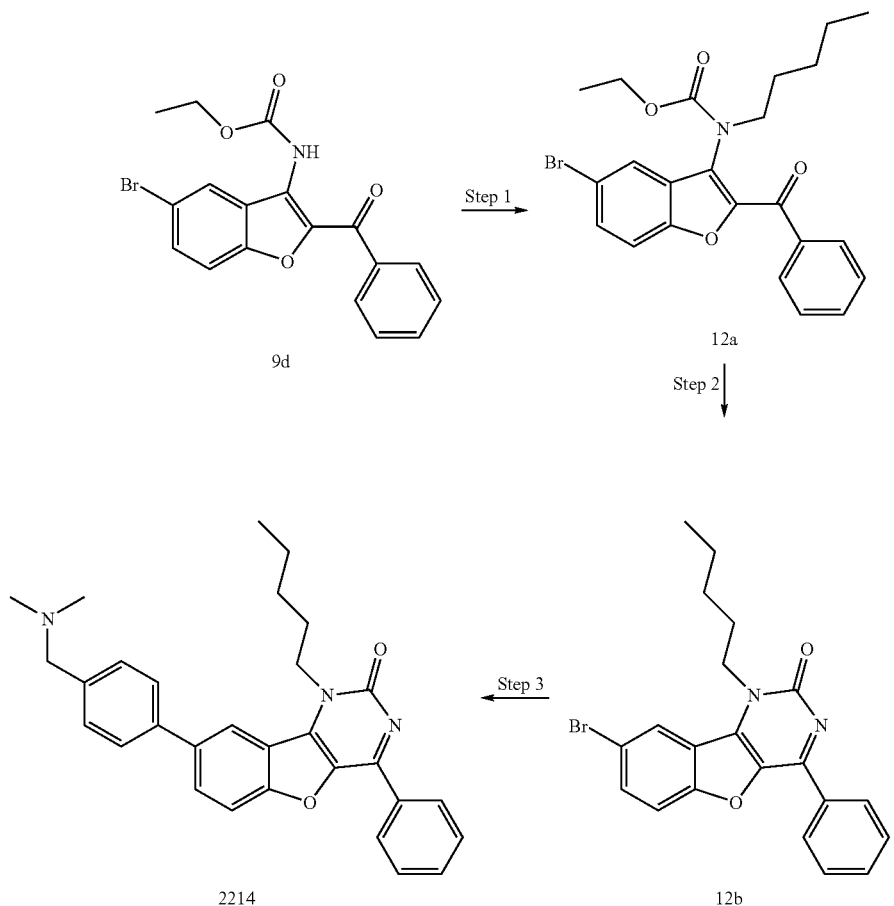

Step 1:

To a mixture of compound 9d (Example 9, step 2) (250 mg, 0.644 mmol) and DMF (3.9 mL) under Ar atm at RT is added NaH (60% in oil, 64.39 mg, 1.61 mmol), and the mixture is allowed to stir at RT for 1 h. 1-Bromopentane (486.4 mg, 3.22 mmol) is added and the mixture is heated at 60° C. for 2 h. The reaction is quenched with saturated $NH_4Cl$ (aq), the mixture is poured into $H_2O$-EtOAc, and the layers are separated. The aqueous phase is extracted with EtOAc and the combined organic layers are washed with water and brine, dried over $Na_2SO_4$ and concentrated under reduced pressure. The residue is purified by combi-flash chromatography (20% EtOAc/Hex) to provide compound 12a (78.8 mg, 26.7%).

Step 2:

A mixture of compound 12a (78.8 mg, 0.172 mmol) and $NH_4OAc$ (1.47 g, 19.1 mmol)) is heated at 150° C. (open to the air) with stirring for 2 h. The mixture is cooled to RT and adjusted to pH>8 by addition of 5N NaOH. The mixture is filtered and the solid is rinsed with water and dried under vacuum to obtain compound 12b (37.9 mg, 53.6%).

Step 3:

To a mixture of compound 12b (37.9 mg, 1 eq), p-N,N-dimethylbenzylamine boronic acid (16.5 mg, 0.092 mmol) and dioxane (0.59 mL)/$H_2O$ (0.26 mL) (bubbled with Ar for 10 min.), is added $K_2CO_3$ (12.7 mg, 0.092 mmol) and cesium fluoride (42 mg, 0.28 mmol), followed by Pd(dppf)Cl$_2$ (6.7 mg, 0.01 mmol). The mixture is heated in a microwave (135° C., 25 min.), then concentrated under reduced pressure. The residue is dissolved in AcOH and purified by prep HPLC to give compound 2214 (15 mg, 35%).

Example 13

Preparation of Compound 2133 (Table 2)

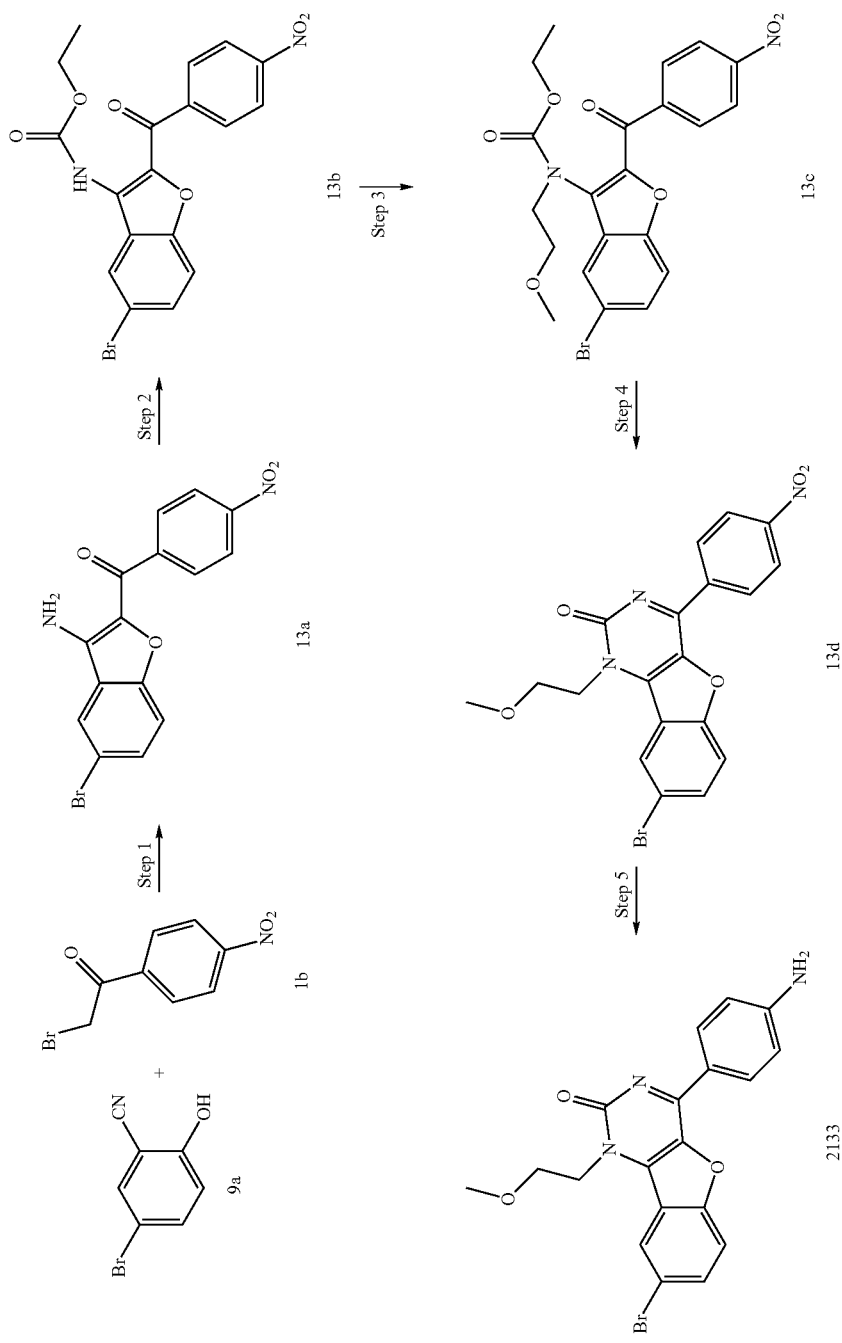

Step 1:
A mixture of 5-bromo-2-hydroxybenzonitrile 9a (Example 9) (5.0 g, 25.25 mmol), 2-bromo-4'-nitroacetophenone 1b (Example 1) (6.2 g, 25.50 mmol), and $Na_2CO_3$ (2.7 g, 25.50 mmol) in acetone (190 mL) is heated at reflux for 24 h. The mixture is filtered to provide compound 13a (11.7 g, >99%).

Step 2:
To a mixture of compound 13a (3.6 g, 9.97 mmol) and $K_2CO_3$ (13 g, 94.70 mmol) in toluene (95 mL) is added ethyl chloroformate (18 mL, 188.29 mmol). The reaction mixture is heated at reflux for 35 h. The mixture is filtered and the resulting solid is air-dried, triturated with water and filtered to provide compound 13b (4.2 g, 97%).

Step 3:
To a stirred mixture of NaH (60% dispersion in mineral oil, 868 mg, 21.70 mmol) in DMF (64 mL) at RT under $N_2$ is added a solution of the carbamate 13b (3.8 g, 8.68 mmol) in DMF (10 mL) dropwise. The mixture is stirred at RT for 1 h and 2-bromoethyl methylether (8.2 mL, 86.79 mmol) is added. The mixture is stirred at RT for 30 min, heated at 90° C. for 1.5 h, then cooled to RT and concentrated under reduced pressure. The residue is diluted with EtOAc (300 mL) and water (300 mL). The layers are separated and the aqueous layer is further extracted with EtOAc (2×100 mL). The combined organic layers are washed with brine, dried ($Na_2SO_4$), filtered and concentrated under reduced pressure. The residue is purified by chromatography (20%-50% EtOAc/Hex) to afford compound 13c (3.8 g, 85%).

Step 4:
A mixture of compound 13c (7.8 g, 15.80 mmol) and ammonium acetate (130 g, 1.95 mol) is heated at 135° C. with stirring for 2 h, then diluted with water (300 mL) and adjusted to pH 8 by addition of 10N NaOH. The precipitate is filtered, and rinsed with water and hexanes to yield compound 13d (5.2 g, 75%).

Step 5:
To a suspension of the nitro compound 13d (1.4 g, 3.15 mmol) in EtOH (16 mL) is added iron (704 mg, 12.61 mmol) followed by 1N aqueous HCl (3.5 mL) and water (1.8 mL). The reaction mixture is heated at reflux for 2 h, then cooled to RT, and the magnetic stirrer with the iron on it is removed from the solution and rinsed with acetonitrile. The mixture is concentrated under reduced pressure and the residue is dried under vacuum to afford HCl salt of compound 2133 (1.4 g, 99%).

Example 14

Preparation of Compound 2193 (Table 2)

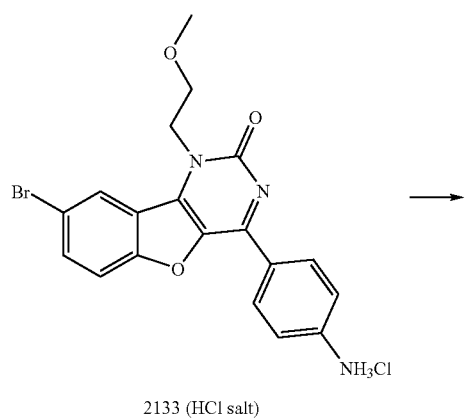

2133 (HCl salt)

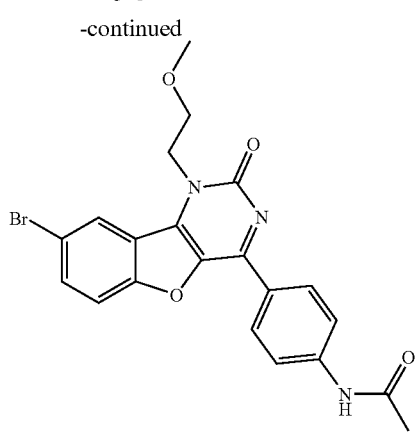

2193

To a mixture of the HCl salt of compound 2133 (Example 13) (100 mg, 1 eq) in DCM (1 mL) at RT is added acetyl chloride (31 μL, 2.0 eq), and the mixture is stirred for 60 min, then concentrated under reduced pressure. The residue is dissolved in DMF (1 mL) and acetic acid (1 mL), filtered on a 0.22 μm Millex filter, and purified by prep HPLC to give compound 2193 (7 mg, 7%).

Example 15

Preparation of Compounds 2174 and 2194 (Table 2)

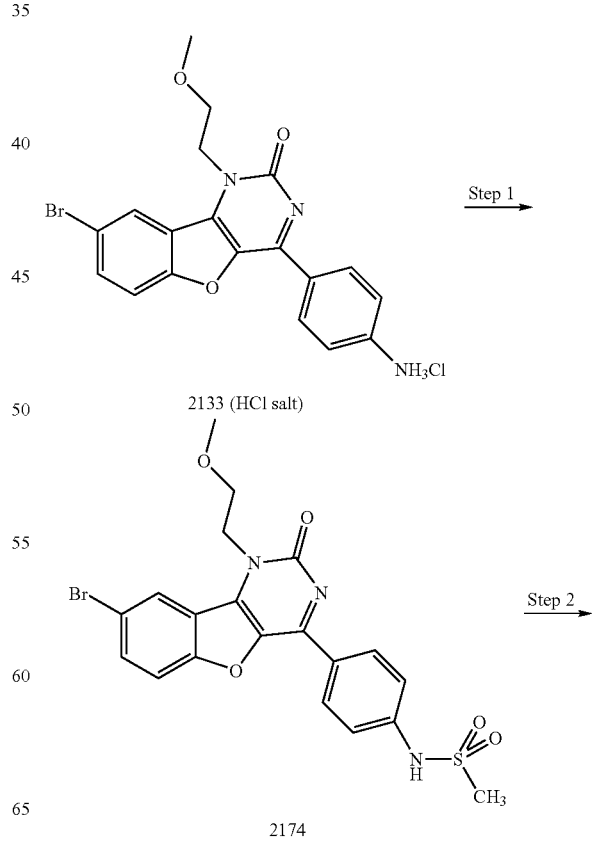

2133 (HCl salt)

2174

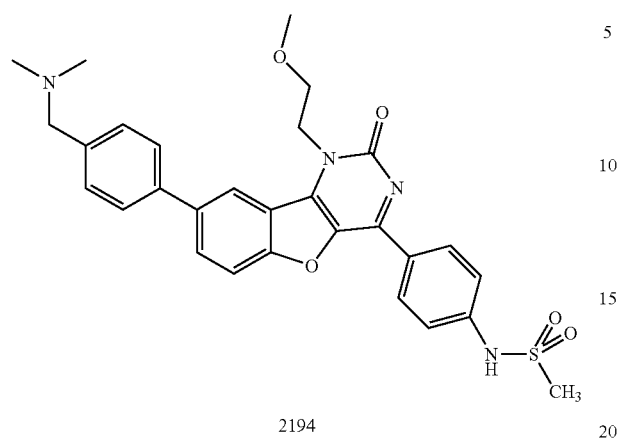

2194

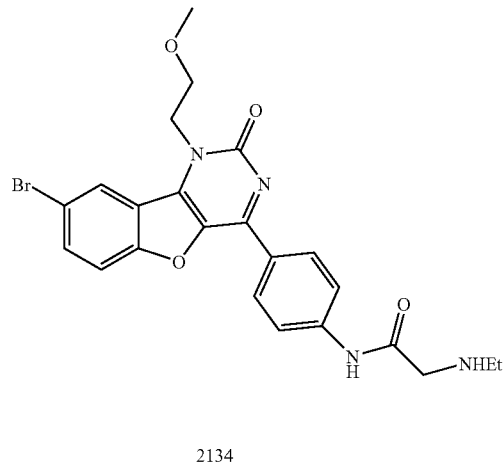

2134

Step 1:

To a mixture of the HCl salt of compound 2133 (Example 13) (126 mg, 1 eq) in DCM (1 mL) at RT is added methanesulfonyl chloride (122 μL, 5 eq) and DMAP (34 mg, 1.0 eq), and the mixture is stirred for 120 min at 50° C. The mixture is then concentrated under reduced pressure and the residue is washed with HCl (1 N), distilled water, then diethyl ether with sonication to give compound 2174 (145 mg, quant.).

Step 2:

To a mixture of compound 2174 (65 mg, 1 eq) in dioxane (1 mL) and water (0.5 mL) at RT is added 4-(N,N-dimethylaminomethyl)phenylboronic acid (35 mg, 1.5 eq), $K_2CO_3$ (55 mg, 3.0 eq) and CsF (60 mg, 3.0 eq). The mixture is degassed with a stream of Ar, then $Pd(dppf)Cl_2 \cdot CH_2Cl_2$ (9.7 mg, 0.1 eq) is added. The mixture is heated in a Biotage microwave at 135° C. for 25 min, and then concentrated under reduced pressure. The residue is dissolved in AcOH and DMSO and purified by prep HPLC to give compound 2194 (6.7 mg, 9%).

Example 16

Preparation of Compound 2134 (Table 2)

To a suspension of the HCl salt of compound 2133 (Example 13) (1.4 g, 3.38 mmol) in DCM (102 mL) is added bromoacetyl bromide (0.3 mL, 3.72 mmol). The reaction mixture is stirred at RT for 15 min and concentrated under reduced pressure, and the residue is suspended in DMF (68 mL). Ethylamine solution (2M in THF) (10.1 mL, 20.28 mmol) is added slowly and the mixture is stirred for 20 h. The suspension is filtered through Celite™ and the filter cake is washed with DMF. The filtrate is concentrated under reduced pressure and the residue is diluted with DCM (200 mL) and water (200 mL). The mixture is filtered affording compound 2134 (1.5 g, 88%).

Example 17

Preparation of Compound 2074 (Table 2)

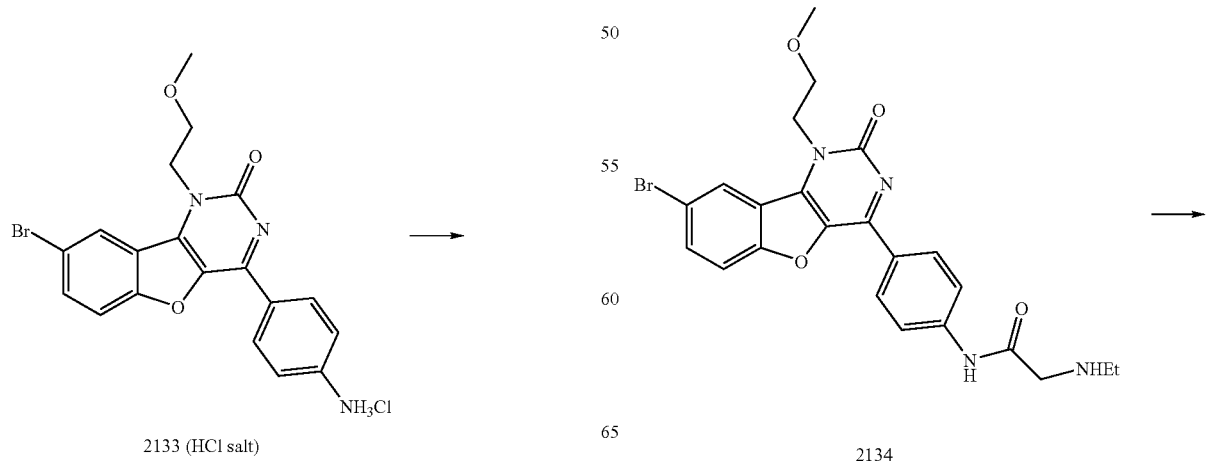

2133 (HCl salt)        2134

-continued

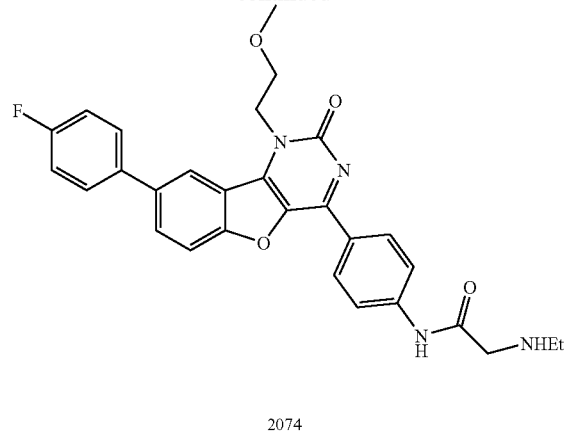

2074

A mixture of compound 2134 (Example 19) (35 mg, 0.07 mmol), 4-fluorophenylboronic acid (18 mg, 0.13 mmol), Pd(dppf)Cl$_2$ DCM complex (5.7 mg, 0.01 mmol) and K$_2$CO$_3$ (29 mg, 0.21 mmol) in 1,4-dioxane (0.7 mL) and water (0.1 mL) is degassed with Ar for 5 min. The mixture is heated in a microwave at 120° C. for 15 min, then concentrated under reduced pressure and the residue is dissolved in AcOH. Purification by prep HPLC affords compound 2074 (13 mg, 36%).

Example 18

Preparation of Compound 2064 (Table 2)

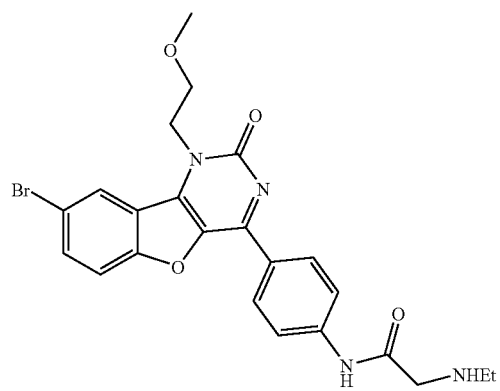

2205

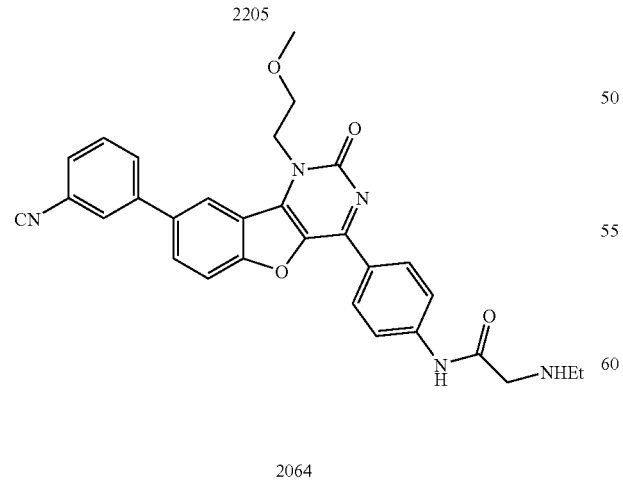

2064

Compound 2064 is prepared using the procedure of Example 17 but replacing 4-fluorophenylboronic acid with 3-cyanophenylboronic acid.

Example 19

Preparation of Compound 2105 (Table 2)

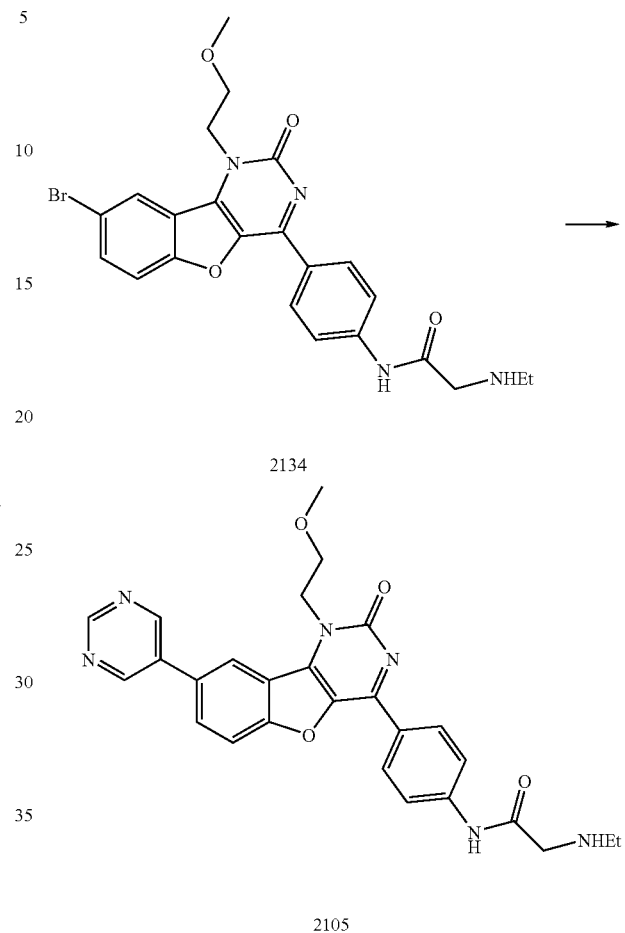

2134

2105

Compound 2105 is prepared using the procedure of Example 17 but replacing 4-fluorophenylboronic acid with 5-pyrimidinylboronic acid.

Example 20

Preparation of Compound 2062 (Table 2)

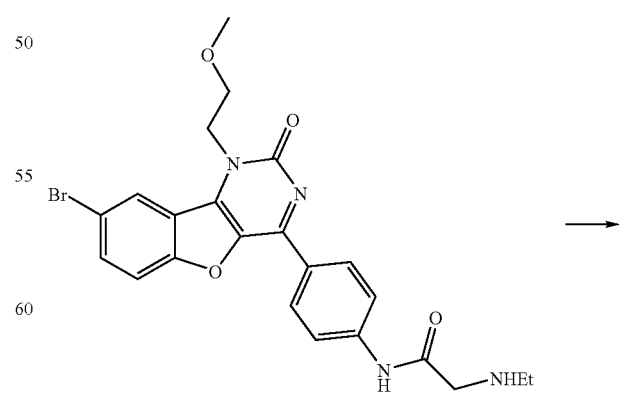

2134

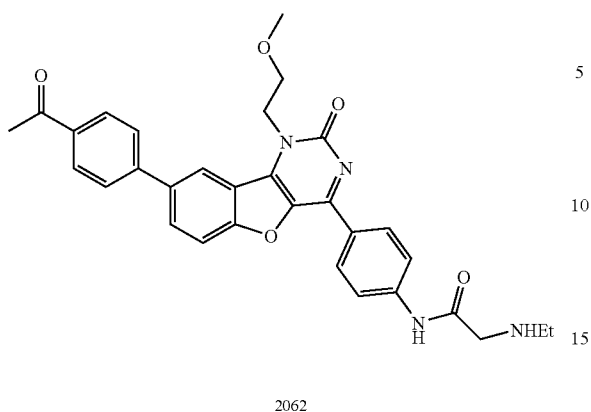

2062

Compound 2062 is prepared using the procedure of Example 17 but replacing 4-fluorophenylboronic acid with 4-acetylphenylboronic acid.

Example 21

Preparation of Compound 2021 (Table 2)

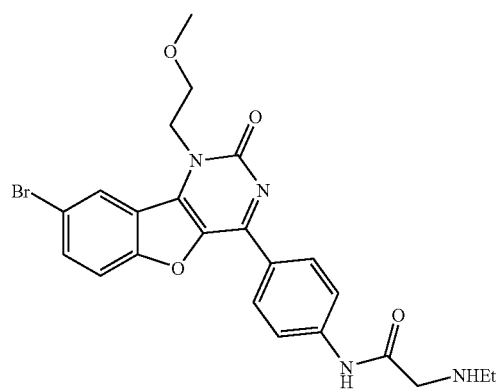

2134

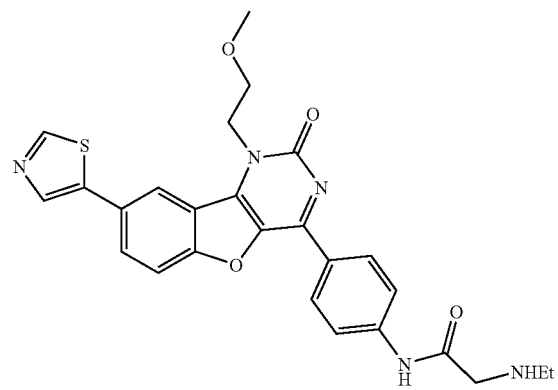

2021

A mixture of compound 2134 (Example 16) (35 mg, 0.07 mmol) in DMF (2 mL) is bubbled with a stream of Ar for 5 min. Pd(PPh$_3$)$_4$ (8 mg, 0.01 mmol) and 5-(tributylstannyl)thiazole (58 mg, 0.15 mmol) are added and the reaction is degassed for an additional one min. The mixture is heated in a microwave at 120° C. for 20 min. Purification by prep HPLC affords compound 2021 (12 mg, 33%).

Example 22

Preparation of Compound 2254 (Table 2)

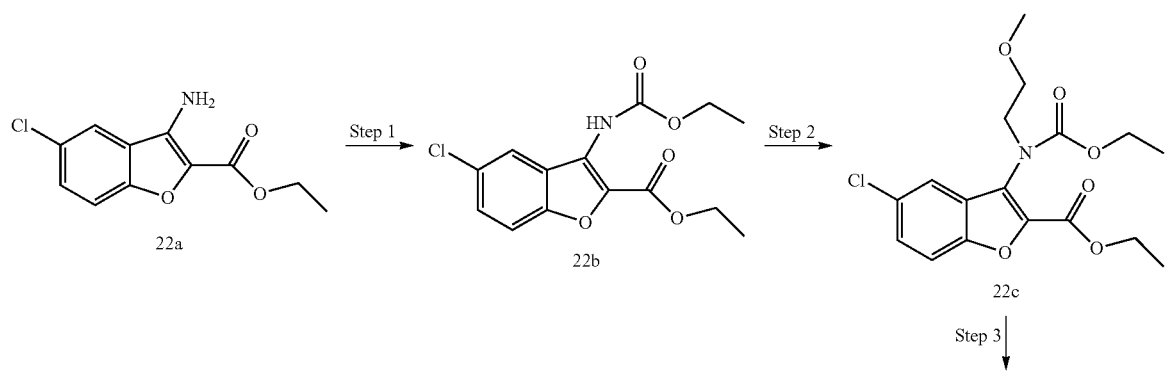

-continued

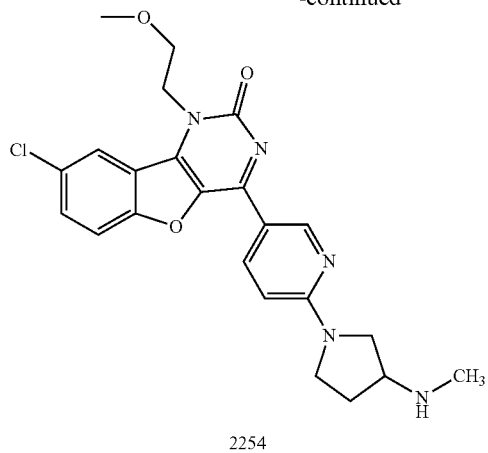

2254

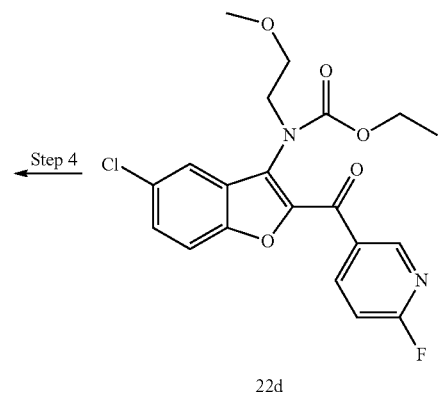

22d

Step 1:

A mixture of the benzofuran 22a (prepared using the method of Example 1, step 1 but replacing compound 1a with 4-chloro-2-cyanophenol, and replacing compound 1b with ethyl 2-bromoacetate) (2.8 g, 1 eq) in toluene/acetonitrile (30 mL/10 mL) and ethyl chloroformate (8 mL, 6 eq) is heated at reflux overnight, then concentrated in vacuo to give compound 22b (3.8 g, 100%).

Step 2:

To a solution of the carbamate 22b (3.8 g, 1 eq) in NMP (20 mL) at RT under $N_2$ is added NaH (660 mg, 1.2 eq). The mixture is stirred at RT for 15 min and a solution of 2-methoxyethyl mesylate/NMP (2.5 g, 1.2 eq/5 mL) is added. The mixture is stirred at RT for 10 min then heated at 90° C. for 1.5 h. The mixture is poured into water then extracted with EtOAc (2×). The organic extract is washed with brine, dried over $MgSO_4$, filtered and concentrated. The residue is purified by flash chromatography on silica gel (10-30% EtOAc/Hex) to give compound 22c (3.0 g, 65%).

Step 3:

To a solution of 2-fluoro-5-bromopyridine (2.2 g, 1.1 eq) and the ester 22c (4.2 g, 1 eq) in THF (80 mL) at −78° C., is added BuLi/hexane (1.6M, 8 mL, 1.2 eq). The mixture is stirred at −78° C. for 1 h, the reaction is quenched by addition of acetic acid, and the mixture is poured in EtOAc/brine and extracted. The organic extract is dried over $MgSO_4$, filtered and concentrated under vacuum. The residue is purified by flash chromatography on silica gel (10-30% EtOAc/Hex) to give compound 22d (4.0 g, 77%).

Step 4:

A mixture of the fluoropyridine 22d (40 mg, 1 eq), 3-methylaminopyrrolidine (15 mg, 1.6 eq), and $Et_3N$ (40 mL, 3 eq) in DMSO (0.8 mL) is heated at 100° C. for 1 h. Ammonium acetate (1.2 g, excess) is added to the hot mixture and heating is continued at 130° C. for 40 min. The mixture is directly purified by prep HPLC (20-35% $CH_3CN$/water) to afford compound 2254 (46 mg, 81%) as a trifluoroacetic acid salt.

Example 23

Preparation of Compound 1071 (Table 1)

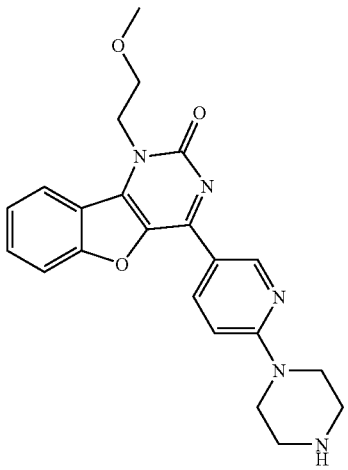

1071

Compound 1071 is prepared according to the method of Example 22 but replacing benzofuran 22a in step 1 with ethyl-3-aminobenzofuran-2-carboxylate and replacing 3-methylaminopyrrolidine in step 4 with piperazine.

Example 24

Preparation of Compound 1076 (Table 1)

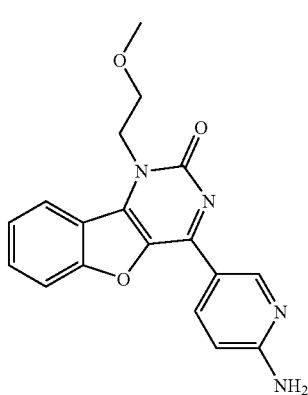

1076

Compound 1076 is prepared according to the method of steps 1 to 3 of Example 22 but replacing benzofuran 22a in step 1 with ethyl-3-aminobenzofuran-2-carboxylate and replacing 2-fluoro-5-bromopyridine in step 3 with 2-amino-5-bromopyridine, followed by the method of step 4 of Example 13.

Example 25

Preparation of Compound 2260 (Table 2)

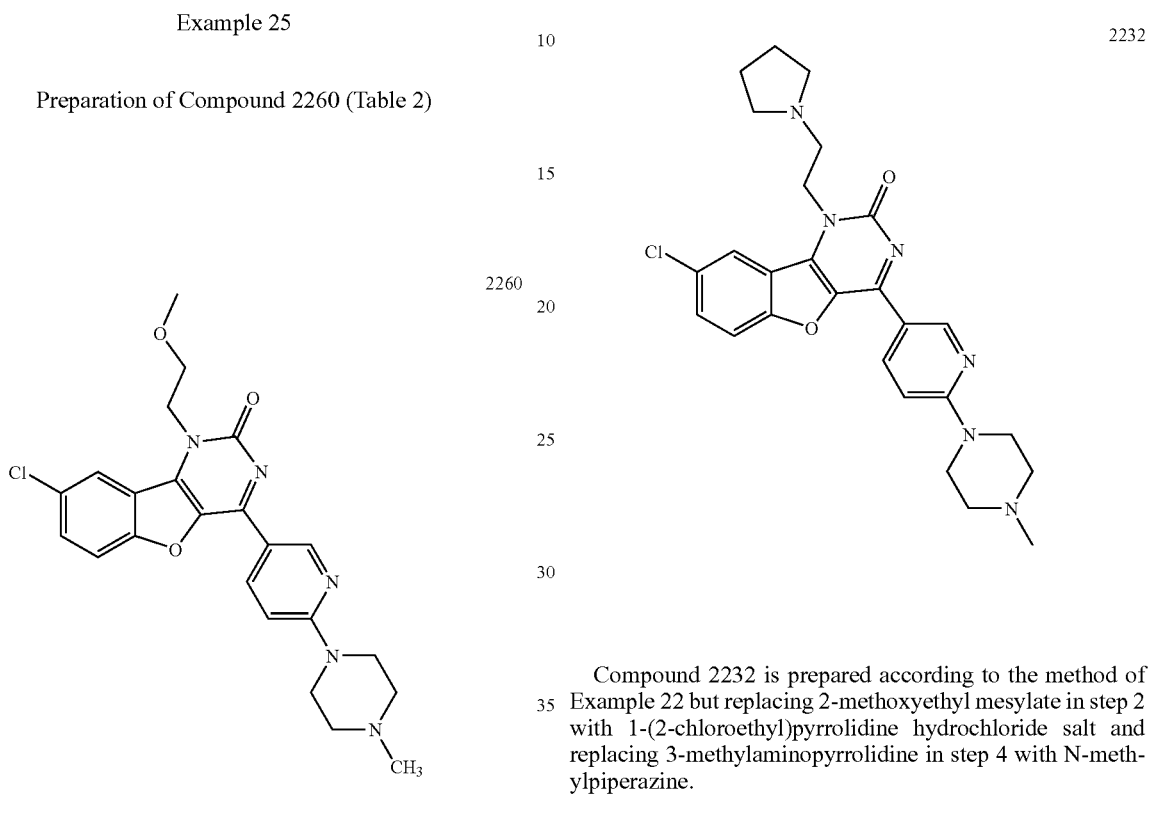

Compound 2260 is prepared according to the method of Example 22 but replacing 3-methylaminopyrrolidine in step 4 with N-methylpiperazine.

Example 26

Preparation of Compound 2232 (Table 2)

Compound 2232 is prepared according to the method of Example 22 but replacing 2-methoxyethyl mesylate in step 2 with 1-(2-chloroethyl)pyrrolidine hydrochloride salt and replacing 3-methylaminopyrrolidine in step 4 with N-methylpiperazine.

Example 27

Preparation of Compound 2213 (Table 2)

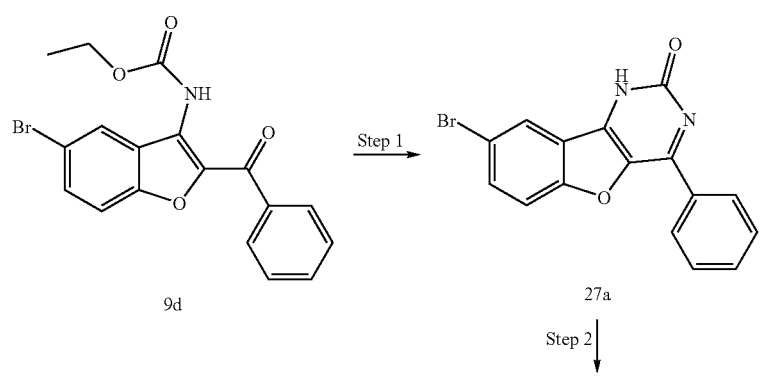

-continued

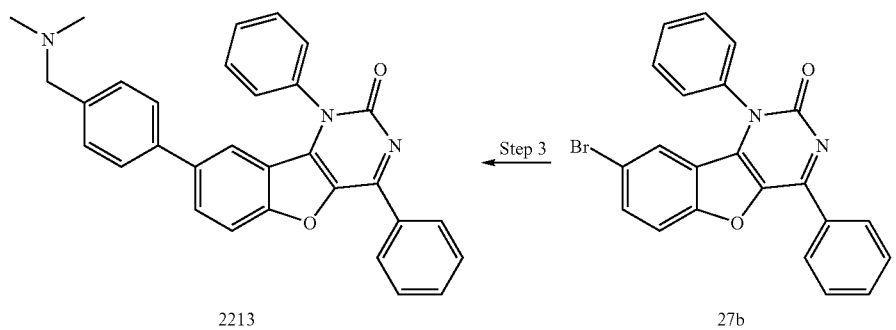

2213       27b

Step 1:

A mixture of compound 9d (Example 9) (1.0 g, 2.58 mmol) and NH$_4$OAc (17.3 g, 224.6 mmol) is heated at 130° C. (open to the air) with stirring for 2 h. The mixture is cooled to RT and 10N NaOH and water are added to adjust the pH to >8. The mixture is filtered and the solid is rinsed with water and hexanes and dried to give compound 27a (0.87 g, 98%).

Step 2:

To a mixture of compound 27a (240 mg, 0.703 mmol), phenyl boronic acid (257.3 mg, 2.11 mmol) and Cu(OAc)$_2$ (0.256 g, 1.41 mmol) is added DCM (2.5 mL) followed by Et$_3$N (0.196 mL) and pyridine (0.114 mL), then 4 Å molecular sieves (0.8 g). The mixture is rapidly stirred at RT under O$_2$ (balloon) overnight. Further portions of phenyl boronic acid (257.3 mg, 2.11 mmol), Cu(OAc)$_2$ (0.256 g, 1.41 mmol), DCM (2.5 mL), Et$_3$N (0.196 mL) and pyridine (0.114 mL) are added and the mixture is rapidly stirred at RT under O$_2$ (balloon) overnight. The mixture is diluted with CH$_2$Cl$_2$, filtered over Celite™, washed with NH$_4$OH (3%) twice, HCl (10%) and brine, dried over MgSO$_4$ and concentrated. The residue is triturated with Et$_2$O and filtered, and the filtrate is washed with ether to obtain compound 27b.

Step 3:

To a mixture of compound 27b (Example 9) (65.6 mg, 0.157 mmol) in dioxane (1 mL) and water (0.4 mL) at RT is added 4-(N,N-dimethylaminomethyl)phenylboronic acid pinacol ester (42.2 mg, 0.236 mmol), K$_2$CO$_3$ (21.7 mg, 0.157 mmol) and CsF (71.6 mg, 0.472 mmol). The mixture is degassed with a stream of Ar, then Pd(dppf)Cl$_2$.CH$_2$Cl$_2$ (11.5 mg, 0.016 mmol) is added. The mixture is heated in a Biotage microwave at 150° C. for 30 min, quenched with 0.1 mL AcOH and then concentrated under reduced pressure. The residue is dissolved in AcOH and DMSO and purified by prep HPLC to give compound 2213 (1.5 mg, 2%).

Example 28

Preparation of Compound 2261 (Table 2)

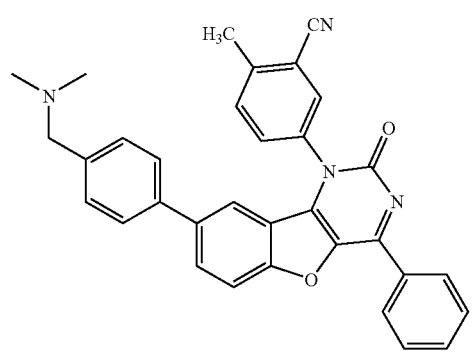

Compound 2261 is prepared according to the method of Example 27 but replacing phenylboronic acid in step 2 with 4-methyl-3-cyanophenylboronic acid.

Example 29

Preparation of Compound 2262 (Table 2)

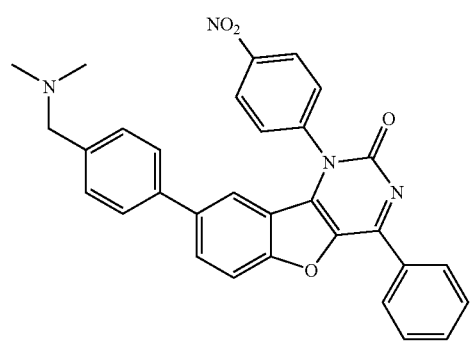

Compound 2262 is prepared according to the method of Example 27 but replacing phenylboronic acid in step 2 with 4-nitrophenylboronic acid.

Example 30

Preparation of Compound 2131 (Table 2)

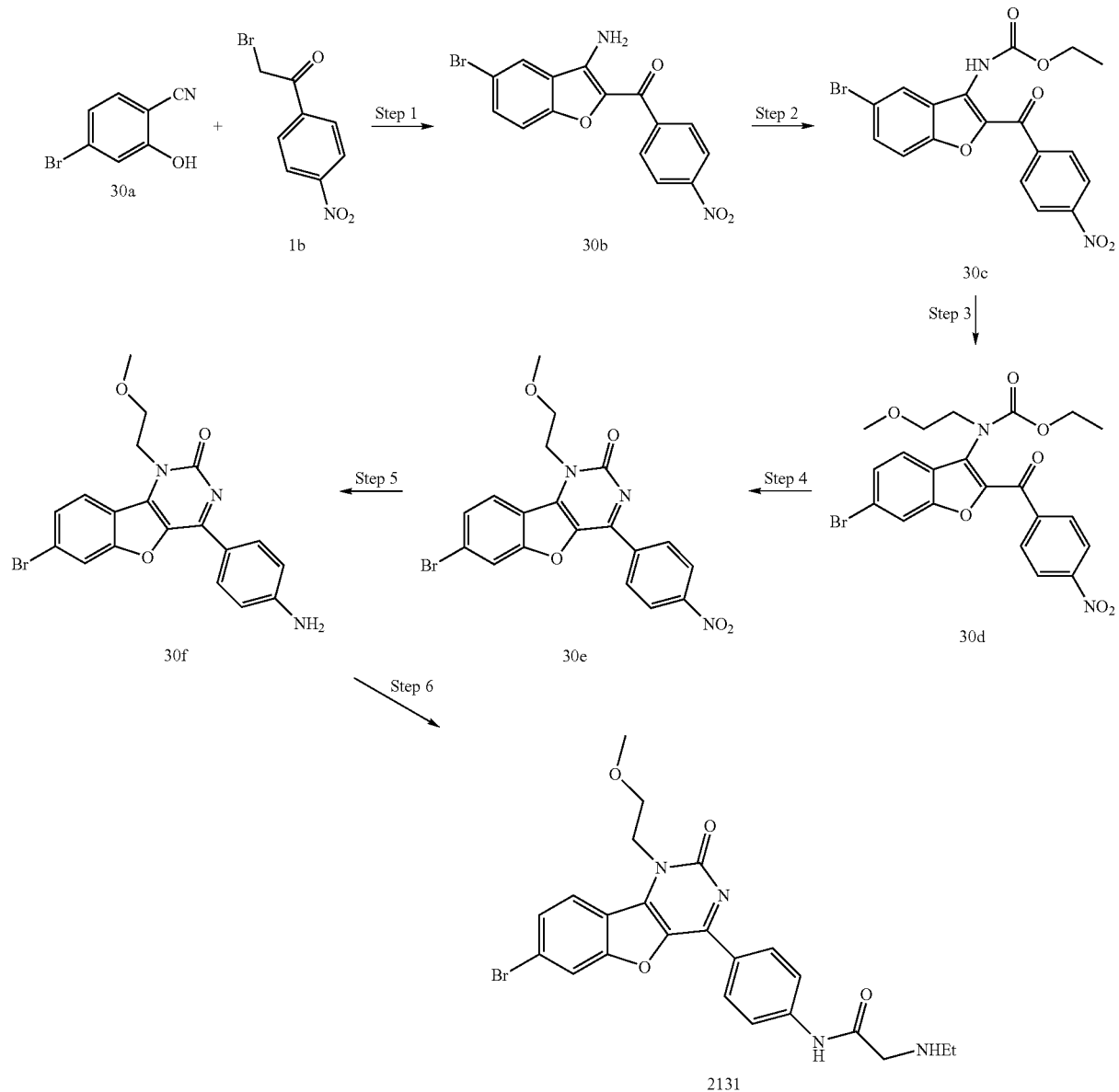

Step 1:

A mixture of 4-bromo-2-hydroxybenzonitrile 30a (5.0 g, 25.25 mmol), 2-bromo-4'-nitroacetophenone 1b (Example 1) (6.2 g, 25.50 mmol), and Na$_2$CO$_3$ (2.7 g, 25.50 mmol) in acetone (190 mL) is heated at reflux for 24 h. The mixture is filtered and the filtered solid is suspended in MeOH (150 mL). 1N NaOH (3 mL) is added and the mixture is heated at 90° C. for 1 h. The resulting precipitate is filtered and air-dried to provide compound 30b (8.3 g, 91%).

Step 2:

To a mixture of compound 30b (8.3 g, 22.9 mmol) and K$_2$CO$_3$ (30 g, 217.3 mmol) in toluene (215 mL) is added ethyl chloroformate (30 mL, 313.6 mmol). The mixture is heated at reflux for 40 h then filtered to provide a solid and a filtrate, which is put aside. The solid is partitioned between DCM and water (1:1, 300 mL) and the aqueous layer is further extracted with DCM (150 mL). The combined organic extracts are washed with brine (150 mL) and combined with the previous filtrate. The combined mixture is then dried (Na$_2$SO$_4$), filtered and concentrated under reduced pressure. The resulting solid is triturated with hexanes and filtered to provide compound 30c (7.9 g, 80%).

Step 3:

To a stirred suspension of NaH (60% dispersion in mineral oil, 852 mg, 21.29 mmol) in DMF (60 mL) at RT under N$_2$ is added a solution of the carbamate 30c (3.7 g, 8.52 mmol) in DMF (10 mL) dropwise. The mixture is stirred at RT for 1 h. To this solution is added 2-bromoethyl methyl ether (8.0 mL, 85.18 mmol). The solution is stirred at RT for 30 min and then heated at 90° C. for 1.5 h. The solution is cooled, diluted with EtOAc (300 mL), washed with water (200 mL) and brine (200 mL), dried (Na$_2$SO$_4$), filtered and concentrated under reduced pressure. The resulting oil is purified by chromatography (15%-25% EtOAc/Hex) to give compound 30d (3.0 g, 72%).

Step 4:

A mixture of the compound 30d (6.1 g, 12.33 mmol) and ammonium acetate (130 g, 1.69 mol) is heated at 135° C. with stirring for 2.5 h. The mixture is cooled, diluted with water (300 mL) and adjusted to pH 8 by addition of 10N NaOH. The precipitate is filtered and rinsed with Et$_2$O to yield compound 30e (4.9 g, 90%).

Step 5:

To a mixture of the nitro compound 30e (1.0 g, 2.25 mmol) and EtOH (10 mL) is added iron (503 mg, 9.00 mmol) followed by 1N aqueous HCl (2.5 mL) and water (1.0 mL). The reaction mixture is heated at 90° C. for 3 h then cooled to RT, the magnetic stirrer is removed from the solution and the iron is rinsed with acetonitrile. The suspension is concentrated under reduced pressure. The residue is coevaporated with toluene (2×20 mL) and dried under vacuum to afford compound 30f (1.0 g, 99%).

Step 6:

To a suspension of the aniline 30f (1.5 g, 3.33 mmol) in DCM (75 mL) is added bromoacetyl bromide (0.3 mL, 3.39 mmol). The reaction mixture is stirred at RT for 30 min, concentrated under reduced pressure and the resulting residue is suspended in DMF (50 mL). Ethylamine (2M in THF) (8.3 mL, 16.64 mmol) is added dropwise and the mixture is stirred for 20 h. The suspension is filtered through Celite™ and the filter cake is washed with DMF. The filtrate is concentrated under reduced pressure, and the residue is diluted with DCM (300 mL) and water (200 mL), and the mixture is filtered. The filtrate is extracted with DCM (2×200 mL) and the organic layers are combined, washed with brine, dried (Na$_2$SO$_4$), filtered and concentrated under reduced pressure. The residue is combined with the solid that is previously filtered, triturated with Et$_2$O and filtered to afford compound 2131 (1.5 g, 90%).

Example 31

Preparation of Compound 2132 (Table 2)

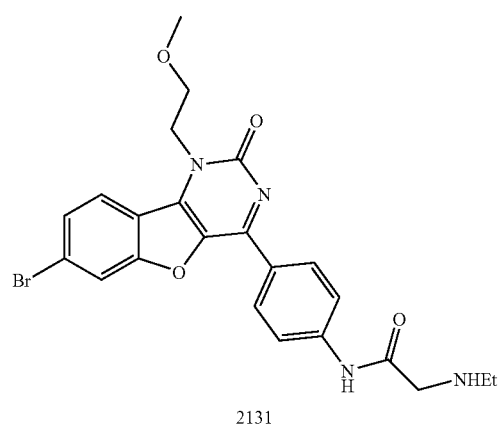

2131

-continued

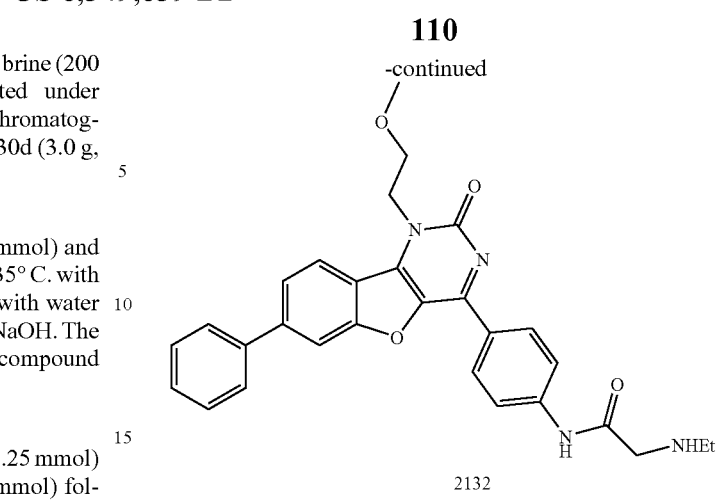

2132

A mixture of compound 2131 (Example 30) (50 mg, 0.10 mmol), phenylboronic acid (15 mg, 0.12 mmol), Pd(dppf)Cl$_2$ DCM complex (7.3 mg, 0.01 mmol) and K$_2$CO$_3$ (42 mg, 0.30 mmol) in 1,4-dioxane (2 mL) and water (1 mL) is heated in a sealed tube at 80° C. for 2 h. The solution is diluted with EtOAc (10 mL) and water (10 mL). The layers are separated and the aqueous layer is further extracted with EtOAc (2×10 mL). The combined organic layers are washed with brine (30 mL), dried (Na$_2$SO$_4$), filtered and concentrated under reduced pressure. Purification by prep HPLC affords compound 2132 (10 mg, 20%).

Example 32

Preparation of Compound 2085 (Table 2)

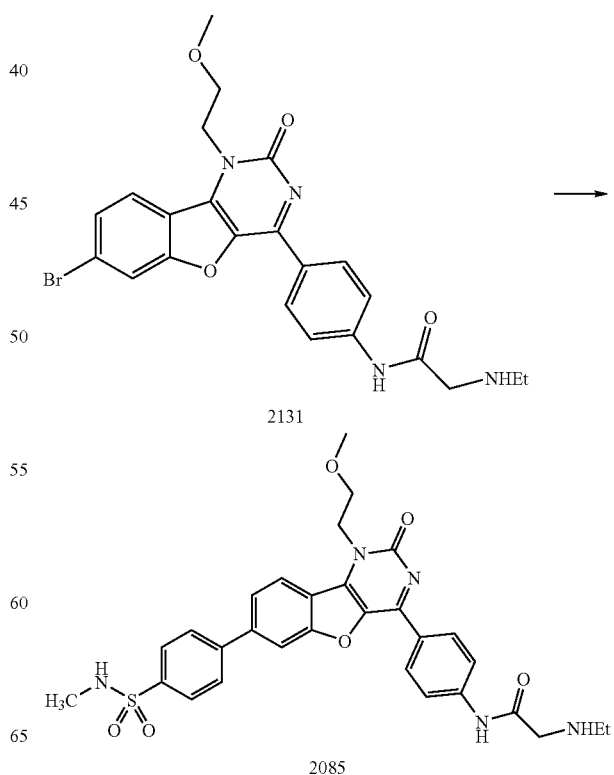

A mixture of compound 2131 (Example 30) (35 mg, 0.07 mmol), 4-(methylaminosulphonyl)benzeneboronic acid (30 mg, 0.14 mmol), Pd(dppf)Cl$_2$ DCM complex (5.1 mg, 0.01 mmol) and K$_2$CO$_3$ (29 mg, 0.21 mmol) in 1,4-dioxane (1 mL) and water (0.5 mL) is degassed with N$_2$ for 5 min and heated in a microwave at 120° C. for 15 min. The resulting solution is concentrated under reduced pressure and the residue is dissolved in an AcOH/DMSO (1:1) solution. Purification by prep HPLC affords compound 2085 (8 mg, 19%).

Example 33

Preparation of Compounds 2137, 2060 and 2069 (Table 2)

aqueous layer is further extracted with EtOAc (2×10 mL). The combined organic layers are washed with brine (30 mL), dried (Na$_2$SO$_4$), filtered and concentrated under reduced pressure to afford compound 2137 (95 mg, 99%).

Step 2:

To a mixture of compound 2137 (90 mg, 0.19 mmol) in THF (3 mL) and MeOH (1 mL) is added 1N aqueous LiOH solution (0.4 mL, 0.38 mmol). The mixture is stirred at RT for 2 h, concentrated under reduced pressure and coevaporated with toluene (2×5 mL) to afford compound 2060 (85 mg, 97%).

Step 3:

To a mixture of compound 2060 (20 mg, 0.04 mmol) and 3-methoxybenzylamine (22 μL, 0.17 mmol) in DMF (2 mL)

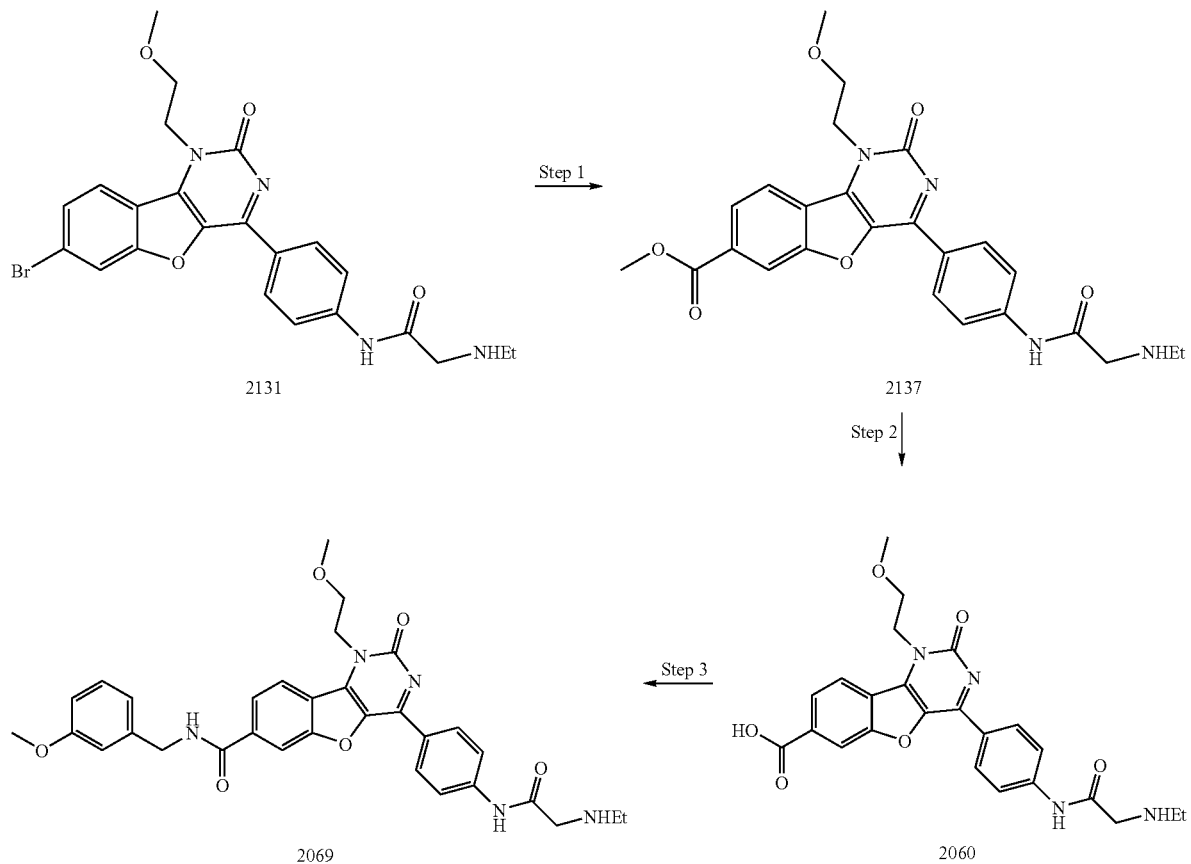

Step 1:

To a mixture of compound 2131 (Example 30) (100 mg, 0.20 mmol) in DMSO (4 mL) and MeOH (2 mL) is added Et$_3$N (0.1 mL, 1 mmol) followed by Pd(OAc)$_2$ (14 mg, 0.02 mmol) and dppf (11 mg, 0.02 mmol). The resulting mixture is purged with CO(g) and heated at 85° C. under 1 atm. of CO(g) for 3 h. The solution is cooled to RT, diluted with EtOAc (10 mL) and water (10 mL). The layers are separated and the is added Et$_3$N (124, 0.09 mmol) followed by TBTU (21 mg, 0.06 mmol). The mixture is stirred at RT for 3 h. AcOH (100 μL) is added and the mixture is purified by prep HPLC to afford compound 2069 (7 mg, 28%).

Example 34

Preparation of Compound 2154 (Table 2)

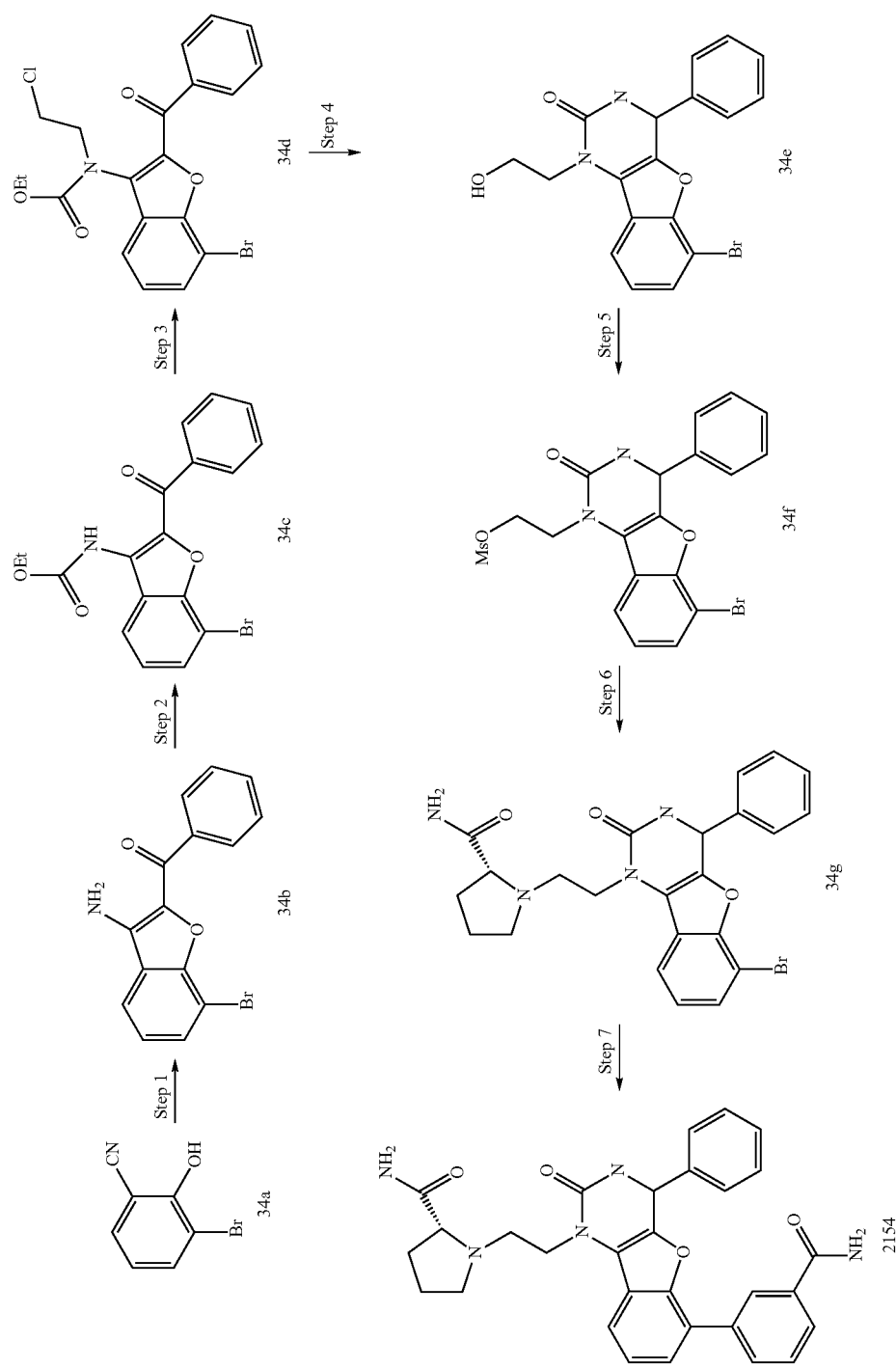

Step 1:
To a mixture of compound 34a (10 g, 50.5 mmol) and bromoacetophenone (compound 10b, Example 10) (10.02 g, 50.34 mmol) in acetone (240 mL) is added Na$_2$CO$_3$ (5.88 g, 55.4 mmol). The mixture is stirred at 75° C. for 16 h. The mixture is concentrated, the residue is taken up in MeOH (240 mL) and NaOH (10 N, ~1 mL) is added. The mixture is reheated to 65° C. and stirred for an additional 15 min. The solid is filtered, washed with 1:1 ether/Hex and dried under vacuum to afford compound 34b (13.4 g). The filtrate is further concentrated and the solid is filtered and washed with a solution of 1:1 ether/Hex to afford additional compound 34b (4.89 g, total yield>99%).
Step 2:
To a mixture of amino benzofuran 34b (9 g, 28 mmol) and K$_2$CO$_3$ (37 g, 269 mmol) in anhydrous toluene (225 mL) is added ethyl chloroformate (22.5 mL, 235 mmol). The stirred mixture is heated at reflux for 16 h., then concentrated and the residue is taken up in EtOAc (500 mL), washed with H$_2$O (3×) and brine (1×), dried (Na$_2$SO$_4$), filtered and concentrated to afford compound 34c (8.44 g, 76%).
Step 3:
To a mixture of carbamate 34c (702 mg, 1.80 mmol) in anhydrous DMF (3.5 mL) is added NaH (60% dispersion, 87 mg, 2.17 mmol) at RT portionwise and the mixture is stirred for 45 min at RT. 2-chloroethyl p-toluenesulphonate (0.46 mL, 2.53 mmol) is added, stirring is continued at RT for 30 min, then the mixture is heated to 90 C and stirred for 3 h. The solution is cooled to RT, diluted with EtOAc (100 mL), washed with H$_2$O(1×) and brine (3×), dried (Na$_2$SO$_4$), filtered and concentrated. The residue is purified by chromatography to afford compound 34d (680 mg, 83%).
Step 4:
A mixture of chlorocarbamate 34d (5.9 g, 13.0 mmol) and NH$_4$OAc (61 g) is heated at 140 C in an open flask for 2 h then H$_2$O (43 mL) and 10 N NaOH (pH adjusted to >8) are added. The mixture is stirred at RT for 15 min, taken up in MeOH (80 mL) and treated with 10 N NaOH (~4.5 mL). The mixture is heated at reflux for an additional 15 min, the mixture is concentrated and the residue is dried under high vacuum. The crude product is co-evaporated with toluene (3×), triturated with ether and filtered to afford the product 34e (5.18 g, >99%).
Step 5:
To a mixture of alcohol 34e (2.5 g, 6.49 mmol) in DCM (68 mL) is added Et$_3$N (2.3 mL, 16.4 mmol) followed by the dropwise addition of methanesulphonyl chloride (0.64 mL, 8.3 mmol) at RT. The mixture is stirred for 1 h at RT. DCM (250 mL) is added, and the mixture is washed with brine (1×), dried (Na$_2$SO$_4$), filtered and concentrated to afford the product 34f (2.88 g).
Step 6:
To a mixture of product 34f (2.88 g) in anhydrous DMF (43 mL) is added (D)-Pro-NH$_2$ (2.09 g, 18 mmol) followed by Et$_3$N (4.2 mL, 30.4 mmol) and NaI (28 mg). The mixture is heated to 70 C and allowed to stir overnight. The mixture is cooled, and the precipitate is filtered and washed with water (1×) followed by ether to afford compound 34g (1.09 g).
Step 7:
To a mixture of compound 34g (40 mg, 0.08 mmol), (3-aminocarbonylphenyl)boronic acid (27 mg, 0.16 mmol), Pd(dppf)Cl$_2$(6 mg, 0.008 mmol) and K$_2$CO$_3$ (34 mg, 0.24 mmol) in a microwave vessel (2-5 mL) is added a degassed mixture of 4:1 dioxane/H$_2$O (2 mL; 10 min). The mixture is heated in a microwave at 120° C. for 15 min. The solution is concentrated and the residue (96.6 mg) is dissolved in AcOH/DMSO and purified by preparative chromatography to afford compound 2154 (21.7 mg, 50%).

Example 35

Preparation of Compound 2155 (Table 2)

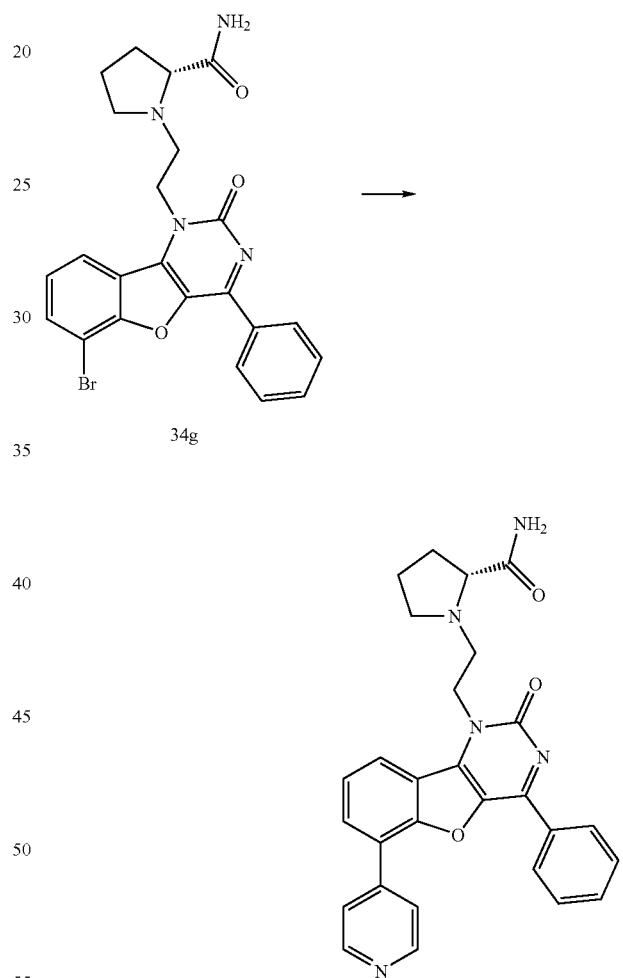

To a mixture of compound 34g (Example 34) (40 mg, 0.08 mmol), pyridine-4-boronic acid (20 mg, 0.16 mmol), Pd(dppf)Cl$_2$(6 mg, 0.008 mmol) and K$_2$CO$_3$(34 mg, 0.24 mmol) in a microwave vessel (2-5 mL) is added a degassed solution of 4:1 dioxane/H$_2$O (2 mL, 10 min) and the mixture is heated in a microwave at 120° C. for 15 min. The mixture is concentrated, and the residue (81 mg) is dissolved in AcOH/DMSO and purified by preparative chromatography to afford compound 2155 (17 mg, 42%).

Example 36

Preparation of Compound 2172 (Table 2)

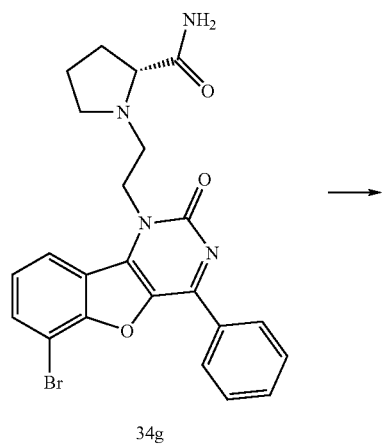

34g

→

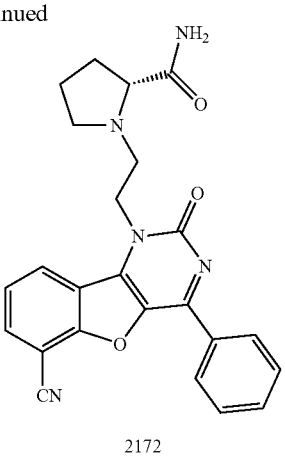

2172

A mixture of compound 34g (Example 34) (40 mg, 0.08 mmol), Zn(CN)$_2$ (40 mg, 0.34 mmol) and Pd(PPh$_3$)$_4$ (48 mg, 0.04 mmol) in DMA (3 mL) in a 2-5 mL microwave vessel is degassed under Ar for 10 min and heated in a microwave apparatus at 125° C. for 45 min. The precipitate (52 mg) is filtered, dissolved in a 3:1 solution of AcOH/DMSO (2 mL) and purified by preparative chromatography to afford compound 2172 (14.9 mg, 42%).

Example 37

Preparation of Compounds 4003 and 4001 (Table 4)

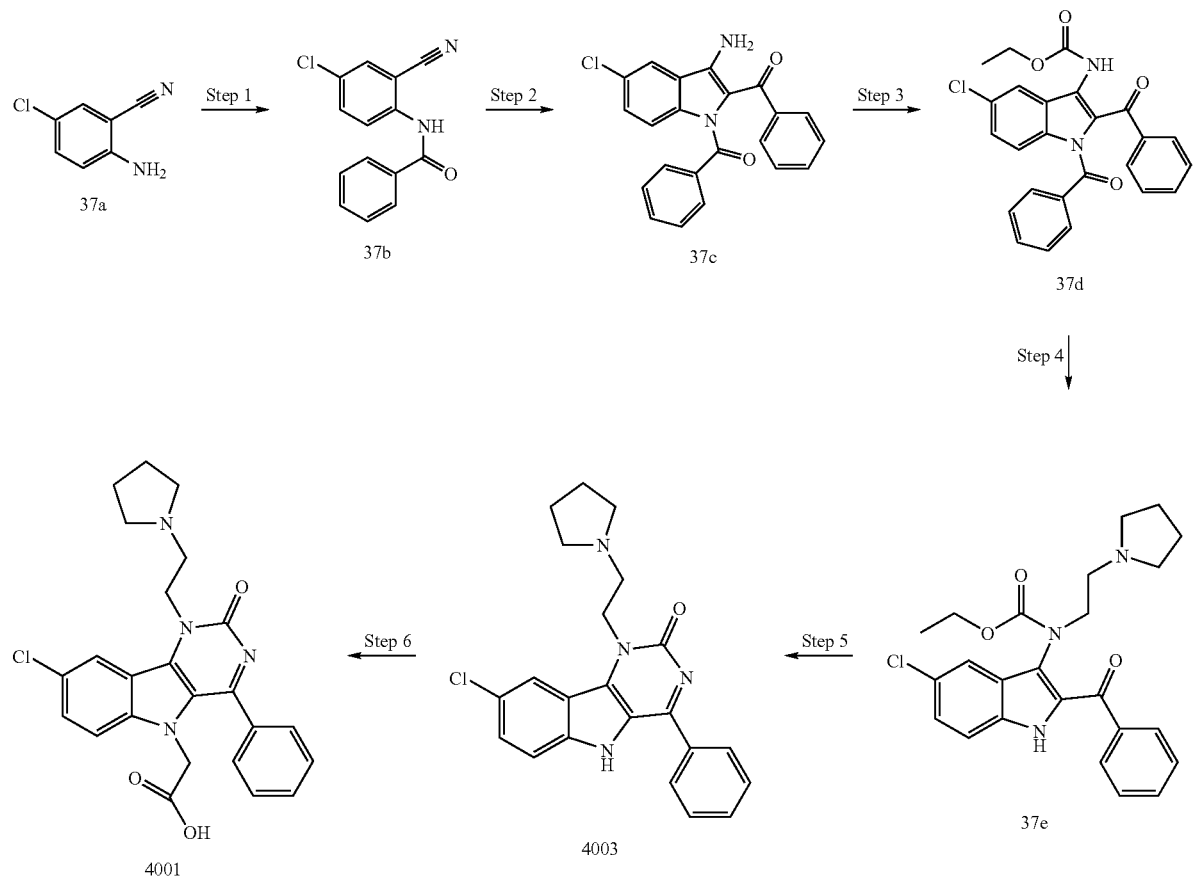

Step 1:

To a stirred mixture of 5-chloro-2-aminobenzonitrile 37a (10.4 g, 1 eq) in DCM (120 mL) are added pyridine (8.8 g, 1.5 eq) and benzoyl chloride (10.4 g, 1.1 eq). The reaction mixture is stirred at RT for 3 h, then diluted with DCM (300 mL) and washed with $H_2O$ (400 mL) and brine (400 mL). The organic extract is dried ($Na_2SO_4$), filtered, and concentrated under reduced pressure. The residue is triturated with pentane to afford compound 37b (16.5 g, 94%).

Step 2:

To a stirred mixture of the benzamide 37b (11.5 g, 1 eq) in DMF (100 mL) is added 2-bromoacetophenone (compound 9b, Example 9) (13.4 g, 1.5 eq) followed by cesium carbonate (24.3 g, 1.7 eq), and the reaction mixture is stirred at RT for 12 h. The mixture is diluted with EtOAc (400 mL), washed with brine, dried over $Na_2SO_4$ filtered and concentrated under reduced pressure. The residue is purified by flash chromatography (10% EtOAc/Hex) to afford compound 37c (13 g, 77%).

Step 3:

To a stirred solution of aminoindole 37c (5 g, 1 eq) in toluene (50 mL) is added $K_2CO_3$ (11 g, 6 eq) followed by ethyl chloroformate (8.7 mL, 6 eq) and the reaction mixture is refluxed for about 5 h. The reaction mixture is filtered through Celite™, the Celite bed is washed with DCM, and the filtrate is concentrated under reduced pressure. The residue is purified by flash chromatography (10% EtOAc/Hex) to afford compound 37d (4.5 g, 71%)

Step 4:

To a stirred solution of the carbamate 37d (4.0 g, 1 eq) in DMSO (30 mL) are added N-(2-chloro ethyl)pyrrolidine HCl (2.3 g, 1.5 eq), followed by $Cs_2CO_3$ (8.7 g, 3 eq), and the reaction mixture is heated to 60° C. for about 5 h. The reaction mixture is diluted with EtOAc (200 mL) and washed with water and brine. The organic layer is separated, dried over anhydrous sodium sulphate, filtered and concentrated under reduced pressure. The residue is purified by flash chromatography (10% MeOH/DCM) to afford compound 37e (2.8 g, 71%).

Step 5:

A mixture of the ketone 37e (1.8 g, 1 eq) and ammonium acetate (25.4 g, excess) is heated to 140° C. for about 30 min. The reaction mixture is adjusted to basic pH with sat.

$Na_2CO_3$ and the solid is filtered, washed with water and dried. The solid is dissolved in 20% MeOH/DCM, washed with brine, dried over anhydrous sodium sulphate, filtered and concentrated under reduced pressure. The residue is washed with ether and ethanol to afford compound 4003 (0.8 g, 44%).

Step 6:

To a stirred solution of compound 4003 (262 mg, 1 eq) in DMSO (6 mL) are added ethyl bromoacetate (82 μL, 1.1 eq), followed by NaH (29 mg, 1.1 eq), and the reaction mixture is stirred at RT for about 18 h. The reaction mixture is diluted with DCM and washed with water (2×) and brine. The organic layer is separated, dried over $MgSO_4$, filtered and concentrated under reduced pressure. The residue is purified by flash chromatography (5% MeOH/DCM) (21 mg, 7%). A solution of the purified residue (20 mg, 1 eq) and 1M NaOH (125 μL, 3 eq) in DMSO (0.5 mL) is stirred at RT for 30 min, then acidified by addition of AcOH. The mixture is purified by prep HPLC (10-25% $CH_3CN$/water) to afford compound 4001 (9 mg, 45%) as the TFA salt.

Example 38

Preparation of Compound 2280 (Table 2)

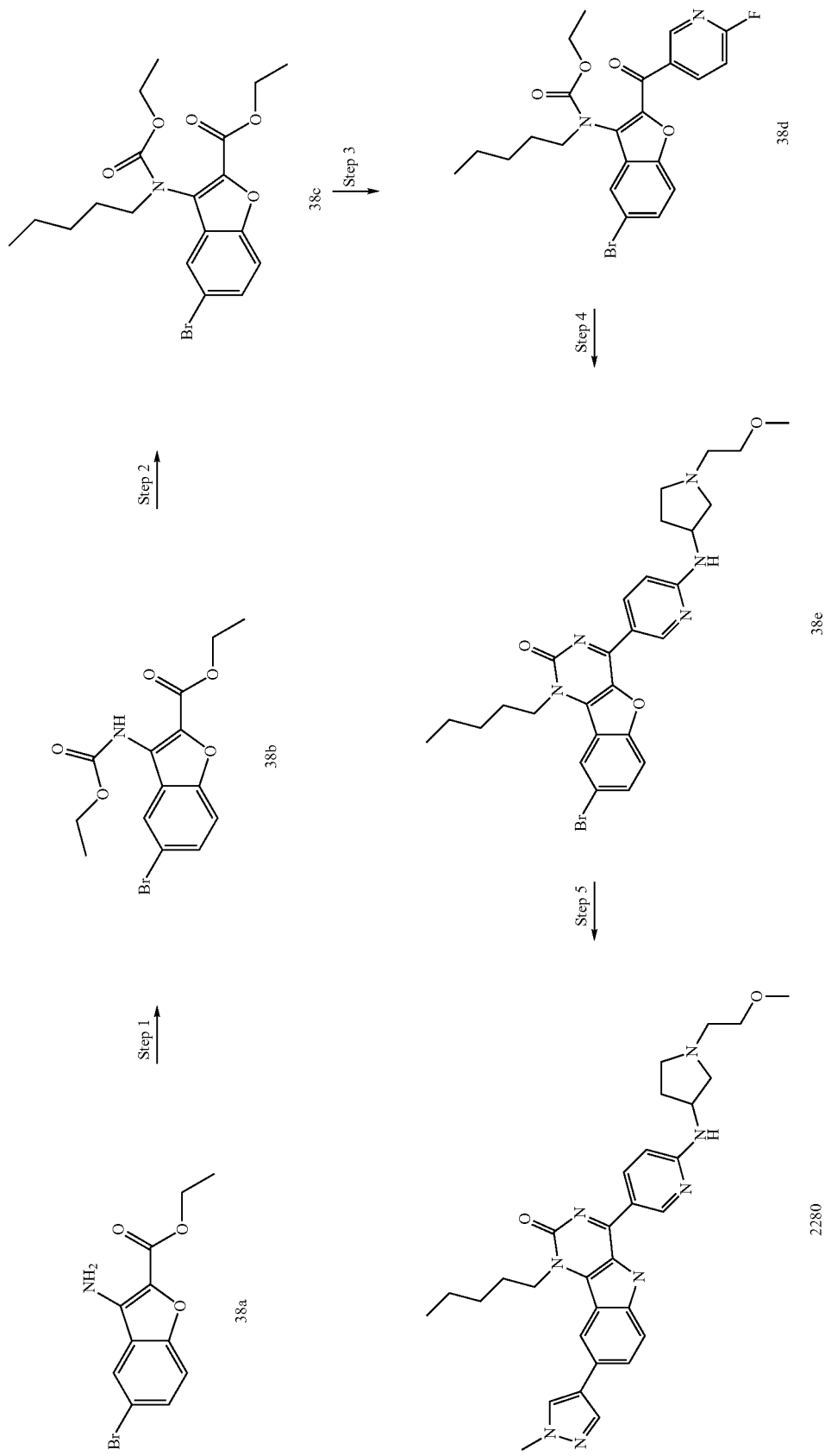

Step 1:

A mixture of the benzofuran 38a (prepared using the method of Example 1, step 1 but replacing compound 1a with 4-bromo-2-cyanophenol, and replacing compound 1b with ethyl 2-bromoacetate (6.0 g, 1 eq) in toluene/acetonitrile (75 mL/45 mL) and ethyl chloroformate (10 mL, 5 eq) is heated at reflux overnight, then concentrated under reduced pressure to give compound 38b (7.4 g, 100%).

Step 2:

To a stirred mixture of the carbamate 38b (4.0 g, 1 eq) in DMSO (15 mL) is added cesium carbonate (8.3 g, 2.2 eq). The mixture is stirred for 5 min and 1-bromopentane is then added (1.9 mL, 1.4 eq). The reaction mixture is stirred at RT for 24 h. The mixture is diluted with EtOAc (300 mL) and water (300 mL). The two layers are sepapared and the aqueous layer is extracted with EtOAc (2×300 mL). The combined organic layers are washed with brine, dried over $Na_2SO_4$ filtered and concentrated under reduced pressure. The residue is purified by flash chromatography (0-30% EtOAc/Hex) to afford compound 38c (4.7 g, 98%).

Step 3:

To a stirred solution of the carbamate 38c (4 g, 1 eq) and 5-bromo-2-fluoropyridine (1.2 mL, 1.2 eq) in THF (50 mL) at −78° C. is added n-BuLi (2.4 M solution in pentane, 4.3 mL, 1.1 eq) dropwise over a 1 h period. The reaction mixture is stirred at −78° C. for one more hour. The reaction is stopped by the dropwise addition of AcOH (1 mL) and silica gel. The mixture is concentrated under reduced pressure. The residue is purified by flash chromatography (0-25% EtOAc/Hex) to afford compound 38d (2.2 g, 49%).

Step 4:

3-(t-Butoxycarbonylamino)pyrrolidine (1 g, 1 eq) is dissolved in DMF (15 mL) and NaH 60% in oil (258 mg, 1.2 eq) is added followed by 2-bromoethyl methyl ether (656 μL, 1.3 eq). Water (150 mL) and EtOAc (150 mL) are added and the two layers are separated. The aqueous layer is extracted with EtOAc (2×150 mL). The combined organic layers are washed with brine, dried over $MgSO_4$ filtered and concentrated under reduced pressure. The residue is purified by flash chromatography (100% EtOAc). The isolated compound (300 mg, 23%) is dissolved in dioxane (2 mL) and HCl 4 M solution in dioxane (5 mL, 20 eq) is added. The solution is stirred for 1 h and the reaction mixture is then concentrated and co-evaporated with toluene to afford 1-(2-methoxy-ethyl)-pyrrolidin-3-ylamine 2HCl (266 mg, 100%).

To a stirred solution of the carbamate 38d (150 mg, 1 eq) in DMSO (1.5 mL) are added the prepared 1-(2-methoxy-ethyl)-pyrrolidin-3-ylamine 2HCl (137 mg, 2.0 eq), followed by $Et_3N$ (263 μL, 6 eq), and the reaction mixture is heated to 50° C. for 20 h. The reaction mixture is diluted with DCM (75 mL) and water (75 mL). The two layers are separated and the aqueous layer is extracted with DCM (3×75 mL). The combined organic layers are washed with brine, dried over $Na_2SO_4$, filtered and concentrated under reduced pressure. The residue is purified by flash chromatography (0-10% MeOH/DCM). The intermediate product is treated with $NH_4OAc$ (1.0 g, excess) and the mixture is heated at 150° C. for 30 min. The reaction mixture is cooled and NaOH 10 M solution in water (1 mL) is added. Water (30 mL) and DCM (30 mL) are added to the resulting suspension and the two layers are separated. The organic layer is washed with water and brine (2×30 mL). The organic layer is washed with brine, dried over $Na_2SO_4$, filtered and concentrated under reduced pressure to afford 38e (53 mg, 30%).

Step 5:

A mixture of the bromide 38e (53 mg, 1 eq), 1-methyl-4-(4,4,5,5-tetramethyl-1,3,2-dioxaborolan-2-yl)-1H pyrazole (40 mg, 2 eq), Pd(dppf)Cl$_2$ DCM complex (7.8 mg, 0.1 eq), $K_2CO_3$ (40 mg, 3 eq) and CsF (43 mg, 3 eq) in 1,4-dioxane (1.5 mL) and water (0.5 mL) is degassed with Ar for 5 min. The mixture is heated in a microwave at 135° C. for 25 min. The reaction mixture is treated with AcOH (0.5 mL). Purification by prep HPLC affords compound 2280 (19 mg, 36%).

Example 39

Preparation of Compound 2288 (Table 2)

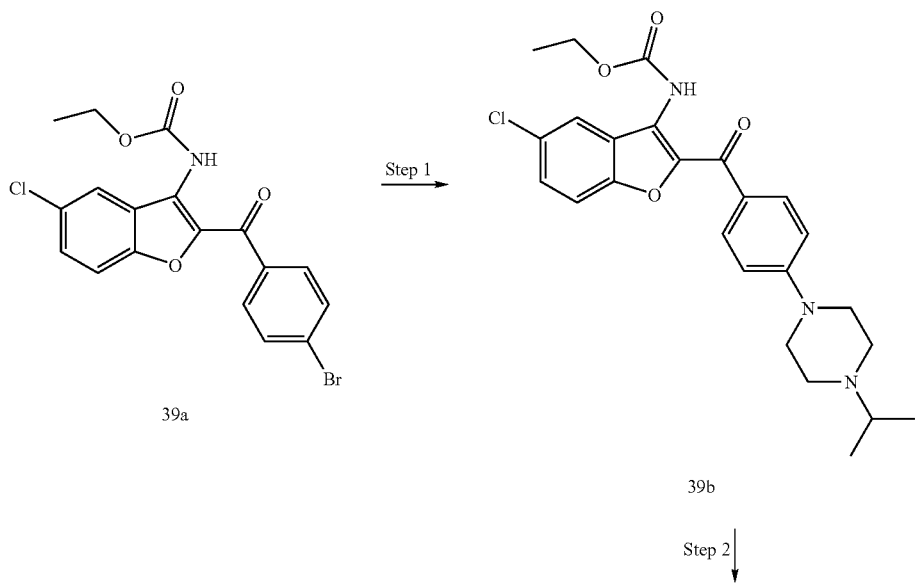

39a

Step 1 →

39b

Step 2 ↓

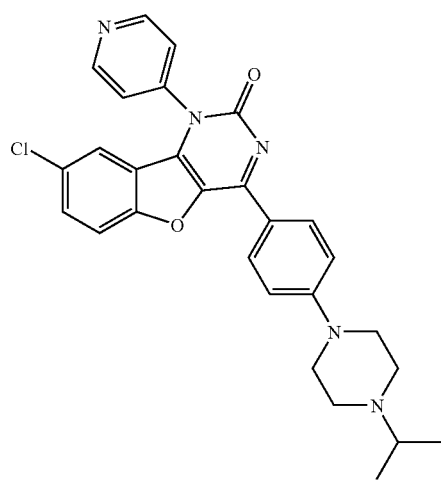

2288

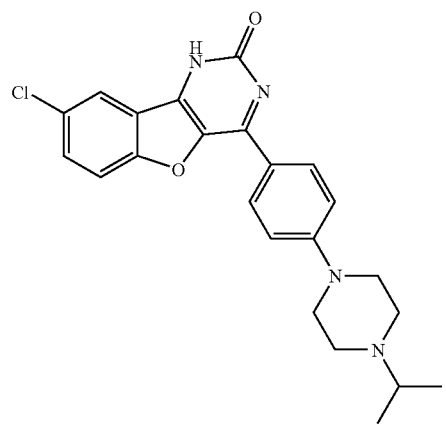

39c

Compound 39a is prepared using the method of example 9, steps 1 and 2 but replacing 5-bromo-2-hydroxybenzonitrile with 5-chloro-2-hydroxybenzonitrile and 2-bromoacetophenone with 2,4'-dibromoacetophenone.

Step 1:

A mixture of compound 39a (250.0 mg, 0.591 mmol), N-isopropylpiperazine (113.8 mg, 0.887 mmol) and K₂CO₃ (251.1, 1.18 mmo) in DME (4.8 mL) is degassed with N₂ for 15 min. After this time, bis(tri-t-butylphosphine)palladium (0) (30.2 mg, 0.059 mmol) is added and the reaction mixture is stirred at 100° C. for 6 h. After this time, the reaction mixture is evaporated under reduced pressure, triturated with Et₂O to give compound 39b (275 mg, 99%).

Step 2:

Compound 39c is prepared from compound 39b using the method of example 27 step 1.

Step 3:

Compound 2288 is prepared according to the method of Example 27 step 2 but replacing phenylboronic acid in with 4-pyridineboronic acid.

Example 40

Preparation of Compound 2297 (Table 2)

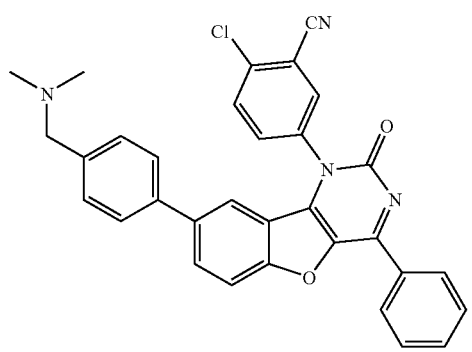

2297

Compound 2297 is prepared according to the method of Example 27 but replacing phenylboronic acid in step 2 with 4-chloro-3-cyanophenylboronic acid.

Example 41

Preparation of Compound 2300 (Table 2)

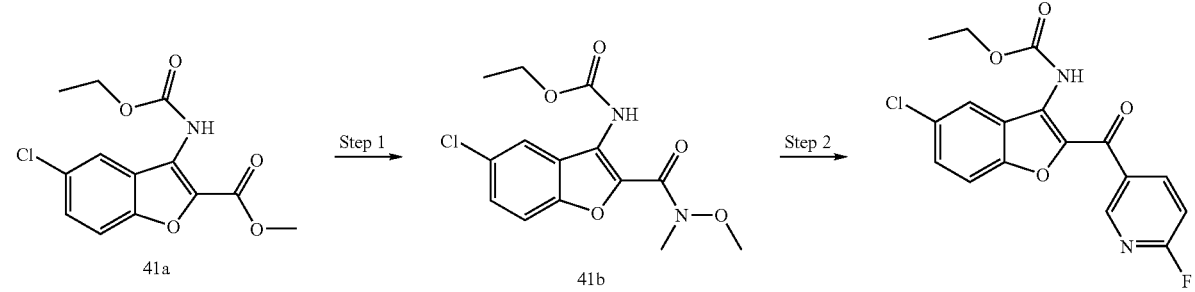

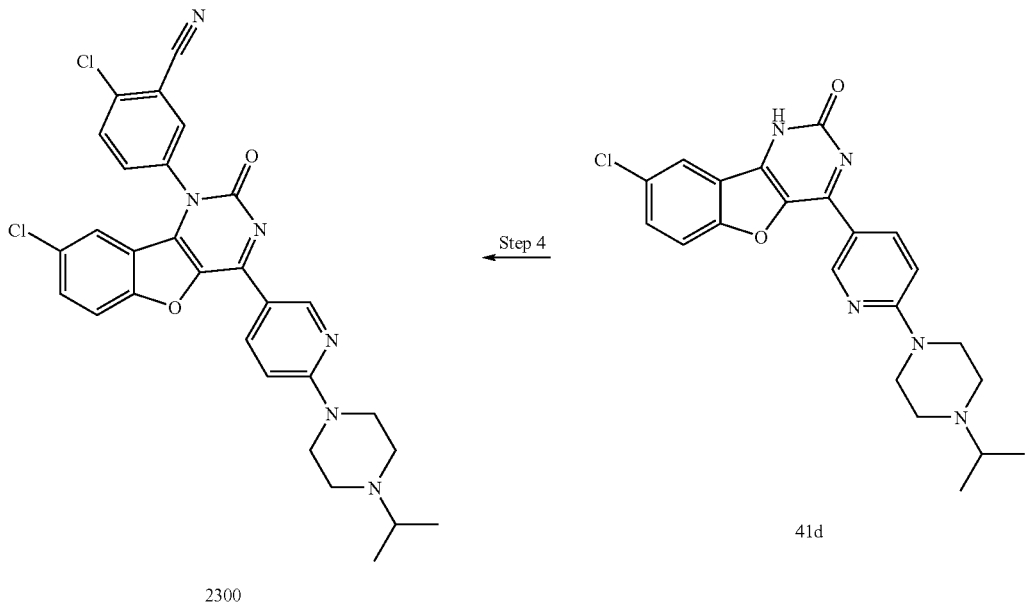

2300

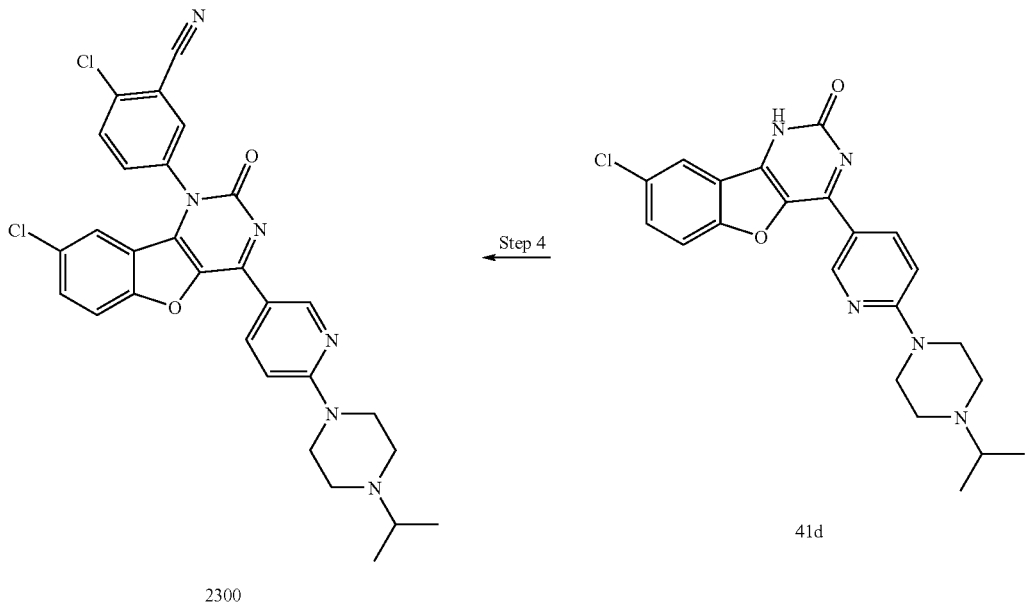

Step 4

41d

Step 1:

A mixture of 41a (5.0 g, 16.04 mmol) in THF (25 mL) is treated with LiOH—H₂O (875 mg, 20.8 mmol) dissolved in H₂O (25 mL). The mixture is allowed to stir at RT overnight, and is then acidified (pH ca. 2-3) with 1M HCl. The reaction mixture is poured into a H₂O (50 mL)/EtOAc (50 mL) mixture and the layers are separated. The aq phase is extracted once more with EtOAc (50 mL) and the combined organic layers are washed (H₂O, brine), dried (MgSO₄) and concentrated in vacuo. The acid (3.57, 12.6 mmol) thus obtained and N,O-dimethylhydroxylamine hydrochloride (1.6 g, 16.4 mmol) are mixed in DMF (37 mL). This solution is then treated with (i-Pr)₂NEt (11.0 mL, 62.9 mmol) followed by HATU (6.2 g, 16.4 mmol) and the solution is then allowed to stir at RT for 3 h. After this time, the reaction mixture is poured into H₂O/EtOAc (50 mL: 50 mL) mixture and the layers are separated. The aq phase is extracted once more with EtOAc (50 mL) and the combined organic layers are washed (H₂O, brine), dried (MgSO₄) and concentrated in vacuo to obtain compound 41b (3.0 g, 73%).

Step 2:

Compound 41c is prepared from compound 41b using the method of example 22 step 3.

Step 3:

A mixture of 41c (2.2 g, 6.1 mmol), N-methylpiperazine (0.81 mL, 7.3 mmol), and Et₃N (2.5 mL, 17.6 mmol) in DMSO (50.0 mL) is heated at 100° C. for 1 h. After this time, NH₄OAc (50.0 g) is added to the reaction mixture and is heated at 130° C. for 40 min. The reaction mixture is then quenched with water and the precipitate thus obtained is filtered. The filtrate is then washed with water (50 mL), extracted by Et₂O (50 mL) to obtain compound 41d (950 mg, 40%).

Step 4:

Compound 2300 is prepared according to the method of Example 27, but replacing phenylboronic acid with 4-chloro-3-cyanophenylboronic acid in step 2 and replacing 4-(N,N-dimethylaminomethyl)phenylboronic acid with N-methyltetrahydroisoquinoline-5-boronic acid pinacol ester in step 3.

Example 42

Preparation of Compound 2307 (Table 2)

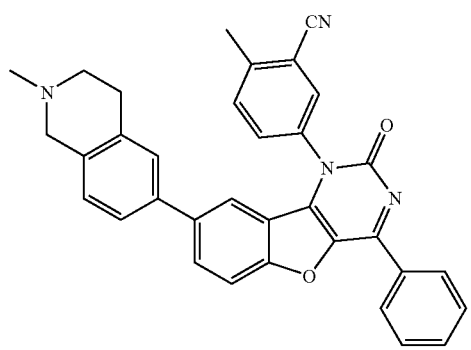

2307

Compound 2307 is prepared according to the method of Example 27 but replacing phenylboronic acid in step 2 with 4-methyl-3-cyanophenylboronic acid and replacing 4-(N,N-dimethylaminomethyl)phenylboronic acid in step 3 with 4-N-methyltetrahydroisoquinolineboronic acid pinacol ester.

Example 43
Preparation of Compound 2321 (Table 2)
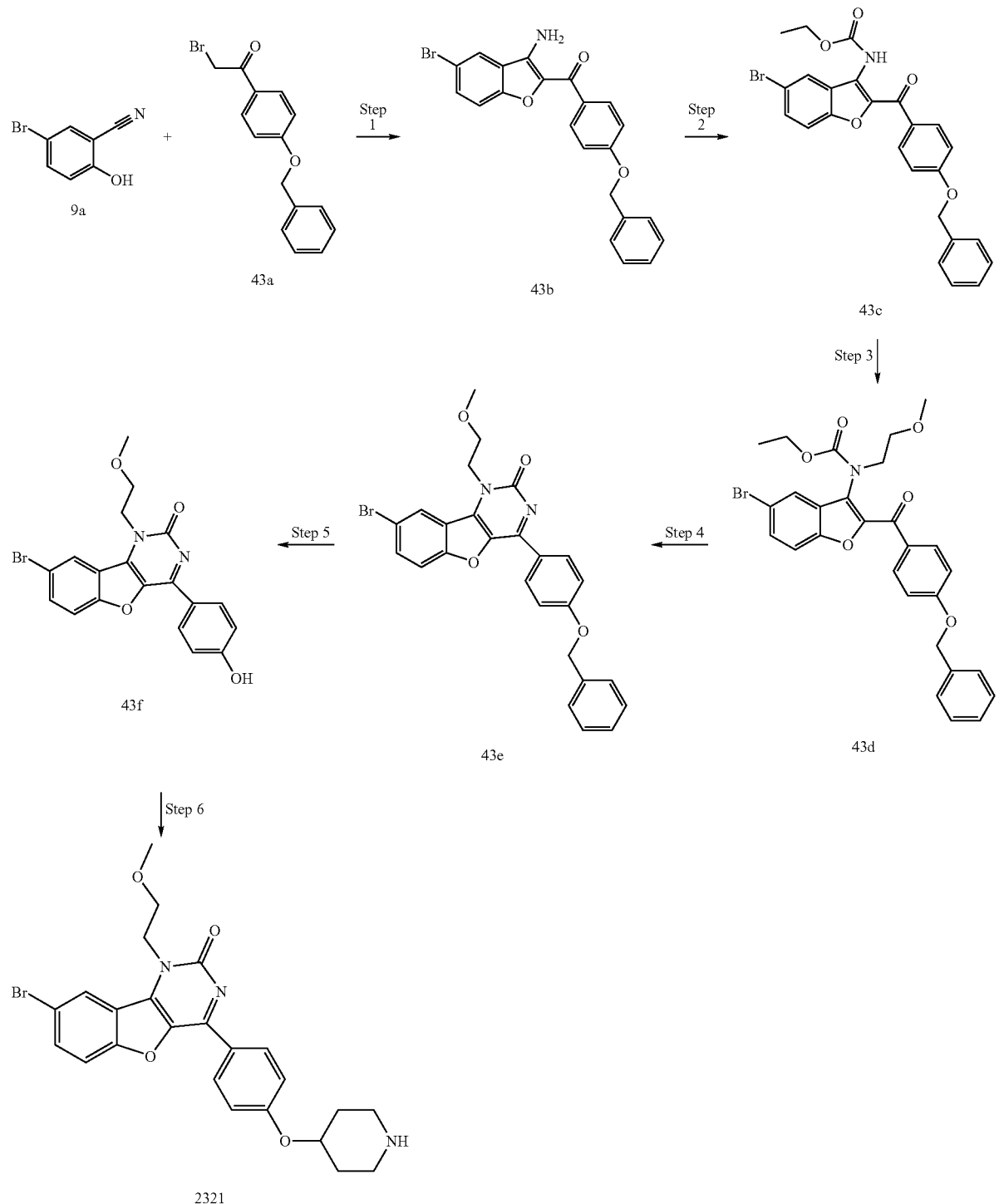
Step 1:
A mixture of 5-bromo-2-hydroxybenzonitrile 9a (Example 9) (0.83 g, 4.19 mmol), 2-bromo-4'-benzyloxyacetophenone 43a (1.2 g, 4.19 mmol), and Na₂CO₃ (0.45 g, 4.19 mmol) in acetone (30 mL) is heated at reflux for 18 h. The solvent is removed and dissolved in methanol (30 mL). One drop of NaOH 10N is added and heated to reflux for 1 h. The mixture is filtered to provide compound 43b (1.64 g, 93%).

Step 2:

To a mixture of compound 43b (1.64 g, 3.84 mmol) and K$_2$CO$_3$ (5.1 g, 36.9 mmol) in toluene (37 mL) is added ethyl chloroformate (3.16 mL, 33.0 mmol). The reaction mixture is heated at reflux for 20 h. The residue is diluted with EtOAc (100 mL) and water (50 mL). The layers are separated and the aqueous layer is further extracted with EtOAc (2×100 mL). The combined organic layers are washed with brine, dried (Na$_2$SO$_4$), filtered and concentrated under reduced pressure to afford compound 43c (1.64 g, 84%).

Step 3:

To a stirred mixture of NaH (60% dispersion in mineral oil, 400 mg, 10 mmol) in DMF (15 mL) at RT under N$_2$ is added a solution of the carbamate 43c (1.65 g, 3.34 mmol) in DMF (5 mL) dropwise. The mixture is stirred at RT for 1 h and 2-bromoethyl methylether (3.14 mL, 33.4 mmol) is added. The mixture is stirred at RT for 30 min, heated at 90° C. for 1.5 h, then cooled to RT and concentrated under reduced pressure. The residue is diluted with EtOAc (150 mL) and water (150 mL). The layers are separated and the aqueous layer is further extracted with EtOAc (2×50 mL). The combined organic layers are washed with brine, dried (Na$_2$SO$_4$), filtered and concentrated under reduced pressure. The residue is purified by chromatography (0%-20% EtOAc/Hex) to afford compound 43d (1.4 g, 76%).

Step 4:

A mixture of compound 43d (1.4 g, 2.53 mmol) and ammonium acetate (25 g, 0.32 mol) is heated at 135° C. with stirring for 2 h, then diluted with water (50 mL) and adjusted to pH 8 by addition of 10N NaOH. The precipitate is filtered, and rinsed with water and hexanes to yield compound 43e (1.03 g, 80%).

Step 5:

Benzyl compound 43e (0.64 g, 1.27 mmol) is dissolved in TFA (4 mL) and stirred for 7 days. Methanol is added and the precipitate is filtered to yield compound 43f (0.5 g, 95%).

Step 6:

Phenol 43f (0.06 g, 0.144 mmol), N-Boc-4-hydroxypiperidine (0.145 g, 0.72 mmol) and triphenylphosphine (0.151 g, 0.58 mmol) are dissolved in DCM (0.8 mL) and diisopropylazodicarboxylate (0.114 mL, 0.578 mmol) is added. The reaction is stirred for 20 min and TFA (0.5 mL) is added and stirred for 1 h. The solvent is removed under reduced pressure. The residue is dissolved in AcOH and DMSO and purified by prep HPLC to give compound 2321 (0.032 g, 36%).

Example 44

Preparation of Compound 2327 (Table 2)

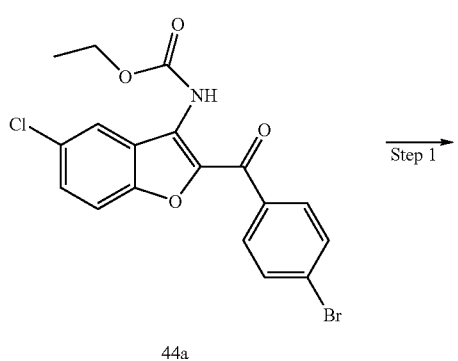

44a

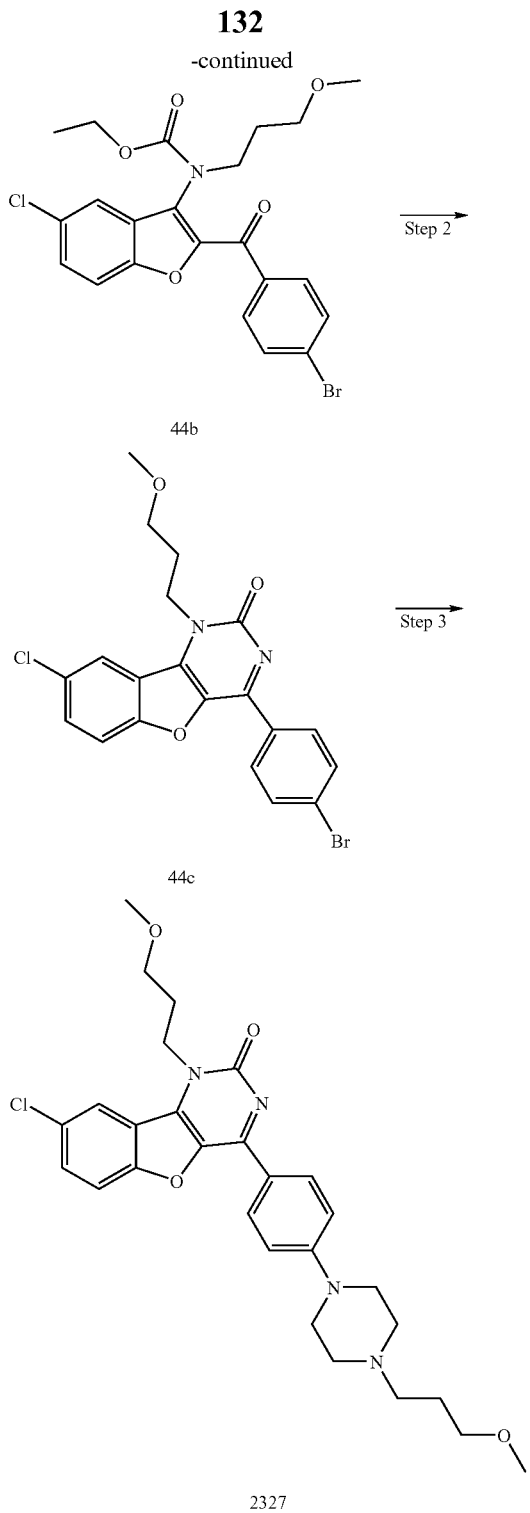

Step 1:

Cesium carbonate (2.15 g, 6.6 mmol) and carbamate 44a (0.93 g, 2.2 mmol) are dissolved in DMSO (5.3 mL) under N$_2$ atm. 2-bromopropylmethylether (0.51 g, 3.3 mmol) is added. The mixture is stirred at RT for 24 h. The residue is diluted with EtOAc (150 mL) and water (150 mL). The layers are separated and the aq layer is further extracted with EtOAc (2×50 mL). The combined organic layers are washed with brine, dried (Na$_2$SO$_4$), filtered and concentrated under reduced pressure. The residue is purified by chromatography (10%-40% EtOAc/Hex) to afford compound 44b (0.7 g, 64%).

Step 2:

A mixture of compound 44b (0.7 g, 1.4 mmol) and ammonium acetate (25 g, 0.05 mol) is heated at 135° C. with stirring for 30 min, then diluted with water (10 mL). The precipitate is filtered, rinsed with water and diethylether to yield compound 44c (0.574 g, 91%).

Step 3:

A mixture of compound 44c (50.0 mg, 0.112 mmol), 1-(3-methoxypropyl)-piperazine (26 mg, 0.168 mmol) and potassium phosphate (47 mg, 0.223 mmol) in DME (0.9 mL) is degassed with $N_2$ for 15 min. After this time, bis(tri-t-butylphosphine)palladium(0) (5.7 mg, 0.011 mmol) is added and the reaction mixture is stirred at 100° C. for 6 h. AcOH and DMSO is added and purified by prep HPLC to give compound 2327 (0.013 g, 19%).

Example 45

Preparation of Compound 2304 (Table 2)

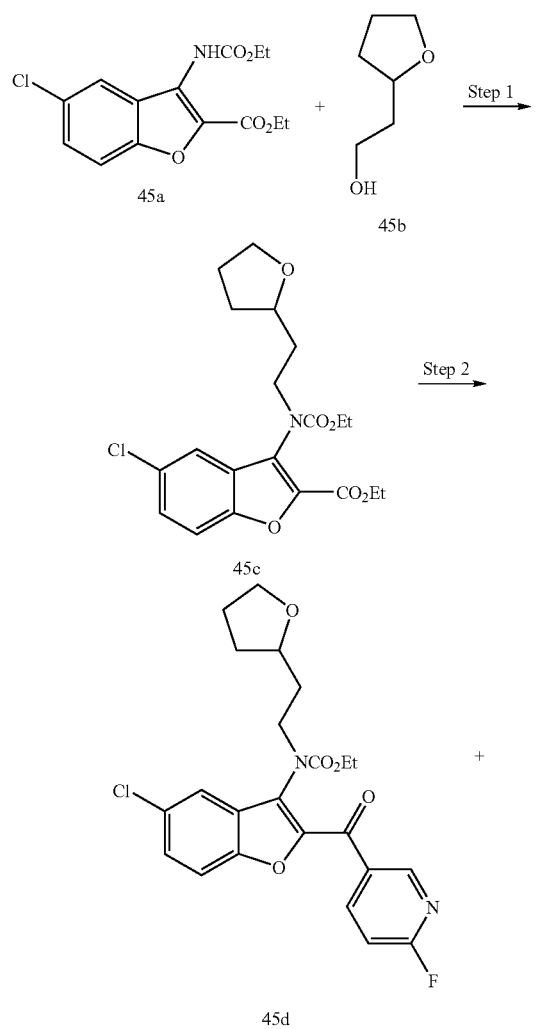

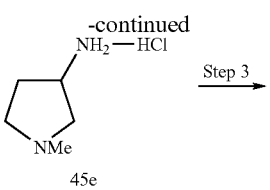

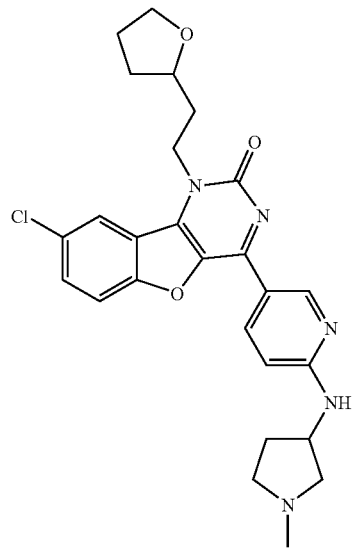

Preparation of N-methyl-3-aminopyrrolidine dihydrochloride salt (used in step 3): To a solution of 3-t-butoxycarbonylaminopyrrolidine (3 g, 3.2 mmoles, 2.6 eq) and formaldehyde (37% in $H_2O$, 3.2 mL, 42 mmoles, 2.5 eq) in DCE (64 mL) is added sodium triaceotoxyborohydride (5.1 g, 24 mmoles, 1.5 eq) at RT. The mixture is stirred at RT for 2 h and the solvents removed in vacuo. The residue is partitioned between sat $NaHCO_3$ and EtOAc (3×100 mL), the layers separated and the aq phase is extracted once more. The combined organic layers are pooled, washed with brine, dried ($Na_2SO_4$), filtered and concentrated to afford N-methyl-3-t-butoxycarbonyl aminopyrrolidine (1.8 g).

The prepared N-methyl-3-t-butoxycarbonylaminopyrrolidine (1.8 g, 8.9 mmoles) is dissolved in HCl/dioxane (4N, 44 mL, 256 mmoles) and allowed to stir at RT for 45 min. The dioxane is removed by concentration and N-methyl-3-aminopyrrolidine dihydrochloride salt is dried under high vacuum (1.7 g).

Step 1:

A mixture of carbamate 45a (0.80 g, 2.57 mmol), $PPh_3$ (3.80 g, 14.5 mmol) and the alcohol 45b (1.50 g, 12.9 mmol, which is prepared by $LiAlH_4$ reduction of the corresponding ester as described in WO2008/101867A1, herein incorporated by reference) in THF (25 mL) is treated with DIAD (2.53 mL, 12.8 mmol) at 0° C. After stirring at RT 48 h the reaction mixture is concentrated and the residue purified by column chromatography (Isco Combiflash, 80 g column, 0 to 100% EtOAc in Hex) to obtain 45c (1.01 g, 96%).

Step 2:

A solution of 45c (1.00 g, 2.45 mmol) and 5-bromo-2-fluoropyridine (867.3 mg, 4.93 mmol) in THF (25 mL) at −78° C. is treated with nBuLi (2.00 mL, 3.20 mmol) and the mixture is allowed to stir for 30 min. HPLC-MS shows the reaction to be incomplete. A further portion of 5-bromo-2-floropyridine (0.5 mL) and 0.25 eq nBuLi is added and stirring continued for 30 min. The reaction is treated with a solution of AcOH in THF (ca. 3:1, excess), allowed to warm to RT and treated with sat NH₄Cl. The reaction mixture is poured into H₂O-EtOAc and the layers separated. The aq phase is extracted with EtOAc and the combined organic layers washed (H₂O, brine), dried (Na₂SO₄) and concentrated in vacuo. The residue is purified by column chromatography (Isco Combiflash, 80 g column, 0 to 100% EtOAc in Hex) to obtain 45d (776.8 mg, 69%).

Step 3:

A solution of 45d (50 mg, 0.108 mmol) and NEt₃ (0.03 mL, 0.215 mmol) in DMSO (1 mL) is treated with 45e (29.4 mg, 0.17 mmol) and the solution is heated at 100° C. for 3 h. This crude reaction mixture is treated with NH₄OAc (1.5 g, 77.1 mmol) and the mixture is heated at 130° C. for 3.5 h. The reaction is cooled, diluted with DMSO (0.5 mL) and HOAc (ca. 0.1 mL) and purified by prep HPLC(CH₃CN—H₂O-TFA) to obtain the TFA salt of 2304 (32.7 mg, 50%).

Example 46

Preparation of Compound 2296 (Table 2)

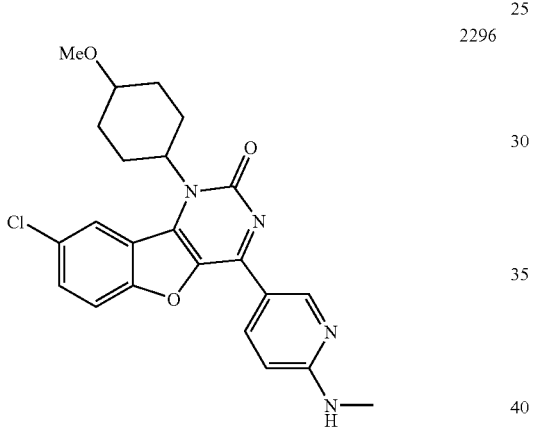

2296

Compound 2296 is prepared following the method of example 45, substituting alcohol 45b in step 1 with 4-methoxycyclohexane (Chemsampco) and substituting amine 45e in step 3 with N-methylamine hydrochloride.

Example 47

Preparation of Compound 2264 (Table 2)

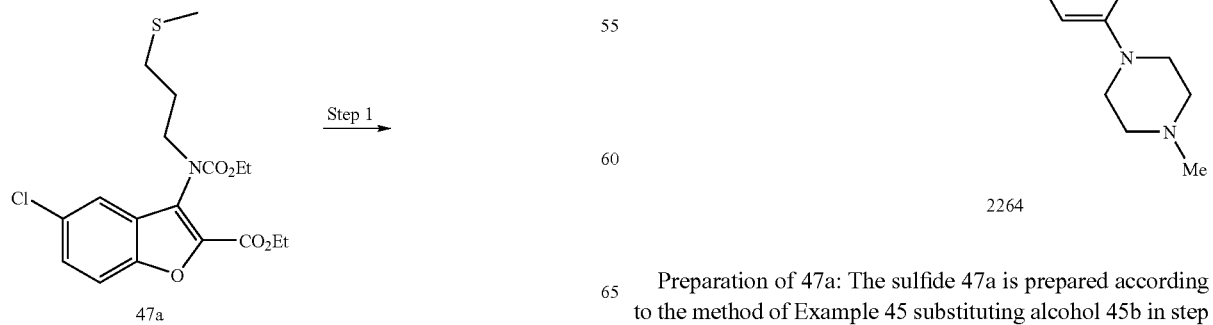

Preparation of 47a: The sulfide 47a is prepared according to the method of Example 45 substituting alcohol 45b in step 1 with 3-thiomethyl-1-propanol.

Step 1:

To a suspension of the sulfide 47a (140 mg, 0.35 mmol) in CH$_2$Cl$_2$ (5 mL) at 0° C. is added mCPBA (345 mg, 1.40 mmol) portion-wise. The reaction mixture is allowed to stir overnight while warming to RT. HPLC-MS shows complete conversion, no starting material is remained, however ca. 10-15% of the sulfoxide is observed. A further 200 mg of mCPBA is added and stirring is continued overnight. The mixture is concentrated in vacuo and purified by column chromatography (Isco Combiflash, 12 g column, 0 to 100% EtOAc in Hex) to obtain 47b (112.2 mg, 74%).

Step 2:

Intermediate 47c is prepared according to the method of Example 45. The crude material is used as is in subsequent steps.

Step 3:

Compound 2264 is prepared according to the method of Example 45 substituting amine 45e with 47d in step 3 (10.6 mg, 14%).

Example 48

Preparation of Compound 2297 (Table 2)

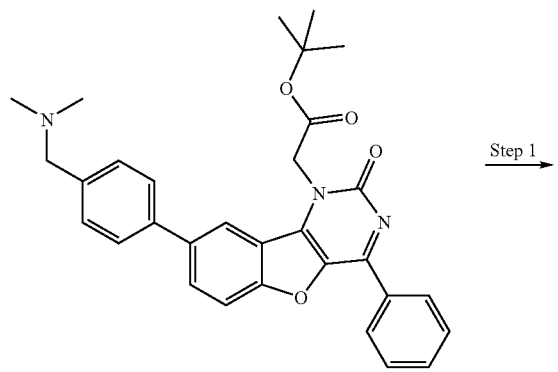

48a

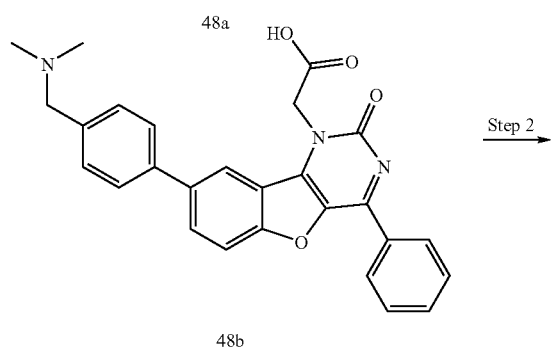

48b

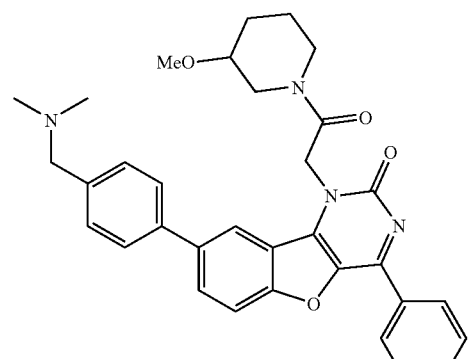

2297

Preparation of 48a: The ester 48a is prepared by the method of Example 12 substituting t-butyl 2-bromoacetate for 1-bromopentane in step 1.

Step 1:

The ester 48a (1.04 g, 2.04 mmol) is suspended in CH$_2$Cl$_2$ (20 mL) and TFA (5 mL) added. The mixture is allowed to stir at RT for 2 h and then concentrated in vacuo to afford 48b. The crude material is used as is in subsequent steps (1.02 g, 88%).

Step 2:

A solution of 48b (52.5 mg, 0.093 mmol) in DMF (1 mL) is treated with iPr$_2$NEt (0.1 mL, 0.56 mmol) followed by HATU (44.0 mg, 0.12 mmol) and the solution allowed to stir for 5 min. To this solution is then added 3-methoxypiperidine (115.0 mg, 1.00 mmol) and the solution is stirred for another hour. The mixture is treated with HOAc (0.2 mL), filtered and purified by prep HPLC to obtain the TFA salt of 2297 (2.4 mg, 4%).

Example 49

Preparation of Compound 5030 (Table 5)

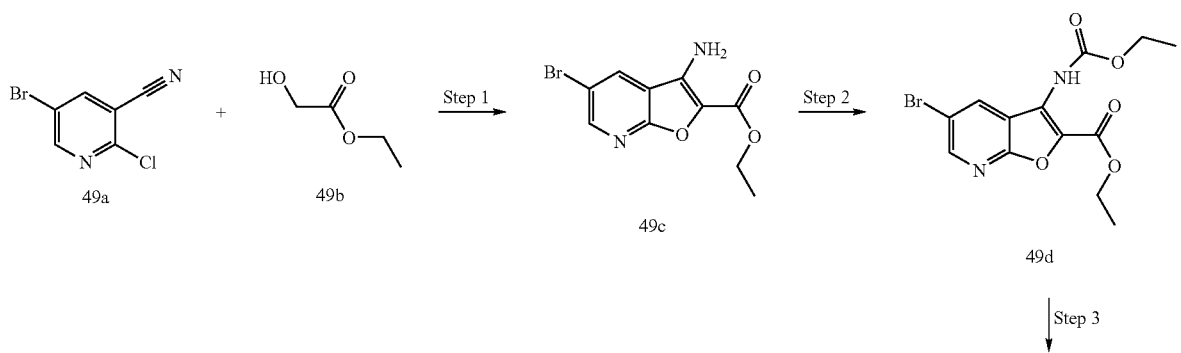

Step 3

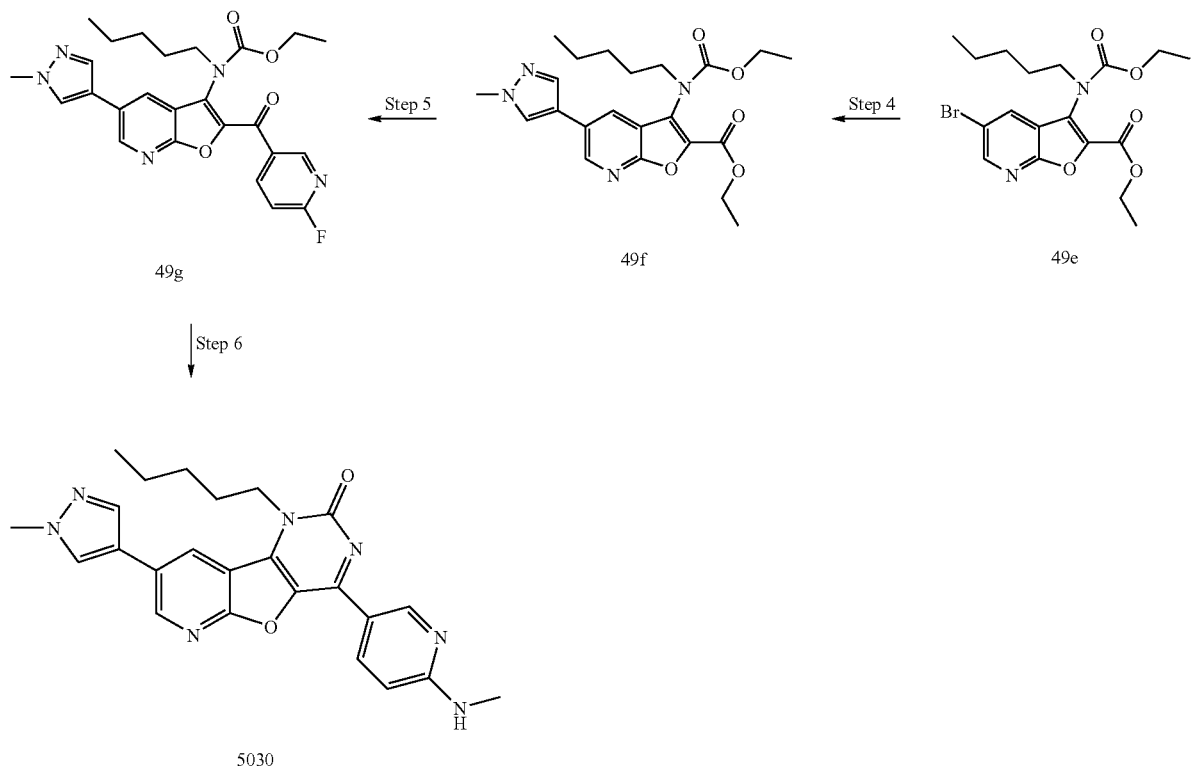

Step 1:
To a stirred mixture of the pyridine 49a (5.00 g, 1.0 eq), the alcohol 49b (2.28 mL, 1.05 eq), CuI (0.100 g, 0.02 eq) is added $Cs_2CO_3$ (16.5 g, 2.2 eq) and heated at 70° C. during 4 h. The reaction mixture is cooled down to RT, poored into $H_2O$ (500 mL) and allowed to stand for 1 h until precipitation. The suspension is filtered, triturated with $Et_2O$/Hexanes (1:1), dried with toluene azeotrope to give 49c (4.00 g, 61%).

Step 2:
To a stirred solution of 49c (4.00 g, 1 eq) in toluene (30 mL), is added ethyl chloroformate (2.68 mL, 2 eq) and heated at reflux during 18 h. The mixture is cooled down to RT diluted with EtOAc/$H_2O$/$NaHCO_3$(sat), the aqueous phase is extracted with EtOAc, the combined organic extracts are washed with brine, dried over $Na_2SO_4$ and concentrated. The resulting residue is triturated in hexanes to give 49d (5.00 g, 96%).

Step 3:
To a stirred mixture of 49d (1.00 g, 1 eq) in DMSO (10 mL), is added $Cs_2CO_3$ (4.12 g, 2.3 eq). After stirring for 5 min, 1-bromopentane (0.97 mL, 1.4 eq) is added and the solution is stirred at RT during 18 h. The reaction mixture is quenched with $H_2O$, extracted with EtOAc (3×). The combined organic extracts are washed with $H_2O$ (3×), brine, dried over $Na_2SO_4$ and concentrated. The resulting residue is purified by flash chromatography Hex/EtOAc (5 to 25%) to give 49e (2.20 g, 92%).

Step 4:
To a suspension of 1-methyl-4-(4,4,5,5-tetramethyl-1,3,2-dioxaborolan-2-yl)-1H pyrazole (1.24 g, 1.7 eq) in dioxane (12 mL, bubbled with Ar during 10 min), is added 49e (1.50 g, 1 eq), $K_2CO_3$ (1.26 g, 2.6 eq) and CsF (1.38 g, 2.6 eq). Pd(dppf)$Cl_2$ $CH_2Cl_2$ complex (0.29 mg, 0.1 eq) is added and the mixture is heated in the microwave (135° C., 25 min). The solution is concentrated, diluted with $H_2O$/EtOAc, extracted with EtOAc, the combined organic extracts are washed with brine, dried over $Na_2SO_4$ and concentrated. The resulting residue is purified by flash chromatography Hex/EtOAc (1:1) to give 49f (1.05 g, 70%).

Step 5:
To a solution of 2-fluoro-5-bromopyridine (0.17 mL, 1.2 eq) and the ester 49f (0.600 g, 1 eq) in THF (10 mL) at −78° C., is added BuLi/hexane (2.3 M, 0.68 mL, 1.1 eq). The mixture is stirred at −78° C. for 1 h, the reaction is quenched by addition of acetic acid, and the mixture is poured in EtOAc/brine and extracted with EtOAc. The organic extract is dried over $MgSO_4$, filtered and concentrated under vacuum. The residue is purified by flash chromatography on silica gel Hex/EtOAc (0 to 20%) to give compound 49g (0.426 g, 63%).

Step 6:
To a stirred solution of 49g (34 mg, 1 eq) in DMSO (0.5 mL), is added a solution of methylamine (71 μL, 2 M in THF, 2 eq) and heated at 50° C. during 30 min. Ammonium acetate (500 mg) is added and the solution is heated at 140° C. during 4 h. The solution is diluted with $H_2O$/AcOH and purified by prep HPLC to give 5030 (12 mg, 38%).

Example 50

Preparation of Compound 5004 (Table 5)

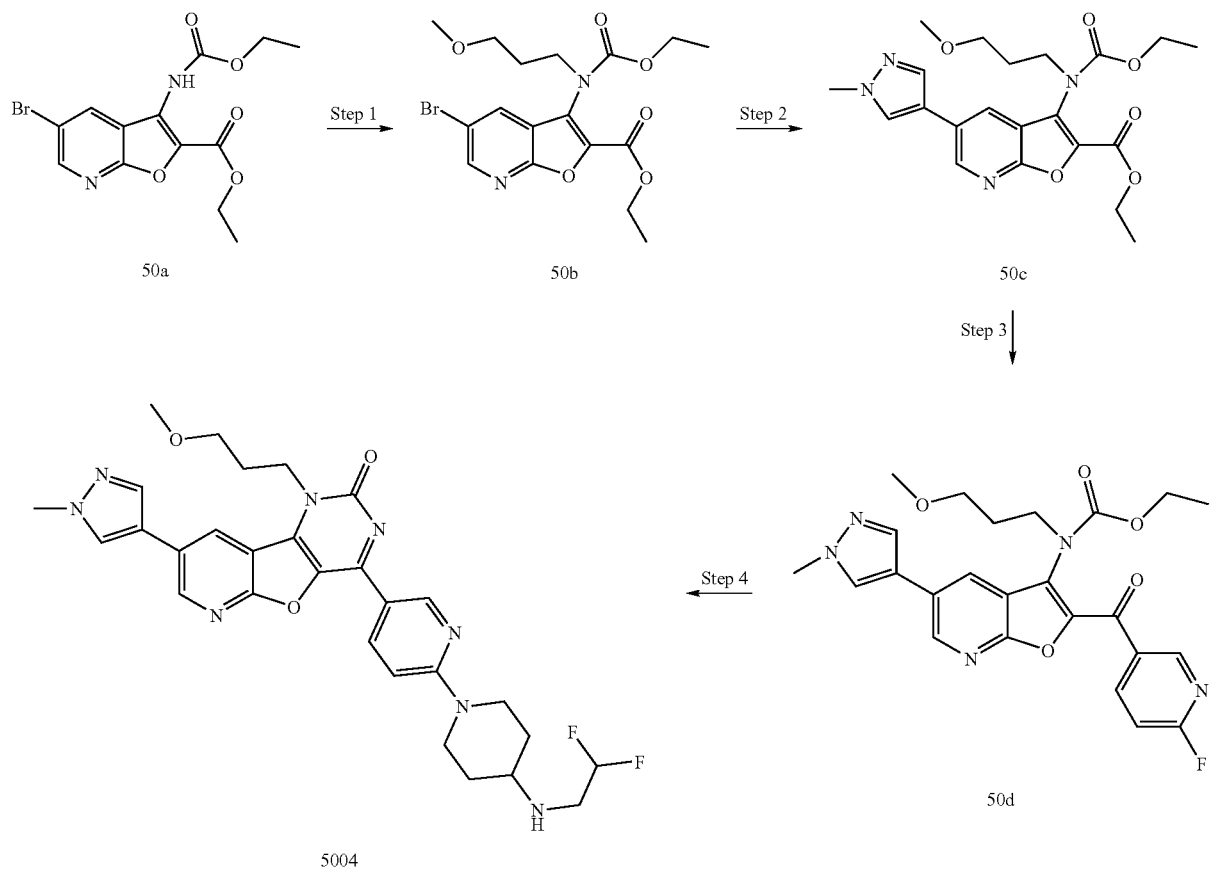 [SMILES: CCOC(=O)Nc1c(C(=O)OCC)oc2ncc(Br)cc12 ; CCOC(=O)c1oc2ncc(Br)cc2c1N(CCCOC)C(=O)OCC ; CCOC(=O)c1oc2ncc(-c3cnn(C)c3)cc2c1N(CCCOC)C(=O)OCC ; COCCCn1c(=O)nc(-c2ccc(N3CCC(NCC(F)F)CC3)nc2)c2oc3ncc(-c4cnn(C)c4)cc3c21 ; CCOC(=O)N(CCCOC)c1c(C(=O)c2ccc(F)nc2)oc2ncc(-c3cnn(C)c3)cc12]

Step 1:

To a stirred mixture of 50a (2.50 g, 1 eq) in DMSO (15 mL), is added Cs$_2$CO$_3$ (4.11 g, 1.8 eq). After stirring for 5 min, 2-bromoethyl methylether (1.2 mL, 1.5 eq) is added and the solution is stirred at RT during 18 h. The reaction mixture is quenched with H$_2$O, extracted three times with EtOAc, the combined organic extracts are washed with H$_2$O (three times), brine, dried over Na$_2$SO$_4$ and concentrated. The resulting residue is purified by flash chromatography Hex/EtOAc (10 to 60%) to give 50b (2.90 g, 97%).

Step 2:

To a suspension of 1-methyl-4-(4,4,5,5-tetramethyl-1,3,2-dioxaborolan-2-yl)-1H pyrazole (1.24 g, 1.7 eq) in dioxane (12 mL, bubbled with Ar during 10 min), is added 50b (1.50 g, 1 eq), K$_2$CO$_3$ (1.26 g, 2.6 eq) and CsF (1.38 g, 2.6 eq). Pd(dppf)Cl$_2$ CH$_2$Cl$_2$ complex (0.29 mg, 0.1 eq) is added and the mixture is heated in the microwave (135° C., 25 min). The solution is concentrated, diluted with H$_2$O/EtOAc, extracted with EtOAc, the combined organic extracts are washed with brine, dried over Na$_2$SO$_4$ and concentrated. The resulting residue is purified by flash chromatography Hex/EtOAc (1:1) to give 50c (1.44 g, 96%).

Step 3:

To a solution of 2-fluoro-5-bromopyridine (0.11 mL, 1.2 eq) and the ester 50c (0.400 g, 1 eq) in THF (10 mL) at −78° C., is added BuLi/hexane (0.9 M, 1.2 mL, 1.1 eq). The mixture is stirred at −78° C. for 1 h, the reaction is quenched by addition of acetic acid, and the mixture is poured in EtOAc/brine and extracted. The organic extract is dried over MgSO$_4$, filtered and concentrated under vacuum. The residue is purified by flash chromatography on silica gel Hex/EtOAc (1:1) to give compound 50d (0.350 g, 78%).

Step 4:

To a stirred solution of 1-Boc-4-piperidone (0.300 g, 1 eq) and 2,2-difluoroethylamine (0.244 g, 2 eq) in 1,2-dichloroethane (6 mL) is added NaBH(OAc)$_3$ (0.640 mg, 2 eq). After 18 h, the solution is diluted with CH$_2$Cl$_2$, washed with NaHCO$_3$ (sat.), brine, dried over Na$_2$SO$_4$ and concentrated. The resulting residue is purified by flash chromatography Hex/EtOAc (1:1) to give the corresponding N-Boc piperidine (0.360 g, 90%). The obtained N-Boc piperidine (29 mg, 1.5 eq) is dissolved in a solution HCl in dioxane (4 M, 0.5 mL) and stirred during 30 min at RT. The solution is concentrated, the resulting residue is dissolved in DMSO (0.5 mL), Et$_3$N (40 µL, 4 eq) is added followed by 50d (35 mg, 1 eq). The solution is heated at 50° C. for 1 h and ammonium acetate (500 mg) is added and the heating is pursued at 140° C. during 4 h. The solution is diluted with H$_2$O/AcOH and purified by prep HPLC to give 5004 (10 mg, 24%).

Example 51

Preparation of Compound 5008 (Table 5)

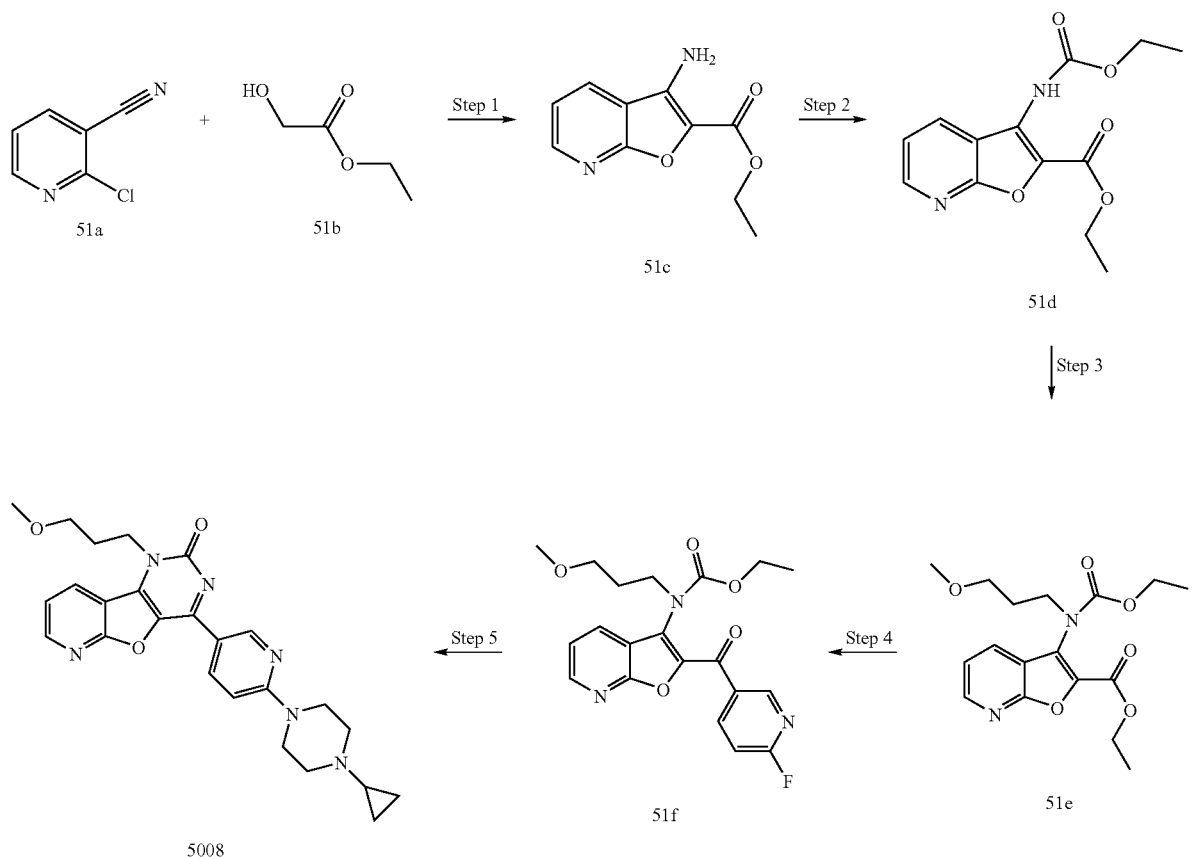

Step 1:

To a stirred mixture of the pyridine 51a (2.00 g, 1.0 eq), the alcohol 51b (1.43 mL, 1.05 eq), CuI (0.05 g, 0.02 eq) is added Cs$_2$CO$_3$ (10.3 g, 2.2 eq) and heated at 70° C. during 4 h. The reaction mixture is cooled down to RT, poured into H$_2$O (300 mL) and allowed to stand for 1 h until precipitation. The suspension is filtered, triturated with Et$_2$O/Hex (1:1), dried with toluene azeotrope to give 51c (2.0 g, 70%).

Step 2:

To a stirred solution of 51c (2.00 g, 1 eq) in toluene (15 mL), is added ethyl chloroformate (1.85 mL, 2 eq) and heated at reflux during 18 h. The mixture is cooled down to RT diluted with EtOAc/H$_2$O/NaHCO$_3$(sat), the aqueous phase is extracted with EtOAc, the combined organic extracts are washed with brine, dried over Na$_2$SO$_4$ and concentrated. The resulting residue is triturated in hexanes to give 51d (2.40 g, 90%).

Step 3:

To a stirred mixture of 51d (1.00 g, 1 eq) in DMSO (8 mL), is added Cs$_2$CO$_3$ (3.51 g, 3 eq). After stirring for 5 min, 2-bromoethyl methylether (0.62 mL, 1.5 eq) is added and the solution is stirred at RT during 18 h. The reaction mixture is quenched with H$_2$O, extracted with EtOAc (3×), the combined organic extracts are washed with H$_2$O (3×), brine, dried over Na$_2$SO$_4$ and concentrated. The resulting residue is purified by flash chromatography Hex/EtOAc (1:1) to give 51e (1.20 g, 98%).

Step 4:

To a solution of 2-fluoro-5-bromopyridine (0.11 mL, 1.5 eq) and the ester 51e (0.250 g, 1 eq) in THF (4 mL) at −78° C. is added BuLi/hexane (1.57 M, 0.54 mL, 1.2 eq). The mixture is stirred at −78° C. for 1 h, the reaction is quenched by addition of acetic acid, and the mixture is poured in EtOAc/brine and extracted. The organic extract is dried over MgSO₄, filtered and concentrated under vacuum. The residue is purified by flash chromatography on silica gel Hex/EtOAc (3:7) to give compound 51f (0.143 g, 50%).

Step 5:

To a stirred solution of 51f (50 mg, 1 eq) in DMSO (0.5 mL), is added 1-cyclopropylpiperazine (38 mg, 2 eq), Et₃N (19 µL, 1.1 eq) and heated at 50° C. during 2 h. Ammonium acetate (500 mg) is added and the solution is heated at 140° C. during 1 h. The solution is diluted with H₂O/AcOH and purified by prep HPLC to give 5008 (8 mg, 13%).

Example 52

Preparation of Compound 5001 (Table 5)

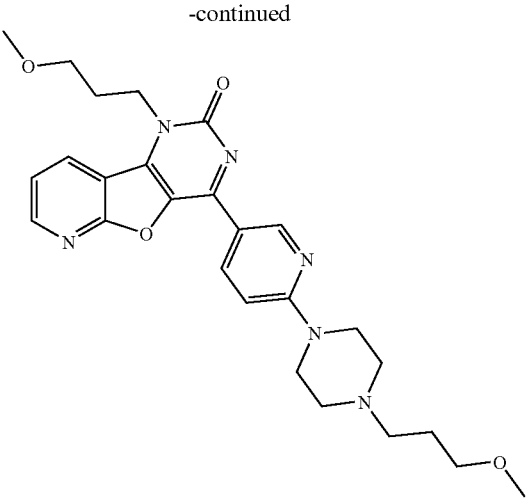

5001

Step 1:

To a stirred solution of 51f (57 mg, 1 eq) in DMSO (0.5 mL), is added 1-(3-methoxypropyl)piperazine (30 mg, 1.3 eq), Et₃N (21 µL, 1.1 eq) and heated at 50° C. during 2 h. Ammonium acetate (600 mg) is added and the solution is heated at 140° C. during 1 h. The solution is diluted with H₂O/AcOH and purified by prep HPLC to give 5001 (29 mg, 42%).

Example 53

Preparation of Compound 2281 (Table 2)

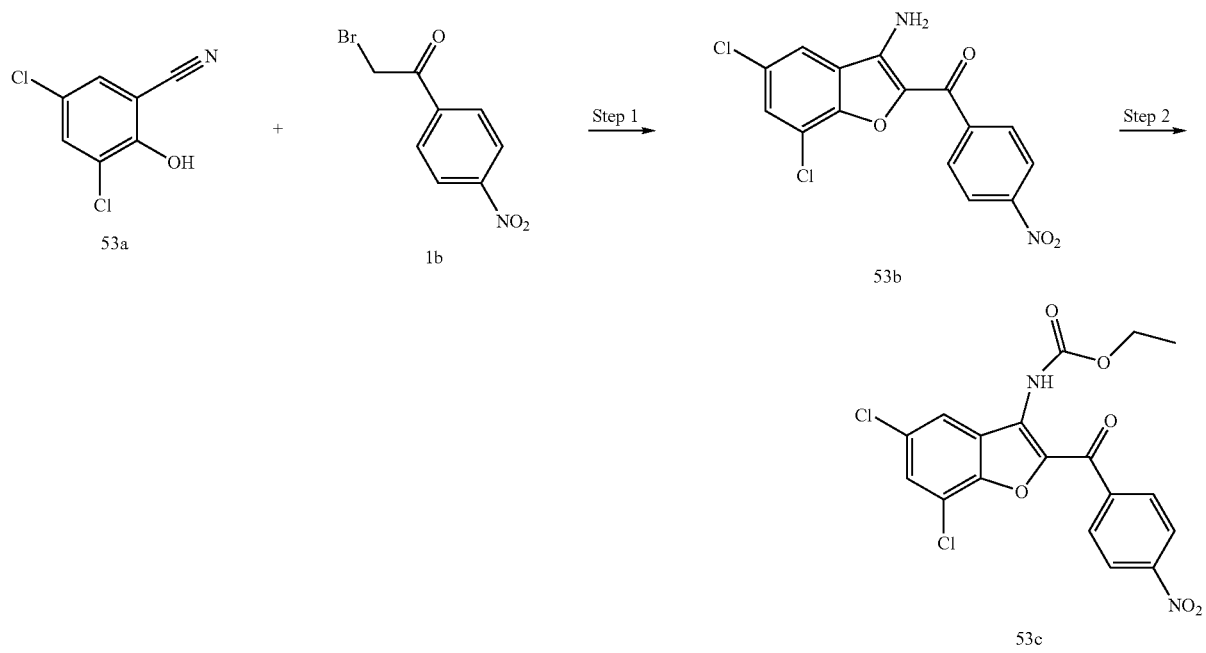

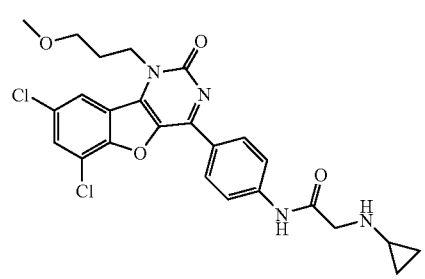
2281

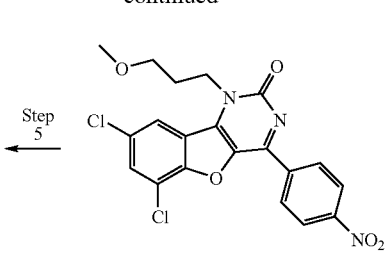
53e

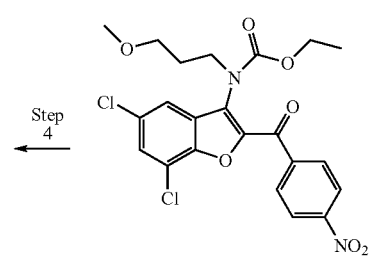
53d

Step 1:
To a stirred mixture of the phenol 53a (2.00 g, 1.0 eq), the bromoketone 1b (2.60 g, 1.0 eq) and acetone (80 mL) at RT is added Na$_2$CO$_3$ (1.13 g, 1.0 eq). The mixture is stirred at reflux for 18 h and filtered, and the filtrate is concentrated. The residue is suspended in MeOH, and NaOH (1 N, 0.1 mL, 0.01 eq) is added. The mixture is stirred at reflux for 2 h and concentrated to give compound 53b (3.35 g, 90%).

Step 2:
To a stirred mixture of compound 53b (3.00 g, 1.0 eq), K$_2$CO$_3$ (8.85 g, 7.3 eq) and toluene (50 mL) at RT under N$_2$ is added ethyl chloroformate (5.7 mL, 7.0 eq). The mixture is stirred at reflux for 18 h and then filtered. The filtrate is concentrated and the residue is triturated with hexanes to give compound 53c (3.40 g, 95%).

Step 3:
To a stirred mixture of 53c (2.00 g, 1 eq) in DMSO (20 mL), is added Cs$_2$CO$_3$ (4.63 g, 3 eq). After stirring for 5 min, 2-bromoethyl methylether (0.80 mL, 1.5 eq) is added and the solution is stirred at RT during 18 h. The reaction mixture is quenched with H$_2$O, extracted with EtOAc (3×), the combined organic extracts are washed with H$_2$O (3×), brine, dried over Na$_2$SO$_4$ and concentrated. The resulting residue is purified by flash chromatography to give 53d (1.10 g, 47%).

Step 4:
A mixture of compound 53d (1.10 g, 1 eq) and ammonium acetate (8 g) is heated at 135° C. with stirring for 2 h, then diluted with water (300 mL) and adjusted to pH ~8 by addition of 10N NaOH. The precipitate is filtered, and rinsed with water and hexanes to yield compound 53e (1.00 g, quant.).

Step 5:
To a suspension of the nitro compound 53e (1.00 g, 1 eq) in EtOH (27 mL) is added iron (0.47 g, 4 eq) followed by 1N aqueous HCl (4.3 mL) and water (2.6 mL). The reaction mixture is heated at reflux for 2 h, cooled to RT and the magnetic stirrer with the iron on it is removed from the solution and rinsed with acetonitrile. The mixture is concentrated under reduced pressure and the residue is dried under vacuum. To a suspension of obtained crude (0.100 g, 1 eq) in DCM (2 mL) is added bromoacetyl bromide (26 µL, 1.3 eq). The reaction mixture is stirred at RT for 15 min and concentrated under reduced pressure, and the residue is suspended in DMF (2 mL). Cyclopropylamine (80 µL, 5 eq) is added slowly and the mixture is stirred for 2 h. The suspension is filtered through Celite™ and purified by prep HPLC to afford compound 2281 (8 mg, 7%).

Example 54

Preparation of Compound 5029 (Table 5)

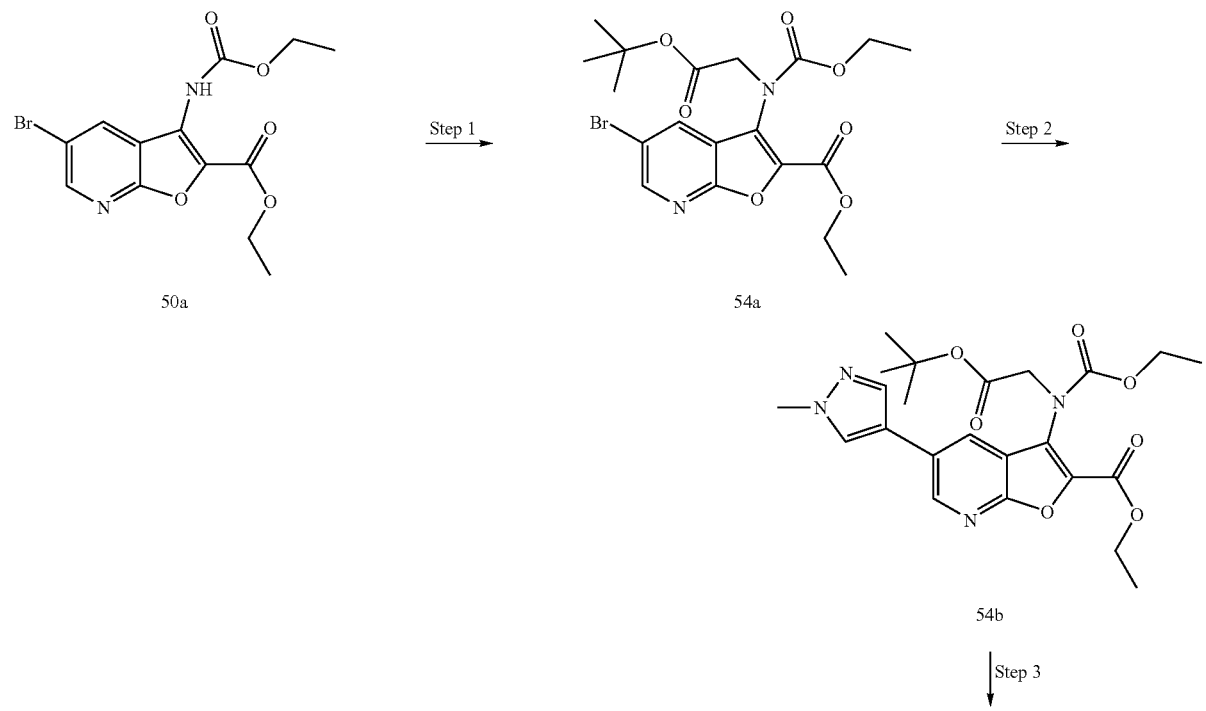

-continued

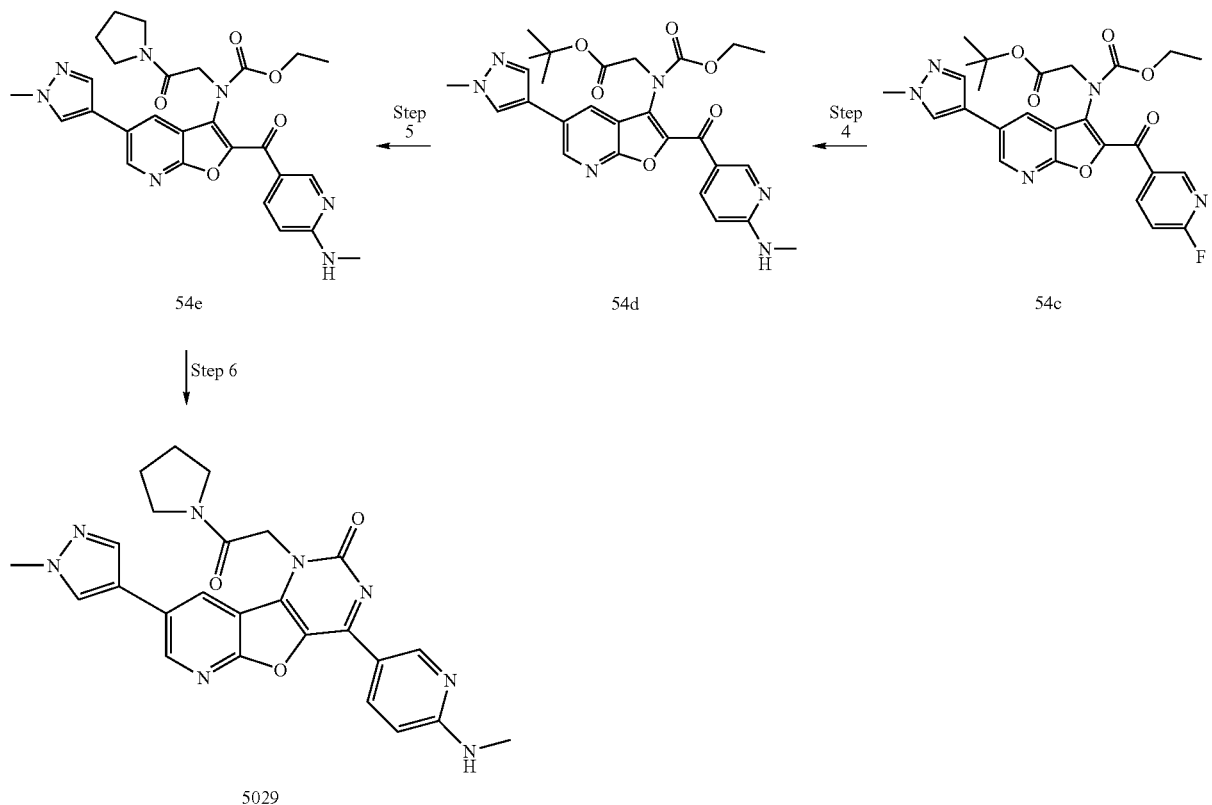

Step 1:
To a stirred mixture of 50a (0.500 g, 1 eq) in DMSO (4 mL), is added Cs$_2$CO$_3$ (1.05 g, 2.3 eq). After stirring for 5 min, tert-butyl bromoacetate (0.31 mL, 1.5 eq) is added and the solution is stirred at RT during 18 h. The reaction mixture is quenched with H$_2$O, extracted with EtOAc (3×), the combined organic extracts are washed with H$_2$O (3×), brine, dried over Na$_2$SO$_4$ and concentrated. The resulting residue is purified by flash chromatography Hex/EtOAc (0 to 25%) to give 54a (0.600 g, 91%).

Step 2:
To a suspension of 1-methyl-4-(4,4,5,5-tetramethyl-1,3,2-dioxaborolan-2-yl)-1H pyrazole (0.530 g, 2 eq) in dioxane (15 mL, bubbled with Ar during 10 min), is added 54a (0.600 g, 1 eq), K$_2$CO$_3$ (0.527 g, 3 eq) and CsF (0.580 g, 3 eq). Pd(dppf)Cl$_2$ CH$_2$Cl$_2$ complex (103 mg, 0.1 eq) is added and the mixture is heated in the microwave (135° C., 25 min). The solution is concentrated, diluted with H$_2$O/EtOAc, extracted with EtOAc, the combined organic extracts are washed with brine, dried over Na$_2$SO$_4$ and concentrated. The resulting residue is purified by flash chromatography Hex/EtOAc (1:1) to give 54b (0.340 g, 57%).

Step 3:
To a solution of 2-fluoro-5-bromopyridine (84 µL, 1.2 eq) and the ester 54b (0.320 g, 1 eq) in THF (10 mL) at −78° C., is added BuLi/hexane (1.2 M, 0.62 mL, 1.1 eq). The mixture is stirred at −78° C. for 1 h, the reaction is quenched by addition of acetic acid, and the mixture is poured in EtOAc/brine and extracted. The organic extract is dried over MgSO$_4$, filtered and concentrated under vacuum. The residue is purified by flash chromatography on silica gel CH$_2$Cl$_2$/acetone (0 to 20%) to give compound 54c (0.280 g, 79%).

Step 4:
To a stirred solution of 54c (50 mg, 1 eq) in THF (0.5 mL), is added a solution of methylamine (0.19 mL, 2 M in THF, 4 eq) and heated at 50° C. during 30 min. The solution is diluted with H$_2$O, extracted with EtOAc, the combined organic extracts are washed with brine, dried over Na$_2$SO$_4$ and concentrated to give 54d (50 mg, quant.).

Step 5:
To a stirred solution of 54d (50 mg, 1 eq) in CH$_2$Cl$_2$ (1 mL), is added TFA (0.1 mL). After stirring for 5 h, the solution is concentrated under vacuum to give the corresponding acid (44 mg, quant.). The obtained acid (44 mg, 1 eq) is dissolved in DMF (1 mL) and iPr$_2$NEt (484, 3 eq), pyrrolidine (194, 2.5 eq) followed by HATU (44 mg, 1.25 eq) are added successively. The resulting solution is stirred at RT during 18 h, diluted with H$_2$O/EtOAc, the organic phase is washed with H$_2$O, brine, dried over Na$_2$SO$_4$ and concentrated to give 54e (45 mg, 92%).

Step 6:
To a stirred solution of 54e (45 mg, 1 eq) in DMSO (0.5 mL), is added ammonium acetate (600 mg) and heated at 140° C. during 1 h. The solution is diluted with H$_2$O, basified to pH ~8 with NaOH 10N and filtered. The resulting solid is dissolved in H$_2$O/MeCN, 1 eq of a solution of HCl (1 N) is added and the solution is lyophilized to give 5029 (27 mg, 66%) as HCl salt.

Example 55

Preparation of Compound 2283 (Table 3)

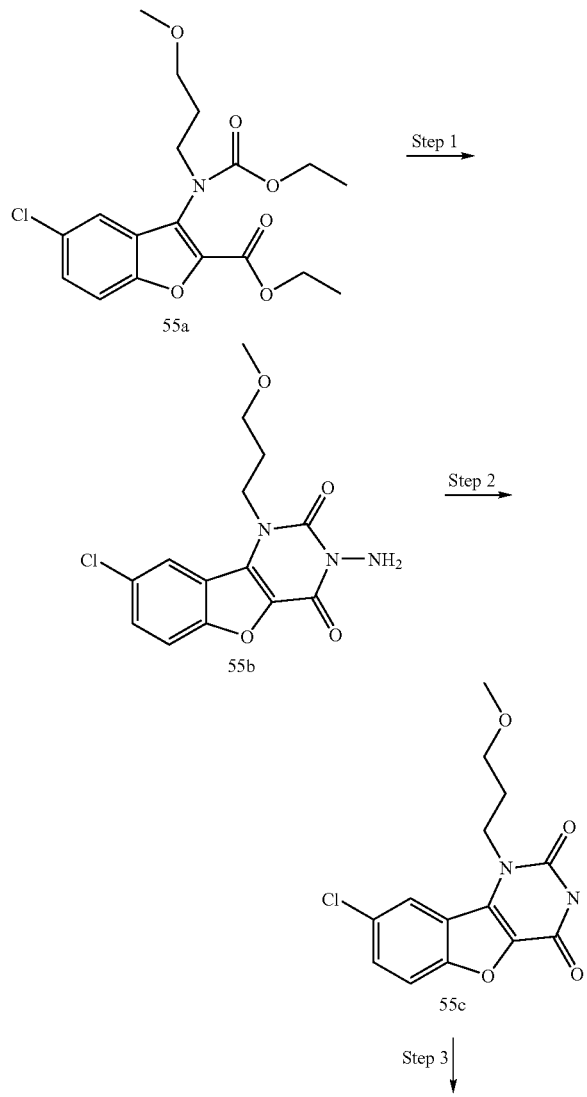

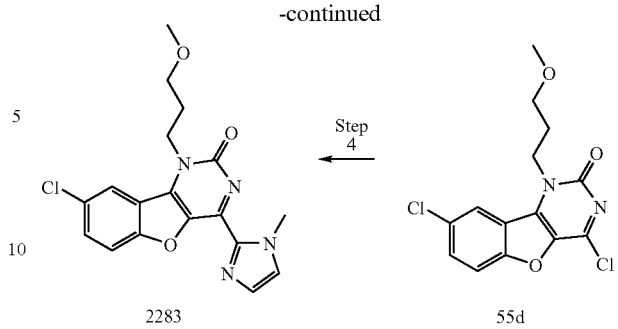

Step 1:
55a (300 mg, 0.78 mmol, 1 eq) is solubilized in EtOH (10 mL) then hydrazine hydrate (0.341 mL) is added. The reaction mixture is stirred at reflux overnight. Reaction mixture is cooled down to RT (precipitate) and filtered to obtain 55b (202 mg, 80%).

Step 2:
A suspension of 55b in 50% AcOH aq. is warmed up to 45-50° C. Sodium nitrite (129 mg, 3 eq) is added portionwise and reaction mixture is stirred at 45-50° C. for 1 h. Reaction mixture is cooled down to RT and water is added. The suspension is filtered to afford 55c (180 mg, 93%).

Step 3:
To a mixture of 55c (100 mg, 0.324 mmol, 1 eq), DIEA (112.9 µL, 0.648 mmol, 2 eq) at −10° C. is added $POCl_3$ (2.96 mL, 32.4 mmol). The mixture is warmed to RT. After 2 h the reaction is completed. The solvent is removed under reduced pressure. The crude material is then diluted with EtOAc, and the organic solution is washed with water, dried over $MgSO_4$ and filtered. HPLC shows ~6% of the hydrolized Chloro adduct. The crude 55d (100 mg, 94%) is used without any further purification for the next step.

Step 4:
55d (50 mg, 0.53 mmol), 1-methyl-2-(tributylstannyl)imidazol (85 mg, 0.23 mmol, 1.5 eq), CuI (5.8 mg, 0.031 mmol, 0.2 eq) and the $Pd(PPh_3)_4$ (17.7 mg, 0.015 mmol, 0.1 eq) are dissolved in DMF (1.5 mL). The resulting solution is stirred at RT for 15 min and warmed up to 55° C. for 12 h. After cooling to RT AcOH (200 µL is added and the reaction is filtered over Millex. The resulting solution is purified using the prep HPLC to afford 2283 (15 mg, 26%).

Example 56

Preparation of Compound 2276 (Table 2)

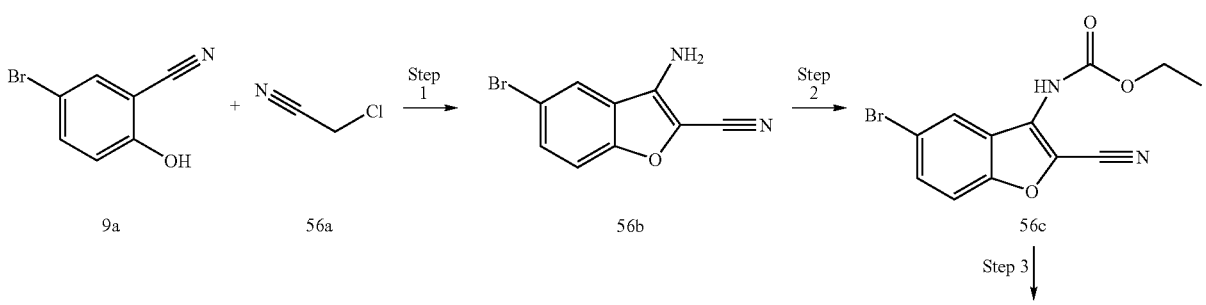

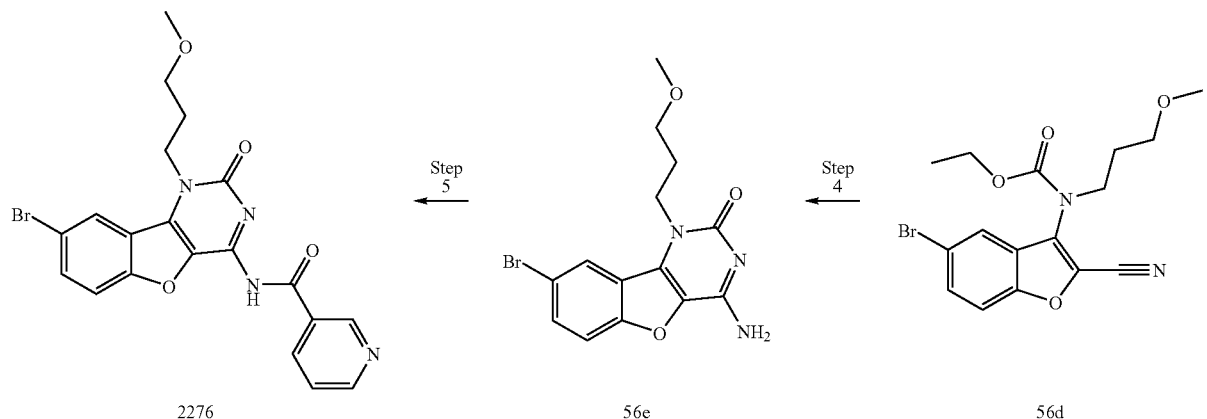

Step 1:

A mixture of 9a (2 g, 10.1 mmol), 56a (0.641 mL, 10.1 mmol) and K$_2$CO$_3$ (4.18 g, 30.3 mmol) in CH$_3$CN (25 mL) is stirred at reflux for 13 h. The suspension is filtered off and the CH$_3$CN is removed. The crude is dissolved with EtOAc, and the organic is washed with water, dried over MgSO$_4$, filtered and concentrated under reduced pressure to afford 56b (2.2 g, 92%).

Step 2:

56b (2 g, 8.43 mmol) and the K$_2$CO$_3$ (5.8 g, 42.2 mmol, 5 eq) are stirred in toluene (30 mL) and ethyl chloroformate (4.84 g, 50.6 mmol, 6 eq) is added. The reaction mixture is stirred at reflux for 20 h. The solution is cooled down, H$_2$O is added and the aqueous phase is washed with EtOAc (2×), the combined organic extracts are washed with brine, dried over Na$_2$SO$_4$, filtered and concentrated to afford 56c (2.6 g, 99%), which is used without purification for the next step.

Step 3:

To a DMF (10 mL) solution of 56c (2.6 g, 8.4 mmol), 1-bromo-3-methoxypropane (1.28 g, 8.4 mmol) is added K$_2$CO$_3$ (3.5 g, 25.2 mmol, 3 eq) and the resulting mixture is warmed up to 110° C. and stirred over night. The reaction is then cooled down to RT and diluted with water and the organic material is extracted with EtOAc, dried over MgSO$_4$, filtered and concentrated under reduced pressure. The crude is purified using the combiflash eluting with 10-40% EtOAc/Hex to afford 56d (2.5 g, 78%).

Step 4:

56d (100 mg, 0.262 mmol), and ammonium acetate (3 g, 39 mmol) are stirred at 140° C. for 2 h and the reaction is cooled down to RT. NaOH 10N (2 mL) was added and the resulting suspension is filtered, rinsed with water and hexanes to afford 56e (90 mg, 97%).

Step 5:

To a mixture of 56e (55 mg, 0.156 mmol), TBTU (65 mg, 0.20 mmol) and nicotinic acid (25 mg, 0.20 mmol) in DMF (1 mL) is added Et$_3$N (65.2 µL, 0.46 mmol). After 1 h, one extra equivalent of all reagents are added and the resulting mixture is stirred for 1 h. The reaction is then acidified using AcOH (500 µL) and filtered over Millex. Purification using prep HPLC gives 2276 (6 mg, 8.4%).

Example 57

Preparation of Compound 5005 (Table 5)

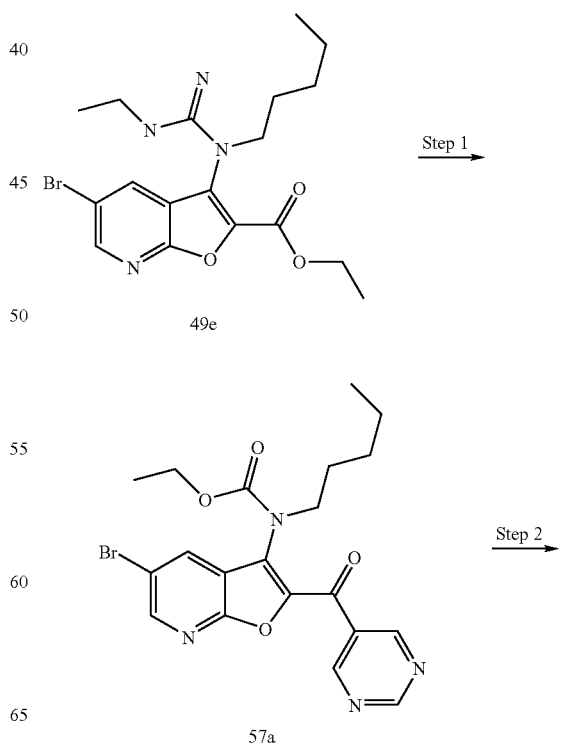

-continued

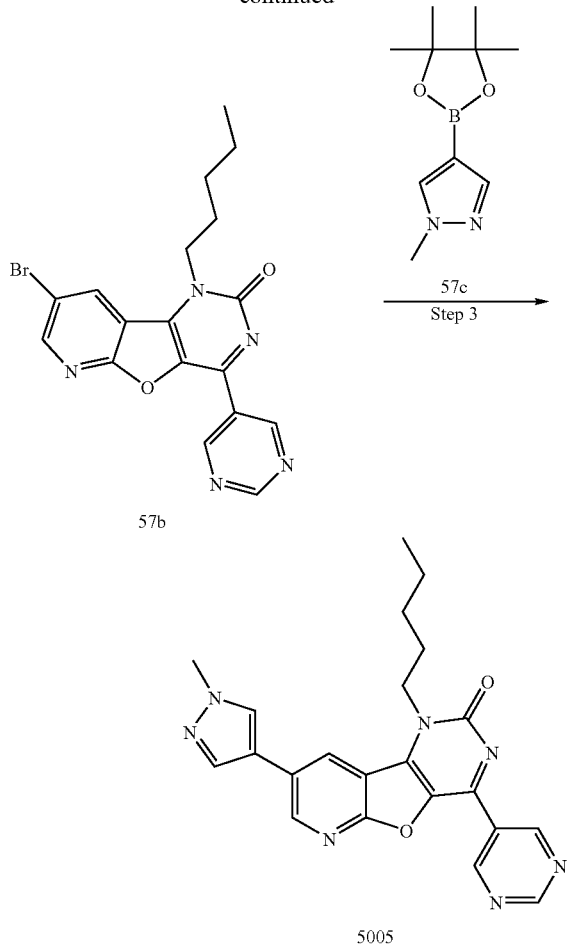

with MeOH/AcOH (1:1, 2 mL) filtered over Milex and purified using prep HPLC (MeOH, Ammonium formate) to afford 5005 (15 mg, 30%).

Example 58

Preparation of Compound 5017 (Table 5)

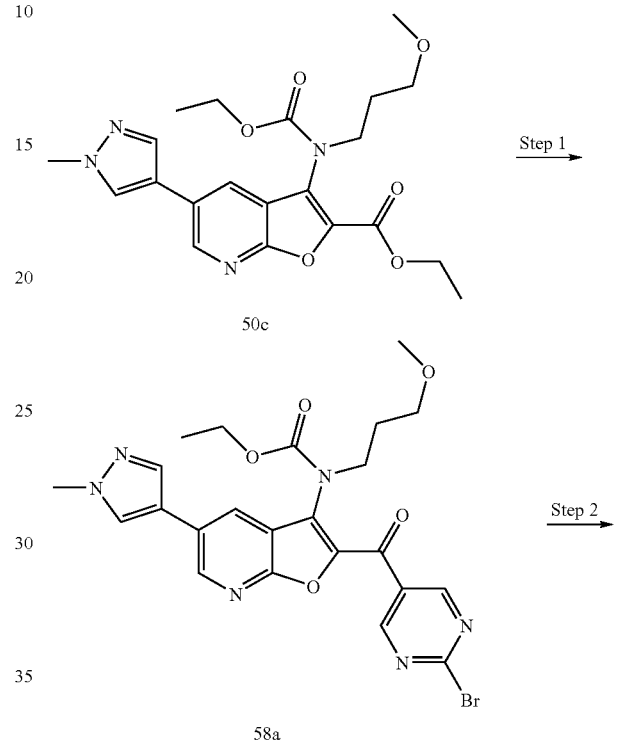

Step 1:

5-Bromopyrimidine (159.5 mg, 1.004 mmol) is placed in an oven flame-dried round-bottom flask and anhydrous THF (3 mL) is added under $N_2$. The solution is then cooled to −78° C. After 3 min n-BuLi (0.627 mL, 1.004 mmol) 1.6 M in THF solution in hexanes is added dropwise over 2 min. The mixture is then stirred at −78° C. for 1 h and a solution of 49e (286 mg, 0.669 mmol) in THF (3 mL) is added dropwise and stirred for 1 h. The reaction is quenched with silica gel. The volatiles are removed followed by a Combiflash purification (10-70% EtOAc/Hex) to afford 57a (139.7 mg, 45%).

Step 2:

Ammonium acetate (400 mg) is added to 57a (139.7 mg, 0.303 mmol) and the mixture is warmed up to 130° C. for 30 min. The resulting mixture is cooled down to RT and quenched with 10N NaOH (3 mL). The mixture is washed with DCM (2×), dried over $MgSO_4$, filtered and concentrated under reduced pressure to afford 57b (125 mg, 0.302 mmol) which is used without any further purification for the next step.

Step 3:

To a suspension of the boronic ester 57c (50 mg, 0.242 mmol) in dioxane (2 mL) (bubbled with Ar during 10 min), are added 57b (50 mg, 0.121 mmol), $K_2CO_3$ (50.2 mg, 0.363 mmol) and CsF (55 mg, 0.363 mmol). The $Pd(PPh_3)_4$ (10 mg, 0.012 mmol) is added and the mixture is heated in the microwave (135° C., 25 min). The solution is concentrated, diluted Step 1:

1,4-dibromopyrazine (350 mg, 1.473 mmol) and 50c (423 mg, 0.982 mmol) are placed in an oven flame-dried round-bottom flask and anhydrous THF (12 mL) is added. The mixture is stirred at RT until a clear solution is obtained. The mixture is stirred under $N_2$ and cooled in a dry-ice/acetone bath (−78° C.) for 15 min. 1.2 M n-BuLi solution in hexanes (1.23 mL, 1.473 mmol) is added dropwise over 50 min. The mixture is then stirred at −78° C. for 1 h. The reaction is quenched with silica gel. Purification using the combiflash eluting with 50/50 EtOAc/Hex followed by 10% MeOH/ EtOAc) gives 58a (332 mg, 0.612 mmol).

Step 2:

Methylpiperazine (35.2 μL, 0.316 mmol) is added to a DMSO (0.5 mL) solution of 58a (86 mg, 0.158 mmol) and the resulting solution is stirred at RT for 15 min. The ammonium acetate (400 mg) is added and the mixture is warmed up to 130° C. for 30 min. The resulting mixture is cooled down to RT and diluted with EtOAc. The organic material is washed with sat aq solution of NaHCO$_3$ and brine. Aq. phase is washed with DCM and the combined organic layers are dried over MgSO$_4$, filtered and concentrated under reduced pressure. Purification by prep HPLC gives 5017 (30 mg, 0.059 mmol).

Example 59

Preparation of Compound 2263 (Table 2)

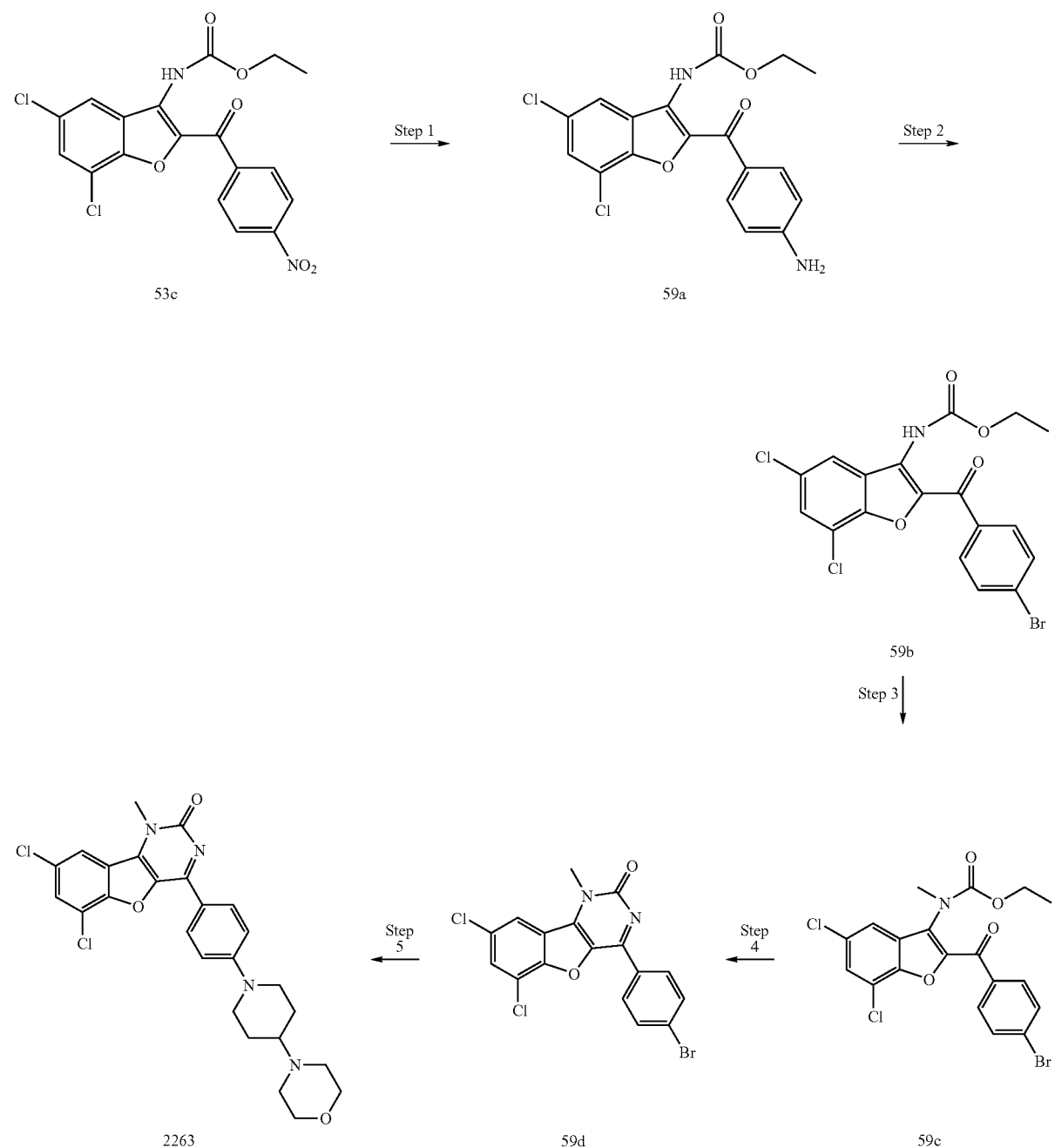

Step 1:

53c (1.6 g, 1 eq) is suspended in anhydrous THF (40 mL), under $N_2$, then 1N aqueous HCl (15 mL, 4 eq) and tin powder are added (3.59 g, 8 eq). The suspension is heated at reflux for 2 h. Additional tin (1.80 g, 4 eq) and 1N aqueous HCl are added and reaction is complete after 2 h. The reaction mixture is cooled down, diluted with EtOAc and saturated aq. $NaHCO_3$, and partitioned in separatory funnel. The aqueous layer is extracted with EtOAc (2×). The organic layer is washed with brine, dried with $MgSO_4$, filtered and evaporated under reduced pressure. 59a thus obtained is dried under high vacuum (960 mg, 65%).

Step 2:

To a stirred suspension of copper (II) bromide (709 mg, 1.2 eq) and tert-butyl nitrite (503 μL 1.6 eq) in $CH_3CN$ (8 mL) at RT is added portionwise a suspension of 59a (840 mg, 1 eq) in $CH_3CN$ (12 mL). The solution is stirred at RT for 3 h. To this mixture is then added 1N aq HCl (5 mL), then water. The precipitate is collected by suction filtration. After drying under suction for 1 h, the residue is suspended in toluene (~10 mL) and the mixture is evaporated under reduced pressure (azeotropic distillation) and dried under high vacuum to obtain bromide 59b, used in the next step without further purification (864 mg, 88%).

Step 3:

59b (434 mg, 1 eq) is dissolved in DMSO (5 mL), and cesium carbonate (650 mg, 2.1 eq) is added at RT. Mixture is stirred for 5 min, iodomethane (70 μL is then added and the mixture is stirred at 45° C. for 45 min. The mixture is diluted with ethyl acetate, and washed with sat aq $NaHCO_3$ (2×). The organic phase is dried with $MgSO_4$, filtered, and evaporated under reduced pressure. The crude product is purified using a CombiFlash Companion with 10% to 40% EtOAc in hexanes gradient to obtain 59c (324 mg, 72%).

Step 4:

59c (324 mg, 1 eq) and ammonium acetate (3.5 g) are mixed and heated to 130° C. under vigorous stirring for 5 h. Cooled down, then water (~25 mL) is added, and the precipitate is filtered under suction, dried for 2 h under suction, then the solid is collected in a round bottom flask suspended in toluene (ca. 10 mL) and the mixture is evaporated under reduced pressure (azeotropic distillation). Product 59d is used in the subsequent step without purification (244 mg, 84%).

Step 5:

59d (75 mg, 1 eq), 4-morpholinopiperidine (45 mg, 1.5 eq), and anhydrous potassium phosphate (75 mg, 2.0 eq), are dissolved in anhydrous DME (1.5 mL). Solution is degassed with Ar under sonication for 5 min. Bis(tri-butylphosphine)palladium(0) is added to the reaction mixture, and heated at 100° C. for 6 h. The reaction mixture is cooled down and concentrated under reduced pressure. Redissolved in DMSO and AcOH and purified by prep HPLC 2263 is obtained after lyophilization (19 mg, 21%).

Example 60

Preparation of Compound 2273 (Table 2)

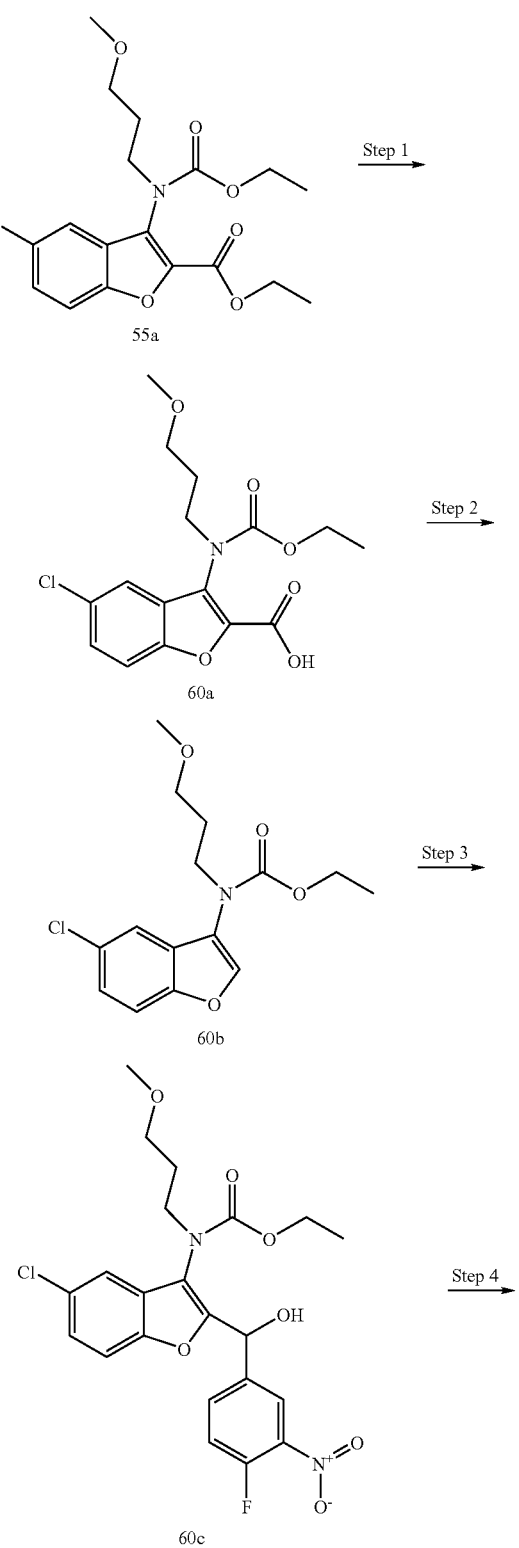

161
-continued
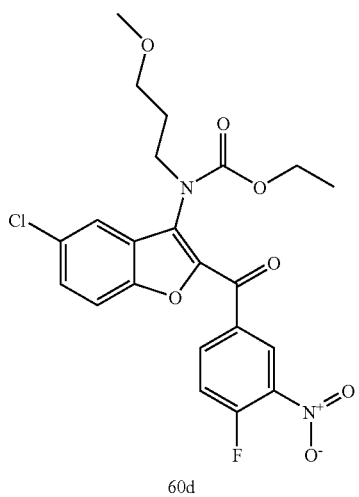
60d
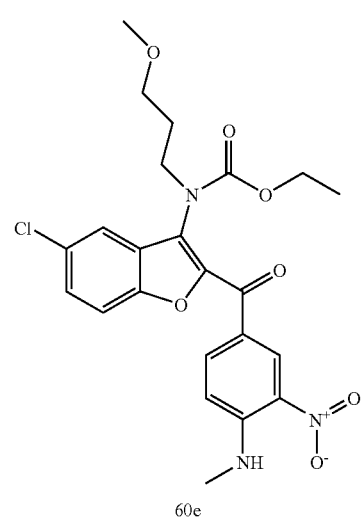
60e
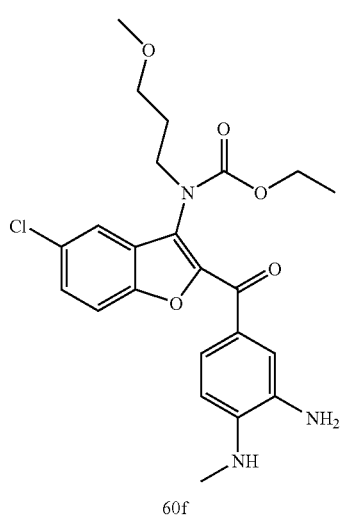
60f
162
-continued
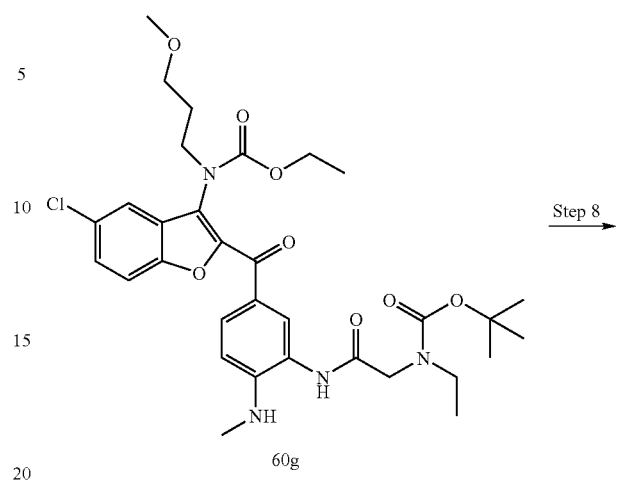
60g
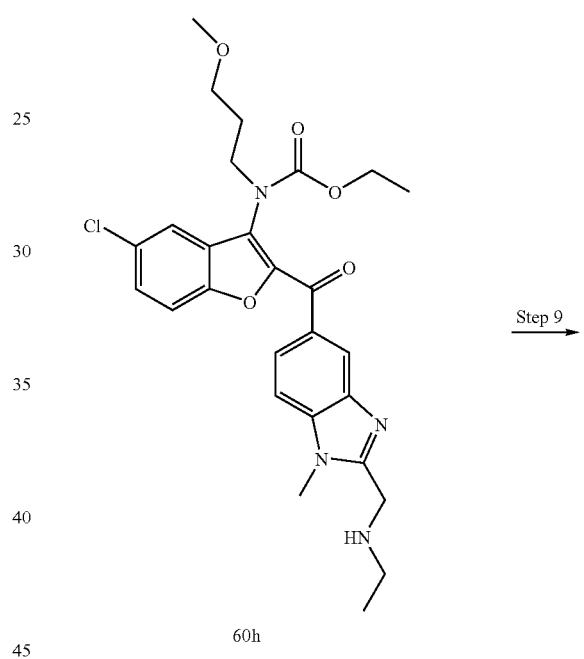
60h
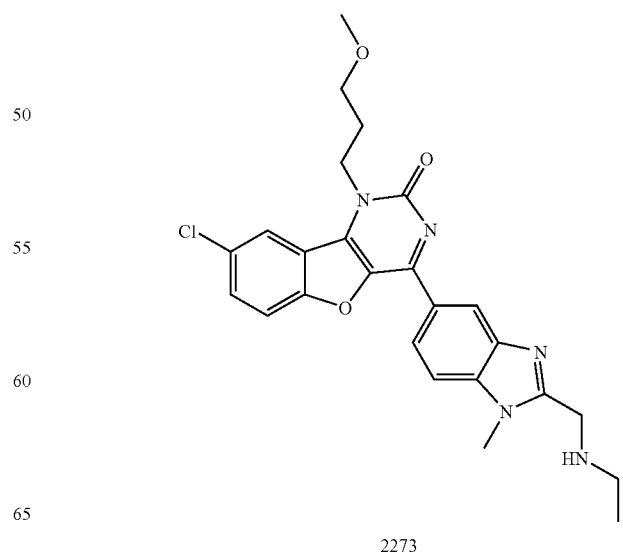
2273
Step 5
Step 6
Step 7
Step 8
Step 9

Step 1:
A mixture of KOH (1.69 g, 2.1 eq) and ester 55a (5.51 g, 1 eq) in MeOH/H₂O (75 mL/25 mL) is stirred at reflux for 2 h. The reaction mixture is cooled down, diluted with water, neutralized with HCl 1N (30 mL, 2.1 eq) and concentrated under reduced pressure. The resulting crude residue is extracted with EtOAc (2×). The organic phase is washed with brine, dried with Na₂SO₄, filtered and concentrated. The resulting oil is subjected to high vacuum for 18 h to obtain 60a (4.88 g, 95%), used without further purification in step 2.

Step 2:
60a (4.25 g, 1 eq) is dissolved in quinoline (15 mL) in a 10-20 mL Biotage microwave vial equipped with a magnetic stirrer. The solution is degassed with N₂ for 15 min. Copper powder is then added to the mixture, and it is heated in a Biotage microwave at 220° C. for 2 h (CAUTION! Pressure increase due to CO₂ evolution). The reaction mixture is then diluted with EtOAc (200 mL), washed with 0.5 N aq HCl (3×200 mL). The aqueous layer is re-extracted with EtOAc (2×). The combined organic layers are washed successively with 1N aq NaOH, water, and brine. The organic phase is dried with MgSO₄, filtered and evaporated. 60b (2.74 g, 74%) is obtained after purification by silica gel flash chromatography (20:80 EtOAc:Hex).

Step 3:
60b (510 mg, 1 eq) is dried by azeotropic distillation using toluene prior to the reaction. The product is then dissolved in situ with THF (9 mL) and cooled to −78° C., under N₂. A solution of LDA (2.0M in THF/Hex/ethylbenzene, 1.06 mL, 1.3 eq) is added slowly over a period of 5 min, and after a further 15 min of stirring at −78° C., 4-chloro-3-nitrobenzaldehyde (364 mg, 1.2 eq) is added in one addition. Reaction mixture is stirred for 10 min, and then a solution of ammonium chloride is added. Mixture is extracted with EtOAc, washed with brine, dried with Na₂SO₄, filtered and evaporated. 60c (665 mg, 82%) is obtained after purification by Combiflash Companion chromatography instrument (40 g column, 10:90 to 30:70 EtOAc:Hex).

Step 4:
Product 60c (477 mg, 1 eq) is dissolved in DCM (8 mL), cooled to 0° C., and Dess-Martin periodinane (448 mg, 1.1 eq) is added in one portion. The reaction mixture is warmed to RT and stirred for 2 h, under N₂. Aqueous 10% sodium thiosulfate is added. The mixture is extracted with EtOAc, and the organic layer is washed with aq sodium bicarbonate, brine and dried with MgSO₄. The solvent is evaporated under reduced pressure. Crude product is purified by silica gel flash chromatography (10% to 50% EtOAc in Hex) to obtain 60d (500 mg, 63%)

Step 5:
Product 60d (500 mg, 1 eq) is dissolved in THF (4 mL) and DMSO (3 mL). Methylamine solution (2.0M in THF, 1.2 mL, 2.4 eq) and DIPEA (350 µL, 2 eq) are added. The solution is heated at 65° C. for 2 h. Cooled down; reaction mixture is diluted with EtOAc. The organic phase is washed with sat aq sodium bicarbonate, brine, and dried with MgSO₄. The organic phase is filtered and the solvent is evaporated under reduced pressure. Compound 60e (368 mg, 74%) is dried under high vacuum for 1 h and used in the next step without further purification.

Step 6:
60e (668 mg, 1 eq) is dissolved in THF (5.5 mL) and tin powder (275 mg, 1.7 eq) and 1N aqueous HCl (5.3 mL, 3.9 eq) are added to the solution at RT. After 1 h, 1N aq NaOH (5.3 mL, 3.9 eq) is added to the suspension, followed by brine. The reaction mixture is then extracted with EtOAc (20 mL). The organic phase is washed with brine, dried over Na₂SO₄, filtered, and concentrated under reduced pressure. After drying under high vacuum, 60f is obtained (588 mg, 94%).

Step 7:
N-tert-butoxycarbonyl-N-ethylglycine (50 mg, 1 eq) is dissolved in DMF (1 mL), and DIPEA (50 µL, 2.5 eq) is added, followed by HATU (49 mg, 1.2 eq) at RT. After stirring for 10 min, aniline 60f (50 mg, 1 eq) is added. The reaction mixture is stirred at RT for 16 h. The mixture is diluted with EtOAc, and washed twice with sat aq sodium bicarbonate. The organic phase is washed with brine, dried with Na₂SO₄, filtered and concentrated under reduced pressure to obtain 60 g, which is used in the next step without further purification.

Step 8:
Crude 60 g is dissolved in acetic acid (2 mL) and stirred at 80° C. for 3 h. The solution is then concentrated under reduced pressure (45 min). The residue is dissolved in DCM (2 mL) and TFA (0.6 mL) and stirred for 1 h at RT. The reaction mixture is then concentrated under reduced pressure and dried under high vacuum to obtain 60 h which is used in the next step as is.

Step 9:
A mixture of 60 h and ammonium acetate is heated to 130° C. After 2 h, the mixture is cooled down, and dissolved in DMSO, AcOH, MeOH with the addition of a few drops of water and purified by prep HPLC (water/ACN system with 0.06% TFA as a phase modifier) to obtain 2273 after lyophilization. (24 mg, 45% over 4 steps)

Example 61

Preparation of Compound 2275 (Table 2)

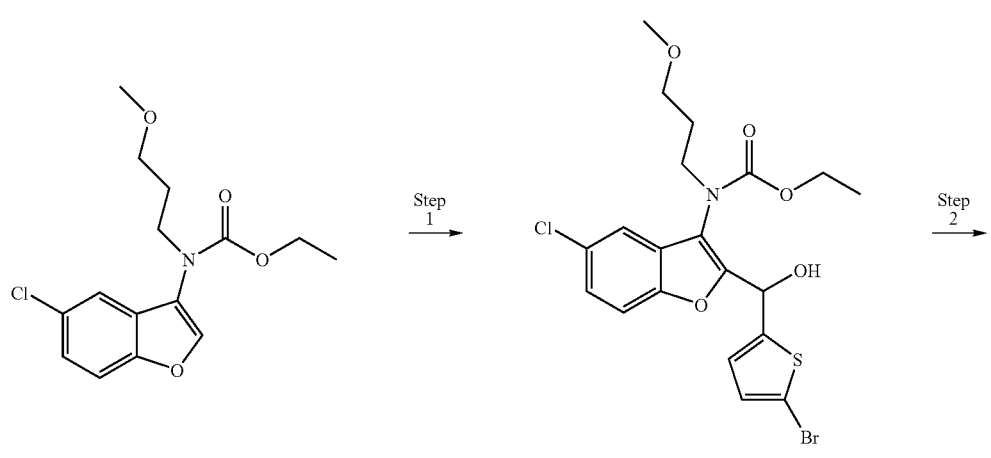

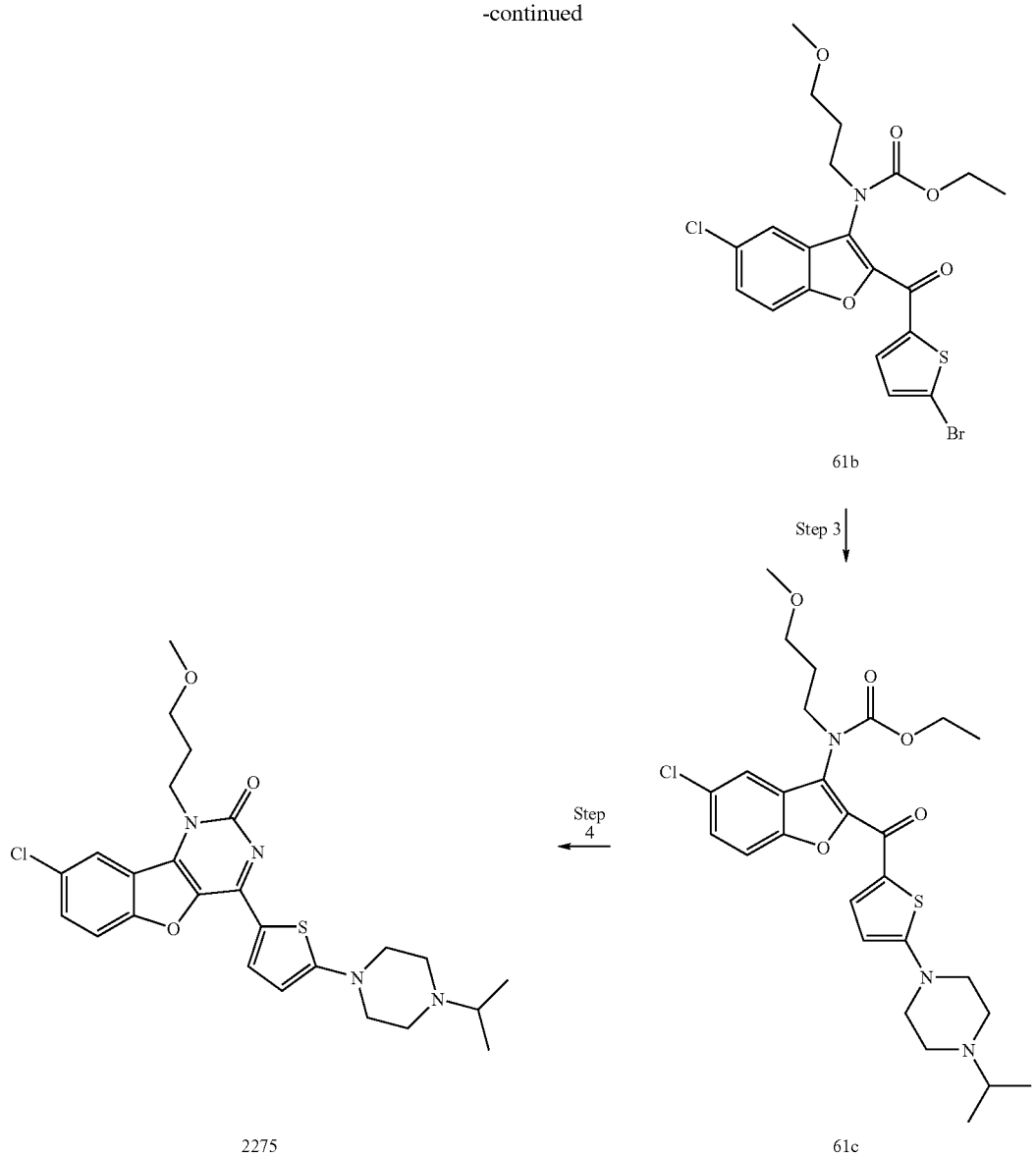

Step 1:

Intermediate 60b (200 mg, 1 eq) is dried by azeotropic distillation using toluene prior to the reaction. The product is then dissolved in situ with THF (3 mL) and cooled to −78° C., under $N_2$. A solution of LDA (0.8M in THF/Hex, 1.6 mL, 2.0 eq) is added slowly over a period of 5 min, and after a further 15 min of stirring at −78° C., 5-bromothiophene-2-carboxaldehyde (147 mg, 1.2 eq) is added in one addition. After stirring for another 15 min, a solution of ammonium chloride is added to the reaction mixture. Mixture is extracted with EtOAc, washed with brine, dried with $Na_2SO_4$, filtered and evaporated. Purification by Combiflash Companion chromatography instrument (40 g silica column, 10:90 to 30:70 EtOAc:Hex eluent gradient) gives 61a (211 mg, 65%).

Step 2:

To a mixture of intermediate 61a (200 mg, 1 eq) dissolved in DCM is added Dess-Martin periodinane (208 mg, 1.3 eq) at 0° C. under $N_2$. After 1 h, the reaction is quenched with aq. sodium thiosulfate and the resulting mixture is extracted with DCM. The organic layer is dried with $Na_2SO_4$ then filtered and evaporated under reduced pressure. The crude residue is purified by chromatography on silica gel using a 5% to 25% EtOAc:Hex to obtain 61b (92 mg, 46%).

Step 3:

Intermediate 61b (70 mg, 1 eq) is dissolved in DMF (1 mL), N-iso-propylpiperazine (95 mg, 3 eq) and DIPEA (49 μl, 2 eq) are added, and the reaction mixture is heated at 95° C. for 18 h. After about 80% conversion, the reaction mixture is diluted with EtOAc and the organic mixture is washed with sat. aq. sodium bicarbonate. The organic phase is washed with brine, dried with $Na_2SO_4$, and concentrated under reduced pressure to obtain 61c, which is used without further purification in the next step.

Step 4:

A mixture of product 61c and ammonium acetate is heated to 130° C. After 2 h, the mixture is cooled down, and the mixture is dissolved in DMSO, AcOH, MeOH with the addition of a few drops of water and purified by prep HPLC (water/ACN system with 0.06% TFA as a phase modifier). After lyophilization compound 2275 is obtained (7 mg, 10% over 2 steps).

Example 62

Preparation of Compound 2287 (Table 2)

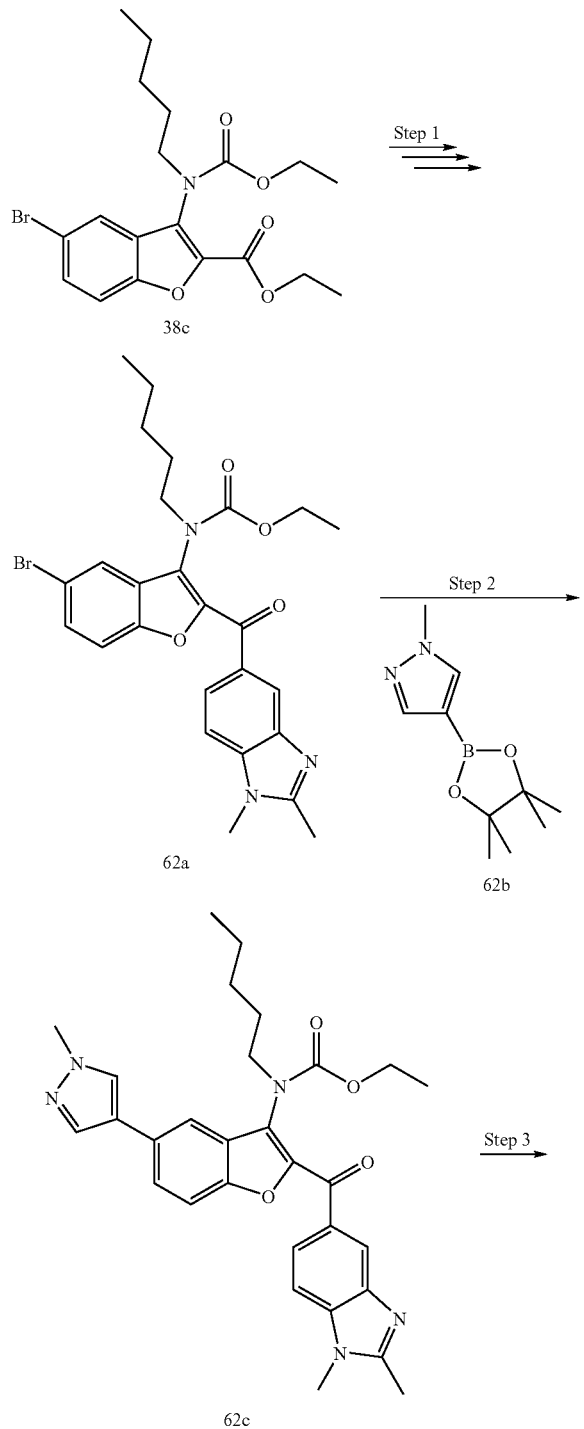

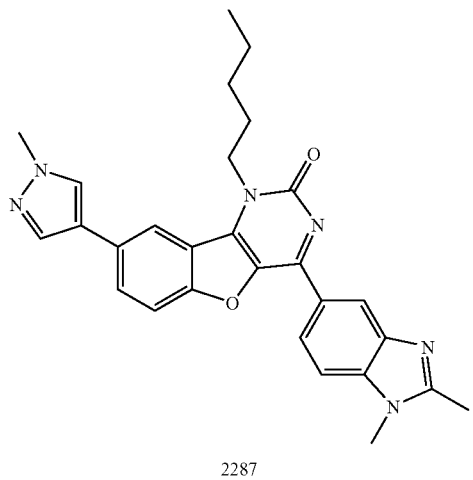 [SMILES: CCCCCn1c(=O)nc(-c2ccc3c(c2)nc(C)n3C)c2oc3ccc(-c4cnn(C)c4)cc3c21]

Step 1:

62a is prepared using the same chemistry as described in example 60, steps 1 to 8, using 38c, instead of 55a as starting material.

Step 2:

62a (125 mg, 1 eq), boronic ester 62b (99 mg, 2.0 eq), $K_2CO_3$ (102 mg, 3.1 eq) and cesium fluoride (108 mg, 3.0 eq) are dissolved in 1,4-dioxane (2.7 mL) and water (0.7 mL) in a 2-5 mL Biotage microwave vial equipped with a stirring magnet. The mixture is degassed with Ar under sonication for 15 minutes, and Pd(dppf)Cl$_2$: dichloromethane complex (19 mg, 0.1 eq) is added. The vial is capped and the reaction mixture is subjected to microwave irradiation in a Biotage microwave system at 135° C. for 25 min. The reaction mixture is then concentrated under reduced pressure, re-dissolved in EtOAc, and washed successively with sat aq sodium bicarbonate and brine. The organic phase is dried with $Na_2SO_4$, filtered, evaporated to obtain 62c, used without further purification in the next step.

Step 3:

A mixture of product 62c, ammonium acetate (800 mg) and DMSO (1 mL) is heated to 125° C. After 2 h, the mixture is cooled down, and the mixture is diluted with AcOH and purified by prep HPLC (water/ACN system with 0.06% TFA as a phase modifier). After lyophilization, compound 2287 is obtained (4 mg, 3.3% over 2 steps)

Example 63
Preparation of Compound 2325 (Table 2)
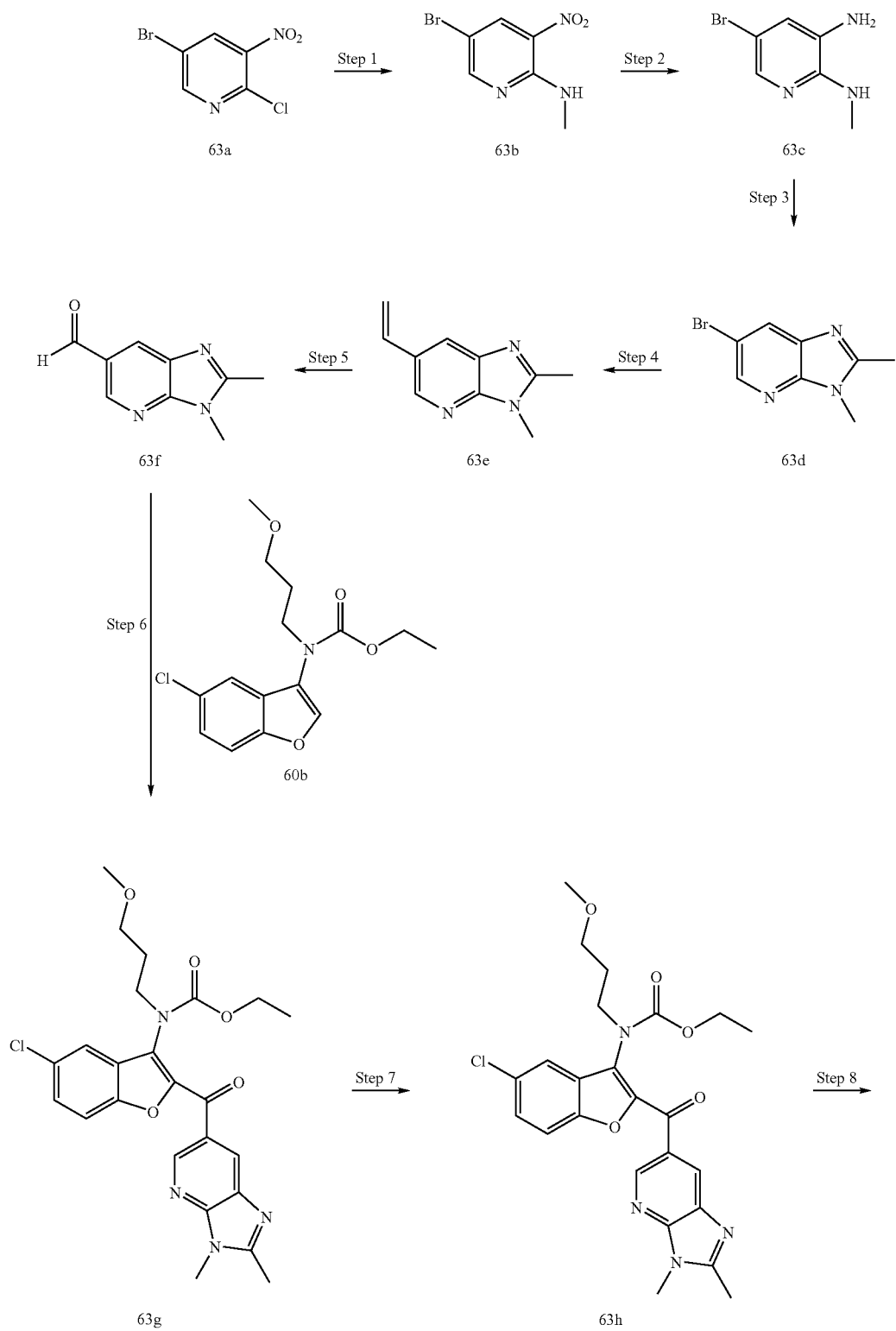

-continued

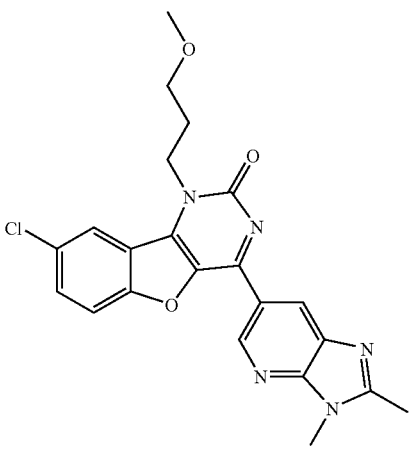

2325

Step 1:

63a (3 g, 1.0 eq) is dissolved in THF (13 mL), and then cooled to 0° C. Methylamine solution (2M in THF, 20.8 mL, 3.3 eq), is slowly added to the reaction mixture (exothermic). The reaction mixture is stirred for 30 min at 0° C. and diluted with EtOAc. Organic layer is washed with sat aq sodium bicarbonate. The aqueous layer is re-extracted with EtOAc (2×). The organic phase is washed with brine, dried with $MgSO_4$, filtered and concentrated under reduced pressure to obtain 63b which dried under high vacuum for 16 h (2.95 g, quantative yield).

Step 2:

63b (2.95 g, 1 eq) is dissolved in THF (51 mL) and 1N aq HCl (50 mL, 3.9 eq) and tin powder (2.57 g, 1.70 eq) are added and stirred at RT for 3 h. 1N NaOH (50 mL) is added, followed by brine. The mixture is extracted with EtOAc (3×). The organic layer is washed with brine, dried over $Na_2SO_4$, filtered and concentrated under vacuum. The obtained 63c is dried under high vacuum and used in the subsequent step without further purification (1.98 g, 77%).

Step 3:

63c (1.00 g, 1 eq) is dissolved in DMF (2.8 mL) and trimethyl orthoacetate (2.87 mL, 3.5 eq). Reaction mixture is stirred at 100° C. for 1 h, then acetic acid (570 µL, 2 eq) is added and heating is pursued for 16 h. After cooling, the reaction mixture is diluted with EtOAc and the resulting solution is washed with a 1:1 brine:sat aq sodium bicarbonate. The aqueous layer is re-extracted with EtOAc (3×), and the combined organic extracts are evaporated under reduced pressure to obtain 63d, used without further purification in the following step (944 mg, 84%).

Step 4:

63d (651 mg, 1 eq) is dissolved in DMF (9 mL) in a sealable tube, and tributyl(vinyl)tin (1.00 mL, 1.2 eq) is added. The mixture is degassed with Ar under sonication for 10 min. Palladium (0) tetrakis(triphenylphosphine) (333 mg, 0.1 eq) is added to the mixture. The sealed tube is capped, and the mixture is stirred at 100° C. for 2 h. The reaction mixture is diluted with EtOAc, washed with sat aq sodium bicarbonate. The aqueous layer is re-extracted with EtOAc (2×). The combined organic extracts are washed with brine; silica (10 g) is added, and the mixture is evaporated under reduced pressure until a dry powder is obtained. The compound impregnated on silica is then purified by flash chromatography on silica gel (0.5% to 8% MeOH in DCM) to obtain compound 63e is obtained (270 mg, 54%).

Step 5:

Product 63e is dissolved in a $THF:H_2O$ mixture (5 mL:5 mL); the solution is cooled to 0° C., then osmium tetroxide (425 µL of a 2.5% solution in tert-butanol, 0.02 eq) is added, followed by sodium periodate (798 mg, 2.2 eq). The reaction mixture is gradually warmed to RT, and stirred for 12 h. The solvent is evaporated under reduced pressure. The crude residue is diluted with EtOAc, washed with water and brine. The aqueous fraction is re-extracted with 2-methyltetrahydrofuran (30 mL). The combined organic layers are dried with $MgSO_4$, filtered, and evaporated under reduced pressure to isolated 63f (201 mg, 74%). 63f is further dried by azeotropic distillation with toluene and kept under Ar atm at 0° C.

Step 6:

Intermediate 60b (140 mg, 1 eq) is dried by azeotropic distillation using toluene prior to the reaction. The product is then dissolved in situ with THF (3 mL) and cooled to −78° C., under $N_2$. A solution of LDA (0.7 M in THF/Hex, 1.5 mL, 2.2 eq) is added slowly over a period of 5 min, and stirring continued for another 15 min at −78° C. Aldehyde 63f (120 mg, 1.4 eq) is added in one addition. The temperature of the reaction mixture is rapidly increased to 0° C., upon which the aldehyde 63f is solubilized. Reaction mixture is stirred for 15 min and then few drops of 1N aq HCl are added. Silica (1 g) is added to the reaction mixture, solvent is evaporated until a solid is obtained. The compound impregnated on silica is then purified by flash chromatography (1% to 5% MeOH in DCM) to obtain compound 63g (59 mg, 25%).

Step 7:

To compound 63g (59 mg, 1 eq) dissolved in DCM is added Dess-Martin periodinane (208 mg, 1.3 eq) at 0° C. under $N_2$. After 1 hour, silica (1 g) is added to the reaction mixture and the solvent is evaporated. The product is purified using flash chromatography (1% to 5% MeOH in DCM) to obtain compound 63h (34 mg, 55%).

Step 8:

A mixture of 63h, ammonium acetate (300 mg) and DMSO (500 µL) is heated at 135° C.

After 2 h, the mixture is cooled down, diluted with AcOH and purified by prep HPLC (water/ACN system with 0.06% TFA as a phase modifier). After lyophilization compound 2325 is obtained (15 mg, 52%).

Example 64

Preparation of Compound 2270 (Table 2)

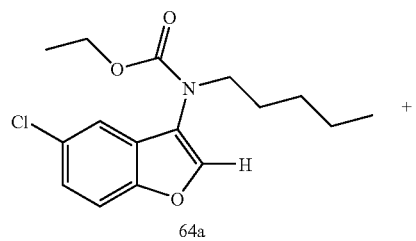
64a

+

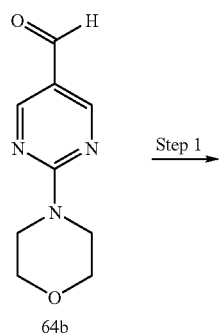
64b

→ Step 1

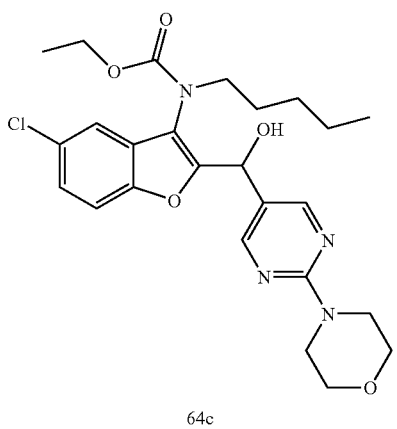
64c

→ Step 2

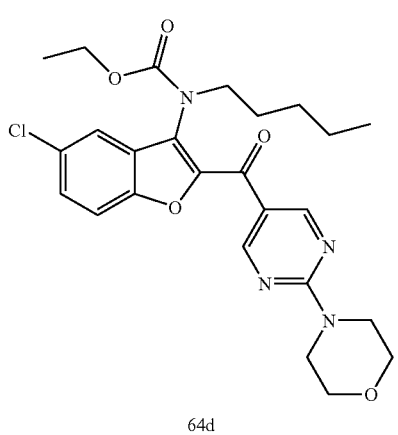
64d

→ Step 3

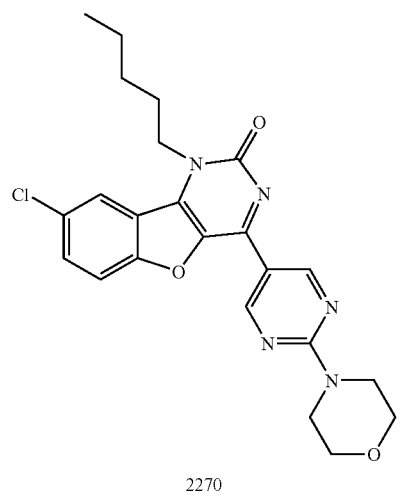 [SMILES: CCCCCn1c(=O)nc(-c2cnc(N3CCOCC3)nc2)c2oc3ccc(Cl)cc3c21]
2270

Step 1:

Compound 64a is prepared using same procedure described in example 60 to prepare 60b, using 38c as starting material.

A solution of benzofuran 64a (150 mg, 1.0 eq) in THF is cooled to −78° C. BuLi (0.41 mL of a 1.3 M solution in hexanes) is added dropwise over 10 min. The resulting solution is stirred at −78° C. for 20 min. A solution of aldehyde 64b (140 mg, 1.5 eq) in THF is added to the benzofuran solution at −78° C. The resulting solution is stirred at −78° C. for 2 h. Sat. solution of NH$_4$Cl is added and the mixture is extracted with EtOAc (3×). The combined organic layers are washed with brine, dried over MgSO$_4$, filtered and purified by flash chromatography on silica gel (0-5% MeOH/CH$_2$Cl$_2$) to provide compound 64c (219 mg, 89%)

Step 2:

A mixture of benzofuran 64c (219 mg, 1.0 eq), Dess-Martin reagent (221 mg, 1.2 eq) in CH$_2$Cl$_2$ is stirred at RT for 1 h. Silica gel is poured into the mixture then evaporated to a residue. Purification by flash chromatography on silica gel (0-15% MeOH/CH$_2$Cl$_2$) affords compound 64d (151 mg, 69%).

Step 3:

A mixture of benzofuran 64d (151 mg, 1.0 eq) and NH$_4$OAc (1 g, 46 eq) is heated at 140° C. (open air) with stirring for 1.5 h. The mixture is diluted in EtOAc, washed with H$_2$O (2×), NaHCO$_3$ (2×), then dried over MgSO$_4$. The residue is purified by prep HPLC to provide compound 2270 (2.3 mg, 2%).

Example 65

Preparation of Compound 3003 (Table 3)

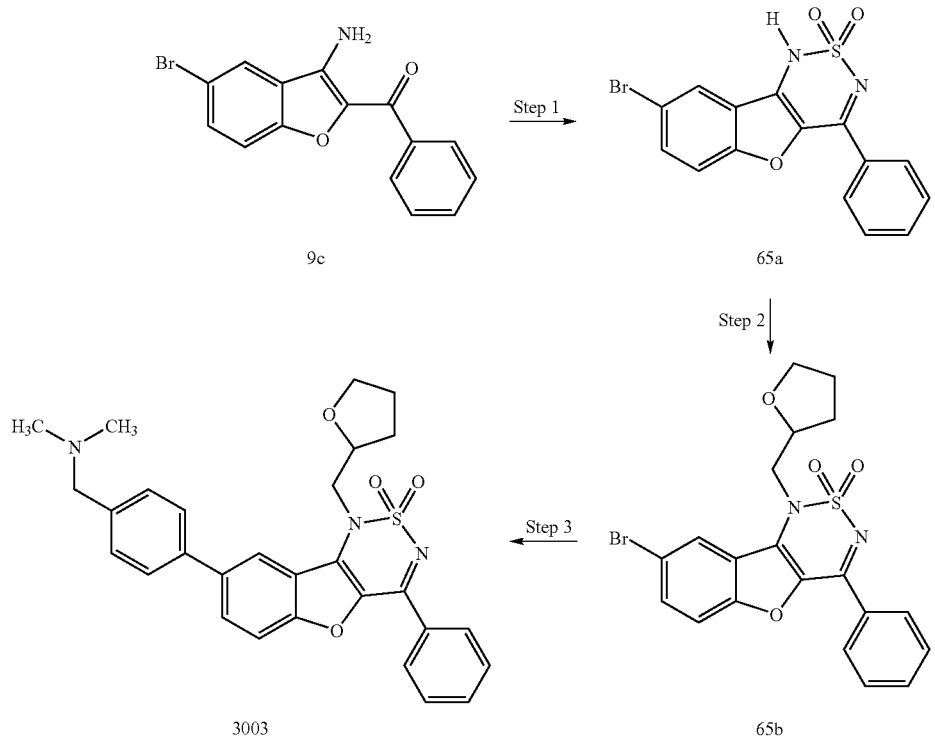 [SMILES: Nc1c(C(=O)c2ccccc2)oc2ccc(Br)cc12 ; O=S1(=O)N=C(c2ccccc2)c2oc3ccc(Br)cc3c2N1 ; CN(C)Cc1ccc(-c2ccc3oc4c(c3c2)N(CC2CCCO2)S(=O)(=O)N=C4c2ccccc2)cc1 ; O=S1(=O)N=C(c2ccccc2)c2oc3ccc(Br)cc3c2N1CC1CCCO1 ; "3003" ; "65b"]

Step 1:

Formic acid (0.75 mL, 200 mmol) is added dropwise to neat chlorosulfonyl isocyanate (1.74 mL, 20 mmol) at 0° C. with rapid stirring and stirring is continued at RT until gas evolution ceases (~1 h). The mixture is dissolved in DCM (6 mL) and allowed to stir until no further gas evolution is observed to give a mixture which is ~3 M in chlorosulfonamide. The chlorosulfonamide mixture (3.26 mL, 9.49 mmol,) is added to a mixture of compound 9c (Example 9, step 1) (1.5 g, 4.75 mmol) and pyridine (0.8 mL, 9.49 mmol) in DCM at 0° C. The mixture is allowed to warm to RT for 12 h and is filtered. The solid is taken up in EtOH (10 mL) and sodium ethoxide (4.6 mL, 14.2 mmol) is added. The mixture is allowed to stir for 12 h and then acidified with 10% HCl (100 mL) and filtered. The solid is mixed with EtOAc and the mixture is washed ($H_2O$), dried ($MgSO_4$), filtered and concentrated under reduced pressure. The residue is triturated with $Et_2O$ to obtain compound 65a (1.20 g, 67%).

Step 2:

A mixture of sulfonamide 65a (50 mg, 0.133 mmol), 2-bromomethyltetrahydrofuran (109 mg, 0.40 mmol) and $K_2CO_3$ (55.0 mg, 0.40 mmol) in DMF is heated at 110° C. for 6 h, then cooled to RT and diluted with EtOAc. The organic phase is washed with brine (2×) and water, dried ($MgSO_4$), filtered and concentrated under reduced pressure to provide compound 65b.

Step 3:

A mixture of compound 65b (50 mg, 0.128 mmol), 4-((N,N-dimethylaminomethyl) phenylboronic acid pinacol ester (67 mg, 0.256 mmol), $Pd(dppf)Cl_2$ (9.7 mg, 0.013 mmol), $K_2CO_3$ (55.0 mg, 0.40 mmol) and CsF (40.4 mg, 0.27 mmol) in dioxane (2 mL) and $H_2O$ (0.5 mL) is allowed to stir for 1 min and is then heated in a microwave reaction vessel at 135° C. for 25 min. The mixture is concentrated under reduced pressure and the residue is diluted with AcOH/DMF (1.5/1.5) mL, filtered and purified by prep HPLC to give compound 3003 (17 mg, 74%).

Example 66

Preparation of Compounds for Biological Assays

Diluted solutions of stock solutions of compounds of Formula I in DMSO are prepared in assay buffer in Eppendorf tubes 16 h prior to their use in the biological assay, using a minimal supplementary volume of 75 μL of assay buffer in addition to the volume required in the assay. The samples are vortexed for 10 min at RT and incubated for 16 h at 4° C. The equilibrated solutions are centrifuged at 16 000 g for 5 min in a centrifuge equipped with an internal chiller, which is pre-equilibrated at 4° C., and the supernatant is collected. The portion of supernatant required for the serial dilutions in the biological assay is transferred to the compound dilution plate and a 75 μL portion of the remaining supernatant is transferred to a 1.4 mL tube (Micronic). A 25 μL volume of DMSO is promptly added and the sample is submitted for concentration determination by HPLC, along with the stock solution of the compound in DMSO as a standard for concentration determination analysis.

Example 67

HIV Reverse Transcriptase Assay ($IC_{50}$)

The assay used to measure inhibition of HIV reverse transcriptase is as described in WO 2006/034583, pages 52-53, incorporated herein by reference, except that 1 mM of ATP was added to the reaction mixture.

Example 68

C8166 HIV-1 Luciferase Assay ($EC_{50}$)

The assay used to measure inhibition of HIV replication is as described in WO 2004/050643, pages 73-75, incorporated herein by reference, with the following modifications:

Preparation of Compounds

Serial dilutions of HIV-1 inhibitors are prepared in complete media from DMSO stock solutions. Eleven serial dilutions of desired concentration are prepared in a 1 mL deep well titer plate (96 wells). The 12th well contains complete media with no inhibitor and serves as the positive control. All samples contain the same concentration of DMSO (<0.1% DMSO). Inhibitor is added, to triplicate wells, of a 96 well tissue culture treated clear view black microtiter plate (Corning Costar catalogue #3904). The total volume per well is 200 μL of media containing the cells and inhibitor. The last row is reserved for uninfected C8166 LTRluc cells to serve as the background blank control and the first row is media alone.

Infection of Cells

Count C8166 LTRluc cells and place in a minimal volume of complete RPMI 1640 in a tissue culture flask (ex. 30×106 cells in 10 mL media/25 cm² flask). Infect cells with HIV-1 at a moi of 0.005. Incubate cells for 1.5 h at 37° C. on a rotating rack in a 5% $CO_2$ incubator. Resuspend cells in complete RPMI to give a final concentration of 25,000-cells/well. Add cells to wells of 96 well microtiter plate containing inhibitors. Add 25,000 uninfected C8166-LTRluc cells/well in 200 μL complete RPMI to last row for background control. Incubate cells at 37° C. in 5% $CO_2$ incubator for 3 days.

Luciferase Assay

50 μL Steady Glo (luciferase substrate $T_{1/2}$=5 hours Promega catalogue # E2520) is added to each well of the 96 well plate. The relative light units (RLU) of luciferase are determined using a luminescence plate reader. The calculated % inhibition values are used to determine $EC_{50}$, slope factor (n) and maximum inhibition ($I_{max}$).

Tables of Compounds

The following tables list compounds representative of the invention. All compounds listed in Tables 1 to 5 are tested in the assay described in Example 67 or the assay described in Example 68 or both. Compounds show an $IC_{50}$ value in the range of 100 μM or less, and mostly in a range of 50 μM or less and/or compounds tested in the assay of Example 68 showed $EC_{50}$ value in the range of 100 μM or less. Specific $IC_{50}$ and $EC_{50}$ values are provided in Table 6 for representative compounds drawn from the tables.

Retention times ($t_R$) for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

| Cpd | R¹ | R² | $t_R$ (min) | MS (M + H)⁺ |
|---|---|---|---|---|
| 1001 | pyrrolidinyl-ethyl | phenyl | 1.49 | 360.2 |
| 1002 | $CH_3$ | 4-(2-(4-methylpiperazin-1-yl)acetamido)phenyl | 1.13 | 432.2 |

TABLE 1-continued

| Cpd | R¹ | R² | $t_R$ (min) | MS $(M+H)^+$ |
|---|---|---|---|---|
| 1003 | CH₃CH₂CH₂— | 4-(NHC(O)CH₂N(CH₃)₂)phenyl | 3.55 | 405.2 |
| 1004 | CH₃OCH₂CH₂— | 4-(NHC(O)CH₂N(CH₃)₂)phenyl | 3.18 | 421.2 |
| 1005 | CH₃OCH₂CH₂— | 4-(NHC(O)CH₂-morpholinyl)phenyl | 2.93 | 463.1 |
| 1006 | CH₃OCH₂CH₂— | 3-(NHC(O)CH₂-pyrrolidinyl)phenyl | 2.70 | 447.1 |
| 1007 | CH₃OCH₂CH₂— | 4-(NHC(O)CH₂N(iPr)(CH₃))phenyl | 3.08 | 449.1 |

TABLE 1-continued

| Cpd | R¹ | R² | $t_R$ (min) | MS $(M+H)^+$ |
|---|---|---|---|---|
| 1008 | CH₃OCH₂CH₂— | *p*-substituted phenyl-NHC(O)CH₂-N(piperidine-4-C(O)NHCH₃) | 2.92 | 518.1 |
| 1009 | CH₃OCH₂CH₂— | *p*-substituted phenyl-NHC(O)CH₂-NHCH₂CH₃ | 2.61 | 421.1 |
| 1010 | CH₃OCH₂CH₂— | *p*-substituted phenyl-NHC(O)CH(CH₃)N(CH₃)₂ | 2.99 | 435.2 |
| 1011 | CH₃OCH₂CH₂— | phenyl-NHC(O)N(CH₃)₂ | 3.45 | 391.2 |
| 1012 | CH₃OCH₂CH₂— | *p*-substituted phenyl-NHC(O)CH₂-N(3-oxopiperazin-1-yl) | 3.44 | 476.2 |

TABLE 1-continued

| Cpd | R¹ | R² | $t_R$ (min) | MS (M + H)⁺ |
|---|---|---|---|---|
| 1013 | CH₃OCH₂CH₂— | 4-(NHCOCH₂N(Et)CH₂CH₂OCH₃)phenyl | 3.95 | 479.3 |
| 1014 | CH₃OCH₂CH₂— | 4-(NHCOCH₂-(4-methylpiperazin-1-yl))phenyl | 3.06 | 476.2 |
| 1015 | CH₃CH₂CH₂— | 3-(NHCOCH₂N(CH₃)₂)phenyl | 3.62 | 405.2 |
| 1016 | CH₃OCH₂CH₂— | 4-(NHC(O)NHCH₂CH₂-pyrrolidin-1-yl)phenyl | 3.43 | 476.2 |
| 1017 | CH₃OCH₂CH₂— | 4-(NHC(O)NHN(CH₃)₂)phenyl | 3.82 | 422.2 |
| 1018 | CH₃OCH₂CH₂— | 4-(C(O)-piperazin-1-yl)phenyl | 2.30 | 433.2 |

TABLE 1-continued
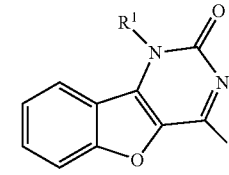
| Cpd | R¹ | R² | $t_R$ (min) | MS $(M + H)^+$ |
|---|---|---|---|---|
| 1019 | CH₃OCH₂CH₂— | 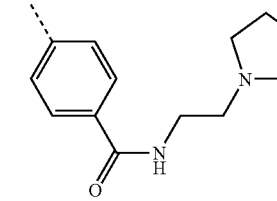 | 2.45 | 461.3 |
| 1020 | CH₃OCH₂CH₂— | 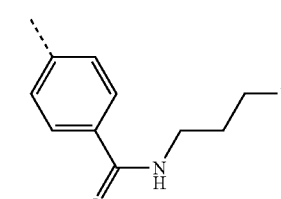 | 2.47 | 475.3 |
| 1021 | CH₃OCH₂CH₂— | 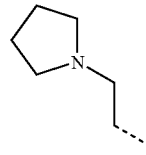 | 2.39 | 449.3 |
| 1022 | 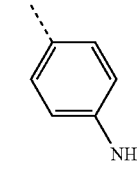 | 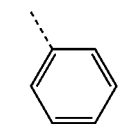 | 1.21 | 375.2 |
| 1023 | (CH₃)₂NCH₂CH₂— | 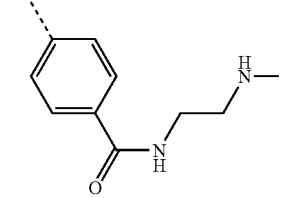 | 1.41 | 334.2 |
| 1024 | CH₃OCH₂CH₂— | 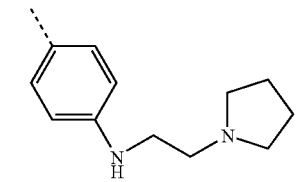 | 2.38 | 421.2 |
| 1025 | CH₃OCH₂CH₂— |  | 1.30 | 433.3 |

TABLE 1-continued

| Cpd | R¹ | R² | $t_R$ (min) | MS $(M + H)^+$ |
|---|---|---|---|---|
| 1026 | CH₃OCH₂CH₂— | 4-[C(O)NHCH₂CH₂N(CH₃)₂]-phenyl | 1.36 | 435.3 |
| 1027 | 2-methylpyrrolidin-1-yl-ethyl | phenyl | 1.62 | 374.3 |
| 1028 | 3-carbamoylpiperidin-1-yl-ethyl | phenyl | 1.49 | 417.3 |
| 1029 | isobutylamino-ethyl | phenyl | 2.06 | 362.3 |
| 1030 | propargylamino-ethyl | phenyl | 1.82 | 344.2 |
| 1031 | ethylamino-ethyl | phenyl | 1.98 | 348.3 |
| 1032 | furan-2-ylmethylamino-ethyl | phenyl | 1.97 | 386.2 |
| 1033 | cyclopropylmethylamino-ethyl | phenyl | 2.00 | 360.3 |

TABLE 1-continued

| Cpd | R¹ | R² | $t_R$ (min) | MS $(M+H)^+$ |
|---|---|---|---|---|
| 1034 | furan-3-ylmethyl-NH-CH₂- | phenyl | 1.96 | 386.3 |
| 1035 | H₃CO-CH₂CH₂-N(CH₂CH₃)-CH₂- | phenyl | 1.66 | 392.3 |
| 1036 | CH₃OCH₂CH₂— | 4-(OCH₂CH₂N(CH₃)₂)phenyl | 2.45 | 408.3 |
| 1037 | pyrrolidin-1-yl-propyl | 4-(NHC(O)CH₂NHCH₂CH₃)phenyl | 1.96 | 460.3 |
| 1038 | CH₃OCH₂CH₂— | phenyl-CH₂-N⁺(CH₃)₂(CH₂CH₂NH₂) Br⁻ | 1.28 | 421.3 |
| 1039 | CH₃OCH₂CH₂— | 4-(CH₂NHCH₂CH₂N(CH₃)₂)phenyl | 1.32 | 421.3 |

TABLE 1-continued

| Cpd | R¹ | R² | $t_R$ (min) | MS $(M+H)^+$ |
|---|---|---|---|---|
| 1040 | CH₃OCH₂CH₂— | 4-(2-(dimethylamino)ethoxymethyl)phenyl | 1.61 | 422.3 |
| 1041 | CH₃OCH₂CH₂— | 4-((dimethylamino)methyl)phenyl | 1.38 | 378.2 |
| 1042 | pyrrolidin-1-ylpropyl | 4-cyanophenyl | 1.66 | 385.3 |
| 1043 | 1-propyl-piperidine-3-carboxylic acid | phenyl | 1.74 | 418.3 |
| 1044 | CH₃OCH₂CH₂— | 4-(N-(2-(dimethylamino)ethyl)-N-methylcarbamoyl)phenyl | 1.57 | 449.3 |
| 1045 | CH₃OCH₂CH₂— | 4-((cyclopentylamino)methyl)phenyl | 1.81 | 418.4 |

TABLE 1-continued
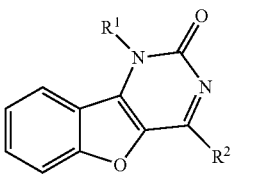
| Cpd | R¹ | R² | $t_R$ (min) | MS $(M + H)^+$ |
|---|---|---|---|---|
| 1046 | CH₃OCH₂CH₂— | 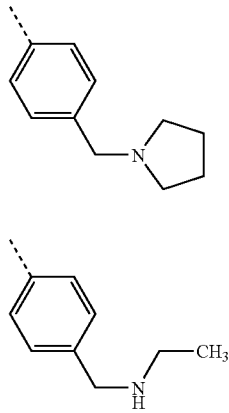 | 1.67 | 404.3 |
| 1047 | CH₃OCH₂CH₂— | 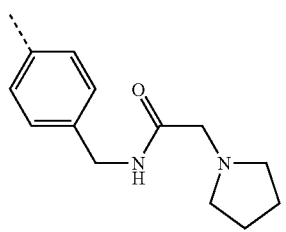 | 1.62 | 378.3 |
| 1048 | CH₃OCH₂CH₂— | 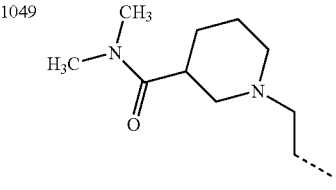 | 1.69 | 461.4 |
| 1049 | 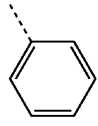 | 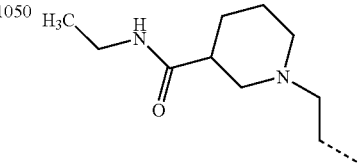 | 1.91 | 445.4 |
| 1050 | 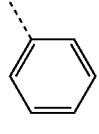 | 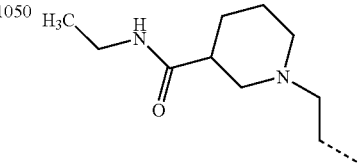 | 1.96 | 445.4 |
| 1051 | CH₃ | 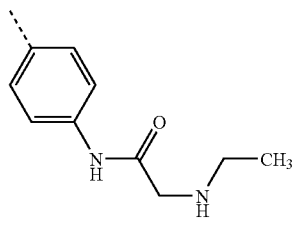 | 1.35 | 377.3 |

TABLE 1-continued

| Cpd | R¹ | R² | $t_R$ (min) | MS (M + H)⁺ |
|---|---|---|---|---|
| 1052 | OCH₃─CH₂CH₂─N(H)─C(O)─[piperidine-3-yl]─N─CH₂CH₂─ | phenyl | 1.63 | 475.5 |
| 1053 | morpholine-N─C(O)─[piperidine-3-yl]─N─CH₂CH₂─ | phenyl | 1.64 | 487.4 |
| 1054 | H₃CO─CH₂CH₂─N(CH₃)─C(O)─[piperidine-3-yl]─N─CH₂CH₂─ | phenyl | 1.68 | 489.4 |
| 1055 | H₃C─CH₂CH₂─N(CH₃)─C(O)─[piperidine-3-yl]─N─CH₂CH₂─ | phenyl | 1.78 | 473.5 |
| 1056 | CH₃OCH₂CH₂─ | 2-OCH₃, 3-NHC(O)CH₂-pyrrolidinyl phenyl | 1.35 | 477.4 |
| 1057 | morpholine-N─CH₂CH₂─ | 2-OH phenyl | 1.42 | 392.1 |
| 1058 | CH₃─ | 3-OCH₂CH₂N(CH₃)₂ phenyl | 1.24 | 364.1 |

TABLE 1-continued

| Cpd | R¹ | R² | $t_R$ (min) | MS $(M+H)^+$ |
|---|---|---|---|---|
| 1059 | H₃C-N(piperidin-4-yl) | phenyl | 1.41 | 360.1 |
| 1060 | CH₃— | phenyl | 1.09 | 292.0 |
| 1061 | CH₃— | 4-methoxyphenyl | 1.64 | 307.0 |
| 1062 | CH₃— | 3-aminophenyl | 1.10 | 292.0 |
| 1063 | CH₃— | 4-(2-(dimethylamino)acetamido)phenyl | 1.13 | 377.0 |
| 1064 | CH₃— | 4-(2-(4-methylpiperazin-1-yl)acetamido)phenyl | 1.13 | 432.2 |
| 1065 | CH₃— | 3-(methylamino)phenyl | | |

TABLE 1-continued
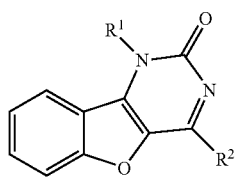
| Cpd | R¹ | R² | $t_R$ (min) | MS $(M + H)^+$ |
|---|---|---|---|---|
| 1066 | CH₃OCH₂CH₂— | 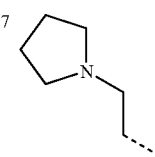 | 2.42 | 435.3 |
| 1067 | 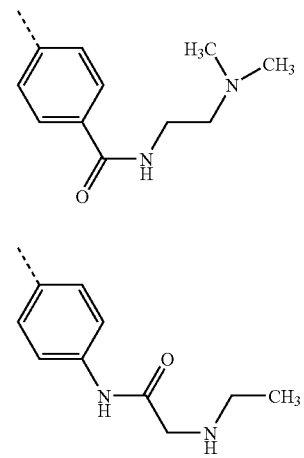 | 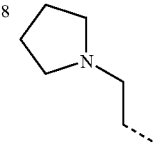 | 1.11 | 460.3 |
| 1068 | 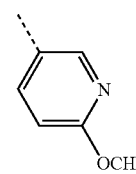 | 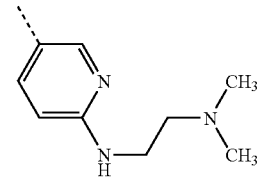 | 1.88 | 391.3 |
| 1069 | CH₃OCH₂CH₂— | 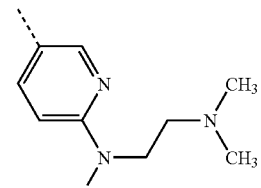 | 2.44 | 408.4 |
| 1070 | CH₃OCH₂CH₂— | 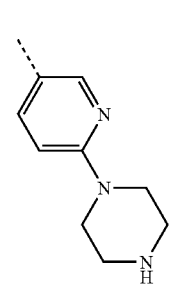 | 2.65 | 422.4 |
| 1071 | CH₃OCH₂CH₂— |  | 2.54 | 406.3 |

TABLE 1-continued

| Cpd | R¹ | R² | $t_R$ (min) | MS $(M + H)^+$ |
|---|---|---|---|---|
| 1072 | CH₃OCH₂CH₂— | 5-(4-methylpiperazin-1-yl)pyridin-2-yl | 2.60 | 420.4 |
| 1073 | CH₃OCH₂CH₂— | 5-(4-isopropylpiperazin-1-yl)pyridin-2-yl | 2.69 | 448.4 |
| 1074 | CH₃OCH₂CH₂— | 5-((piperidin-4-ylmethyl)amino)pyridin-2-yl | 2.03 | 434.3 |
| 1075 | CH₃OCH₂CH₂— | 5-((2-(pyrrolidin-1-yl)ethyl)amino)pyridin-2-yl | 1.13 | 434.4 |
| 1076 | CH₃OCH₂CH₂— | 5-(6-aminopyridin-3-yl) | 1.10 | 337.3 |
| 1077 | CH₃OCH₂CH₂— | 5-(pyrrolidin-1-yl)pyridin-2-yl | 1.26 | 391.3 |

TABLE 1-continued
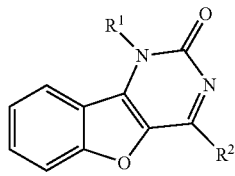
| Cpd | R¹ | R² | $t_R$ (min) | MS (M + H)⁺ |
|---|---|---|---|---|
TABLE 2
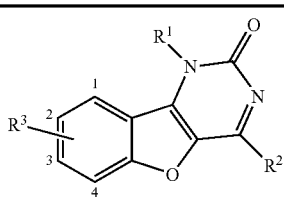
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2001 | pyrrolidinylethyl | phenyl | Cl | 2 | 2.95 | 394.2 |
| 2002 | pyrrolidinylethyl | 4-(NHC(O)CH₂NHCH₂CH₃)phenyl | Cl | 2 | 2.47 | 494.3 |
| 2003 | pyrrolidinylethyl | phenyl | NH₂ | 3 | 2.31 | 375.3 |
| 2004 | pyrrolidinylethyl | phenyl | Br | 2 | 3.02 | 438.2 |
| 2005 | H₃CO-CH₂-pyrrolidinylethyl | phenyl | Cl | 2 | 3.06 | 438.3 |

TABLE 2-continued

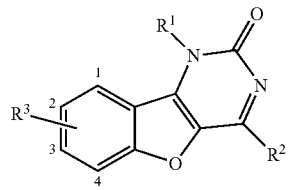

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2006 | pyrrolidin-1-ylethyl | phenyl | CH$_3$C(=O)NH— | 3 | 2.68 | 417.3 |
| 2007 | 2-carbamoylpyrrolidin-1-ylethyl | phenyl | Cl | 2 | 2.79 | 437.3 |
| 2008 | 3-(dimethylamino)pyrrolidin-1-ylethyl | phenyl | Cl | 2 | 2.73 | 437.3 |
| 2009 | 3,3-difluoropyrrolidin-1-ylethyl | phenyl | Cl | 2 | 3.14 | 430.2 |
| 2010 | pyrrolidin-1-ylethyl | phenyl | CH$_3$O— | 4 | 2.88 | 390.4 |
| 2011 | CH$_3$OCH$_2$CH$_2$— | 4-(ethylaminoacetamido)phenyl | 3-(hydroxymethyl)phenyl | 3 | 2.87 | 527.3 |

TABLE 2-continued

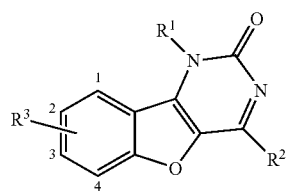

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2012 | CH₃OCH₂CH₂— | 4-(NHC(O)CH₂NHCH₂CH₃)phenyl | pyridin-3-yl | 3 | 2.35 | 498.3 |
| 2013 | CH₃OCH₂CH₂— | 4-(NHC(O)CH₂NHCH₂CH₃)phenyl | phenyl | 2 | 3.16 | 397.2 |
| 2014 | CH₃OCH₂CH₂— | 4-(NHC(O)CH₂NHCH₂CH₃)phenyl | pyridin-4-yl | 2 | 2.33 | 498.2 |
| 2015 | CH₃OCH₂CH₂— | 4-(NHC(O)CH₂NHCH₂CH₃)phenyl | 4-(hydroxymethyl)phenyl | 2 | 2.54 | 527.2 |
| 2016 | CH₃OCH₂CH₂— | 4-methoxyphenyl | 4-((dimethylamino)methyl)phenyl | 2 | 3.14 | 484.2 |
| 2017 | CH₃OCH₂CH₂— | 4-methoxyphenyl | 2-methyl-1,2,3,4-tetrahydroisoquinolin-7-yl | 2 | 3.14 | 496.2 |

TABLE 2-continued

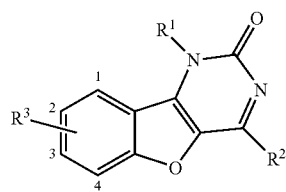

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2018 | CH₃OCH₂CH₂— | 4-(NHC(O)CH₂NHCH₂CH₃)phenyl | 3-(2-hydroxyethyl)phenyl | 2 | 2.97 | 541.1 |
| 2019 | CH₃OCH₂CH₂— | 4-(NHC(O)CH₂NHCH₂CH₃)phenyl | 2-methyl-1,2,3,4-tetrahydroisoquinolin-7-yl | 3 | 2.61 | 566.2 |
| 2020 | 1-(carbamoyl)pyrrolidin-1-yl-propyl | 4-fluorophenyl | Cl | 2 | 2.97 | 455.0 |
| 2021 | CH₃OCH₂CH₂— | 4-(NHC(O)CH₂NHCH₂CH₃)phenyl | thiazol-5-yl | 2 | 2.81 | 504.1 |
| 2022 | CH₃OCH₂CH₂— | 4-(NHC(O)CH₂NHCH₂CH₃)phenyl | pyridin-2-yl | 2 | 2.42 | 498.1 |
| 2023 | 2-(3,3-difluoropyrrolidin-1-yl)ethyl | 4-fluorophenyl | 2-methyl-1,2,3,4-tetrahydroisoquinolin-6-yl | 2 | 2.93 | 559.2 |

TABLE 2-continued

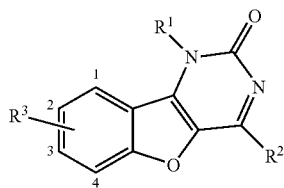

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2024 | 3,3-difluoropyrrolidin-1-yl-ethyl | 4-fluorophenyl | 4-((dimethylamino)methyl)phenyl | 2 | 2.92 | 547.2 |
| 2025 | 2-carbamoylpyrrolidin-1-yl-ethyl | 4-fluorophenyl | 2-methyl-1,2,3,4-tetrahydroisoquinolin-6-yl | 2 | 2.81 | 566.2 |
| 2026 | 2-carbamoylpyrrolidin-1-yl-ethyl | 4-fluorophenyl | 4-((dimethylamino)methyl)phenyl | 2 | 2.80 | 554.2 |
| 2027 | 2-carbamoylpyrrolidin-1-yl-ethyl | phenyl | Br | 2 | 2.94 | 482.5 |
| 2028 | 2-carbamoylpyrrolidin-1-yl-ethyl | phenyl | Br | 2 | 2.94 | 480.6 |
| 2029 | 3-acetamidopyrrolidin-1-yl-ethyl | phenyl | Br | 2 | 2.95 | 494.6 |
| 2030 | (3S)-3-hydroxypyrrolidin-1-yl-ethyl | phenyl | Br | 2 | 2.94 | 453.6 |

TABLE 2-continued

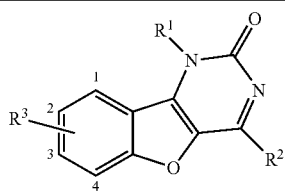

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2031 | (S)-3-hydroxypyrrolidin-1-yl-ethyl | phenyl | Br | 2 | 2.94 | 453.6 |
| 2032 | (S)-3-fluoropyrrolidin-1-yl-ethyl | phenyl | Br | 2 | 3.06 | 455.5 |
| 2033 | 3-(dimethylamino)pyrrolidin-1-yl-ethyl | phenyl | Br | 2 | 2.77 | 481.3 |
| 2034 | 3-(Boc-amino)pyrrolidin-1-yl-ethyl | phenyl | Br | 2 | 3.40 | 553.3 |
| 2035 | 2-(hydroxymethyl)pyrrolidin-1-yl-ethyl | phenyl | Br | 2 | 2.97 | 470.3 |
| 2036 | 2-methoxyethyl(methyl)amino-ethyl | phenyl | Br | 2 | 3.09 | 456.3 |
| 2037 | 2-carbamoylpyrrolidin-1-yl-ethyl | phenyl | thiazol-5-yl | 2 | 2.89 | 486.3 |
| 2038 | 3-(N-methylacetamido)pyrrolidin-1-yl-ethyl | phenyl | Br | 2 | 3.04 | 509.3 |

TABLE 2-continued

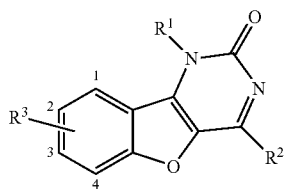

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2039 | CH₃OCH₂CH₂— | 4-(NHC(O)CH₂NHCH₂CH₃)-phenyl | 1-methyl-1,2,3,4-tetrahydroquinolin-7-yl | 2 | 2.82 | 566.2 |
| 2040 | (S)-2-carbamoylpyrrolidin-1-yl-ethyl | 4-fluorophenyl | Cl | 2 | 2.81 | 455.1 |
| 2041 | (S)-2-carbamoylpyrrolidin-1-yl-ethyl | phenyl | thiazol-5-yl | 2 | 2.92 | 486.3 |
| 2042 | (S)-3-acetamidopyrrolidin-1-yl-ethyl | phenyl | thiazol-5-yl | 2 | 2.71 | 500.3 |
| 2043 | (S)-3-hydroxypyrrolidin-1-yl-ethyl | phenyl | thiazol-5-yl | 2 | 2.91 | 459.3 |
| 2044 | (R)-3-hydroxypyrrolidin-1-yl-ethyl | phenyl | thiazol-5-yl | 2 | 2.90 | 459.3 |
| 2045 | (S)-2-(methoxymethyl)pyrrolidin-1-yl-ethyl | phenyl | thiazol-5-yl | 2 | 2.96 | 487.3 |

TABLE 2-continued

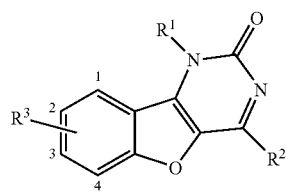

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2046 | (CH$_3$)$_2$N-pyrrolidin-3-yl-N-propyl | phenyl | thiazol-5-yl | 2 | 2.78 | 486.3 |
| 2047 | (3-aminopyrrolidin-1-yl)propyl | phenyl | thiazol-5-yl | 2 | 2.74 | 458.3 |
| 2048 | (3-aminopyrrolidin-1-yl)propyl | phenyl | thiazol-5-yl | 2 | 2.74 | 458.3 |
| 2049 | (2-hydroxymethylpyrrolidin-1-yl)propyl | phenyl | thiazol-5-yl | 2 | 2.95 | 473.3 |
| 2050 | CH$_3$OCH$_2$CH$_2$N(CH$_3$)propyl | phenyl | thiazol-5-yl | 2 | 3.04 | 461.3 |
| 2051 | CH$_3$OCH$_2$CH$_2$— | 4-(NHC(O)CH$_2$NHCH$_2$CH$_3$)phenyl | thiazol-5-yl | 3 | 2.81 | 504.0 |
| 2052 | CH$_3$OCH$_2$CH$_2$— | 4-(NHC(O)CH$_2$NHCH$_2$CH$_3$)phenyl | thiazol-4-yl | 2 | 2.87 | 504.1 |

TABLE 2-continued

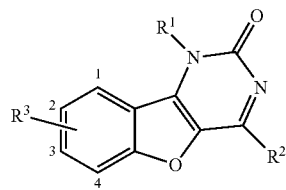

Site designates the attachment site (1, 2, 3 or 4) for $R^3$.

| Cpd | $R^1$ | $R^2$ | $R^3$ | Site | $t_R$ (min) | MS (M + H)+ |
|---|---|---|---|---|---|---|
| 2053 | $CH_3OCH_2CH_2$— | 4-(NHC(O)CH$_2$NHCH$_2$CH$_3$)phenyl | 2-thiazolyl | 2 | 2.90 | 504.1 |
| 2054 | $CH_3OCH_2CH_2$— | 4-(NHC(O)CH$_2$NHCH$_2$CH$_3$)phenyl | 1-methyl-1H-pyrazol-4-yl | 2 | 2.77 | 501.1 |
| 2055 | $CH_3OCH_2CH_2$— | 4-(NHC(O)CH$_2$NHcyclopropyl)phenyl | 5-thiazolyl | 2 | 2.84 | 516.0 |
| 2056 | 1-(2-(N-ethyl-N-acetylamino)pyrrolidin-1-yl)ethyl | phenyl | Br | 2 | 3.18 | 523.3 |
| 2057 | 1-(2-(N-ethyl-N-acetylamino)pyrrolidin-1-yl)ethyl | phenyl | 5-thiazolyl | 2 | 3.14 | 528.3 |
| 2058 | $CH_3OCH_2CH_2$— | 4-(NHC(O)CH$_2$NHCH$_2$CH$_3$)phenyl | 3-fluorophenyl | 2 | 3.28 | 515.2 |

TABLE 2-continued
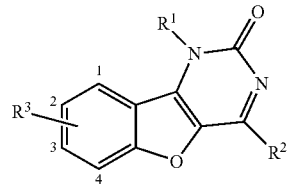
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2059 | ![structure with H₃CO, NH, C=O, pyrrolidine N, propyl] | [phenyl] | Cl | 2 | 3.01 | 495.4 |
| 2060 | $CH_3OCH_2CH_2$— | [phenyl-NHC(O)CH₂NHCH₂CH₃] | —COOH | 3 | 2.51 | 465.2 |
| 2061 | $CH_3OCH_2CH_2$— | [phenyl-NHC(O)CH₂NHCH₂CH₃] | [4-methoxyphenyl] | 2 | 3.23 | 527.2 |
| 2062 | $CH_3OCH_2CH_2$— | [phenyl-NHC(O)CH₂NHCH₂CH₃] | [4-acetylphenyl] | 2 | 3.08 | 539.2 |
| 2063 | $CH_3OCH_2CH_2$— | [phenyl-NHC(O)CH₂NHCH₂CH₃] | [2-furyl] | 2 | 2.93 | 487.2 |

TABLE 2-continued

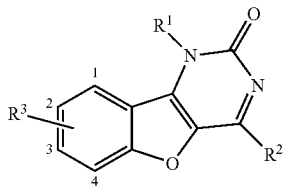

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2064 | $CH_3OCH_2CH_2$— | 4-(NHC(O)CH$_2$NHCH$_2$CH$_3$)phenyl | 3-cyanophenyl | 2 | 3.14 | 522.2 |
| 2065 | $CH_3OCH_2CH_2$— | 4-(NHC(O)CH$_2$NHCH$_2$CH$_3$)phenyl | 3,5-dimethylphenyl | 2 | 3.53 | 525.2 |
| 2066 | $CH_3OCH_2CH_2$— | 4-(NHC(O)CH$_2$NHCH$_2$CH$_3$)phenyl | 1-methylindol-5-yl | 2 | 3.35 | 550.2 |
| 2067 | $CH_3OCH_2CH_2$— | 4-(NHC(O)CH$_2$NHCH$_2$CH$_3$)phenyl | —COOCH$_3$ | 2 | 2.75 | 479.1 |
| 2068 | $CH_3OCH_2CH_2$— | 4-(NHC(O)CH$_2$NHCH$_2$CH$_3$)phenyl | —COOH | 2 | 2.47 | 465.1 |

TABLE 2-continued
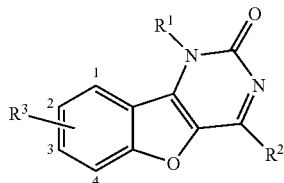
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2069 | CH₃OCH₂CH₂— | 4-(NHC(O)CH₂NHCH₂CH₃)phenyl | 3-methoxybenzyl-NHC(O)- | 3 | 2.51 | 584.3 |
| 2070 | CH₃OCH₂CH₂— | 4-(NHC(O)CH₂NHCH₂CH₃)phenyl | Cl | 2 | 2.70 | 455.4 |
| 2071 | CH₃OCH₂CH₂— | 4-(NHC(O)CH₂NHCH₂CH₃)phenyl | pyridin-3-yl | 2 | 2.35 | 498.2 |
| 2072 | CH₃OCH₂CH₂— | 4-(NHC(O)CH₂NHCH₂CH₃)phenyl | 4-(CH₃NHC(O))phenyl | 2 | 2.80 | 554.2 |
| 2073 | CH₃OCH₂CH₂— | 4-(NHC(O)CH₂NHCH₂CH₃)phenyl | 3-hydroxyphenyl | 2 | 2.90 | 513.2 |

TABLE 2-continued

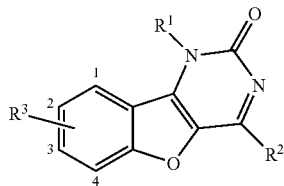

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2074 | $CH_3OCH_2CH_2$— | 4-(NHC(O)CH₂NHCH₂CH₃)phenyl | 4-fluorophenyl | 2 | 3.27 | 515.2 |
| 2075 | $CH_3OCH_2CH_2$— | 4-(NHC(O)CH₂NHCH₂CH₃)phenyl | 4-(pyrrolidin-1-ylcarbonyl)phenyl | 2 | 3.04 | 594.3 |
| 2076 | $CH_3OCH_2CH_2$— | 4-(NHC(O)CH₂NHCH₂CH₃)phenyl | 3-(methylsulfonyl)phenyl | 2 | 2.89 | 575.2 |
| 2077 | $CH_3OCH_2CH_2$— | 4-(NHC(O)CH₂NHCH₂CH₃)phenyl | 3-(methylsulfonylamino)phenyl | 2 | 2.91 | 590.2 |
| 2078 | $CH_3OCH_2CH_2$— | 4-(NHC(O)CH₂NHCH₂CH₃)phenyl | 2,4-dioxo-1,2,3,4-tetrahydropyrimidin-5-yl | 2 | 2.35 | 531.2 |

TABLE 2-continued

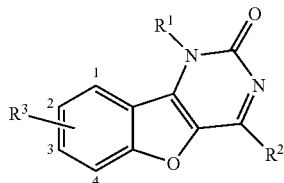

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2079 | CH₃OCH₂CH₂— | 4-(NHCOCH₂NHCH₂CH₃)phenyl | 6-methoxypyridin-3-yl | 2 | 2.94 | 528.2 |
| 2080 | CH₃OCH₂CH₂— | 4-(NHCOCH₂NHCH₂CH₃)phenyl | 3-(hydroxymethyl)phenyl | 2 | 2.49 | 527.2 |
| 2081 | CH₃OCH₂CH₂— | 4-(NHCOCH₂NHCH₂CH₃)phenyl | 4-((dimethylamino)methyl)phenyl | 2 | 2.00 | 554.3 |
| 2082 | CH₃OCH₂CH₂— | 4-(NHCOCH₂NHCH₂CH₃)phenyl | imidazo[1,2-a]pyridin-6-yl | 2 | 2.44 | 537.2 |
| 2083 | CH₃OCH₂CH₂— | 4-(NHCOCH₂NHCH₂CH₃)phenyl | 4-(N-methylsulfamoyl)phenyl | 2 | 2.90 | 590.2 |

TABLE 2-continued

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2084 | CH₃OCH₂CH₂— | 4-(NHCOCH₂NHCH₂CH₃)phenyl | 4-(hydroxymethyl)phenyl | 3 | 2.86 | 527.2 |
| 2085 | CH₃OCH₂CH₂— | 4-(NHCOCH₂NHCH₂CH₃)phenyl | 4-(SO₂NHCH₃)phenyl | 3 | 2.93 | 590.2 |
| 2086 | CH₃OCH₂CH₂— | 4-(NHCOCH₂NHCH₂CH₃)phenyl | 4-methoxyphenyl | 3 | 3.26 | 527.2 |
| 2087 | CH₃OCH₂CH₂— | 4-(NHCOCH₂NHCH₂CH₃)phenyl | —NH₂ | 3 | 2.28 | 463.2 |
| 2088 | CH₃OCH₂CH₂— | 4-(NHCOCH₂NHCH₂CH₃)phenyl | 3-(NHCOCH₃)phenyl | 3 | 2.63 | 554.2 |

TABLE 2-continued

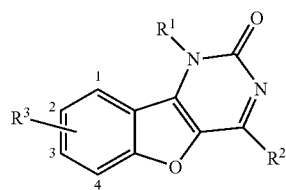

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2089 | CH₃OCH₂CH₂— | 4-(NHC(O)CH₂NHCH₂CH₃)-phenyl | 2-furyl | 3 | 3.12 | 487.2 |
| 2090 | CH₃OCH₂CH₂— | 4-(NHC(O)CH₂NHCH₂CH₃)-phenyl | 3-HO-phenyl | 3 | 2.94 | 513.2 |
| 2091 | CH₃OCH₂CH₂— | 4-(NHC(O)CH₂NHCH₂CH₃)-phenyl | 3-(N,N-dimethylcarbamoyl)-phenyl | 3 | 2.62 | 568.2 |
| 2092 | CH₃OCH₂CH₂— | 4-(NHC(O)CH₂NHCH₂CH₃)-phenyl | 2,3-dihydrobenzofuran-5-yl | 3 | 3.24 | 539.2 |
| 2093 | 2-(pyrrolidin-1-yl)ethyl | phenyl | CH₂=CH— | 2 | 3.08 | 386.4 |
| 2094 | 2-(pyrrolidin-1-yl)ethyl | phenyl | 4-(HOCH₂)-phenyl | 2 | 3.09 | 466.4 |

TABLE 2-continued

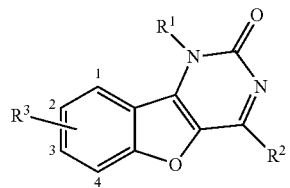

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2095 | CH₃OCH₂CH₂— | 4-(NHC(O)CH₂NHCH₂CH₃)phenyl | 1H-1,2,3-triazol-4-yl | 3 | 2.16 | 488.3 |
| 2096 | CH₃OCH₂CH₂— | 4-(NHC(O)CH₂NHCH₂CH₃)phenyl | 4-(CH₃OCH₂)phenyl | 2 | 3.18 | 541.3 |
| 2097 | CH₃OCH₂CH₂— | 4-NH₂-phenyl | 3-(HOCH₂)phenyl | 3 | 2.97 | 442.2 |
| 2098 | CH₃OCH₂CH₂— | 4-NH₂-phenyl | CH₂=CH— | 2 | 3.03 | 362.2 |
| 2099 | CH₃OCH₂CH₂— | 4-(NHC(O)CH₂NHCH₂CH₃)phenyl | 3-((CH₃)₂NCH₂)phenyl | 2 | 2.12 | 554.3 |
| 2100 | CH₃OCH₂CH₂— | 4-(NHC(O)CH₂NHCH₂CH₃)phenyl | 3-(CH₃OCH₂)phenyl | 2 | 3.08 | 541.3 |

TABLE 2-continued

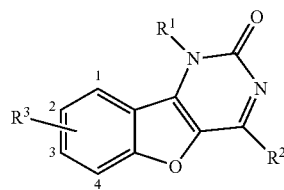

Site designates the attachment site (1, 2, 3 or 4) for R³.

| Cpd | R¹ | R² | R³ | Site | $t_R$ (min) | MS (M+H)⁺ |
|---|---|---|---|---|---|---|
| 2101 | CH₃OCH₂CH₂— | 4-(NHC(O)CH₂NHCH₂CH₃)phenyl | 3-(C(O)N(CH₃)₂)phenyl... N-methyl benzamide | 2 | 2.90 | 568.3 |
| 2102 | CH₃OCH₂CH₂— | 4-aminophenyl | 3-(hydroxymethyl)phenyl | 2 | 3.04 | 442.2 |
| 2103 | CH₃OCH₂CH₂— | 4-(NHC(O)CH₂NHCH₂CH₃)phenyl | 2-methyl-1,2,3,4-tetrahydroisoquinolin-6-yl | 2 | 2.56 | 566.3 |
| 2104 | CH₃OCH₂CH₂— | 4-(NHC(O)CH₂NHCH₂CH₃)phenyl | 6-methylpyridin-3-yl | 2 | 1.85 | 512.3 |
| 2105 | CH₃OCH₂CH₂— | 4-(NHC(O)CH₂NHCH₂CH₃)phenyl | pyrimidin-5-yl | 2 | 2.11 | 499.2 |
| 2106 | CH₃OCH₂CH₂— | 4-aminophenyl | 4-((dimethylamino)methyl)phenyl | 2 | 2.16 | 469.3 |

TABLE 2-continued

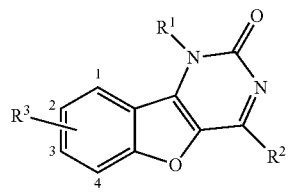

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2107 | CH₃OCH₂CH₂— | 4-aminophenyl | 2-methyl-1,2,3,4-tetrahydroisoquinolin-6-yl | 2 | 2.16 | 481.3 |
| 2108 | CH₃OCH₂CH₂— | phenyl | 2-methyl-1,2,3,4-tetrahydroisoquinolin-6-yl | 2 | 3.10 | 466.1 |
| 2109 | CH₃OCH₂CH₂— | phenyl | 4-((dimethylamino)methyl)phenyl | 2 | 3.09 | 454.2 |
| 2110 | CH₃OCH₂CH₂— | 4-(2-(ethylamino)acetamido)phenyl | 6-oxo-1,6-dihydropyridin-3-yl | 2 | 2.51 | 514.2 |
| 2111 | CH₃OCH₂CH₂— | 4-(2-(ethylamino)acetamido)phenyl | 6-aminopyridin-3-yl | 2 | 2.41 | 514.3 |
| 2112 | CH₃OCH₂CH₂— | 4-(2-(ethylamino)acetamido)phenyl | 4-acetamidophenyl | 2 | 2.86 | 554.3 |
| 2113 | CH₃OCH₂CH₂— | 4-methoxyphenyl | 2-methyl-1,2,3,4-tetrahydroisoquinolin-6-yl | 2 | 3.14 | 496.2 |

TABLE 2-continued

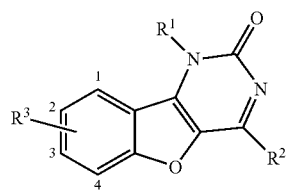

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2114 | CH$_3$OCH$_2$CH$_2$— | 4-(NHC(O)CH$_2$NHCH$_2$CH$_3$)-phenyl | 2-methyl-1,2,3,4-tetrahydroisoquinolin-7-yl | 2 | 2.59 | 566.2 |
| 2115 | CH$_3$OCH$_2$CH$_2$— | 4-(NHC(O)CH$_2$NHCH$_2$CH$_3$)-phenyl | 2-methyl-1,2,3,4-tetrahydroisoquinolin-5-yl | 2 | 2.59 | 566.2 |
| 2116 | CH$_3$OCH$_2$CH$_2$— | 4-(NHC(O)CH$_2$NHCH$_2$CH$_3$)-phenyl | 2-methyl-1,2,3,4-tetrahydroisoquinolin-8-yl | 2 | 2.61 | 566.2 |
| 2117 | 2-(pyrrolidin-1-yl)ethyl | phenyl | pyridin-3-yl | 2 | 2.54 | 437.4 |
| 2118 | 2-(pyrrolidin-1-yl)ethyl | phenyl | 3-(hydroxymethyl)phenyl | 2 | 3.12 | 466.4 |
| 2119 | 2-(3,3-difluoropyrrolidin-1-yl)ethyl | phenyl | pyridin-3-yl | 2 | 2.59 | 473.4 |

TABLE 2-continued

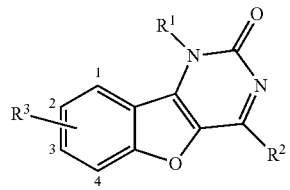

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2120 | 3,3-difluoropyrrolidinyl-propyl | phenyl | 3-(hydroxymethyl)phenyl | 2 | 3.20 | 502.4 |
| 2121 | 2-carbamoylpyrrolidinyl-ethyl | phenyl | pyridin-3-yl | 2 | 2.50 | 480.4 |
| 2122 | 2-carbamoylpyrrolidinyl-ethyl | phenyl | 3-(hydroxymethyl)phenyl | 2 | 3.05 | 509.4 |
| 2123 | CH₃OCH₂CH₂— | 4-cyanophenyl | 2-methyl-1,2,3,4-tetrahydroisoquinolin-6-yl | 2 | 3.10 | 491.2 |
| 2124 | CH₃OCH₂CH₂— | 4-cyanophenyl | 4-((dimethylamino)methyl)phenyl | 2 | 3.10 | 479.2 |
| 2125 | CH₃OCH₂CH₂— | 4-(2-(ethylamino)acetamido)phenyl | 2-methyl-1,2,3,4-tetrahydroisoquinolin-6-yl | 3 | 2.58 | 566.3 |

TABLE 2-continued

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2126 | CH₃OCH₂CH₂— | 4-(NHC(O)CH₂NHCH₂CH₃)phenyl | 4-(N(CH₃)₂CH₂)phenyl | 3 | 2.58 | 554.3 |
| 2127 | CH₃OCH₂CH₂— | 4-(NHC(O)CH₂NHCH₂CH₃)phenyl | 3-(N(CH₃)₂CH₂)phenyl | 3 | 2.62 | 554.5 |
| 2128 | pyrrolidin-1-yl-propyl | phenyl | 2-methyl-1,2,3,4-tetrahydroisoquinolin-6-yl | 2 | 2.80 | 505.4 |
| 2129 | 3,3-difluoropyrrolidin-1-yl-ethyl | phenyl | 2-methyl-1,2,3,4-tetrahydroisoquinolin-6-yl | 2 | 2.86 | 541.5 |
| 2130 | 2-carbamoylpyrrolidin-1-yl-ethyl | phenyl | 2-methyl-1,2,3,4-tetrahydroisoquinolin-6-yl | 2 | 2.75 | 548.5 |
| 2131 | CH₃OCH₂CH₂— | 4-(NHC(O)CH₂NHCH₂CH₃)phenyl | Br | 3 | 2.77 | 499.2 |

TABLE 2-continued

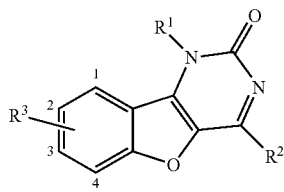

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2132 | $CH_3OCH_2CH_2-$ | 4-(NHC(=O)CH$_2$NHCH$_2$CH$_3$)phenyl | phenyl | 3 | 3.32 | 497.3 |
| 2133 | $CH_3OCH_2CH_2-$ | 4-(NH$_2$)phenyl | Br | 2 | 3.14 | 414.0 |
| 2134 | $CH_3OCH_2CH_2-$ | 4-(NHC(=O)CH$_2$NHCH$_2$CH$_3$)phenyl | Br | 2 | 2.78 | 499.0 |
| 2135 | $CH_3OCH_2CH_2-$ | 4-(NHC(=O)CH$_2$NHCH$_2$CH$_3$)phenyl | $CH_2=CH-$ | 2 | 3.09 | 447.2 |
| 2136 | $CH_3OCH_2CH_2-$ | 4-(NHC(=O)CH$_2$NHCH$_2$CH$_3$)phenyl | $CH_3C(=O)-$ | 3 | 2.36 | 463.3 |
| 2137 | $CH_3OCH_2CH_2-$ | 4-(NHC(=O)CH$_2$NHCH$_2$CH$_3$)phenyl | $CH_3OC(=O)-$ | 3 | 2.82 | 479.2 |

TABLE 2-continued

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2138 | pyrrolidine-2-carboxamide, N-propyl | phenyl | 2-methyl-1,2,3,4-tetrahydroisoquinolin-6-yl | 3 | 2.64 | 548.1 |
| 2139 | pyrrolidine-2-carboxamide, N-propyl | phenyl | 4-((dimethylamino)methyl)phenyl | 3 | 2.65 | 536.1 |
| 2140 | pyrrolidine-2-carboxamide, N-propyl | phenyl | thiazol-5-yl | 3 | 2.90 | 486.2 |
| 2141 | pyrrolidine-2-carboxamide, N-propyl | phenyl | Br | 3 | 3.02 | 481.1 |
| 2142 | pyrrolidine-2-carboxamide, N-propyl | phenyl | 1-methyl-1H-pyrazol-4-yl | 3 | 2.85 | 483.2 |
| 2143 | pyrrolidine-2-carboxamide, N-propyl | phenyl | 4-carbamimidoylphenyl | 3 | 2.83 | 522.2 |
| 2144 | pyrrolidine-2-carboxamide, N-propyl | phenyl | 5-(hydroxymethyl)pyridin-3-yl | 3 | 2.35 | 510.2 |

TABLE 2-continued

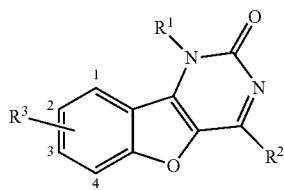

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2145 | prolinamide-ethyl | phenyl | 2-thiazolyl | 2 | 2.99 | 486.0 |
| 2146 | prolinamide-ethyl | phenyl | phenyl | 2 | 3.30 | 479.1 |
| 2147 | prolinamide-ethyl | phenyl | 3-(hydroxymethyl)phenyl | 2 | 3.05 | 509.1 |
| 2148 | prolinamide-ethyl | phenyl | 3-pyridyl | 2 | 2.49 | 480.1 |
| 2149 | prolinamide-ethyl | phenyl | 4-(dimethylaminomethyl)phenyl | 2 | 2.74 | 536.1 |
| 2150 | prolinamide-ethyl | phenyl | 2-amino-5-thiazolyl | 2 | 2.49 | 501.1 |
| 2151 | prolinamide-ethyl | phenyl | 5-(hydroxymethyl)-3-pyridyl | 2 | 2.39 | 510.1 |

TABLE 2-continued

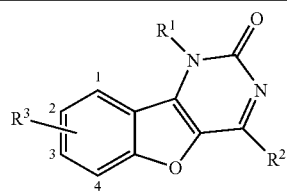

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2152 | pyrrolidine-2-carboxamide N-ethyl | phenyl | phenyl | 4 | 3.17 | 479.2 |
| 2153 | pyrrolidine-2-carboxamide N-ethyl | phenyl | 3-cyanophenyl | 4 | 3.05 | 504.2 |
| 2154 | pyrrolidine-2-carboxamide N-ethyl | phenyl | 3-carbamoylphenyl | 4 | 2.57 | 522.2 |
| 2155 | pyrrolidine-2-carboxamide N-ethyl | phenyl | pyridin-4-yl | 4 | 2.17 | 480.2 |
| 2156 | pyrrolidine-2-carboxamide N-ethyl | phenyl | 4-((dimethylamino)methyl)phenyl | 4 | 2.35 | 536.3 |
| 2157 | pyrrolidine-2-carboxamide N-ethyl | phenyl | 1-methyl-1H-pyrazol-4-yl | 2 | 2.79 | 483.2 |
| 2158 | pyrrolidine-2-carboxamide N-ethyl | phenyl | 2-(2-methoxyethyl)-1,2,3,4-tetrahydroisoquinolin-6-yl | 3 | 2.57 | 592.3 |

TABLE 2-continued
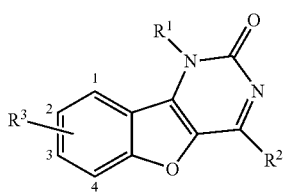
Site designates the attachment site (1, 2, 3 or 4) for $R^3$.
| Cpd | $R^1$ | $R^2$ | $R^3$ | Site | $t_R$ (min) | MS (M + H)+ |
|---|---|---|---|---|---|---|
| 2159 | | | | 3 | 2.69 | 588.3 |
| 2160 | | | | 3 | 2.66 | 606.4 |
| 2161 | | | | 3 | 2.60 | 534.3 |
| 2162 | | | | 3 | 2.52 | 534.3 |
| 2163 | | | | 3 | 2.77 | 548.2 |
| 2164 | | | | 3 | 2.87 | 562.3 |
| 2165 | | | | 3 | 2.45 | 533.2 |

TABLE 2-continued

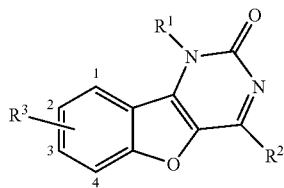

Site designates the attachment site (1, 2, 3 or 4) for R³.

| Cpd | R¹ | R² | R³ | Site | t_R (min) | MS (M + H)⁺ |
|---|---|---|---|---|---|---|
| 2166 | pyrrolidine-2-carboxamide N-propyl | phenyl | isoindoline-5-yl | 3 | 2.44 | 520.2 |
| 2167 | pyrrolidine-2-carboxamide N-propyl | phenyl | 1,2,3,4-tetrahydroisoquinolin-6-yl | 3 | 2.47 | 534.3 |
| 2168 | pyrrolidine-2-carboxamide N-propyl | phenyl | 1-oxo-1,2,3,4-tetrahydroisoquinolin-6-yl | 3 | 2.74 | 548.2 |
| 2169 | pyrrolidine-2-carboxamide N-propyl | phenyl | 1-oxo-2,3-dihydro-1H-inden-5-yl | 3 | 3.02 | 533.2 |
| 2170 | pyrrolidine-2-carboxamide N-propyl | phenyl | 2-oxo-2,3-dihydrobenzoxazol-5-yl | 3 | 2.90 | 536.2 |
| 2171 | CH₃OCH₂CH₂— | phenyl | 4-((dimethylamino)methyl)phenyl | 2 | 2.99 | 468.2 |
| 2172 | pyrrolidine-2-carboxamide N-propyl | phenyl | —CN | 4 | 2.70 | 428.1 |

TABLE 2-continued

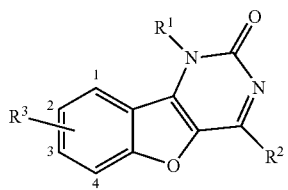

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2173 | pyrrolidine-2-carboxamide-N-propyl | phenyl | 4-(hydroxymethyl)phenyl | 3 | 2.82 | 509.2 |
| 2174 | CH₃OCH₂CH₂— | 4-(methylsulfonamido)phenyl | Br | 2 | 3.43 | 492.0 |
| 2175 | pyrrolidine-2-carboxamide-N-propyl | phenyl | 2-(5-carboxy)thiazolyl | 2 | 2.82 | 530.1 |
| 2176 | pyrrolidine-2-carboxamide-N-propyl | phenyl | 4-(carboxymethyl)pyrazolyl | 2 | 2.72 | 527.1 |
| 2177 | pyrrolidine-2-carboxamide-N-propyl | phenyl | 4-(2-(piperazin-1-yl)-2-oxoethyl)pyrazolyl | 2 | 2.51 | 595.2 |
| 2178 | pyrrolidine-2-carboxamide-N-propyl | phenyl | 2-(1H-imidazolyl) | 2 | 2.32 | 469.1 |

TABLE 2-continued

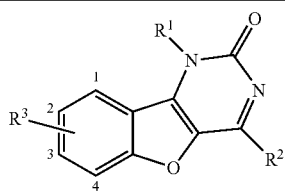

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2179 | pyrrolidine-2-carboxamide-N-propyl | phenyl | 2-methyl-1H-imidazol-4-yl | 2 | 2.42 | 483.1 |
| 2180 | pyrrolidine-2-carboxamide-N-propyl | phenyl | 2,4-dimethylthiazol-5-yl | 2 | 2.71 | 514.1 |
| 2181 | pyrrolidine-2-carboxamide-N-propyl | phenyl | 1-methyl-1H-imidazol-2-yl | 2 | 2.30 | 483.1 |
| 2182 | pyrrolidine-2-carboxamide-N-propyl | phenyl | 1-methyl-1H-pyrazol-5-yl | 2 | 2.38 | 483.1 |
| 2183 | pyrrolidine-2-carboxamide-N-propyl | phenyl | 1-methyl-1H-imidazol-4-yl | 2 | 2.39 | 483.1 |
| 2184 | pyrrolidine-2-carboxamide-N-propyl | phenyl | 4-(4-aminophenyl)-1H-pyrazol-1-yl | 2 | 2.69 | 560.2 |
| 2185 | pyrrolidine-2-carboxamide-N-propyl | phenyl | 1-(2-aminoethyl)-1H-pyrazol-4-yl | 2 | 2.67 | 513.2 |

TABLE 2-continued

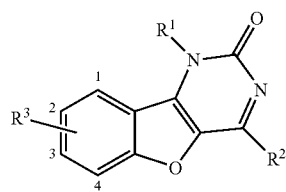

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2186 | pyrrolidine-2-carboxamide N-ethyl | phenyl | —COOCH₃ | 4 | 2.75 | 461.2 |
| 2187 | CH₃OCH₂CH₂— | 4-(2-(cyclopropylamino)acetamido)phenyl | Br | 2 | 2.93 | 511.1 |
| 2188 | pyrrolidine-2-carboxamide N-ethyl | phenyl | (2-methylthiazol-5-yl)(pyrrolidin-1-yl)methanone | 2 | 2.93 | 583.1 |
| 2189 | pyrrolidine-2-carboxamide N-ethyl | phenyl | pyridin-3-yl N-oxide | 2 | 2.52 | 496.1 |
| 2190 | pyrrolidine-2-carboxamide N-ethyl | phenyl | 2-methyl-1,2,3,4-tetrahydroisoquinolin-6-yl | 2 | 2.64 | 548.2 |
| 2191 | CH₃CH₂OCH₂CH₂— | phenyl | 4-((dimethylamino)methyl)phenyl | 2 | 3.05 | 468.3 |
| 2192 | pyrrolidine-2-carboxamide N-ethyl | phenyl | —COOH | 4 | 2.35 | 447.2 |

TABLE 2-continued

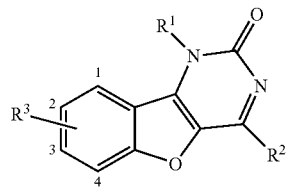

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2193 | CH₃OCH₂CH₂— | 4-(NHC(O)CH₃)-phenyl | Br | 2 | 3.31 | 456.0 |
| 2194 | CH₃OCH₂CH₂— | 4-(NHS(O)₂CH₃)-phenyl | 4-((CH₃)₂NCH₂)-phenyl | 2 | 2.70 | 547.2 |
| 2195 | 1-(CH₂CH₂-)-pyrrolidine-2-carboxamide | phenyl | 4-(imidazol-1-ylmethyl)-phenyl | 3 | 2.54 | 559.2 |
| 2196 | 1-(CH₂CH₂-)-pyrrolidine-2-carboxamide | phenyl | —CONHCH₂CH₃ | 4 | 2.50 | 474.3 |
| 2197 | 1-(CH₂CH₂-)-pyrrolidine-2-carboxamide | phenyl | pyridin-4-ylmethyl-NHC(O)— | 4 | 2.10 | 537.2 |
| 2198 | 1-(CH₂CH₂-)-pyrrolidine-2-carboxamide | phenyl | HOOC-CH₂-NHC(O)— | 4 | 2.27 | 504.2 |
| 2199 | 1-(CH₂CH₂-)-pyrrolidine-2-carboxamide | phenyl | pyridin-3-yl-NHC(O)— | 4 | 2.20 | 523.2 |

TABLE 2-continued

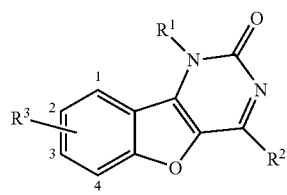

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2200 | (S)-pyrrolidine-2-carboxamide N-propyl | phenyl | —CONH₂ | 4 | 2.21 | 446.2 |
| 2201 | CH₃OCH₂CH₂CH₂— | phenyl | Br | 2 | 3.87 | 413.0 |
| 2202 | CH₃OCH₂CH₂CH₂— | phenyl | pyridin-3-yl | 2 | 2.73 | 412.2 |
| 2203 | CH₃OCH₂CH₂CH₂— | phenyl | 2-methyl-1,2,3,4-tetrahydroisoquinolin-6-yl | 2 | 3.00 | 480.2 |
| 2204 | (S)-pyrrolidine-2-carboxamide N-propyl | phenyl | phenyl | 3 | 3.49 | 479.2 |
| 2205 | (S)-pyrrolidine-2-carboxamide N-propyl | phenyl | —CN | 3 | 2.66 | 428.1 |
| 2206 | (S)-pyrrolidine-2-carboxamide N-propyl | 4-fluorophenyl | 4-((dimethylamino)methyl)phenyl | 2 | 2.71 | 554.2 |
| 2207 | (S)-pyrrolidine-2-carboxamide N-propyl | 4-fluorophenyl | thiazol-2-yl | 2 | 3.06 | 504.1 |

TABLE 2-continued

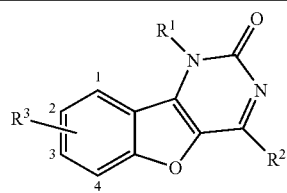

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2208 | (S)-prolinamide-N-ethyl | 4-fluorophenyl | 1-(carbamoylmethyl)pyrazol-4-yl | 2 | 2.67 | 544.2 |
| 2209 | (S)-prolinamide-N-ethyl | 4-fluorophenyl | pyridin-3-yl | 2 | 2.36 | 498.2 |
| 2210 | (S)-prolinamide-N-ethyl | 4-fluorophenyl | 3-(hydroxymethyl)phenyl | 2 | 3.18 | 527.2 |
| 2211 | (S)-prolinamide-N-ethyl | 4-fluorophenyl | 2-methyl-1,2,3,4-tetrahydroisoquinolin-6-yl | 2 | 2.73 | 566.2 |
| 2212 | 4-methoxybutyl | phenyl | 4-(dimethylaminomethyl)phenyl | 2 | 3.14 | 482.2 |
| 2213 | phenyl | phenyl | 4-(dimethylaminomethyl)phenyl | 2 | 3.21 | 472.2 |
| 2214 | n-butyl | phenyl | 4-(dimethylaminomethyl)phenyl | 2 | 3.49 | 465.0 |
| 2215 | 2-morpholinoethyl | phenyl | —NO₂ | 2 | 1.35 | 421.1 |

TABLE 2-continued
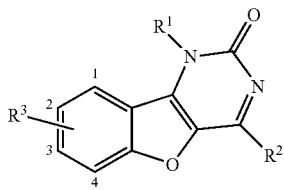
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2216 | 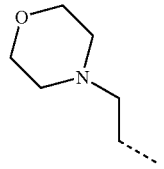 | 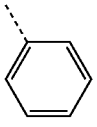 | —NH₂ | 2 | 1.06 | 391.1 |
| 2217 | 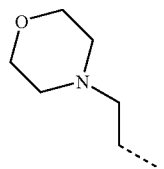 | 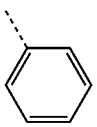 | —OCH₃ | 3 | 1.38 | 406.1 |
| 2218 | 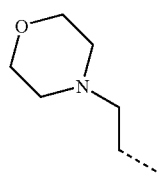 | 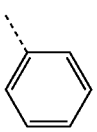 | Cl | 2 | 1.44 | 410.1 |
| 2219 | 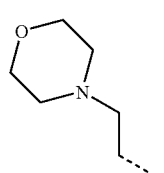 | 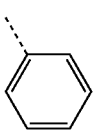 | OH | 3 | 1.19 | 392.1 |
| 2220 | 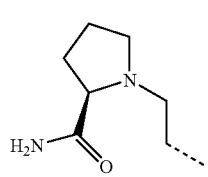 | 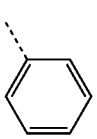 | 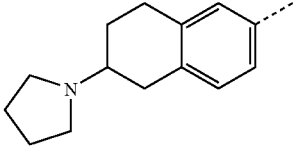 | 3 | 2.67 | 602.5 |
| 2221 | 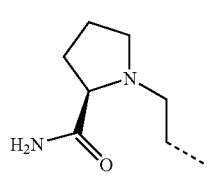 | 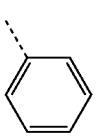 | 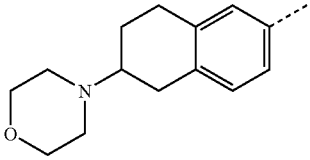 | 3 | 2.61 | 618.4 |
| 2222 | 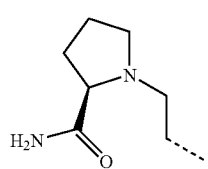 | 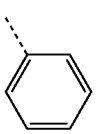 | 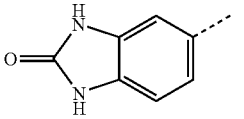 | 3 | 2.62 | 535.2 |

TABLE 2-continued

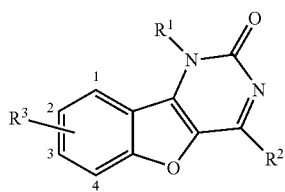

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2223 | (S)-pyrrolidine-2-carboxamide | phenyl | 3-amino-1H-indazol-6-yl | 3 | 2.53 | 534.2 |
| 2224 | (S)-pyrrolidine-2-carboxamide | phenyl | indolin-5-yl | 3 | 2.45 | 520.2 |
| 2225 | (S)-pyrrolidine-2-carboxamide | phenyl | 1-(2-morpholino-2-oxoethyl)-1H-pyrazol-4-yl | 2 | 2.72 | 596.2 |
| 2226 | (S)-pyrrolidine-2-carboxamide | phenyl | 1-(carbamoylmethyl)-1H-pyrazol-4-yl | 2 | 2.62 | 526.1 |
| 2227 | (S)-pyrrolidine-2-carboxamide | phenyl | 5-methyl-1,3,4-thiadiazol-2-yl | 2 | 2.74 | 501.1 |
| 2228 | (S)-pyrrolidine-2-carboxamide | phenyl | 2-methylthiazol-4-yl | 2 | 2.96 | 500.1 |
| 2229 | (S)-pyrrolidine-2-carboxamide | phenyl | 3-amino-1-methyl-1H-pyrazol-4-yl | 2 | 2.55 | 498.2 |

TABLE 2-continued

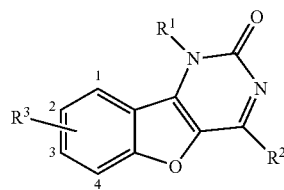

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2230 | (S)-pyrrolidine-2-carboxamide N-propyl | phenyl | 4-aminobenzyl-pyrazol-1-yl | 2 | 2.62 | 574.2 |
| 2231 | (S)-pyrrolidine-2-carboxamide N-propyl | phenyl | 2-hydroxyethyl-pyrazol-1-yl | 2 | 2.67 | 513.2 |
| 2232 | pyrrolidin-1-yl-propyl | 6-(4-methylpiperazin-1-yl)pyridin-3-yl | Cl | 2 | 2.40 | 492.6 |
| 2233 | CH$_3$OCH$_2$CH$_2$— | 6-(ethylamino)pyridin-3-yl | Cl | 2 | 2.61 | 399.2 |
| 2234 | CH$_3$OCH$_2$CH$_2$— | 6-(3,5-dimethylpiperazin-1-yl)pyridin-3-yl | Cl | 2 | 2.90 | 468.3 |

TABLE 2-continued
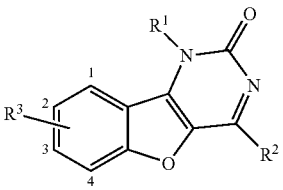
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2235 | CH₃OCH₂CH₂— | 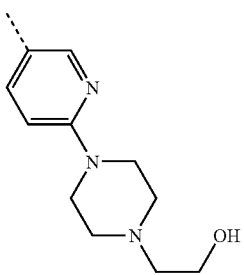 | Cl | 2 | 2.80 | 484.2 |
| 2236 | CH₃OCH₂CH₂— | 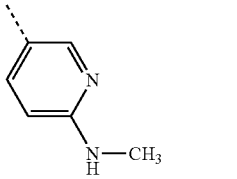 | Cl | 2 | 2.47 | 385.2 |
| 2237 | CH₃OCH₂CH₂— | 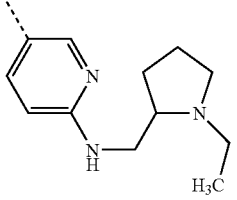 | Cl | 2 | 2.93 | 482.3 |
| 2238 | CH₃OCH₂CH₂— | 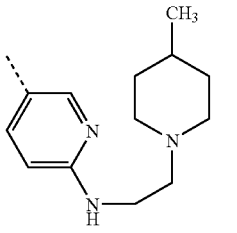 | Cl | 2 | 2.94 | 496.4 |
| 2239 | CH₃OCH₂CH₂— | 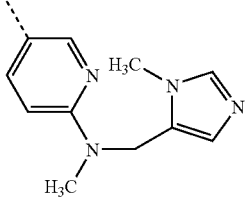 | Cl | 2 | 2.66 | 479.3 |

TABLE 2-continued

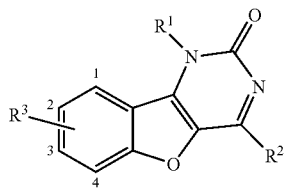

Site designates the attachment site (1, 2, 3 or 4) for $R^3$.

| Cpd | $R^1$ | $R^2$ | $R^3$ | Site | $t_R$ (min) | MS (M + H)$^+$ |
|---|---|---|---|---|---|---|
| 2240 | CH$_3$OCH$_2$CH$_2$— | 5-pyridyl-N(CH$_3$)-CH$_2$-(1-methylpyrrolidin-3-yl) | Cl | 2 | 2.69 | 482.4 |
| 2241 | CH$_3$OCH$_2$CH$_2$— | 5-pyridyl-(4-hydroxypiperidin-1-yl) | Cl | 2 | 2.56 | 455.3 |
| 2242 | CH$_3$OCH$_2$CH$_2$— | 5-pyridyl-NH-CH$_2$-(piperidin-4-yl) | Cl | 2 | 2.62 | 468.3 |
| 2243 | CH$_3$OCH$_2$CH$_2$— | 5-pyridyl-(2-((dimethylamino)methyl)morpholin-4-yl) | Cl | 2 | 2.83 | 498.3 |
| 2244 | CH$_3$OCH$_2$CH$_2$— | 5-pyridyl-N(CH$_3$)-CH$_2$-(1-methylpiperidin-4-yl) | Cl | 2 | 2.64 | 496.4 |

TABLE 2-continued
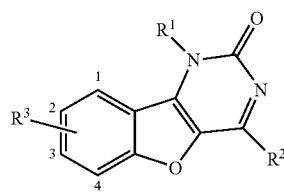
Site designates the attachment site (1, 2, 3 or 4) for $R^3$.
| Cpd | $R^1$ | $R^2$ | $R^3$ | Site | $t_R$ (min) | MS (M + H)$^+$ |
|---|---|---|---|---|---|---|
| 2245 | CH$_3$OCH$_2$CH$_2$— | | Cl | 2 | 2.60 | 482.3 |
| 2246 | CH$_3$OCH$_2$CH$_2$— | | Cl | 2 | 2.91 | 443.3 |
| 2247 | CH$_3$OCH$_2$CH$_2$— | | Cl | 2 | 2.68 | 465.3 |
| 2248 | CH$_3$OCH$_2$CH$_2$— | | Cl | 2 | 2.92 | 498.4 |
| 2249 | CH$_3$OCH$_2$CH$_2$— | | Cl | 2 | 3.06 | 482.4 |
| 2250 | CH$_3$OCH$_2$CH$_2$— | | Cl | 2 | 2.64 | 482.3 |

TABLE 2-continued
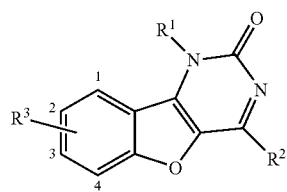
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2251 | CH₃OCH₂CH₂— | pyridine-pyrrolidine-C(O)NH₂ | Cl | 2 | 2.73 | 468.3 |
| 2252 | CH₃OCH₂CH₂— | pyridine-NH-(N-methylpyrrolidine) | Cl | 2 | 2.71 | 454.3 |
| 2253 | CH₃OCH₂CH₂— | pyridine-pyrrolidine-NHC(O)CH₃ | Cl | 2 | 2.74 | 482.3 |
| 2254 | CH₃OCH₂CH₂— | pyridine-pyrrolidine-NHCH₃ | Cl | 2 | 2.59 | 454.3 |
| 2255 | pyrrolidine-propyl | pyridine-(N-methylpiperazine) | thiazole | 2 | 2.48 | 542.4 |

TABLE 2-continued
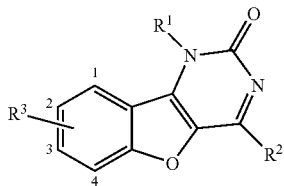
Site designates the attachment site (1, 2, 3 or 4) for $R^3$.
| Cpd | $R^1$ | $R^2$ | $R^3$ | Site | $t_R$ (min) | MS (M + H)$^+$ |
|---|---|---|---|---|---|---|
| 2256 | pyrrolidine-2-carboxamide-N-propyl | 5-(4-methylpiperazin-1-yl)pyridin-2-yl | Cl | 2 | 2.38 | 536.4 |
| 2257 | $CH_3$— | 5-(4-methylpiperazin-1-yl)pyridin-2-yl | Br | 2 | 2.64 | 456.2 |
| 2258 | $CH_3OCH_2CH_2$— | 5-(4-methylpiperazin-1-yl)pyridin-2-yl | Br | 2 | 2.80 | 500.3 |
| 2259 | pyrrolidine-2-carboxamide-N-propyl | 5-(4-methylpiperazin-1-yl)pyridin-2-yl | Br | 2 | 2.28 | 582.3 |

TABLE 2-continued

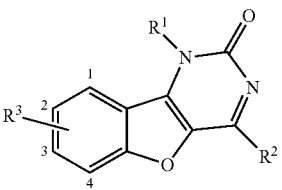

Site designates the attachment site (1, 2, 3 or 4) for $R^3$.

| Cpd | $R^1$ | $R^2$ | $R^3$ | Site | $t_R$ (min) | MS $(M+H)^+$ |
|---|---|---|---|---|---|---|
| 2260 | $CH_3OCH_2CH_2$— | 5-(4-methylpiperazin-1-yl)pyridin-2-yl | Cl | 2 | 2.87 | 454.3 |
| 2261 | 2-methyl-5-cyanophenyl | phenyl | 4-(N,N-dimethylaminomethyl)phenyl | 2 | 3.11 | 511.2 |
| 2262 | 4-nitrophenyl | phenyl | 4-(N,N-dimethylaminomethyl)phenyl | 2 | 3.11 | 517.2 |
| 2263 | $CH_3$— | 4-(4-morpholinopiperidin-1-yl)phenyl | Cl, Cl | 2, 4 | 2.93 | 513.2/ |
| 2264 | methylsulfonylpropyl | 6-(4-methylpiperazin-1-yl)pyridin-3-yl | Cl | 2 | 2.57 | 516.3 |

TABLE 2-continued
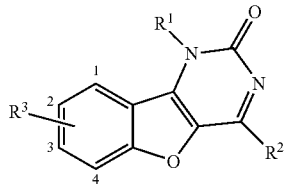
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2265 | | | Cl, Cl | 2, 4 | 3.06 | 489.2 |
| 2266 | | | Cl, Cl | 2, 3 | 1.52 | 489.1 |
| 2267 | | | Br | 2 | 1.55 | 524.3 |
| 2268 | | | | 2 | 1.30 | 528.5 |

TABLE 2-continued
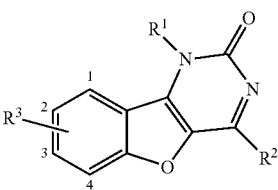
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2269 | 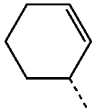 | 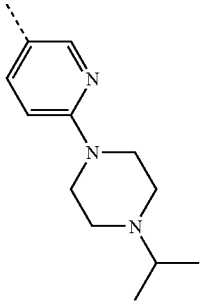 | Cl | 2 | 3.22 | 504.3 |
| 2270 |  | 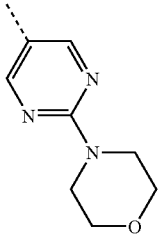 | Cl | 2 | 4.02 | 454.3 |
| 2271 | 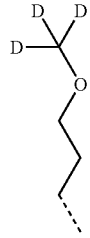 | 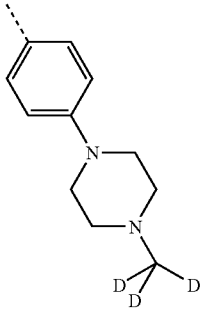 | Cl | 2 | 2.88 | 473.2 |
| 2272 | 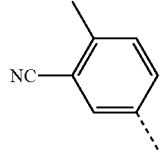 | 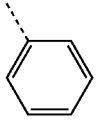 | 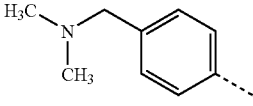 | 2 | 3.12 | 511.2 |
| 2273 |  | 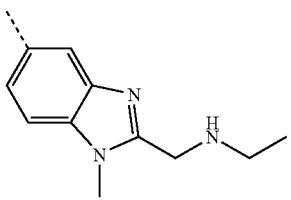 | Cl | 2 | 2.89 | 480.2 |

TABLE 2-continued
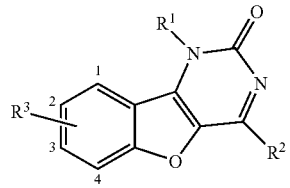
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2274 | | | Cl | 2 | 3.3 | 493.3 |
| 2275 | | | Cl | 2 | 2.83 | 501.2 |
| 2276 | | | Br | 2 | 3.05 | 457.0 |
| 2277 | | | Cl | 2 | 2.74 | 553.4 |

TABLE 2-continued

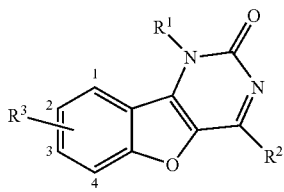

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2278 | 2-methoxyphenylmethyl | 4-(4-isopropylpiperazin-1-yl)phenyl | Cl | 2 | 3.21 | 529.2 |
| 2279 | 3-methoxypropyl | 5-[cyclopropyl(1-methylpiperidin-4-yl)amino]pyrazin-2-yl | Cl | 2 | 2.84 | 523.4 |
| 2280 | pentyl | 5-{[1-(2-methoxyethyl)pyrrolidin-3-yl]amino}pyridin-2-yl | 1,4-dimethyl-1H-pyrazol-4-yl | 2 | 2.82 | 556.5 |
| 2281 | 3-methoxypropyl | 4-[(cyclopropylaminoacetyl)amino]phenyl | Cl, Cl | 2, 4 | 3.15 | 515.1 |
| 2282 | 3-methoxypropyl | 4-[(ethylaminoacetyl)amino]phenyl | Cl, Cl | 2, 3 | 3.12 | 503.1 |

TABLE 2-continued

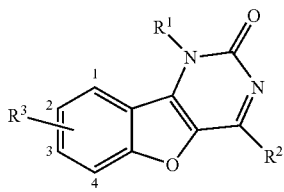

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2283 | methoxypropyl | 1-methylimidazol-2-yl | Cl | 2 | 2.59 | 373.2 |
| 2284 | pentyl | 1-methyl-2-(ethylaminomethyl)benzimidazol-5-yl | Cl | 2 | 3.21 | 478.1 |
| 2285 | pyrrolidinyl-carbonylmethyl | phenyl | 4-(dimethylaminomethyl)phenyl | 2 | 2.81 | 507.3 |
| 2286 | methoxypropyl | 1-methyl-2-(2-methylaminoethyl)benzimidazol-5-yl | Cl | 2 | 2.74 | 480.2 |
| 2287 | pentyl | 1,2-dimethylbenzimidazol-5-yl | 1-methylpyrazol-4-yl | 2 | 2.83 | 481.2 |
| 2288 | pyridin-4-yl | 4-(4-isopropylpiperazin-1-yl)phenyl | Cl | 2 | 2.62 | 500.2 |

TABLE 2-continued
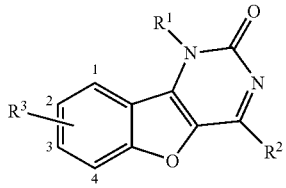
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2289 | CF₃-(chain) | 4-(4-pyrrolidin-1-yl-piperidin-1-yl)phenyl | Cl | 2 | 3.2 | 559.1 |
| 2290 | ethoxypropyl | 5-(2-aminoethylamino)pyridin-2-yl | CF₃ | 2 | 2.7 | 462.2 |
| 2291 | 2,2-difluoropropyl | phenyl | 2-methyl-1,2,3,4-tetrahydroisoquinolin-6-yl | 2 | 3.05 | 472.2 |
| 2292 | 4-nitrophenyl | phenyl | 2-methyl-1,2,3,4-tetrahydroisoquinolin-6-yl | 2 | 3.14 | 529 |
| 2293 | ethoxypropyl | 2-(4-(pyridin-4-yl)piperazin-1-yl)pyridin-4-yl | Br | 2 | 2.78 | 575.3 |

TABLE 2-continued

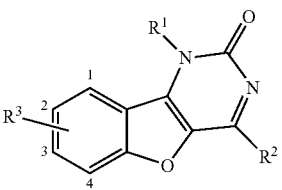

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2294 | 4-methoxyphenyl | 4-(4-isopropylpiperazin-1-yl)phenyl | Cl | 2 | 3.16 | 529.1 |
| 2295 | 3-methoxypropyl | 1-methyl-2-((2-methoxyethylamino)methyl)benzimidazol-5-yl | Cl | 2 | 2.82 | 453.1 |
| 2296 | 4-methoxycyclohexyl | 6-(methylamino)pyridin-3-yl | Cl | 2 | 2.99 | 439.2 |
| 2297 | 2-chloro-5-cyanophenyl | phenyl | 4-((dimethylamino)methyl)phenyl | 2 | 3.16 | 531.1 |
| 2298 | 3-methoxypropyl | 1-methylbenzimidazol-5-yl | NC | 2 | 2.58 | 414.1 |
| 2299 | morpholin-4-yl-carbonylmethyl | phenyl | 4-((dimethylamino)methyl)phenyl | 2 | 2.79 | 523.3 |

TABLE 2-continued
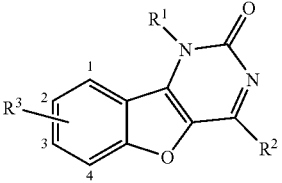
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2300 | 2-Cl, 5-CN-phenyl | 6-(4-isopropylpiperazin-1-yl)pyridin-3-yl | Cl | 2 | 3.22 | 559.1 |
| 2301 | 4-methylphenyl | 4-(4-isopropylpiperazin-1-yl)phenyl | Cl | 2 | 3.3 | 513.3 |
| 2302 | 2-CN, 5-methyl-phenyl | 6-(4-isopropylpiperazin-1-yl)pyridin-3-yl | Cl | 2 | 3.04 | 511.2 |
| 2303 | 2-(tetrahydrofuran-2-yl)ethyl | 6-(4-methylpiperazin-1-yl)pyridin-3-yl | Cl | 2 | 2.94 | 494.4 |

TABLE 2-continued

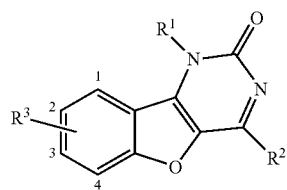

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2304 | tetrahydrofuran-2-ylethyl | 5-(1-methylpyrrolidin-3-ylamino)pyridin-2-yl | Cl | 2 | 2.81 | 494.4 |
| 2305 | tetrahydrofuran-2-ylmethyl | phenyl | 2-methyl-1,2,3,4-tetrahydroisoquinolin-6-yl | 2 | 2.97 | 492.1 |
| 2306 | pyridin-3-yl | phenyl | 4-(dimethylaminomethyl)phenyl | 2 | 2.82 | 473.2 |
| 2307 | 2-chloro-5-cyanophenyl | phenyl | 2-methyl-1,2,3,4-tetrahydroisoquinolin-6-yl | 2 | 3.12 | 523.1 |
| 2308 | 2-(piperidin-1-yl)-2-oxoethyl | phenyl | 4-(dimethylaminomethyl)phenyl | 2 | 2.89 | 521.3 |
| 2309 | 2-(3-methoxypiperidin-1-yl)-2-oxoethyl | phenyl | 4-(dimethylaminomethyl)phenyl | 2 | 2.88 | 551.3 |
| 2310 | N-cyclopropylcarbamoylmethyl | phenyl | 4-(dimethylaminomethyl)phenyl | 2 | 2.82 | 493.3 |

TABLE 2-continued
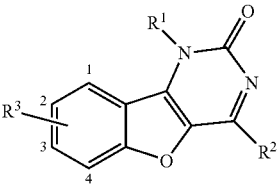
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2311 | F₃C-(CH₂)₅- | 4-(4-pyrrolidin-1-yl-piperidin-1-yl)phenyl | Cl | 2 | 3.26 | 573.3 |
| 2312 | n-hexyl | pyrimidin-5-yl | Br | 2 | 3.62 | 415.1 |
| 2313 | 4-(methylsulfonyl)phenyl | 6-(4-methylpiperazin-1-yl)pyridin-3-yl | Cl | 2 | 2.79 | 550.1 |
| 2314 | 3-(methylsulfonyl)phenyl | 6-(4-methylpiperazin-1-yl)pyridin-3-yl | Cl | 2 | 2.77 | 550.2 |

TABLE 2-continued

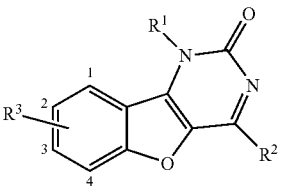

Site designates the attachment site (1, 2, 3 or 4) for R³.

| Cpd | R¹ | R² | R³ | Site | $t_R$ (min) | MS (M + H)⁺ |
|---|---|---|---|---|---|---|
| 2315 | D₃C-CH₂-CH₂-CH₂-O-CH₂-⁓ (CD₃ methyl ether butyl chain) | 4-(4-methylpiperazin-1-yl)phenyl | Cl | 2 | 2.88 | 470.2 |
| 2316 | HOOC-CH₂-CH₂-⁓ | phenyl | 4-((dimethylamino)methyl)phenyl | 2 | 2.81 | 453.0 |
| 2317 | CH₃-O-CH₂-CH₂-CH₂-CH₂-⁓ | 1,2-dimethyl-1H-benzimidazol-5-yl | thiazol-5-yl | 2 | 2.65 | 486.1 |
| 2318 | 4-methoxyphenyl | phenyl | 4-((dimethylamino)methyl)phenyl | 2 | 3.08 | 502.1 |
| 2319 | HOOC-CH₂-CH₂-⁓ | 6-(4-isopropylpiperazin-1-yl)pyridin-3-yl | Cl | 2 | 3.44 | 482.2 |

TABLE 2-continued
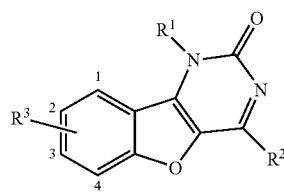
Site designates the attachment site (1, 2, 3 or 4) for $R^3$.
| Cpd | $R^1$ | $R^2$ | $R^3$ | Site | $t_R$ (min) | MS (M + H)$^+$ |
|---|---|---|---|---|---|---|
| 2320 | | | Br | 2 | 3.06 | 510.2 |
| 2321 | | | Br | 2 | 2.96 | 498.1 |
| 2322 | | | Cl | 2 | 2.9 | 537.2 |
| 2323 | | | Br | 2 | 2.92 | 486.1 |
| 2324 | | | Cl | 2 | 2.97 | 483.2 |

TABLE 2-continued
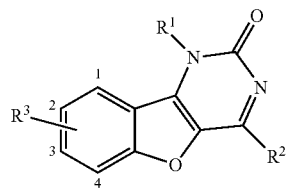
Site designates the attachment site (1, 2, 3 or 4) for R³.
| Cpd | R¹ | R² | R³ | Site | $t_R$ (min) | MS (M + H)⁺ |
|---|---|---|---|---|---|---|
| 2325 | methoxybutyl | 2,3-dimethylimidazo[4,5-b]pyridin-6-yl | Cl | 2 | 2.76 | 438.1 |
| 2326 | methoxybutyl | 4-(2-(cyclobutylamino)acetamido)phenyl | Cl | 2 | 3.02 | 495.2 |
| 2327 | methoxybutyl | 4-(4-(3-methoxypropyl)piperazin-1-yl)phenyl | Cl | 2 | 2.98 | 525.2 |
| 2328 | methoxybutyl | 4-(N-methyl-N-(2-morpholinoethyl)amino)phenyl | Cl | 2 | 2.93 | 511.2 |

TABLE 3
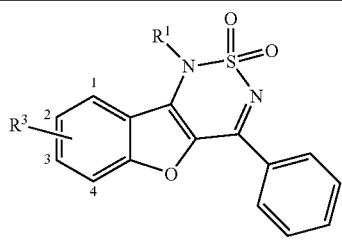
Site designates the attachment site (1, 2, 3 or 4) for $R^3$.
| Cpd | $R^1$ | $R^3$ | Site | $t_R$ (min) | MS $(M + H)^+$ |
|---|---|---|---|---|---|
| 3001 | $CH_3OCH_2CH_2-$ | H₃C-N(CH₃)-CH₂-C₆H₄- | 2 | 3.43 | 490.2 |
| 3002 | $CH_3-$ | H₃C-N(CH₃)-CH₂-C₆H₄- | 2 | 3.74 | 446.2 |
| 3003 | tetrahydrofuran-2-ylmethyl | H₃C-N(CH₃)-CH₂-C₆H₄- | 2 | 3.48 | 516.2 |
| 3004 | $CH_3OCH_2CH_2CH_2-$ | H₃C-N(CH₃)-CH₂-C₆H₄- | 2 | 3.90 | 504.2 |
TABLE 4
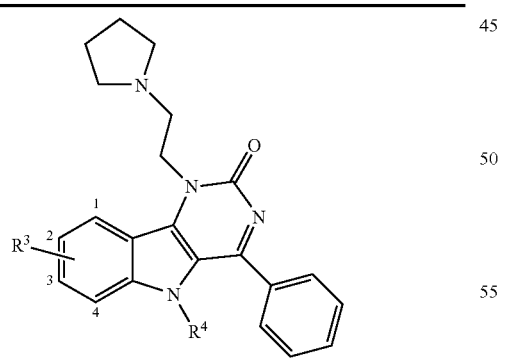
Site designates the attachment site (1, 2, 3 or 4) for $R^3$.
| Cpd | $R^3$ | Site | $R^4$ | $t_R$ (min) | MS $(M + H)^+$ |
|---|---|---|---|---|---|
| 4001 | Cl | 2 | $HOOCCH_2-$ | 2.50 | 453.3 |
| 4002 | Br | 2 | $CH_3-$ | 2.94 | 453.3 |
| 4003 | Cl | 2 | H | 2.64 | 395.4 |

TABLE 5

| Cpd | A₁ | A₂ | A₃ | A₄ | R₁ | R₂ | $t_R$ (min) | MS $(M+H)^+$ |
|---|---|---|---|---|---|---|---|---|
| 5001 | CH | CH | CH | N | CH₃O(CH₂)₃– | 5-(4-(3-methoxypropyl)piperazin-1-yl)pyridin-2-yl | 2.42 | 493.3 |
| 5002 | CH | CH | N | CH | CH₃O(CH₂)₃– | 5-(4-methylpiperazin-1-yl)pyridin-2-yl | 2.18 | 435.2 |
| 5003 | CH | thiazole | CH | N | CH₃O(CH₂)₃– | 5-((1-(3-methoxypropyl)pyrrolidin-3-yl)amino)pyridin-2-yl | 2.52 | 576.4 |
| 5004 | CH | N-methylpyrazole | CH | N | CH₃O(CH₂)₃– | 5-(4-((2,2-difluoroethyl)amino)piperidin-1-yl)pyridin-2-yl | 2.40 | 579.3 |

TABLE 5-continued
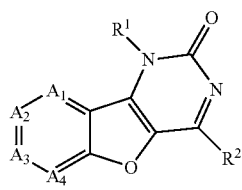
| Cpd | A₁ | A₂ | A₃ | A₄ | R₁ | R₂ | $t_R$ (min) | MS (M + H)⁺ |
|---|---|---|---|---|---|---|---|---|
| 5005 | H | 1-methylpyrazol-4-yl | CH | N | CH₃O(CH₂)₃– | 5-(4-(4,4-difluoropiperidin-1-yl)piperidin-1-yl)pyridin-3-yl | 2.95 | 416.4 |
| 5006 | H | 1-methylpyrazol-4-yl | CH | N | CH₃O(CH₂)₃– | 5-(4-(3-oxopiperazin-1-yl)piperidin-1-yl)pyridin-3-yl | 2.11 | 598.4 |
| 5007 | CH | pyridin-3-yl | CH | N | pentyl | 2-(dimethylamino)pyrimidin-5-yl | 2.08 | 455.3 |
| 5008 | CH | CH | CH | N | CH₃O(CH₂)₃– | 6-(4-cyclopropylpiperazin-1-yl)pyridin-3-yl | 2.39 | 461.3 |

TABLE 5-continued

| Cpd | A₁ | A₂ | A₃ | A₄ | R₁ | R₂ | t_R (min) | MS (M + H)⁺ |
|---|---|---|---|---|---|---|---|---|
| 5009 | CH | 1-methyl-pyrazol-4-yl | CH | N | 3-methoxypropyl | 5-[4-(2-methoxyethyl)piperazin-1-yl]pyridin-2-yl | 2.5 | 559.5 |
| 5010 | CH | 1-methyl-pyrazol-4-yl | CH | N | pentyl | 5-[4-(3-methoxypropyl)piperazin-1-yl]pyridin-2-yl | 2.81 | 571.5 |
| 5011 | CH | 1-methyl-pyrazol-4-yl | CH | N | 3-methoxypropyl | 5-[4-(2-ethoxyethyl)piperazin-1-yl]pyridin-2-yl | 2.58 | 573.5 |
| 5012 | CH | thiazol-5-yl | CH | N | 3-methoxypropyl | 5-[4-(2-ethoxyethyl)piperazin-1-yl]pyridin-2-yl | 2.64 | 576.3 |

TABLE 5-continued
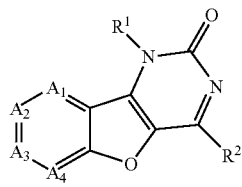
| Cpd | A$_1$ | A$_2$ | A$_3$ | A$_4$ | R$_1$ | R$_2$ | t$_R$ (min) | MS (M + H)$^+$ |
|---|---|---|---|---|---|---|---|---|
| 5013 | N | CH | CH | CH | CH$_3$O(CH$_2$)$_3$- | 5-(4-isopropylpiperazin-1-yl)pyridin-2-yl | 2.48 | 463.3 |
| 5014 | CH | CH | CH | N | CH$_3$O(CH$_2$)$_3$- | 5-(4-isopropylpiperazin-1-yl)pyridin-2-yl | 2.39 | 463.3 |
| 5015 | CH | N-methylpyrazol-4-yl | CH | N | pentyl | 5-[1-(3-methoxypropyl)pyrrolidin-3-ylamino]pyridin-2-yl | 2.72 | 571.5 |
| 5016 | CH | N-methylpyrazol-4-yl | CH | N | pentyl | 5-[4-(2-methoxyethyl)piperazin-1-yl]pyridin-2-yl | 2.78 | 557.5 |

TABLE 5-continued

| Cpd | A₁ | A₂ | A₃ | A₄ | R₁ | R₂ | t_R (min) | MS (M+H)⁺ |
|---|---|---|---|---|---|---|---|---|
| 5017 | CH | N-methyl pyrazol-4-yl | CH | N | CH₃O(CH₂)₃– | 5-(4-methylpiperazin-1-yl)pyridin-2-yl | 2.09 | 516.5 |
| 5018 | CH | thiazol-5-yl | CH | N | CH₃O(CH₂)₃– | 5-[4-(3-methoxypropyl)piperazin-1-yl]pyridin-2-yl | 2.59 | 576.4 |
| 5019 | CH | CH | N | CH | CH₃O(CH₂)₃– | 5-(4-isopropylpiperazin-1-yl)pyridin-2-yl | 2.27 | 463.3 |
| 5020 | CH | N≡C | CH | N | CH₃O(CH₂)₃– | 5-(4-methylpiperazin-1-yl)pyridin-2-yl | 2.45 | 460.3 |

TABLE 5-continued
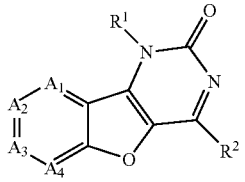
| Cpd | A₁ | A₂ | A₃ | A₄ | R₁ | R₂ | $t_R$ (min) | MS $(M+H)^+$ |
|---|---|---|---|---|---|---|---|---|
| 5021 | CH | H₃C-C | CH | N | CH₃O(CH₂)₃- | 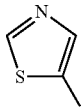 | 2.47 | 449.3 |
| 5022 | CH | 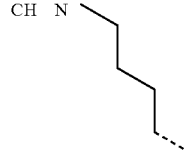 | CH | N | pentyl | 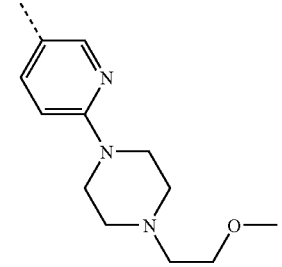 | 2.84 | 560.4 |
| 5023 | CH | 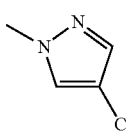 | CH | N | CH₃O(CH₂)₃- | 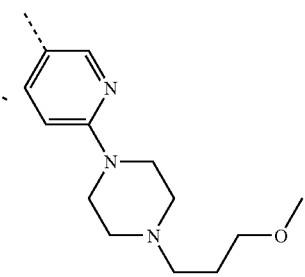 | 2.53 | 573.5 |
| 5024 | CH | N-C | CH | N | pentyl |  | 2.81 | 458.3 |

TABLE 5-continued
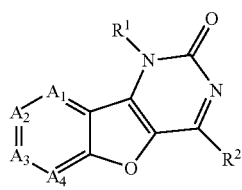
| Cpd | A₁ | A₂ | A₃ | A₄ | R₁ | R₂ | t_R (min) | MS (M + H)⁺ |
|---|---|---|---|---|---|---|---|---|
| 5025 | CH | pyrazole | CH | N | CH₃O-propyl | pyridine-piperidine-piperidine-OMe | 3.72 | 613.7 |
| 5026 | CH | pyrazole | CH | N | CH₃O-propyl | pyrimidine-NHMe | 2.35 | 447.3 |
| 5027 | CH | pyrazole | CH | N | CH₃O-propyl | pyridine-N-methylpiperazine | 2.43 | 515.4 |
| 5028 | CH | thiazole | CH | N | CH₃O-propyl | pyridine-N-methylpiperazine | 2.48 | 518.4 |
| 5029 | CH | pyrazole | CH | N | pentyl | pyridine-NHMe | 2.69 | 444.4 |

TABLE 5-continued

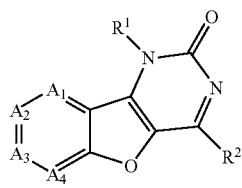

| Cpd | A₁ | A₂ | A₃ | A₄ | R₁ | R₂ | $t_R$ (min) | MS (M + H)⁺ |
|---|---|---|---|---|---|---|---|---|
| 5030 | CH | (pyrazole) | CH | N | (pyrrolidine acyl) | (pyridyl-NH) | 1.98 | 485.3 |

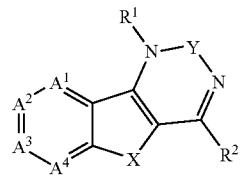

TABLE 6

Representative compounds drawn from Tables 1 to 5 show the following IC₅₀ values when tested in the assay of Example 67 and the following EC₅₀ values when tested in the assay of Example 68.

| Compound | IC₅₀, nM | EC₅₀, nM |
|---|---|---|
| 1001 | 2350 | — |
| 1002 | 11000 | 15000 |
| 1004 | 1150 | 3600 |
| 1005 | 215 | — |
| 1009 | 73 | 675 |
| 1016 | 107 | 6800 |
| 1036 | 633 | 14000 |
| 1051 | 520 | 980 |
| 1056 | 2500 | — |
| 1070 | 310 | 1200 |
| 1073 | 107 | 720 |
| 2001 | 593 | 3700 |
| 2009 | 323 | 2900 |
| 2013 | 33 | 363 |
| 2021 | 20 | 200 |
| 2025 | 35 | 52 |
| 2038 | 250 | 2900 |
| 2039 | 24 | 440 |
| 2115 | 1153 | — |
| 2133 | 760 | 4650 |
| 2194 | 395 | 1500 |
| 2213 | 86 | 235 |
| 2214 | 27 | 99 |
| 2232 | 22 | 240 |
| 2254 | 40 | 210 |
| 2257 | 31 | 190 |
| 2260 | 75 | 890 |
| 2273 | 8 | 58 |
| 2277 | 7 | 92 |
| 2287 | 5 | 18 |
| 2310 | 1000 | — |
| 3003 | >225 | 950 |
| 3004 | >205 | 520 |
| 4001 | 280 | 5800 |
| 5001 | 60 | 590 |
| 5004 | 14 | — |
| 5019 | 25 | 280 |
| 5024 | 6 | 32 |
| 5028 | 4.1 | 21 |
| 5030 | 70 | — |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of the formula (I):

(I)

wherein

R¹ is (C₁₋₆)alkyl, (C₂₋₆)alkenyl, (C₂₋₆)alkynyl, (C₃₋₇)cycloalkyl, (C₃₋₇)cycloalkyl-(C₁₋₆)alkyl, -aryl, aryl-(C₁₋₆)alkyl-, Het or Het-(C₁₋₆)alkyl-, wherein each of the (C₁₋₆)alkyl, (C₂₋₆)alkenyl, (C₂₋₆)alkynyl, (C₃₋₇)cycloalkyl, (C₃₋₇)cycloalkyl-(C₁₋₆)alkyl-, aryl, aryl-(C₁₋₆)alkyl-, Het and Het-(C₁₋₆)alkyl- is optionally substituted with 1 to 3 substituents each independently selected from R¹¹, halo, oxo, —CN, —NO₂, —OR¹¹, —N(R¹²)R¹¹, —C(=O)OR¹¹, —C(=O)N(R¹²)R¹¹, —C(=O)N(R¹²)—SO₂R¹¹, —N(R¹²)—C(=O)R¹²)—C(=O)OR¹¹, —N(R¹²)—C(=O)N(R¹²)R¹¹, —N(R¹²)—SO₂R¹¹, —SR¹¹, —SOR¹¹, —SO₂R¹¹ and —SO₂N(R¹²)R¹¹;

R² is R²¹, —OR²¹, —N(R¹²)R²¹, —C(=O)R²¹, —C(=O)OR²¹, —C(=O)N(R¹²)R²¹, —C(=O)N(R¹²)—SO₂R²¹, —N(R¹²)—C(=O)OR²¹, —N(R¹²)—C(=O)N(R¹²)—SO₂R²¹, —SR²¹, —SOR²¹ or —SO₂N(R¹²)R²¹;

wherein R²¹ is H, (C₁₋₆)alkyl, (C₂₋₆)alkenyl, (C₂₋₆)alkynyl, (C₃₋₇)cycloalkyl, (C₃₋₇)cycloalkyl-(C₁₋₆)alkyl-, aryl, aryl-(C₁₋₆)alkyl-, Het or Het-(C₁₋₆)alkyl-;

wherein each of the (C₁₋₆)alkyl, (C₂₋₆)alkenyl, (C₂₋₆)alkynyl, (C₃₋₇)cycloalkyl, (C₃₋₇)cycloalkyl-(C₁₋₆)alkyl-, aryl, aryl-(C₁₋₆)alkyl-, Het and Het-(C₁₋₆)alkyl- is optionally substituted with 1 to 3 substituents each independently selected from R¹¹, halo, oxo, —CN, —NO₂, —OR¹¹, —N(R¹²)R¹¹, —C(=O)R¹¹, —C(=O)OR¹¹, —C(=O)N(R¹²)R¹¹, —C(=O)N(R¹²)—SO₂R¹¹, —N(R¹²)—C(=O)R¹¹, —N(R$^{12}$)—C(=O)—(C$^{1-3}$)alkyl-N(R$^{12}$)R$^{11}$,
—N($^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is substituted with (C$_{1-6}$)alkyl or Het, wherein each of the (C$_{1-6}$)alkyl and Het is substituted with with 1 to 3 substituents each independently selected from R$^{11}$, halo, oxo, —CN, —NO$_2$, —OR$^{11}$, —N(R$^{12}$)R$^{11}$, —N((C$_{1-6}$)alkyl)$_2$R$^{11}$)$^+$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl—N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

A$^1$, A$^2$, A$^3$ and A$^4$ are each independently selected from N and CR$^3$, wherein R$^3$ is independently in each instance selected from H and R$^{33}$, wherein R$^{33}$ is independently in each instance selected from R$^{32}$, halo, —CN, —NO$_2$, —OR$^{31}$, —N(R$^{12}$)R$^{31}$, —C(=O)R$^{31}$, —C(=O)OR$^{31}$, —C(=O)N(R$^{12}$)R$^{31}$, —C(=O)N(R$^{12}$)—SO$_2$R$^{31}$, —N(R$^{12}$)—C(=O)R$^{31}$, —N(R$^{12}$)—C(=O)OR$^{31}$, —N(R$^{12}$)—C(=O)N(R$^{12}$)R$^{31}$, —N(R$^{12}$)—SO$_2$R$^{31}$, —SR$^{31}$, —SOR$^{31}$, —SO$_2$R$^{31}$ and —SO$_2$N(R$^{12}$)R$^{31}$;

wherein R$^{31}$ is independently in each instance selected from H and R$^{32}$, and R$^{32}$ is independently in each instance selected from (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from R$^{11}$, halo, oxo, —CN, —NO$_2$, —OR$^{11}$, —N(R$^{12}$)R$^{11}$, -C(=O_R$^{11}$, —C(=O)OR$^{11}$, —C(=O)N(R$^{11}$, —C(=O)N(R$^{12}$)—SO$_2$R$^{11}$, —C(=NH)N(R$^{12}$)R$^{11}$, —N(R$^{12}$)—C(=O)R$^{11}$, —N(R$^{12}$)—C(=O)OR$^{11}$, —N(R$^{12}$)—C(=O)N(R12)R11, —N(R$^{12}$)—SO$_2$R11, —SR$_{11}$, —SOR$^{11}$, —SO$_2$R$^{11}$, and —SO$_2$N(R$^{12}$)R$^{11}$;

or wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is substituted with (C$_{1-6}$)alkyl or Het, wherein each of the (C$_{1-6}$)alkyl and Het is substituted with 1 to 3 substituents each independently selected from R$^{11}$, halo, oxo, —CN, —NO$_2$, —OR$^{11}$, —(R$^{12}$)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)OR$^{11}$, —N(R$^{12}$)—C(=O)N(R$^{12}$)R$^{11}$, —N(R$^{12}$)—C(=O)—(C$_{1-3}$)alkyl-N(R12)R11, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

X is O
Y is C=O or SO$_2$;
R$^{11}$ is independently in each instance selected from H, (C$_{1-6}$)alkyl, (C$_{1-6}$)haloalkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —CN, —NO$_2$, —OH, —O(C$_{1-6}$)alkyl, —NH$_2$, —NH(C$_{1-6}$)alkyl, —N((C$_{1-6}$)alkyl)$_2$, —C(=O)—(C$_{1-6}$)alkyl, —COOH, —COO(C$_{1-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$)alkyl, —SO$_2$NH$_2$, —SO$_2$NH(C$_{1-6}$)alkyl, —SO$_2$N((C$_{1-6}$)alkyl)$_2$, —NHC(=O)—(C$_{1-6}$)alkyl, —N((C$_{1-6}$)alkyl)C(=O)—(C$_{1-6}$)alkyl, —NHSO$_2$—(C$_{1-6}$)alkyl and —N((C$_{1-6}$)alkyl)SO$_2$—(C$_{1-6}$)alkyl; and R$^{12}$ is independently in each instance selected from R$^{11}$, —OH, —O(C$_{1-6}$)alkyl, —NH$_2$ —NH(C$_{1-6}$)alkyl and —N((C$_{1-6}$)alkyl)$_2$;

wherein Het is a 4- to 7-membered saturated, unsaturated or aromatic heterocycle having 1 to 4 heteroatoms each independently selected from O, N, and S or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

or a salt thereof

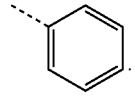

2. A compound according to claim 1, wherein R$^1$ is (C$_{1-6}$)alkyl, (C$_{2-6}$)alkenyl, aryl, Het or Het-(C$_{1-6}$)alkyl-, wherein Het and the Het portion of Het-(C$_{1-6}$)alkyl- are each independently selected from a 5- or 6-membered saturated, unsaturated or aromatic heterocycle having 1 to 3 heteroatoms each independently selected from O, N and S, or an 8- or 9-membered saturated, unsaturated or aromatic heteropolycycle having 1 or 2 N heteroatoms and wherein each of the (C$_{1-6}$)alkyl, (C$_{2-6}$)alkenyl, aryl, Het and Het-(C$_{1-6}$)alkyl- is optionally substituted with 1 to 3 substituents each independently selected from R$^{11}$, halo, —CN, —NO$_2$, —OR$^{11}$, —N(R$^{12}$)R$^{11}$, —C(=O)N)R$^{12}$)R$^{11}$, —N(R$^{12}$)—C(=O)R$^{11}$ and —N(R$^{12}$)—C(=O)OR$^{11}$;

wherein R$^{11}$ and R$^{12}$ are each independently in each instance selected from H, (C$_{1-6}$)alkyl, (C$_{1-6}$)haloalkyl, (C$_{2-6}$)alkynyl, (C$_{3-7}$)cycloalkyl-(C$_{1-6}$)alkyl-, aryl-(C$_{1-6}$)alkyl-, Het and Het-(C$_{1-6}$)alkyl-, wherein Het and the Het portion of Het-(C$_{1-6}$)alkyl- are each independently selected from a 5- or 6-membered saturated, unsaturated or aromatic heterocycle having 1 or 2 heteroatoms each independently selected from O and N, and wherein each of the (C$_{1-6}$)alkyl, (C$_{2-6}$)alkynyl, (C$_{3-7}$)cycloalkyl-(C$_{1-6}$)alkyl-, aryl-(C$_{1-6}$)alkyl-, Het and Het-(C$_{1-6}$)alkyl- are optionally substituted with 1 to 3 substituents each independently selected from (C$_{1-6}$)alkyl, halo, —CN, —OH, —O(C$_{1-6}$)alkyl and —N((C$_{1-6}$)alkyl)$_2$.

3. A compound according to claim 1, wherein R$^1$ is (C$_{1-6}$)alkyl, (C$_{2-6}$)alkenyl, aryl, Het or Het-(C$_{1-6}$)alkyl-, wherein Het and the Het portion of Het-(C$_{1-6}$)alkyl- are each independently selected from

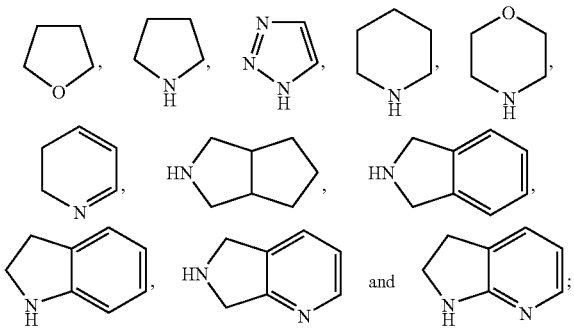

and wherein each of the (C$_{1-6}$)alkyl, (C$_{2-6}$)alkenyl, aryl, Het and Het-(C$_{1-6}$)alkyl- is optionally substituted with 1 to 3 substituents each independently selected from R$^{11}$, halo, —CN, —NO$_2$, —OR", —N(R$^{12}$)R$^{11}$, —C(=O)R$^{11}$, —C(=O)OR$^{11}$, —C(=O)N(R$^{12}$)R$^{11}$, —N(R$^{12}$)—C(=O) R$^{11}$ and —N(R$^{12}$)—C(=O)OR$^{11}$;

wherein R$^{11}$ is independently in each instance selected from H, (C$_{1-6}$)alkyl, (C$_{1-6}$)haloalkyl, (C$_{2-6}$)alkynyl, (C$_{3-7}$)cycloalkyl-(C$_{1-6}$)alkyl-, aryl-(C$_{1-6}$)alkyl-, Het and Het-(C$_{1-6}$)alkyl-, wherein Het and the Het portion of Het-(C$_{1-6}$)alkyl- are each independently selected from

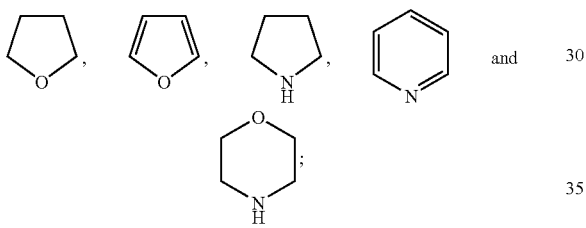

and wherein each of the (C$_{1-6}$)alkyl, (C$_{2-6}$)alkynyl, (C$_{3-7}$) cycloalkyl-(C$_{1-6}$)alkyl-, aryl-(C$_{1-6}$)alkyl-, Het and Het-(C$_{1-6}$) alkyl- are optionally substituted with 1 to 3 substituents each independently selected from (C$_{1-6}$)alkyl, halo, —CN, —OH, O(C$_{1-6}$)alkyl and —N((C$_{1-6}$)alkyl)$_2$; and R$^{12}$ is independently in each instance selected from H and (C$_{1-6}$)alkyl.

4. A compound according to claim 1, wherein R$^2$ is aryl or Het;

wherein each of the aryl and Het is optionally substituted with 1 to 3 substituents each independently selected from R$^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O )N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or wherein each of the aryl and Het is substituted with (C$_{1-6}$)alkyl or Het, wherein each of the (C$_{1-6}$)alkyl and Het is substituted with with 1 to 3 substituents each independently selected from R$^{11}$, halo, oxo, —CN, —NO$_2$, —OR", —N(R$^{12}$)R$^{11}$, —(N((C$_{1-6}$)alkyl)$_2$ R$_{11}$)$^+$, —C(=O)R$^{11}$, —C(=O)OR$^{11}$, —C(=O)N (R$^{12}$)R$^{11}$, —C(=O)N(R$^{12}$)—SO$_2$R$^{11}$, —N(R$^{12}$)—C (=O)R$^{11}$, —N(R$^{12}$)—C(=O)—(C$_{1-3}$)alkyl-N(R$^{12}$) R$^{11}$, —N(R$^{12}$)—C(=O)OR$^{11}$, —N(R12)—C(=O)N (R12)R11, —N(R$^{12}$)—SO$_2$R$^{11}$, SR$^{11}$, —SOR$^{11}$, —SO$_2$R$^{11}$ and —SO$_2$N(R$^{12}$)R$^{11}$;

R$^{11}$ is independently in each instance selected from H, (C$_{1-6}$)alkyl, (C$_{1-6}$)haloalkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl-, wherein each of the (C$_{1-6}$)alkyl, (C$_{2-6}$)alkenyl, (C$_{2-6}$) alkynyl, (C$_{3-7}$)cycloalkyl, (C$_{3-7}$)cycloalkyl-(C$_{1-6}$) alkyl-, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —CN, —NO$_2$, —OH, O(C$_{1-6}$)alkyl, —NH$_2$, —NH (C$_{1-6}$)alkyl, —N((C$_{1-6}$)alkyl)$_2$, —C(=O)—(C$_{1-6}$)alkyl, —COOH, —COO(C$_{l-6}$)alkyl, —C(=O)NH$_2$, —C(=O)NH(C$_{1-6}$)alkyl, —C(=O)N((C$_{1-6}$)alkyl)$_2$, —SH, —S(C$_{1-6}$)alkyl, —SO(C$_{1-6}$)alkyl, —SO$_2$(C$_{1-6}$) alkyl, —SO$_2$NH$_2$, SO$_2$NH(C$_{1-6}$)alkyl, —SO$_2$N((C$_{1-6}$) alkyl)$_2$, —NHC(=O)—(C$_{1-6}$)alkyl, —N((C$_{1-6}$)alkyl)C (=O)—(C$_{1-6}$)alkyl, —NHSO$_2$—(C$_{1-6}$)alkyl and —N((C$_{1-6}$)alkyl)SO$_2$—(C$_{1-6}$)alkyl; and R$^{12}$ is independently in each instance selected from R$^{11}$, —OH, —O(C$_{1-6}$)alkyl, —NH$_2$, —NH(C$_{1-6}$)alkyl and —N((C$_{1-6}$)alkyl)$_2$;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or —SO$_2$

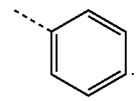

5. A compound according to claim 1, wherein R$^2$ is aryl optionally substituted with 1 or 2 substituents each independently selected from R$^{11}$, halo, —CN, —NO$_2$, —OR$^{11}$, —N(R$^{12}$)R$^{11}$, —C(=O)R$^{11}$, —C(=O)R$^{11}$, —C(=O )N(R$^{12}$)R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)N(R$^{12}$)R$^{11}$ and —N(R$^{12}$)—SO$_2$R$^{11}$;

or R$^2$ is aryl substituted with (C$_{1-6}$)alkyl wherein the (C$_{1-6}$)alkyl is substituted with 1 to 3 substituents each independently selected from R$^{11}$, —OR$^{11}$, —N(R$^{12}$) R$^{11}$, —(N((C$_{1-6}$)alkyl)$_2$R$^{11}$)$^+$ and —N(R$^{12}$)—C(=O) R$^{11}$;

wherein R$^{11}$ is independently in each instance selected from H, (C$_{1-6}$)alkyl, (C$_{1-6}$)haloalkyl, (C$_{3-7}$)cycloalkyl, aryl, aryl-(C$_{1-6}$)alkyl-, Het and Het-(C$_{1-6}$)alkyl-;

wherein Het and the Het portion of Het-(C$_{1-6}$)alkyl- are each independently selected from a 5- or 6-membered saturated, unsaturated or aromatic heterocycle having 1 to 4 heteroatoms each independently selected from O, N and S, or a 9-membered saturated, unsaturated or aromatic heteropolycycle having 1 O heteroatom;

and wherein each of the (C$_{1-6}$)alkyl, (C$_{3-7}$)cycloalkyl, aryl, aryl-(C$_{1-6}$)alkyl-, Het and Het-(C$_{1-6}$)alkyl- are optionally substituted with 1 to 3 substituents each independently selected from (C$_{1-6}$)alkyl, halo, oxo, —OH, —(C$_{1-6}$)alkyl, —NH$_2$, —NH(C$_{1-6}$)alkyl, —N((C$_{1-6}$) alkyl)$_2$, —COO(C$_{1-6}$)alkyl, —C(=O)NH(C$_{1-6}$)alkyl and —C(=O)N((C$_{1-6}$)alkyl)$_2$; and R$^{12}$ is independently in each instance selected from H, (C$_{1-6}$)alkyl, —NH$_2$, —NH(C$_{1-6}$)alkyl and —N((C$_{1-6}$) alkyl)$_2$.

6. A compound according to claim 1, wherein $R^3$ is independently in each instance selected from H and $R^{33}$, wherein $R^{33}$ is independently in each instance selected from $R^{32}$, halo, —CN, —NO$_2$, —OR$^{31}$, —N(R$^{12}$)R$^{31}$, —C(=O)R$^{31}$, —C(=O)OR$^{31}$, —C(=O)N(R$^{12}$)R$^{31}$ and —N(R$^{12}$)—C(=O)R$^{31}$;

wherein $R^{31}$ is independently in each instance selected from H and $R^{32}$ and $R^{32}$ is independently in each instance selected from (C$_{1-6}$)alkyl, (C$_{2-6}$)alkenyl, (C$_{2-6}$)alkynyl, aryl, aryl-(C$_{1-6}$)alkyl-, Het and Het-(C$_{1-6}$)alkyl-, wherein Het and the Het portion of Het-(C$_{1-6}$)alkyl- are each independently selected from a 5- or 6-membered saturated, unsaturated or aromatic heterocycle having 1 to 4 heteroatoms each independently selected from O, N and S, or a 9- or 10-membered saturated, unsaturated or aromatic heteropolycycle having wherever possible 1 or 2 heteroatoms, each independently selected from O and N;

wherein each N heteroatom may, independently and where possible, exist in an oxidized state such that it is further bonded to an oxygen atom to form an N-oxide group;

and wherein each of the (C$_{1-6}$)alkyl, (C$_{2-6}$)alkenyl, (C$_{2-6}$)alkynyl, aryl, aryl-(C$_{1-6}$)alkyl-, Het and Het-(C$_{1-6}$)alkyl- is optionally substituted with 1 to 3 substituents each independently selected from $R^{11}$, halo, oxo, —CN, —OR$^{11}$, —N(R$^{12}$)R$^{11}$, —(C=O)OR$^{11}$, —C(=O)N(R$^{12}$)R$^{11}$, —C(=NH)N(R$^{12}$)R$^{11}$, —N(R$^{12}$)—C(=O)R$^{11}$, —N(R$^{12}$)—SO$_2$R$^{11}$, —SO$_2$R$^{11}$ and —SO$_2$N(R$^{12}$)R$^{11}$;

or wherein each of the (C$_{1-6}$)alkyl, (C$_{2-6}$)alkenyl, (C$_{2-6}$)alkynyl, aryl, aryl-(C$_{1-6}$)alkyl-, Het and Het-(C$_{1-6}$)alkyl- is substituted with (C$_{1-6}$)alkyl wherein the (C$_{1-6}$)alkyl is substituted with 1 to 3 substituents each independently selected from $R^{11}$, —OR$^{11}$, —N(R$^{12}$)R$^{11}$, —C(=O)R$^{11}$, —C(=O)OR$^{11}$ and —C(=O)N(R$^{12}$)R$^{11}$;

wherein $R^{11}$ is independently in each instance selected from H, (C$_{1-6}$)alkyl, (C$_{1-6}$)haloalkyl, (C$_{3-7}$)cycloalkyl, aryl, aryl-(C$_{1-6}$)alkyl-, Het and Het-(C$_{1-6}$)alkyl-; wherein Het and the Het portion of Het-(C$_{1-6}$)alkyl- are each independently selected from a 5- or 6-membered saturated, unsaturated or aromatic heterocycle having 1 or 2 heteroatoms each independently selected from O and N;

and wherein each of the (C$_{1-6}$)alkyl, (C$_{3-7}$)cycloalkyl, aryl, aryl-(C$_{1-6}$)alkyl-, Het and Het-(C$_{1-6}$)alkyl- are optionally substituted with 1 to 3 substituents each independently selected from —OH, —O(C$_{1-6}$)alkyl, —NH$_2$, —N((C$_{1-6}$)alkyl)$_2$, —COOH and —C(=O)NH$_2$; and $R^{12}$ is independently in each instance selected from H and (C$_{1-6}$)alkyl.

7. A compound according to claim 1, wherein Y is C=O.

8. A compound of the formula II

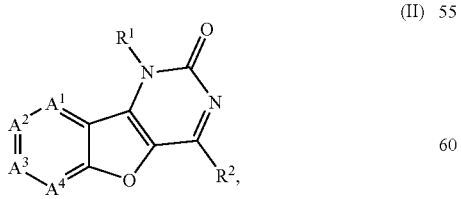

(II)

wherein
$R^1$ is H, (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-, wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from $R^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

$R^2$ is $R^{21}$, wherein $R^{21}$ is (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-;

wherein each of the (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is optionally substituted with 1 to 3 substituents each independently selected from $R^{11}$, halo, oxo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or wherein each of the (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het-(C$_{1-6}$)alkyl- is substituted with (C$_{1-6}$)alkyl or Het, wherein each of the (C$_{1-6}$)alkyl and Het is substituted with with 1 to 3 substituents each independently selected from $R^{11}$, halo, oxo, —CN, —NO$_2$, —OR$^{11}$, —N(R$^{12}$)R$^{11}$, —(N((C$_{1-6}$)alkyl)$_2$R$^{11}$)$^+$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$, —N(R$^{12}$)—C(=O)—(C$_{1-3}$)alkyl-N(R$^{12}$)R$^{11}$, —N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, -13 SOR$^{11}$, —SO$_2$R$^{11}$ and —SO$_2$N(R$^{12}$)R$^{11}$;

provided that when $R^{21}$ is unsubstituted (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-; then $R^1$ is (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het or Het-(C$_{1-6}$)alkyl-, all of which being substituted with at least one substituent selected from $R^{11}$, halo, —OR$^{11}$, oxo, —CN, —NO$_2$, —N(R$^{12}$)R$^{11}$, —C(=O)R$^{11}$, —C(=O)OR$^{11}$, —C(=O)N(R$^{12}$)R$^{11}$, —C(=O)N(R$^{12}$)—SO$_2$R$^{11}$, —N(R$^{12}$)—C(=O)R$^{11}$,—N(R$^{12}$)—C(=O)OR$^{11}$, —N(R$^{12}$)—C(=O)N(R$^{12}$)R$^{11}$, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

and provided that $R^1$ cannot be haloalkyl or alkoxy;

$A^1$, $A^2$, $A^3$ and $A^4$ are each independently selected from N and CR$^3$, wherein $R^3$ is independently in each instance selected from H and $R^{33}$, wherein $R^{33}$ is independently in each instance selected from $R^{32}$, halo, —CN, —NO$_2$, —N(R$^{12}$)R$^{31}$, —C(=O)R$^{31}$, —C(=O)OR$^{31}$, —C(=O)N(R$^{12}$)R$^{31}$, —C(=O)N(R$^{12}$)—SO$_2$R$^{31}$, —N(R$^{12}$)—C(=O)R$^{31}$, —N(R$^{12}$)—C(=O)OR$^{31}$, —N(R$^{12}$)—C(=O)N(R$^{12}$)R$^{31}$, —N(R$^{12}$)—SO$_2$R$^{31}$, —SR$^{31}$, —SOR$^{31}$, —SO$_2$R$^{31}$ and —SO$_2$N(R12)R31;

wherein $R^{31}$ is independently in each instance selected from H and $R^{32}$, and $R^{32}$ is independently in each instance selected from (C$_{1-6}$)alkyl, (C$_{2-6}$)alkenyl, (C$_{2-6}$)alkynyl, (C$_{3-7}$)cycloalkyl, (C$_{3-7}$)cycloalkyl-(C$_{1-6}$)alkyl-, aryl, aryl-(C$_{1-6}$)alkyl-, Het and Het- $(C_{1-6})$alkyl-, wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is optionally substituted with 1 to 3 substituents each independently selected from $R^{11}$, halo, oxo, —CN, —NO$_2$, —OR$^{11}$, —N(R$^{12}$)$_R$$^{11}$, —C(=O)$^{11}$, —C(=O)OR$^{11}$, —C(=O)N(R$^{12}$)R$^{11}$, —C(=O)N(R$^{12}$)—SO$_2$R$^{11}$, —C(=NH)N(R$^{12}$)R$^{11}$, —N(R$^{12}$)—C(=O)R$^{11}$, —N(R$^{12}$)—C(=O)R$^{11}$, —N(R$^{12}$)—C(=O)N(R$^{12}$)R11, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

or wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- is substituted with $(C_{1-6})$alkyl or Het, wherein each of the $(C_{1-6})$alkyl and Het is substituted with 1 to 3 substituents each independently selected from $R^{11}$, halo, oxo, —CN, —NO$_2$, —OR$^{11}$, —N(R$^{12}$)R$^{11}$, —C(=O)NR$^{12}$)R$^{11}$, —C(=O)N(R$^{12}$)—SO$_2$R$^{11}$, —N(R$^{12}$)—C(=O)R$^{11}$, —N(R$^{12}$)—C(=O)OR$^{11}$, —N(R$^{12}$)—C(=O)N(R$^{12}$)R$^{11}$, —N(R$^{12}$)—C(=O)—(C$_{1-3}$)alkyl-N(R$^{12}$)R11, —N(R$^{12}$)—SO$_2$R$^{11}$, —SR$^{11}$, —SOR$^{11}$, —SO$_2$R$^{11}$ and —SO$_2$N(R$^{12}$)R$^{11}$;

$R^{11}$ is independently in each instance selected from H, $(C_{1-6})$alkyl, $(C_{1-6})$haloalkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl-, wherein each of the $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, aryl, aryl-$(C_{1-6})$alkyl-, Het and Het-$(C_{1-6})$alkyl- are optionally substituted with 1 to 3 substituents each independently selected from $(C_{1-6})$alkyl, halo, oxo, —CN, —NO$_2$, —OH, —O $(C_{1-6})$alkyl, —NH$_2$, —NH$(C_{1-6})$alkyl, —N(($C_{1-6}$)alkyl)$_2$, —C(=O)—$(C_{1-6})$alkyl, —COOH, —COO$(C_{1-6})$alkyl, —C(=O)NH$_2$, —C(=O)NH$(C_{1-6})$alkyl, —C(=O)N(($C_{1-6}$)alkyl)$_2$, —SH, —S$(C_{1-6})$alkyl, —SO$(C_{1-6})$alkyl, —SO$_2$$(C_{1-6})$alkyl, —SO$_2$NH$_2$, —SO$_2$NH$(C_{1-6})$alkyl, —SO$_2$N(($C_{1-6}$)alkyl)$_2$, —NHC(=O)—$(C_{1-6})$alkyl, —N(($C_{1-6}$)alkyl)C(=O)—$(C_{1-6})$alkyl, —NHSO$_2$—$(C_{1-6})$alkyl and —N(($C_{1-6}$)alkyl)SO$_2$—$(C_{1-6})$alkyl; and $R^{12}$ is independently in each instance selected from $R^{11}$, —OH, —O$(C_{1-6})$alkyl, —NH$_2$, —NH$(C_{1-6})$alkyl and —N(($C_{1-6}$)alkyl)$_2$;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S;

wherein each N heteroatom may, independently and where possible, exist in an oxidized state such that it is further bonded to an oxygen atom to form an N-oxide group and wherein each S heteroatom may, independently and where possible, exist in an oxidized state such that it is further bonded to one or two oxygen atoms to form the groups SO or SO$_2$;

or a salt thereof.

9. A compound according to claim 8, wherein $R^1$ is $(C_{1-6})$alkyl, $(C_{2-6})$alkenyl, aryl, Het or Het-$(C_{1-6})$alkyl-, wherein Het and the Het portion of Het-$(C_{1-6})$alkyl- are each independently selected from a 5- or 6-membered saturated, unsaturated or aromatic heterocycle having 1 to 3 heteroatoms each independently selected from O, N and S, or an 8- or 9-membered saturated, unsaturated or aromatic heteropolycycle having 1 or 2 N heteroatoms and wherein each of the $(C_{1-6})$alkyl, $(C_{2-6})$alkenyl, aryl, Het and Het-$(C_{1-6})$alkyl- is optionally substituted with 1 to 3 substituents each independently selected from $R^{11}$, halo, —CN, —NO$_2$, —OR$^{11}$, —N(R$^{12}$)$_R$$^{11}$, —C(=O)R$^{11}$, —C(=O)OR$^{11}$, —C(=O)N(R$^{12}$)R$^{11}$, —N(R$^{12}$)—C(=O)R$^{11}$ and —N(R$^{12}$)—C(=O)OR$^{11}$;

wherein $R^{11}$ and $R^{12}$ are each independently in each instance selected from H, $(C_{1-6})$alkyl, $(C_{1-6})$haloalkyl, $(C_{2-6})$alkynyl, $(C_{3-7})$cycloalkyl-$(C_{1-6})$alkyl-, aryl-$(C_{1-6})$alkyl-, Het and Het-$(C_{1-6})$alkyl-, wherein Het and the Het portion of Het-$(C_{1-6})$alkyl- are each independently selected from a 5- or 6-membered saturated, unsaturated or aromatic heterocycle having 1 or 2 heteroatoms each independently selected from O and N, and wherein each of the $(C_{1-6})$alkyl, $(C_{2-6})$alkynyl, $(C_{3-7})$cycloalkyl-$(C_{1-6})$alkyl-, aryl-$(C_{1-6})$alkyl-, Het and Het-$(C_{1-6})$alkyl- are optionally substituted with 1 to 3 substituents each independently selected from $(C_{1-6})$alkyl, halo, —CN, —OH, —O$(C_{1-6})$alkyl and —N(($C_{1-6}$)alkyl)$_2$;

provided that when $R^2$ is $R^{21}$ and $R^{21}$ is unsubstituted $(C_{3-7})$cycloalkyl, $(C_{3-7})$cycloalkyl-$(C_{1-6})$alkyl-, aryl, aryl-$(C_{1-6})$alkyl-, Het or Het-$(C_{1-6})$alkyl-; then $R^1$ is $(C_{1-6})$alkyl, $(C_{2-6})$alkenyl, aryl, Het or Het-$(C_{1-6})$alkyl-, all of which being substituted with at least one substituent selected from $R^{11}$, halo, —CN, —NO$_2$, —OR$^{11}$, —N(R$^{12}$)R$^{11}$, —C(=O)R$^{11}$, —C(=O)OR$^{11}$, —C(=O)N(R$^{12}$)R$^{11}$, —N(R$^{12}$)R$^{11}$ and —N(R$^{12}$)—C(=O)OR$^{11}$;

and provided that $R^1$ cannot be haloalkyl or alkoxy.

10. A compound according to claim 8, wherein $R^2$ is phenyl or Het, wherein Het is a 5- or 6-membered aromatic heterocycle or a 9- or 10-membered aromatic heteropolycycle having 1 or 2 N heteroatom; and wherein the phenyl and Het are substituted with 1 to 3 substituents each independently selected from $R^{11}$, —OR$^{11}$, —N(R$^{12}$)R$^{11}$ and Het, wherein Het is selected from a 5- or 6-membered saturated, unsaturated or aromatic heterocycle having 1 or 2 heteroatoms each independently selected from O and N; and wherein the Het is substituted with 1 to 3 substituents each independently selected from $R^{11}$, —CN, —OR$^{11}$, —N(R$^{12}$)R$^{11}$, —N(R$^{12}$)—C(=O)R$^{11}$ and —SO$_2$N(R$^{12}$)R$^{11}$;

wherein $R^{11}$ and $R^{12}$ are each independently in each instance selected from H, $(C_{1-6})$alkyl, aryl, Het and Het-$(C_{1-6})$alkyl-, wherein Het and the Het portion of Het-$(C_{1-6})$alkyl- are each independently selected from a 5- or 6-membered saturated, unsaturated or aromatic heterocycle having 1 or 2 heteroatoms each independently selected from O and N and wherein each of the $(C_{1-6})$alkyl, aryl, Het and Het-$(C_{1-6})$alkyl- are optionally substituted with 1 to 3 substituents each independently selected from $(C_{1-6})$alkyl, —CN, —OH, —O$(C_{1-6})$alkyl, —NH$(C_{1-6})$alkyl, —N(($C_{1-6}$)alkyl)$_2$, —C(=O)NH$_2$ and —NHC(=O)—$(C_{1-6})$alkyl.

11. A compound according to claim 8, wherein $R^3$ is independently in each instance selected from H, halo, —CN, —NO$_2$, —CH=CH$_2$, —CF$_3$, —N(R$^{12}$)R$^{31}$, —C(=O)R$^{31}$, —C(=O)OR$^{31}$, —C(=O)N(R$^{12}$)R$^{31}$ and —N(R$^{12}$)—C(=O)R$^{31}$, phenyl and Het;

wherein the phenyl and Het are optionally substituted with 1 to 3 substituents each independently selected from $R^{11}$, halo, oxo, —CN, —OR$^{11}$, —N(R$^{12}$)R$^{11}$, —C(=O)R$^{11}$, —C(=O)OR$^{11}$, —C(=O)N(R$^{12}$)R$^{11}$, —C(=NH)N(R$^{12}$)R$^{11}$, —N(R$^{12}$)—C(=O)R$^{11}$, —N(R$^{12}$)—SO$_2$R$^{11}$, —SO$_2$R$^{11}$ and —SO$_2$N(R$^{12}$)R$^{11}$;

or wherein each of the phenyl and Het is substituted with $(C_{1-6})$alkyl wherein the $(C_{1-6})$alkyl is substituted with 1 to 3 substituents each independently selected from $R^{11}$, —OR$^{11}$, —N(R$_{12}$)R$^{11}$, —C(=O)OR$^{11}$, —C(=O)OR$^{11}$ and —C(=O)N(R$^{12}$)R$^{11}$; wherein R$^{31}$ is independently in each instance selected from H, (C$_{1-6}$)alkyl, aryl and Het;

wherein

R$^{11}$ is independently in each instance selected from H, (C$_{1-6}$)alkyl, optionally substituted with 1 to 3 substituents each independently selected from —OH, —(C$_{1-6}$)alkyl, —NH$_2$, —N((C$_{1-6}$)alkyl)$_2$, —COON and —C(=O)NH$_2$; and R$^{12}$ is independently in each instance selected from H and (C$_{1-6}$)alkyl;

wherein Het is selected from

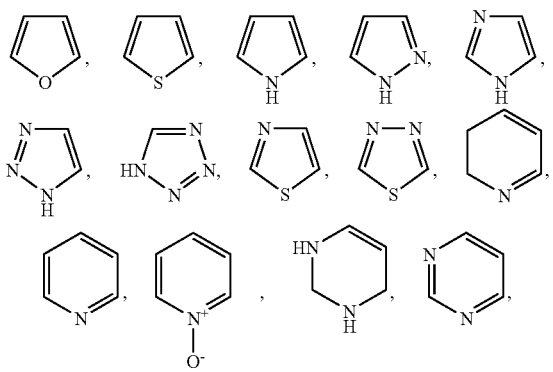

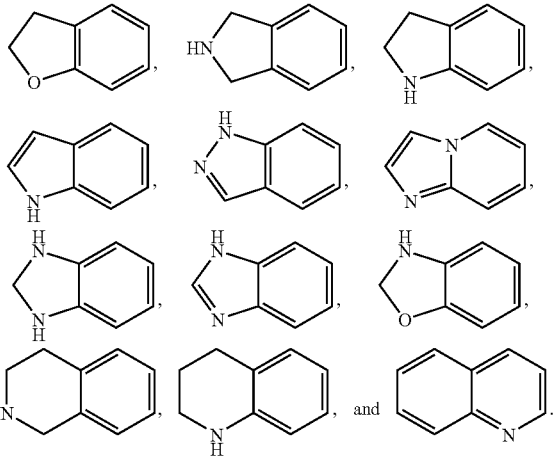

12. A pharmaceutically acceptable salt of a compound according to any one of claims 1-6 or 7-11.

13. A pharmaceutical composition comprising a compound according to any one of claims 1-6 or 7-11 or a pharmaceutically acceptable salt thereof; and one or more pharmaceutically acceptable carriers.

14. A method of treating HIV infection in a human being which comprises administering to a human host infected with HIV a therapeutically effective amount of a compound according to any one of claims 1 to 11, or a pharmaceutically acceptable salt thereof.

* * * * *